(12) United States Patent
Yamashita et al.

(10) Patent No.: US 9,133,129 B2
(45) Date of Patent: Sep. 15, 2015

(54) BICYCLIC COMPOUND

(71) Applicant: TAKEDA PHARMACEUTICAL COMPANY LIMITED, Osaka (JP)

(72) Inventors: Tohru Yamashita, Kanagawa (JP); Takuya Fujimoto, Kanagawa (JP); Ryo Mizojiri, Kanagawa (JP); Kazuko Yonemori, Kanagawa (JP); Hideki Hirose, Kanagawa (JP); Zenichi Ikeda, Kanagawa (JP); Ikuo Fujimori, Kanagawa (JP); Kyoko Toyofuku, Kanagawa (JP); Tsuneo Yasuma, Osaka (JP); Nobuyuki Matsunaga, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/353,622

(22) PCT Filed: Oct. 23, 2012

(86) PCT No.: PCT/JP2012/077357
§ 371 (c)(1),
(2) Date: Apr. 23, 2014

(87) PCT Pub. No.: WO2013/061962
PCT Pub. Date: May 2, 2013

(65) Prior Publication Data
US 2014/0243310 A1   Aug. 28, 2014

(30) Foreign Application Priority Data
Oct. 24, 2011   (JP) .................................. 2011-233457
May 29, 2012   (JP) .................................. 2012-122471

(51) Int. Cl.
| | | |
|---|---|---|
| A61K 31/437 | (2006.01) |
| C07D 471/04 | (2006.01) |
| C07D 231/56 | (2006.01) |
| A61K 31/343 | (2006.01) |
| A61K 31/416 | (2006.01) |
| A61K 31/4184 | (2006.01) |
| A61K 31/422 | (2006.01) |
| A61K 31/423 | (2006.01) |
| A61K 31/4439 | (2006.01) |
| C07D 413/04 | (2006.01) |
| C07D 498/04 | (2006.01) |
| C07D 307/80 | (2006.01) |
| C07D 235/18 | (2006.01) |
| C07D 263/57 | (2006.01) |
| C07D 513/04 | (2006.01) |

(52) U.S. Cl.
CPC ............ *C07D 231/56* (2013.01); *A61K 31/343* (2013.01); *A61K 31/416* (2013.01); *A61K 31/4184* (2013.01); *A61K 31/422* (2013.01); *A61K 31/423* (2013.01); *A61K 31/437* (2013.01); *A61K 31/4439* (2013.01); *C07D 235/18* (2013.01); *C07D 263/57* (2013.01); *C07D 307/80* (2013.01); *C07D 413/04* (2013.01); *C07D 498/04* (2013.01); *C07D 513/04* (2013.01)

(58) Field of Classification Search
CPC ........................... A61K 31/437; C07D 471/04
See application file for complete search history.

(56) References Cited

U.S. PATENT DOCUMENTS

| | | |
|---|---|---|
| 2006/0211656 A1 | 9/2006 | Albert et al. |
| 2009/0023723 A1 | 1/2009 | Cole |
| 2010/0056521 A1 | 3/2010 | Shimizu |
| 2011/0166147 A1 | 7/2011 | Macleod |
| 2011/0230454 A1 | 9/2011 | Shimizu |
| 2011/0263562 A1 | 10/2011 | Yamashita et al. |
| 2012/0010247 A1 | 1/2012 | Kamata et al. |
| 2012/0142714 A1 | 6/2012 | Yasuma et al. |
| 2013/0065883 A1 | 3/2013 | Pastor Fernandez |
| 2013/0252955 A1 | 9/2013 | Shimizu |
| 2014/0179932 A1 | 6/2014 | Shimizu |

FOREIGN PATENT DOCUMENTS

| | | |
|---|---|---|
| EP | 2 133 332 A1 | 12/2009 |
| JP | 2012-106958 | 6/2012 |
| WO | 2004/096757 | 11/2004 |
| WO | 2007/035873 | 3/2007 |
| WO | 2009/024585 | 2/2009 |
| WO | 2010/050445 | 5/2010 |
| WO | 2011/101644 | 8/2011 |
| WO | 2011/136385 | 11/2011 |
| WO | 2012/013716 | 2/2012 |
| WO | 2012/074126 | 6/2012 |
| WO | 2012/108478 | 8/2012 |

OTHER PUBLICATIONS

International Search Report issued Nov. 27, 2012 in International (PCT) Application No. PCT/JP2012/077357.
Extended European Search Report issued May 11, 2015 in corresponding Application No. 12843076.6.

*Primary Examiner* — Samantha Shterengarts
(74) *Attorney, Agent, or Firm* — Wenderoth, Lind & Ponack, L.L.P.

(57) ABSTRACT

The present invention provides a compound represented by the formula (I):

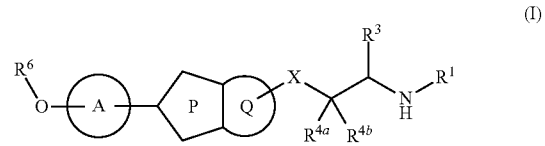

(I)

wherein each symbol is as defined in the specification, or a salt thereof.

12 Claims, No Drawings

BICYCLIC COMPOUND

TECHNICAL FIELD

The present invention relates to a bicyclic compound having an acetyl-CoA carboxylase (in the present specification, sometimes to be abbreviated as ACC) inhibitory action, which is useful for the prophylaxis or treatment of obesity, diabetes, hypertension, hyperlipidemia, cardiac failure, diabetic complications, metabolic syndrome, sarcopenia, cancer and the like.

BACKGROUND OF THE INVENTION

ACC is an enzyme that converts acetyl-CoA to malonyl-CoA, and catalyzes a rate-limiting reaction in metabolism or synthesis of fatty acid. Malonyl-CoA, which is produced by an ACC-catalyzed reaction, inhibits fatty acid oxidation in mitochondria based on the feedback inhibition of carnitine palmitoyl transferase-1 (CPT-1). Accordingly, ACC plays a key role in controlling the balance between use of carbohydrate and fatty acid in the liver and skeletal muscle, and controlling insulin sensitivity in the liver, skeletal muscle and adipose tissue.

A reduced level of malonyl-CoA by ACC inhibition can promote increased fatty acid oxidation, suppression of fatty acid synthesis, decreased secretion of triglyceride (TG)-rich lipoprotein (VLDL) in the liver, regulation of insulin secretion in the pancreas, and improvement in the insulin sensitivity in the liver, skeletal muscle and adipose tissue.

In addition, long-term administration of a compound having an ACC inhibitory action can strikingly decrease the TG content of the liver and adipose tissues and selectively decrease body fat in obese test subjects taking low fat diet, by promoting fatty acid oxidation and suppressing de novo synthesis of fatty acid.

Accordingly, a compound having an ACC inhibitory action is extremely useful for the prophylaxis or treatment of metabolic syndrome, obesity, hypertension, diabetes, cardiovascular diseases associated with atherosclerosis, and the like.

On the other hand, WO 2004/096757 A1 (patent document 1) has reported a compound represented by the formula:

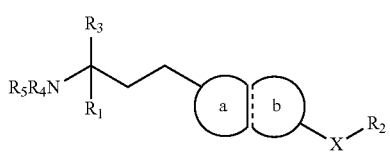

wherein
$R_1$ is $C_{1-6}$ alkyl or the like;
$R_3$ is $Z-X_2$ wherein Z is $CH_2$ or the like; and $X_2$ is OH or the like;
$R_2$ is optionally substituted phenyl (the substituent is an alkoxy group or the like);
X is a bond, O or the like;
$R_4$ and $R_5$ are each independently H, optionally substituted $C_{1-4}$ alkyl, acyl or the like; and
ring a and ring b are each independently aryl, heterocycle or the like,
as an agent for the treatment of lymphocyte-mediated diseases or autoimmune diseases.

US 2012/0010247 A1 (patent document 2) has reported a compound represented by the formula:

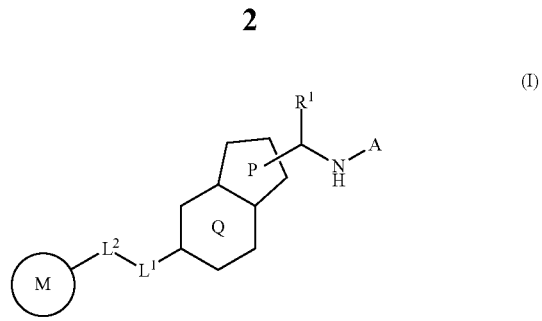

wherein
A is an acyl group or an optionally substituted 5- or 6-membered aromatic ring group;
ring M is an optionally fused 5- to 7-membered ring which is optionally further substituted;
for ring P and ring Q
(1) ring P is an optionally further substituted 5-membered heterocycle, ring Q is an optionally further substituted 6-membered ring, and ring P and ring Q are fused to form an optionally further substituted bicyclic heterocycle, or
(2) ring P is an optionally further substituted 5-membered non-aromatic ring, ring Q is an optionally further substituted 6-membered aromatic ring, and ring P and ring Q are fused to form an optionally further substituted bicyclic non-aromatic ring;
$R^1$ is an optionally substituted $C_{1-6}$ alkyl group or an optionally substituted $C_{3-6}$ cycloalkyl group; and
$L^1$ and $L^2$ are
(1) independently optionally substituted methylene, O, S, SO or $SO_2$, or
(2) $L^1$ and $L^2$ in combination form optionally substituted vinylene, or ethynylene,
provided that
(a) a compound wherein A is an α-aminoisobutyroyl group; and
(b) a compound wherein A is a 5- or 6-membered aromatic ring group substituted by
a group represented by the formula: —CO—(CH$_2$)$_3$—COOR$^{41}$ wherein R$^{41}$ is a hydrogen atom or a $C_{1-6}$ alkyl group, or
a group represented by the formula: —CO—NR$^{42}$—CR$^{43}$R$^{44}$—CR$^{45}$R$^{46}$—COOR$^{47}$ wherein R$^{42}$, R$^{43}$, R$^{44}$, R$^{45}$ and R$^{47}$ are each independently a hydrogen atom or a $C_{1-6}$ alkyl group; and R$^{46}$ is a hydrogen atom, a $C_{1-6}$ alkyl group or a hydroxy group.
are excluded,
as a compound having an ACC inhibitory action.

US 2011/0263562 A1 (patent document 3) has reported a compound represented by the formula:

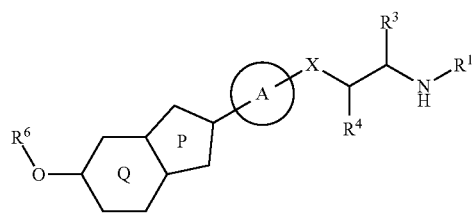

wherein
$R^1$ is a group represented by the formula: —COR$^2$ wherein R$^2$ is a hydrogen atom or a substituent, an optionally substituted 5- or 6-membered aromatic heterocyclic group or an optionally substituted phenyl group;

$R^3$ is a $C_{1-6}$ alkyl group optionally substituted by halogen atom(s), or an optionally substituted $C_{3-6}$ cycloalkyl group;

$R^4$ is a hydrogen atom or a substituent;

X is O, CO, $CR^{5a}R^{5b}$ (wherein $R^{5a}$ and $R^{5b}$ are each independently a hydrogen atom, a halogen atom or an optionally substituted $C_{1-6}$ alkyl group), $NR^{5c}$ (wherein $R^{5c}$ is a hydrogen atom or an optionally substituted $C_{1-6}$ alkyl group), S, SO or $S(O)_2$;

ring A is an optionally further substituted 4- to 7-membered non-aromatic ring (the ring is optionally bridged);

ring P is a 5-membered aromatic heterocycle, ring Q is an optionally further substituted 6-membered ring, and ring P and ring Q are fused to form an optionally further substituted bicyclic aromatic heterocycle; and $R^6$ is an optionally substituted $C_{1-6}$ alkyl group or an optionally substituted $C_{3-6}$ cycloalkyl group.

as a compound having an ACC inhibitory action.

US 2012/0142714 A1 (patent document 4) has reported a compound represented by the formula:

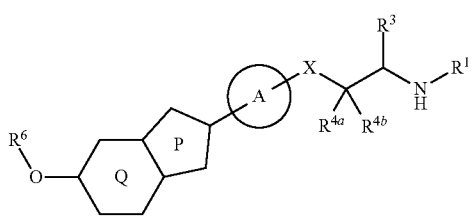

wherein $R^1$ is a group represented by the formula: $-COR^2$ wherein $R^2$ is a hydrogen atom or a substituent, or an optionally substituted 5- or 6-membered aromatic ring group;

$R^3$ is a $C_{1-6}$ alkyl group optionally substituted by halogen atom(s), or an optionally substituted $C_{3-6}$ cycloalkyl group;

$R^{4a}$ and $R^{4b}$ are each independently a hydrogen atom or a substituent;

X is O, CO, $CR^{5a}R^{5b}$ wherein $R^{5a}$ and $R^{5b}$ are each independently a hydrogen atom or a substituent, $NR^{5c}$ wherein $R^{5c}$ is a hydrogen atom or an optionally substituted $C_{1-6}$ alkyl group, S, SO, or $S(O)_2$;

ring A is an optionally further substituted 5- or 6-membered aromatic ring;

for ring P and ring Q, (1) ring P is an optionally further substituted 5-membered aromatic ring, ring Q is an optionally further substituted 6-membered ring, and ring P and ring Q are fused to form an optionally further substituted bicyclic aromatic ring, or (2) ring P is an optionally further substituted 5-membered non-aromatic ring, ring Q is an optionally further substituted 6-membered aromatic ring, and ring P and ring Q are fused to form an optionally further substituted bicyclic non-aromatic ring; and $R^6$ is an optionally substituted $C_{1-6}$ alkyl group or an optionally substituted $C_{3-6}$ cycloalkyl group, as a compound having an ACC inhibitory action.

WO 2012/108478 A1 (patent document 5) has reported a compound represented by the formula:

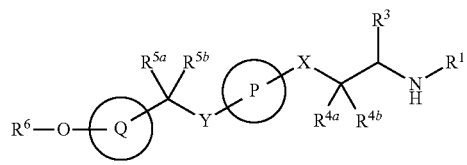

wherein $R^1$ is a group represented by the formula: $-COR^2$ wherein $R^2$ is a hydrogen atom or a substituent, or an optionally substituted 5- or 6-membered aromatic ring group;

$R^3$ is a $C_{1-6}$ alkyl group optionally substituted by halogen atom(s), or an optionally substituted $C_{3-6}$ cycloalkyl group;

$R^{4a}$ and $R^{4b}$ are each independently a hydrogen atom or a substituent, or $R^{4a}$ and $R^{4b}$ in combination optionally form a 3-membered ring or a 4-membered ring, each of which is optionally substituted;

$R^{5a}$ and $R^{5b}$ are each independently a hydrogen atom or a substituent or $R^{5a}$ and $R^{5b}$ in combination optionally form a 3-membered ring or a 4-membered ring, each of which is optionally substituted;

$R^6$ is an optionally substituted $C_{1-6}$ alkyl group or an optionally substituted $C_{3-6}$ cycloalkyl group;

X is O, CO, $CR^{7a}R^{7b}$ wherein $R^{7a}$ and $R^{7b}$ are each independently a hydrogen atom or a substituent, $NR^{7c}$ wherein $R^{7c}$ is a hydrogen atom or an optionally substituted hydrocarbon group, S, SO, or $S(O)_2$;

Y is O, CO, $CR^{8a}R^{8b}$ wherein $R^{8a}$ and $R^{8b}$ are each independently a hydrogen atom or a substituent, $NR^{8c}$ wherein $R^{8c}$ is a hydrogen atom or an optionally substituted hydrocarbon group, S, SO, or $S(O)_2$;

ring P is an optionally further substituted 3- to 7-membered ring; and ring Q is an optionally further substituted 5- or 6-membered aromatic ring, as a compound having an ACC inhibitory action.

JP 2012-106958 A (patent document 6) has reported a compound represented by the formula:

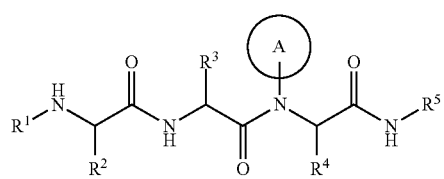

(I)

wherein $R^1$ and $R^4$ are the same or different and each is a hydrogen atom or $C_{1-6}$ alkyl optionally having substituent(s);

$R^2$ is $C_{1-6}$ alkyl optionally having substituent(s);

$R^3$ and $R^5$ are the same or different and each is a cyclic group optionally having substituent(s) or $C_{1-6}$ alkyl optionally having substituent(s); and ring A is a heterocycle optionally having substituent(s), as an IAP antagonist which is a compound useful for the prophylaxis or treatment of cancer and the like.

DOCUMENT LIST

Patent Document

Patent Document 1: WO 2004/096757 A1
Patent Document 2: US 2012/0010247 A1

Patent Document 3: US 2011/0263562 A1
Patent Document 4: US 2012/0142714 A1
Patent Document 5: WO 2012/108478 A1
Patent Document 6: JP 2012-106958 A

SUMMARY OF THE INVENTION

Problems to be Solved by the Invention

There is a demand for the development of a compound having an ACC inhibitory action, which is useful as an agent for the prophylaxis or treatment of obesity, diabetes, hypertension, hyperlipidemia, cardiac failure, diabetic complications, metabolic syndrome, sarcopenia, cancer and the like, and has superior efficacy.

Means of Solving the Problems

The present inventors have found for the first time that a compound represented by the formula (I):

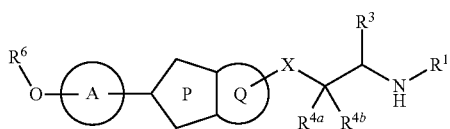

(I)

wherein
$R^1$ is a group represented by the formula: —$COR^2$ wherein $R^2$ is a hydrogen atom or a substituent, or an optionally substituted 5- or 6-membered aromatic ring group;
$R^3$ is a $C_{1-6}$ alkyl group optionally substituted by halogen atom(s), or an optionally substituted $C_{3-6}$ cycloalkyl group;
$R^{4a}$ and $R^{4b}$ are each independently a hydrogen atom or a substituent;
X is O, CO, $CR^{5a}R^{5b}$ wherein $R^{5a}$ and $R^{5b}$ are each independently a hydrogen atom or a substituent, $NR^{5c}$ wherein $R^{5c}$ is a hydrogen atom or an optionally substituted $C_{1-6}$ alkyl group, S, SO, or $S(O)_2$;
ring A is an optionally further substituted 5- or 6-membered aromatic ring;
ring P is an optionally further substituted 5-membered aromatic heterocycle;
ring Q is an optionally further substituted 5- to 7-membered ring; and
$R^6$ is an optionally substituted $C_{1-6}$ alkyl group or an optionally substituted $C_{3-6}$ cycloalkyl group,
or a salt thereof [hereinafter sometimes to be referred to as compound (I)] has a superior ACC inhibitory action, which is useful for the prophylaxis or treatment of obesity, diabetes, hypertension, hyperlipidemia, cardiac failure, diabetic complications, metabolic syndrome, sarcopenia, cancer and the like, and has superior efficacy. Based on this finding, the present inventors have conducted intensive studies and completed the present invention.

Accordingly, the present invention relates to
[1] compound (I);
[2] the compound or salt of the above-mentioned [1], wherein $R^1$ is a group represented by —$COR^2$ wherein $R^2$ is a $C_{1-6}$ alkyl group, a $C_{1-6}$ alkoxy group, or an amino group optionally mono- or di-substituted by $C_{1-6}$ alkyl group(s);
[3] the compound or salt of the above-mentioned [1] or [2], wherein $R^3$ is a $C_{1-6}$ alkyl group optionally substituted by 1 to 3 halogen atoms;

[4] the compound or salt of the above-mentioned [1], [2] or [3], wherein $R^{4a}$ and $R^{4b}$ are both hydrogen atoms;
[5] the compound or salt of the above-mentioned [1], [2], [3] or [4], wherein X is O, CO or $CH_2$;
[6] the compound or salt of the above-mentioned [1], [2], [3], [4] or [5], wherein ring A is a 5- or 6-membered aromatic ring optionally further substituted by 1 to 4 substituents selected from
    (1) a halogen atom,
    (2) a $C_{1-6}$ alkyl group, and
    (3) a $C_{1-6}$ alkoxy group;
[7] the compound or salt of the above-mentioned [1], [2], [3], [4], [5] or [6], wherein ring P and ring Q form

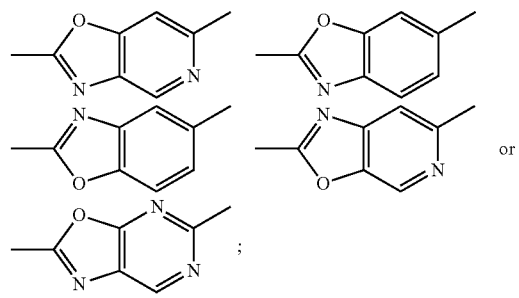

;

[8] the compound or salt of the above-mentioned [1], [2], [3], [4], [5], [6] or [7], wherein $R^6$ is a $C_{1-6}$ alkyl group optionally substituted by 1 to 3 substituents selected from
    (a) a $C_{3-6}$ cycloalkyl group optionally substituted by 1 to 5 halogen atoms,
    (b) a halogen atom,
    (c) a hydroxy group, and
    (d) a $C_{6-14}$ aryl group;
[9] the compound or salt of the above-mentioned [1], wherein $R^1$ is a group represented by —$COR^2$ wherein $R^2$ is a $C_{1-6}$ alkyl group, a $C_{1-6}$ alkoxy group, or an amino group optionally mono- or di-substituted by $C_{1-6}$ alkyl group(s),
$R^3$ is a $C_{1-6}$ alkyl group optionally substituted by 1 to 3 halogen atoms,
$R^{4a}$ and $R^{4b}$ are both hydrogen atoms,
X is O, CO or $CH_2$,
ring A is benzene, pyridine or pyridazine, each of which is optionally further substituted by 1 to 4 substituents selected from
    (1) a halogen atom,
    (2) a $C_{1-6}$ alkyl group, and
    (3) a $C_{1-6}$ alkoxy group,
ring P and ring Q form

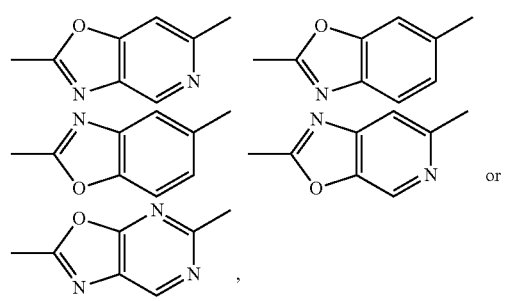

, and
$R^6$ is a $C_{1-6}$ alkyl group optionally substituted by 1 to 3 substituents selected from
  (a) a $C_{3-6}$ cycloalkyl group optionally substituted by 1 to 5 halogen atoms,
  (b) a halogen atom,
  (c) a hydroxy group, and
  (d) a $C_{6-14}$ aryl group;

[10] N-((2S)-1-((2-(4-(cyclopropylmethoxy)-2,5-difluorophenyl)[1,3]oxazolo[4,5-c]pyridin-6-yl)oxy)propan-2-yl)acetamide or a salt thereof;

[11] N-((2S)-1-((2-(4-(((1R)-2,2-difluorocyclopropyl)methoxy)phenyl)[1,3]oxazolo[4,5-c]pyridin-6-yl)oxy)propan-2-yl)acetamide or a salt thereof;

[12] N-((2S)-1-((2-(4-(((1R)-2,2-difluorocyclopropyl)methoxy)-3-fluorophenyl)[1,3]oxazolo[4,5-c]pyridin-6-yl)oxy)propan-2-yl)acetamide or a salt thereof;

[13] a medicament comprising the compound or salt of the above-mentioned [1];

[14] the medicament of the above-mentioned [13], which is an acetyl-CoA carboxylase inhibitor;

[15] the medicament of the above-mentioned [13], which is an agent for the prophylaxis or treatment of obesity or diabetes;

[16] a method of inhibiting acetyl-CoA carboxylase in a mammal, which comprises administering an effective amount of the compound or salt of the above-mentioned [1] to the mammal;

[17] a method for the prophylaxis or treatment of obesity or diabetes in a mammal, which comprises administering an effective amount of the compound or salt of the above-mentioned [1] to the mammal;

[18] the compound or salt of the above-mentioned [1] for use in the prophylaxis or treatment of obesity or diabetes;

[19] use of the compound or salt of the above-mentioned [1] for production of an agent for the prophylaxis or treatment of obesity or diabetes; and the like.

Effect of the Invention

Compound (I) has an ACC inhibitory action, which is useful for the prophylaxis or treatment of obesity, diabetes, hypertension, hyperlipidemia, cardiac failure, diabetic complications, metabolic syndrome, sarcopenia, cancer and the like, and has superior efficacy.

DETAILED DESCRIPTION OF THE INVENTION

The definition of each symbol in the formula (I) is described in detail in the following.

The "halogen atom" in the present specification means, unless otherwise specified, a fluorine atom, a chlorine atom, a bromine atom or an iodine atom.

The "$C_{1-3}$ alkylenedioxy group" in the present specification means, unless otherwise specified, methylenedioxy, ethylenedioxy or the like.

The "$C_{1-6}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

The "$C_{1-6}$ alkoxy group" in the present specification means, unless otherwise specified, methoxy, ethoxy, propoxy, isopropoxy, butoxy, isobutoxy, sec-butoxy, tert-butoxy or the like.

The "$C_{1-6}$ alkoxy-carbonyl group" in the present specification means, unless otherwise specified, methoxycarbonyl, ethoxycarbonyl, propoxycarbonyl, tert-butoxycarbonyl or the like.

The "$C_{1-6}$ alkyl-carbonyl group" in the present specification means, unless otherwise specified, acetyl, propanoyl, butanoyl, isobutanoyl, pentanoyl, isopentanoyl, hexanoyl or the like.

The "optionally substituted $C_{6-14}$ arylsulfonyloxy group" in the present specification means benzenesulfonyloxy group, p-toluenesulfonyloxy group or the like.

The "optionally substituted $C_{1-6}$ alkylsulfonyloxy group" in the present specification means methanesulfonyloxy group, trifluoromethanesulfonyloxy group or the like.

$R^1$ is a group represented by the formula: —$COR^2$ wherein $R^2$ is a hydrogen atom or a substituent, or an optionally substituted 5- or 6-membered aromatic group.

Examples of the "substituent" for $R^2$ include an "optionally substituted hydrocarbon group", an "optionally substituted heterocyclic group", an "optionally substituted hydroxy group", an "optionally substituted amino group", an "optionally substituted sulfanyl group", an "acyl group", a "halogen atom", a "cyano group", a "nitro group", and the like.

Examples of the "hydrocarbon group" of the above-mentioned "optionally substituted hydrocarbon group" include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group and the like.

Examples of the $C_{1-10}$ alkyl group include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Of these, a $C_{1-6}$ alkyl group is preferable.

Examples of the $C_{2-10}$ alkenyl group include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Of these, a $C_{2-6}$ alkenyl group is preferable.

Examples of the $C_{2-10}$ alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Of these, a $C_{2-6}$ alkynyl group is preferable.

Examples of the $C_{3-10}$ cycloalkyl group include cyclopropyl, cyclobutyl, cyclopentyl, cyclohexyl, cycloheptyl, cyclooctyl and the like. Of these, a $C_{3-6}$ cycloalkyl group is preferable.

Examples of the $C_{3-10}$ cycloalkenyl group include 2-cyclopenten-1-yl, 3-cyclopenten-1-yl, 2-cyclohexen-1-yl, 3-cyclohexen-1-yl and the like. Of these, a $C_{3-6}$ cycloalkenyl group is preferable.

Examples of the $C_{4-10}$ cycloalkadienyl group include 2,4-cyclopentadien-1-yl, 2,4-cyclohexadien-1-yl, 2,5-cyclohexadien-1-yl and the like. Of these, a $C_{4-6}$ cycloalkadienyl group is preferable.

The above-mentioned $C_{3-10}$ cycloalkyl group, $C_{3-10}$ cycloalkenyl group and $C_{4-10}$ cycloalkadienyl group are each optionally fused with a benzene ring to form a fused ring group. Examples of the fused ring group include indanyl, dihydronaphthyl, tetrahydronaphthyl, fluorenyl and the like.

In addition, the above-mentioned $C_{3-10}$ cycloalkyl group, $C_{3-10}$ cycloalkenyl group and $C_{4-10}$ cycloalkadienyl group may be each a $C_{7-10}$ bridged hydrocarbon group. Examples of the $C_{7-10}$ bridged hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Moreover, the above-mentioned $C_{3-10}$ cycloalkyl group, $C_{3-10}$ cycloalkenyl group and $C_{4-10}$ cycloalkadienyl group each optionally forms a spiro ring group together with a $C_{3-10}$ cycloalkane, a $C_{3-10}$ cycloalkene or a $C_{4-10}$ cycloalkadiene. Examples of the $C_{3-10}$ cycloalkane, $C_{3-10}$ cycloalkene and $C_{4-10}$ cycloalkadiene include rings corresponding to the above-mentioned $C_{3-10}$ cycloalkyl group, $C_{3-10}$ cycloalkenyl group and $C_{4-10}$ cycloalkadienyl group. Examples of the spiro ring group include spiro[4.5]decan-8-yl and the like.

Examples of the $C_{6-14}$ aryl group include phenyl, naphthyl, anthryl, phenanthryl, acenaphthylenyl, biphenylyl and the like. Of these, a $C_{6-12}$ aryl group is preferable.

Examples of the $C_{7-13}$ aralkyl group include benzyl, phenethyl, naphthylmethyl, biphenylylmethyl and the like.

Examples of the $C_{8-13}$ arylalkenyl group include styryl and the like.

The $C_{1-10}$ alkyl group, $C_{2-10}$ alkenyl group and $C_{2-10}$ alkynyl group, which are exemplified as the above-mentioned "hydrocarbon group", optionally have 1 to 7 (preferably 1 to 3) substituents at substitutable positions.

Examples of the substituent include (1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 so halogen atoms, and
    (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(4) a non-aromatic heterocyclic group (e.g., tetrahydrofuryl, morpholinyl, thiomorpholinyl, piperidyl, pyrrolidinyl, piperazinyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms,
    (d) a halogen atom, and
    (e) an oxo group;
(5) an amino group optionally mono- or di-substituted by substituent(s) selected from
    (a) a $C_{1-6}$ alkyl group optionally substituted by 1 to 3 halogen atoms,
    (b) a $C_{1-6}$ alkyl-carbonyl group optionally substituted by 1 to 3 halogen atoms,
    (c) a $C_{1-6}$ alkoxy-carbonyl group optionally substituted by 1 to 3 halogen atoms,
    (d) a $C_{1-6}$ alkylsulfonyl group (e.g., methylsulfonyl) optionally substituted by 1 to 3 halogen atoms,
    (e) a carbamoyl group optionally mono- or di-substituted by $C_{1-6}$ alkyl group(s) optionally substituted by 1 to 3 halogen atoms, and
    (f) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from
    (a) a halogen atom,
    (b) a $C_{1-6}$ alkoxy group,
    (c) a $C_{6-14}$ aryl group (e.g., phenyl), and
    (d) a heterocyclic group (e.g., tetrahydrofuryl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from
    (a) a halogen atom,
    (b) a carboxy group,
    (c) a $C_{1-6}$ alkoxy group,
    (d) a $C_{1-6}$ alkoxy-carbonyl group optionally substituted by 1 to 3 $C_{6-14}$ aryl groups (e.g., phenyl),
    (e) an amino group optionally mono- or di-substituted by substituent(s) selected from a $C_{1-6}$ alkyl group and a $C_{1-6}$ alkoxy-carbonyl group,
    (f) a heterocyclic group (e.g., tetrahydrofuryl), and
    (g) a $C_{3-10}$ cycloalkyl group (e.g., cyclopropyl, cyclohexyl);
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
    (a) a halogen atom, and
    (b) a $C_{1-6}$ alkyl group optionally substituted by 1 to 3 halogen atoms;
(20) a non-aromatic heterocyclylcarbonyl group (e.g., pyrrolidinylcarbonyl, morpholinylcarbonyl) optionally substituted by 1 to 3 substituents selected from $C_{1-6}$ alkyl groups optionally substituted by 1 to 3 halogen atoms;
(21) a sulfanyl group;
(22) a $C_{1-6}$ alkylsulfanyl group (e.g., methylsulfanyl, ethylsulfanyl) optionally substituted by 1 to 3 substituents selected from
    (a) a halogen atom, and
    (b) a $C_{1-6}$ alkoxy-carbonyl group;
(23) a $C_{7-13}$ aralkylsulfanyl group (e.g., benzylsulfanyl);
(24) a $C_{6-14}$ arylsulfanyl group (e.g., phenylsulfanyl, naphthylsulfanyl);
(25) a cyano group;
(26) a nitro group;

(27) a halogen atom;
(28) a $C_{1-3}$ alkylenedioxy group;
(29) a $C_{1-3}$ alkyleneoxy group (e.g., methyleneoxy, ethyleneoxy);
(30) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(31) a $C_{3-10}$ cycloalkoxy group (e.g., cyclopropoxy, cyclopentyloxy) optionally substituted by 1 to 3 substituents selected from
    (a) a halogen atom (e.g., a fluorine atom), and
    (b) a $C_{1-6}$ alkoxy group (e.g., methoxy)
and the like. When the number of the substituents is not less than 2, the respective substituents may be the same or different.

The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group, which are exemplified as the above-mentioned "hydrocarbon group", optionally have 1 to 3 substituents at substitutable positions.

Examples of the substituent include
(1) the groups exemplified as the substituents for the above-mentioned $C_{1-10}$ alkyl group and the like;
(2) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group, and
    (f) an amino group optionally mono- or di-substituted by $C_{1-6}$ alkyl group(s);
(3) a $C_{2-6}$ alkenyl group (e.g., ethenyl, 1-propenyl) optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group, and
    (f) an amino group optionally mono- or di-substituted by $C_{1-6}$ alkyl group(s);
(4) a $C_{7-13}$ aralkyl group (e.g., benzyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group, and
    (d) a halogen atom;
and the like. When the number of the substituents is not less than 2, the respective substituents may be the same or different.

Examples of the "heterocyclic group" of the above-mentioned "optionally substituted heterocyclic group" include an "aromatic heterocyclic group" and a "non-aromatic heterocyclic group".

Examples of the aromatic heterocyclic group include a 5- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 5- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, and the like.

Preferable examples of the aromatic heterocyclic group include
monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; fused aromatic heterocyclic groups such as
quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl), pyridopyridinyl (e.g., pyrido[2,3-b]pyridin-3-yl), thienopyridyl (e.g., thieno[2,3-b]pyridin-3-yl) and the like; and the like.

Examples of the non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom and a nitrogen atom, and a fused aromatic heterocyclic group. Examples of the fused aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are fused, a group wherein the above-mentioned group is partially saturated, and the like.

Preferable examples of the non-aromatic heterocyclic group include monocyclic non-aromatic heterocyclic groups such as azetidinyl (e.g., 1-azetidinyl, 2-azetidinyl, 3-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like;

fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolyl (e.g., 1,2-dihydroquinolin-4-yl), tetrahydroquinolyl (e.g., 1,2,3,4-tetrahydroquinolin-4-yl), dihydroisoquinolyl (e.g., 1,2-dihydroisoquinolin-4-yl), tetrahydroisoquinolyl (e.g., 1,2,3,4-tetrahydroisoquinolin-4-yl), dihydrophthalazinyl (e.g., 1,4-dihydrophthalazin-4-yl) and the like;

and the like.

The "heterocyclic group" of the "optionally substituted heterocyclic group" optionally has 1 to 3 substituents at substitutable positions. Examples of the substituent include those similar to the substituents that the $C_{3-10}$ cycloalkyl group and the like exemplified as the "hydrocarbon group" of the above-mentioned "optionally substituted hydrocarbon group" optionally has. When the heterocyclic group is a "non-aromatic heterocyclic group", the substituent further includes an oxo group. When the number of the substituents is not less than 2, the respective substituents may be the same or different.

Examples of the above-mentioned "optionally substituted hydroxy group" include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include those similar to the "aromatic heterocyclic group" and "non-aromatic heterocyclic group" exemplified as the "heterocyclic group" of the above-mentioned "optionally substituted heterocyclic group".

The above-mentioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group and heterocyclic group optionally have 1 to 3 substituents at substitutable positions. When the number of the substituents is not less than 2, the respective substituents may be the same or different.

Examples of the substituent for the $C_{1-10}$ alkyl group, $C_{2-10}$ alkenyl group and $C_{1-6}$ alkyl-carbonyl group include those similar to the substituent that the $C_{1-10}$ alkyl group and the like exemplified as the "hydrocarbon group" of the above-mentioned "optionally substituted hydrocarbon group" optionally has.

Examples of the substituent for the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those similar to the substituent that the $C_{3-10}$ cycloalkyl group and the like exemplified as the "hydrocarbon group" of the above-mentioned "optionally substituted hydrocarbon group" optionally has. Examples of the substituent for the heterocyclic group include those similar to the substituent that the "heterocyclic group" of the above-mentioned "optionally substituted heterocyclic group" optionally has.

Examples of the above-mentioned "optionally substituted sulfanyl group" include a sulfanyl group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

Examples of the substituent include those exemplified as the substituents of the above-mentioned "optionally substituted hydroxy group".

Examples of the above-mentioned "optionally substituted amino group" include an amino group optionally mono- or di-substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group and a heterocyclic group, each of which is optionally substituted; an acyl group and the like.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those exemplified as the "hydrocarbon group" of the above-mentioned "optionally substituted hydrocarbon group".

Examples of the heterocyclic group include those similar to the "aromatic heterocyclic group" and "non-aromatic heterocyclic group" exemplified as the "heterocyclic group" of the above-mentioned "optionally substituted heterocyclic group". Of these, a 5- or 7-membered monocyclic aromatic heterocyclic group is preferable.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and heterocyclic group optionally have 1 to 3 substituents at substitutable positions. When the number of the substituents is not less than 2, the respective substituents may be the same or different.

Examples of the substituent for the $C_{1-10}$ alkyl group and $C_{2-10}$ alkenyl group include those similar to the substituent that the $C_{1-10}$ alkyl group and the like exemplified as the "hydrocarbon group" of the above-mentioned "optionally substituted hydrocarbon group" optionally has.

Examples of the substituent for the $C_{3-10}$ cycloalkyl group, $C_{3-10}$ cycloalkenyl group, $C_{6-14}$ aryl group, $C_{7-13}$ aralkyl group and $C_{8-13}$ arylalkenyl group include those similar to the substituent that the $C_{3-10}$ cycloalkyl group and the like exemplified as the "hydrocarbon group" of the above-mentioned "optionally substituted hydrocarbon group" optionally has. Examples of the substituent for the heterocyclic group include those similar to the substituent that the "heterocyclic group" of the above-mentioned "optionally substituted heterocyclic group" optionally has.

Examples of the "acyl group" exemplified as the substituent for the "optionally substituted amino group" include those similar to the "acyl group" below, which is exemplified as the "substituent" for $R^2$.

Examples of the "acyl group" exemplified as the "substituent" for $R^2$ include a group represented by the formula: —$COR^A$, —CO—$CR^A$, —$SO_3R^A$, —$S(O)_2R^A$, —$SOR^A$, —CO—$NR^{A'}R^{B'}$, —CS—$NR^{A'}R^{B'}$ or —$S(O)_2NR^{A'}R^{B'}$ wherein $R^A$ is a hydrogen atom, an optionally substituted hydrocarbon group or an optionally substituted heterocyclic group, $R^{A'}$ and $R^{B'}$ are the same or different and each is a hydrogen atom, an optionally substituted hydrocarbon group or an optionally substituted heterocyclic group, or $R^{A'}$ and $R^{B'}$ form, together with the adjacent nitrogen atom, an optionally substituted nitrogen-containing heterocycle, and the like.

Examples of the "optionally substituted hydrocarbon group" and "optionally substituted heterocyclic group" for $R^A$, $R^{A'}$ or $R^{B'}$ include those similar to the "optionally substituted hydrocarbon group" and "optionally substituted heterocyclic group", which are exemplified as the "substituent" for $R^2$.

Examples of the "nitrogen-containing heterocycle" of the "optionally substituted nitrogen-containing heterocycle" formed by $R^{A'}$ and $R^{B'}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 or 2) substituents at substitutable positions. Examples of the substituent include those similar to the substituent that the "heterocyclic group" of the "optionally substituted heterocyclic group", which is exemplified as the "substituent" for $R^2$, optionally has. When the number of the substituents is not less than 2, the respective substituents may be the same or different.

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
   (a) a $C_{1-6}$ alkyl group optionally substituted by 1 to 3 substituents selected from a halogen atom, a $C_{1-6}$ alkoxy group, a $C_{1-6}$ alkoxy-carbonyl group and a carboxy group, and
   (b) an amino group optionally mono- or di-substituted by $C_{1-6}$ alkoxy-carbonyl group(s);
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl, pyrrolidinocarbonyl) optionally substituted by 1 to 3 substituents selected from a $C_{1-6}$ alkyl group optionally substituted by 1 to 3 halogen atoms; and the like.

$R^2$ is preferably an optionally substituted $C_{1-6}$ alkyl group, an optionally substituted $C_{1-6}$ alkoxy group, an optionally substituted amino group, an optionally substituted non-aromatic heterocyclic group or an optionally substituted aromatic heterocyclic group.

$R^2$ is more preferably a $C_{1-6}$ alkyl group (e.g., methyl), a $C_{1-6}$ alkoxy group (e.g., methoxy), an amino group optionally mono- or di-substituted by $C_{1-6}$ alkyl group(s) (e.g., methyl), a 4- to 7-membered monocyclic non-aromatic heterocyclic group (e.g., azetidinyl) or a 5- to 7-membered aromatic heterocyclic group (e.g., pyrazolyl).

$R^2$ is still more preferably a $C_{1-6}$ alkyl group (e.g., methyl), a $C_{1-6}$ alkoxy group (e.g., methoxy) or an amino group optionally mono- or di-substituted by $C_{1-6}$ alkyl group(s) (e.g., methyl).

$R^2$ is particularly preferably a $C_{1-6}$ alkyl group (e.g., methyl).

The "group represented by the formula: —$COR^2$" for $R^1$ is preferably a group represented by —$COR^2$ wherein $R^2$ is an optionally substituted $C_{1-6}$ alkyl group, an optionally substituted $C_{1-6}$ alkoxy group, an optionally substituted amino group, an optionally substituted non-aromatic heterocyclic group or an optionally substituted aromatic heterocyclic group.

The "group represented by the formula: —$COR^2$" for $R^1$ is more preferably a group represented by —$COR^2$ wherein $R^2$ is a $C_{1-6}$ alkyl group (e.g., methyl), a $C_{1-6}$ alkoxy group (e.g., methoxy), an amino group optionally mono- or di-substituted by $C_{1-6}$ alkyl group(s) (e.g., methyl), a 4- to 7-membered monocyclic non-aromatic heterocyclic group (e.g., azetidinyl) or a 5- to 7-membered aromatic heterocyclic group (e.g., pyrazolyl).

The "group represented by the formula: —$COR^2$" for $R^1$ is still more preferably a group represented by —$COR^2$ wherein $R^2$ is a $C_{1-6}$ alkyl group (e.g., methyl), a $C_{1-6}$ alkoxy group (e.g., methoxy) or an amino group optionally mono- or di-substituted by $C_{1-6}$ alkyl group(s) (e.g., methyl).

The "group represented by the formula: —$COR^2$" for $R^1$ is particularly preferably a group represented by —$COR^2$ wherein $R^2$ is a $C_{1-6}$ alkyl group (e.g., methyl).

Examples of the "5- or 6-membered aromatic ring group" of the "optionally substituted 5- or 6-membered aromatic ring group" for $R^1$ include phenyl, pyrrolyl, pyrazolyl, imidazolyl, triazolyl (1,2,3-triazolyl, 1,2,4-triazolyl, 1,3,4-triazolyl), tetrazolyl, oxazolyl, isoxazolyl, thiazolyl, isothiazolyl, oxadiazolyl, thiadiazolyl, furyl, thienyl, pyridyl, pyridazinyl, pyrimidinyl, pyrazinyl, triazinyl and the like.

The "5- or 6-membered aromatic ring group" is preferably a 5-membered aromatic heterocyclic group, more preferably pyrazolyl, oxazolyl, isoxazolyl, thiazolyl, isothiazolyl, thiadiazolyl or the like, particularly preferably isoxazolyl.

The "5- or 6-membered aromatic ring group" of the "optionally substituted 5- or 6-membered aromatic ring group" for $R^1$ optionally has 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

The "optionally substituted 5- or 6-membered aromatic ring group" for $R^1$ is preferably a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 substituents selected from a $C_{1-6}$ alkyl group (e.g., methyl).

$R^1$ is preferably
(1) a group represented by —$COR^2$ wherein $R^2$ is an optionally substituted $C_{1-6}$ alkyl group, an optionally substituted $C_{1-6}$ alkoxy group, an optionally substituted amino group, an optionally substituted non-aromatic heterocyclic group or an optionally substituted aromatic heterocyclic group; or
(2) an optionally substituted 5- or 6-membered aromatic ring group.

$R^1$ is more preferably
(1) a group represented by —$COR^2$ wherein $R^2$ is a $C_{1-6}$ alkyl group (e.g., methyl), a $C_{1-6}$ alkoxy group (e.g., methoxy), an amino group optionally mono- or di-substituted by $C_{1-6}$ alkyl group(s) (e.g., methyl), a 4- to 7-membered monocyclic non-aromatic heterocyclic group (e.g., azetidinyl) or a 5- to 7-membered monocyclic aromatic heterocyclic group (e.g., pyrazolyl); or
(2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 $C_{1-6}$ alkyl groups (e.g., methyl).

$R^1$ is further more preferably a group represented by —$COR^2$ wherein $R^2$ is a $C_{1-6}$ alkyl group (e.g., methyl), a $C_{1-6}$ alkoxy group (e.g., methoxy), an amino group optionally mono- or di-substituted by $C_{1-6}$ alkyl group(s) (e.g., methyl), a 4- to 7-membered monocyclic non-aromatic heterocyclic group (e.g., azetidinyl) or a 5- to 7-membered monocyclic aromatic heterocyclic group (e.g., pyrazolyl).

$R^1$ is still more preferably a group represented by —$COR^2$ wherein $R^2$ is a $C_{1-6}$ alkyl group (e.g., methyl), a $C_{1-6}$ alkoxy group (e.g., methoxy) or an amino group optionally mono- or di-substituted by $C_{1-6}$ alkyl group(s) (e.g., methyl).

$R^1$ is particularly preferably a group represented by —$COR^2$ wherein $R^2$ is a $C_{1-6}$ alkyl group (e.g., methyl).

$R^3$ is a $C_{1-6}$ alkyl group optionally substituted by halogen atom(s), or an optionally substituted $C_{3-6}$ cycloalkyl group.

The "$C_{1-6}$ alkyl group" of the "$C_{1-6}$ alkyl group optionally substituted by halogen atom(s)" for $R^3$ optionally has preferably 1 to 7, more preferably 1 to 3 halogen atoms, at substitutable positions.

Examples of the "$C_{3-6}$ cycloalkyl group" of the "optionally substituted $C_{3-6}$ cycloalkyl group" for $R^3$ include cyclopropyl, cyclobutyl, cyclopentyl and cyclohexyl.

The "$C_{3-6}$ cycloalkyl group" of the "optionally substituted $C_{3-6}$ cycloalkyl group" for $R^3$ optionally has 1 to 3 substituents at substitutable positions. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

$R^3$ is preferably a $C_{1-6}$ alkyl group (e.g., methyl) optionally substituted by 1 to 3 halogen atoms.

$R^3$ is more preferably a $C_{1-6}$ alkyl group (e.g., methyl).

$R^{4a}$ and $R^{4b}$ are each independently a hydrogen atom or a substituent.

Examples of the "substituent" for $R^{4a}$ or $R^{4b}$ include those similar to the "substituent" for $R^2$.

$R^{4a}$ and $R^{4b}$ are preferably each independently a hydrogen atom or an optionally substituted $C_{1-6}$ alkyl group (e.g., methyl), more preferably each independently a hydrogen atom or a $C_{1-6}$ alkyl group (e.g., methyl), particularly preferably both hydrogen atoms.

$R^6$ is an optionally substituted $C_{1-6}$ alkyl group or an optionally substituted $C_{3-6}$ cycloalkyl group.

The "$C_{1-6}$ alkyl group" of the "optionally substituted $C_{1-6}$ alkyl group" for $R^6$ optionally has 1 to 3 substituents at substitutable positions. Examples of the substituent include those similar to the substituents that the $C_{1-10}$ alkyl group and the like exemplified as the "hydrocarbon group" of the "optionally substituted hydrocarbon group", which is exemplified as the "substituent" for $R^2$, optionally has.

Examples of the "optionally substituted $C_{3-6}$ cycloalkyl group" for $R^6$ include those similar to the "optionally substituted $C_{3-6}$ cycloalkyl group" for $R^3$.

$R^6$ is preferably an optionally substituted $C_{1-6}$ alkyl group.

$R^6$ is more preferably a $C_{1-6}$ alkyl group (e.g., methyl, ethyl, propyl, isopropyl, butyl, isobutyl) optionally substituted by 1 to 3 substituents selected from
(a) a $C_{3-6}$ cycloalkyl group (e.g., cyclopropyl, cyclobutyl) optionally substituted by 1 to 5 substituents selected from
(i) a halogen atom (e.g., a fluorine atom), and
(ii) a $C_{1-6}$ alkyl group (e.g., methyl),
(b) a halogen atom (e.g., a fluorine atom),
(c) a hydroxy group,
(d) a $C_{6-14}$ aryl group (e.g., phenyl), and
(e) a cyano group.

$R^6$ is still more preferably a $C_{1-6}$ alkyl group (e.g., methyl, ethyl, propyl, isopropyl, butyl, isobutyl) optionally substituted by 1 to 3 substituents selected from
(a) a $C_{3-6}$ cycloalkyl group (e.g., cyclopropyl, cyclobutyl) optionally substituted by 1 to 5 halogen atoms (e.g., a fluorine atom),
(b) a halogen atom (e.g., a fluorine atom),
(c) a hydroxy group, and
(d) a $C_{6-14}$ aryl group (e.g., phenyl).

$R^6$ is particularly preferably a $C_{1-6}$ alkyl group (preferably methyl) substituted by $C_{3-6}$ cycloalkyl group(s) (preferably cyclopropyl) optionally substituted by 1 to 3 halogen atoms (preferably a fluorine atom).

X is O, CO, $CR^{5a}R^{5b}$ wherein $R^{5a}$ and $R^{5b}$ are each independently a hydrogen atom or a substituent, $NR^{5c}$ wherein $R^{5c}$ is a hydrogen atom or an optionally substituted $C_{1-6}$ alkyl group, S, SO or $S(O)_2$.

Examples of the "substituent" for $R^{5a}$ or $R^{5b}$ include those similar to the "substituent" for $R^2$.

$R^{5a}$ and $R^{5b}$ are preferably each independently a hydrogen atom or a halogen atom (e.g., a fluorine atom).

$R^{5a}$ and $R^{5b}$ are more preferably both hydrogen atoms.

The "$C_{1-6}$ alkyl group" of the "optionally substituted $C_{1-6}$ alkyl group" for $R^{5c}$ optionally has 1 to 3 substituents at substitutable positions. Examples of the substituent include those similar to the substituents that the $C_{1-10}$ alkyl group and the like exemplified as the "hydrocarbon group" of the "optionally substituted hydrocarbon group", which is exemplified as the "substituent" for $R^2$, optionally has.

$R^{5c}$ is preferably a hydrogen atom or a $C_{1-6}$ alkyl group, more preferably a hydrogen atom.

X is preferably O, CO, $CR^{5a}R^{5b}$ wherein $R^{5a}$ and $R^{5b}$ are each independently a hydrogen atom or a halogen atom (e.g., a fluorine atom), $NR^{5c}$ wherein $R^{5c}$ is a hydrogen atom or a $C_{1-6}$ alkyl group, S, SO or $S(O)_2$.

X is more preferably O, CO, $CH_2$, NH, S, SO or $S(O)_2$.

X is still more preferably O, CO or $CH_2$.

X is particularly preferably C.

Ring P is an optionally further substituted 5-membered aromatic heterocycle.

Examples of the "5-membered aromatic heterocycle" of the "optionally further substituted 5-membered aromatic heterocycle" for ring P include pyrrole, pyrazole, imidazole, triazole (1,2,3-triazole, 1,2,4-triazole, 1,3,4-triazole), tetrazole, oxazole, isoxazole, thiazole, isothiazole, oxadiazole, thiadiazole, furan, thiophene and the like. Among them, oxazole, thiazole, furan, pyrazole, imidazole and 1,2,3-triazole are preferable, oxazole, thiazole, furan, pyrazole and imidazole are more preferable, and oxazole is particularly preferable.

The "5-membered aromatic heterocycle" of the "optionally further substituted 5-membered aromatic heterocycle" for ring P optionally has 1 or 2 substituents at substitutable positions, in addition to ring A. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

Ring P is preferably a 5-membered aromatic heterocycle, more preferably oxazole, thiazole, furan, pyrazole, imidazole or 1,2,3-triazole, more preferably oxazole, thiazole, furan, pyrazole or imidazole, particularly preferably oxazole.

Ring Q is an optionally further substituted 5- to 7-membered ring.

Examples of the "5- to 7-membered ring" of the "optionally further substituted 5- to 7-membered ring" for ring Q include benzene, a $C_{5-7}$ cycloalkane, a $C_{5-7}$ cycloalkene, a $C_{5-7}$ cycloalkadiene, a 5- to 7-membered aromatic heterocycle and a 5- to 7-membered non-aromatic heterocycle.

Examples of the "$C_{5-7}$ cycloalkane" include cyclopentane, cyclohexane and cycloheptane. Among them, cyclohexane is preferable.

Examples of the "$C_{5-7}$ cycloalkene" include cyclopentene, cyclohexene and cycloheptene. Among them, cyclohexene is preferable.

Examples of the "$C_{5-7}$ cycloalkadiene" include 2,4-cyclopentadiene, 2,4-cyclohexadiene, 2,5-cyclohexadiene, 2,4-cycloheptadiene, 2,5-cycloheptadiene and the like. Among them, 2,4-cyclohexadiene and 2,5-cyclohexadiene are preferable, and 2,4-cyclohexadiene is particularly preferable.

Examples of the "5- to 7-membered aromatic heterocycle" include pyrrole, pyrazole, imidazole, triazole (1,2,3-triazole, 1,2,4-triazole, 1,3,4-triazole), tetrazole, oxazole, isoxazole, thiazole, isothiazole, oxadiazole, thiadiazole, furan, thiophene, pyridine, pyridazine, pyrimidine, pyrazine, triazine and the like. Among them, a 6-membered nitrogen-containing aromatic heterocycle (preferably pyridine, pyridazine, pyrimidine, pyrazine, more preferably pyridine, pyrimidine, still more preferably pyridine) is preferable.

Examples of the "5- to 7-membered non-aromatic heterocycle" include pyrrolidine, piperidine, morpholine, piperazine, hexamethylenimine, oxazolidine, thiazolidine, imidazolidine, oxazoline, thiazoline, imidazoline, dioxole, dioxolane, dihydrooxadiazole, pyran, dihydropyran, tetrahydropyran, thiopyran, dihydrothiopyran, tetrahydrothiopyran, dihydrofuran, tetrahydrofuran, pyrazolidine, pyrazoline, dihydropyridine, tetrahydropyridine, dihydropyrimidine, tetrahydropyrimidine, dihydrotriazole, tetrahydrotriazole and the like. Among them, a 5- or 6-membered (preferably 6-membered) nitrogen-containing non-aromatic heterocycle (preferably pyrrolidine, piperidine, piperazine, dihydropyrimidine, tetrahydropyridine, particularly preferably tetrahydropyridine) is preferable.

The "5- to 7-membered ring" of the "optionally further substituted 5- to 7-membered ring" for ring Q is preferably a 6-membered ring, more preferably benzene, cyclohexane, cyclohexene, 2,4-cyclohexadiene, 2,5-cyclohexadiene, a 6-membered nitrogen-containing aromatic heterocycle (preferably pyridine, pyridazine, pyrimidine or pyrazine, more preferably pyridine or pyrimidine, particularly preferably pyridine) or a 6-membered nitrogen-containing non-aromatic heterocycle (preferably pyrrolidine, piperidine, piperazine, dihydropyrimidine or tetrahydropyridine, particularly preferably tetrahydropyridine), still more preferably benzene, pyridine, pyrimidine, tetrahydropyridine, cyclohexane, cyclohexene or 2,4-cyclohexadiene, particularly preferably benzene, pyridine or cyclohexane.

The "5- to 7-membered ring" of the "optionally further substituted 5- to 7-membered ring" for ring Q optionally has 1 to 3 substituents at substitutable positions, in addition to group —X—. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

Preferable Examples of additional substituent for the "5- to 7-membered ring" of the "optionally further substituted 5- to 7-membered ring" for ring Q include a halogen atom (e.g., a fluorine atom, a chlorine atom).

Ring Q is preferably an optionally further substituted 6-membered ring.

Ring Q is more preferably benzene, cyclohexane, cyclohexene, 2,4-cyclohexadiene, 2,5-cyclohexadiene, a 6-membered nitrogen-containing aromatic heterocycle (preferably pyridine, pyridazine, pyrimidine or pyrazine, more preferably pyridine or pyrimidine, particularly preferably pyridine) or a 6-membered nitrogen-containing non-aromatic heterocycle (preferably pyrrolidine, piperidine, piperazine, dihydropyrimidine or tetrahydropyridine, particularly preferably tetrahydropyridine), each of which is optionally further substituted by 1 to 3 halogen atoms (e.g., a fluorine atom, a chlorine atom).

Ring Q is more preferably benzene, pyridine, pyrimidine, tetrahydropyridine, cyclohexane, cyclohexene or 2,4-cyclohexadiene, each of which is optionally further substituted by 1 to 3 halogen atoms (e.g., a fluorine atom, a chlorine atom).

Ring Q is particularly preferably benzene or pyridine or cyclohexane, each of which is optionally further substituted by 1 to 3 halogen atoms (preferably a fluorine atom).

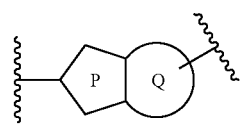

in the formula (I) means that ring P and ring Q are fused to form an "optionally further substituted heterobicycle".

For example, when ring P is oxazole, and ring Q is benzene, examples of the "optionally further substituted heterobicycle" formed by fusion of ring P and ring Q include
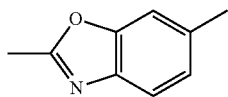
and the like.
Preferable specific examples of the "heterobicycle" of the "optionally further substituted heterobicycle" formed by fusion of ring P and ring Q include
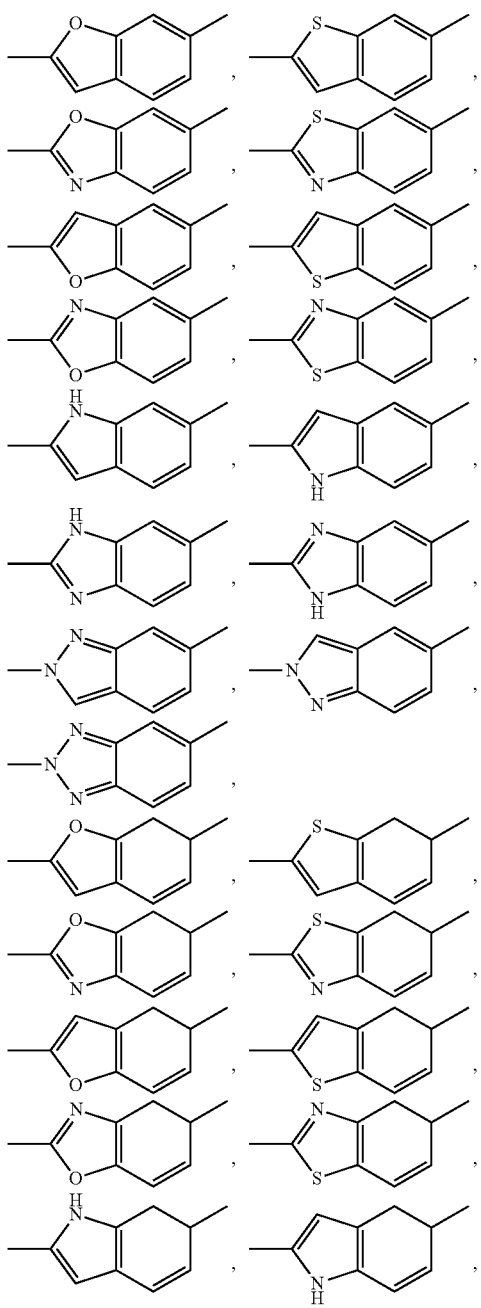
-continued
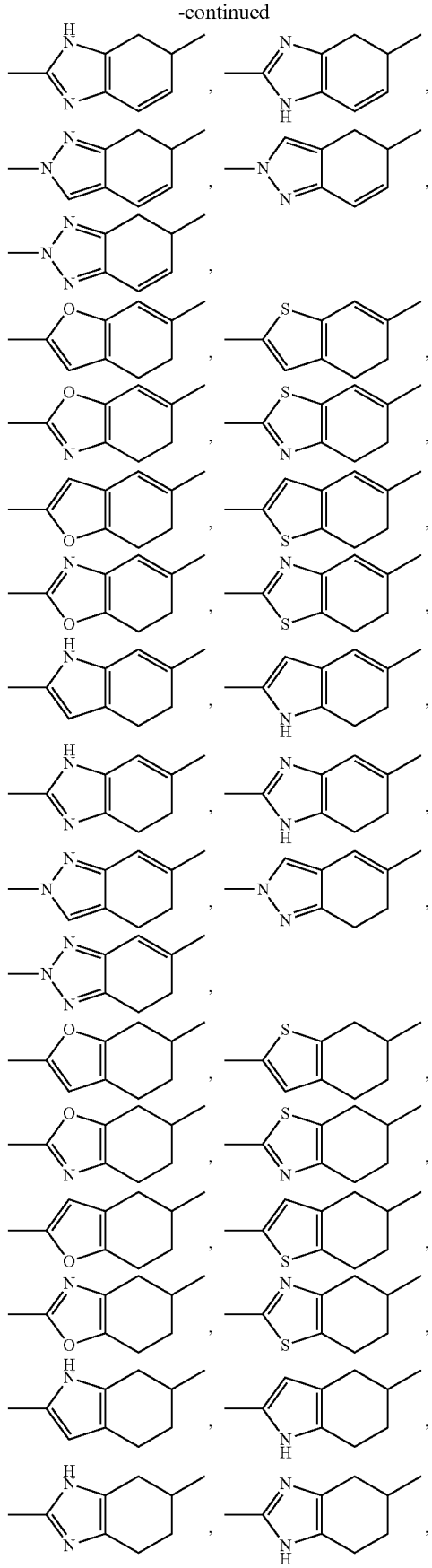

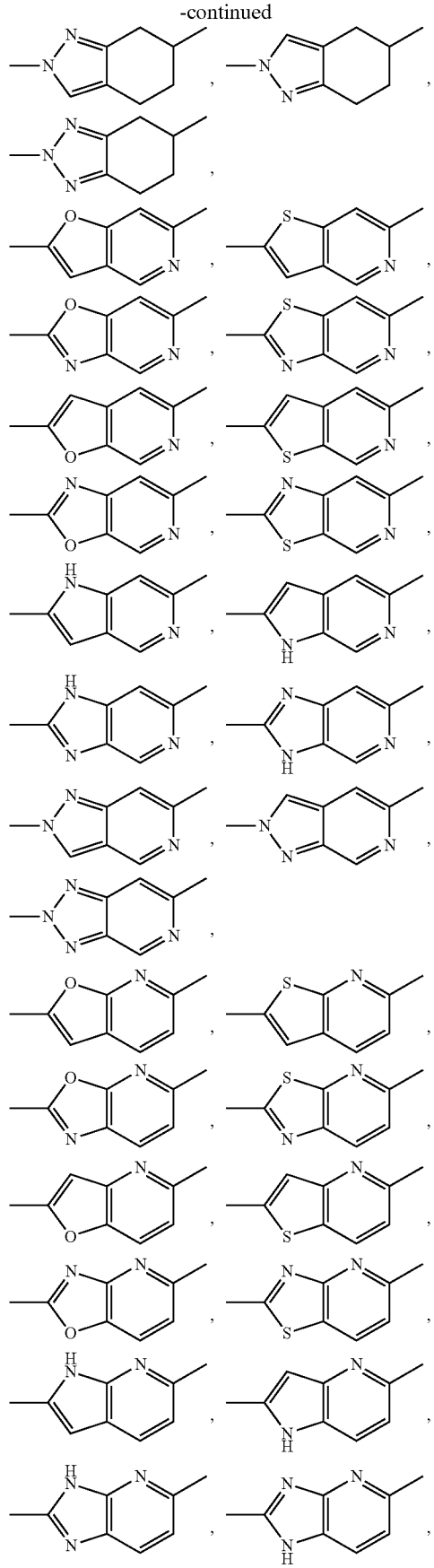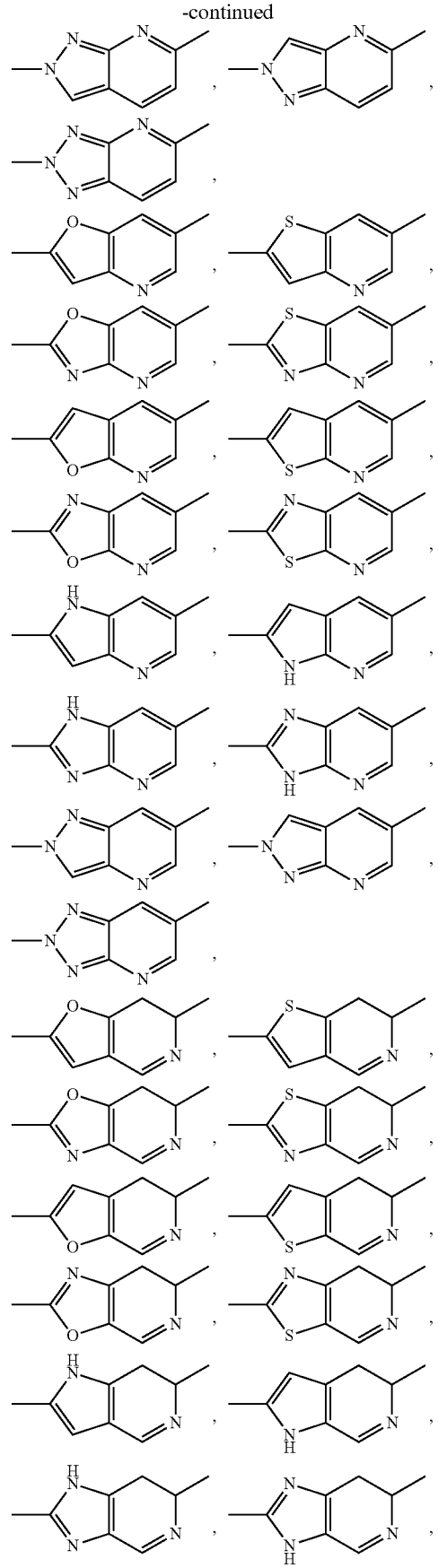

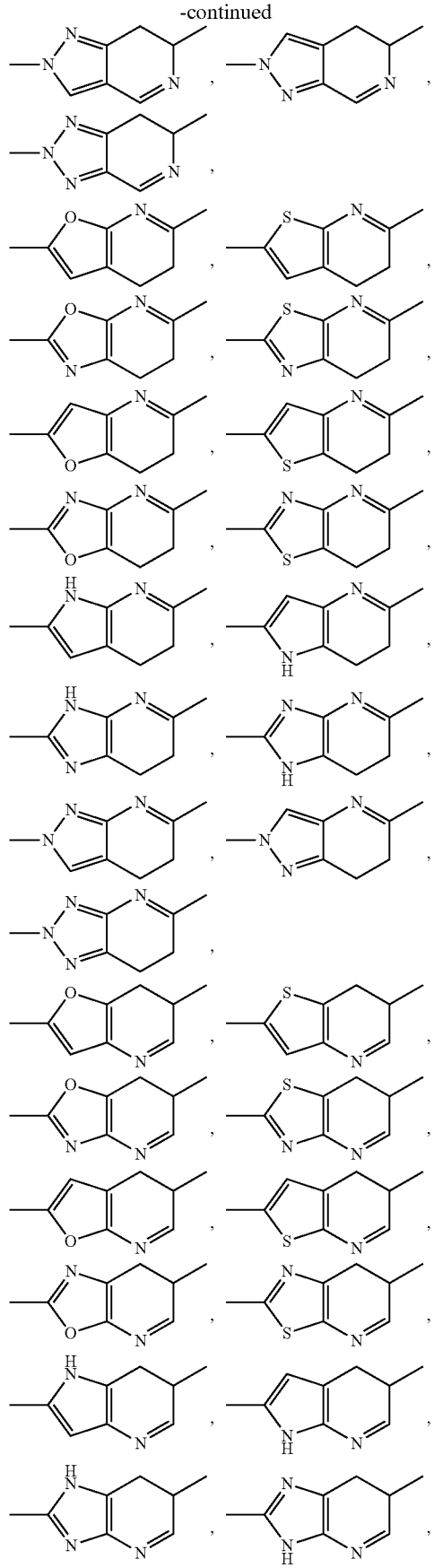
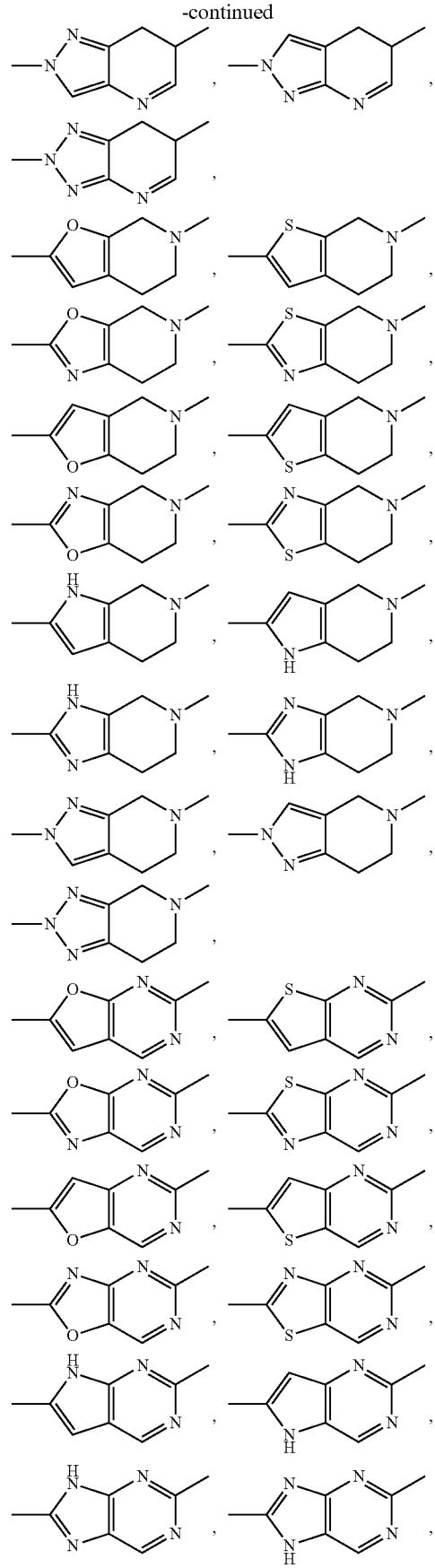

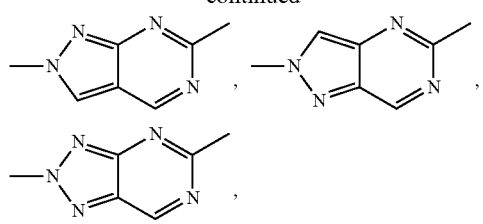

and the like.

The "heterobicycle" of the "optionally further substituted heterobicycle" formed by fusion of ring P and ring Q optionally has 1 to 3 substituents at substitutable positions on ring P and ring Q, in addition to group —X— and ring A. Examples of the substituent include those similar to the substituents that the $C_{3-10}$ cycloalkyl group and the like exemplified as the "hydrocarbon group" of the "optionally substituted hydrocarbon group", which is exemplified as the "substituent" for $R^2$, optionally has.

Preferable Examples of additional substituent for the "heterobicycle" of the "optionally further substituted heterobicycle" formed by fusion of ring P and ring Q include preferably a halogen atom (e.g., a fluorine atom, a chlorine atom).

The "heterobicycle" of the "optionally further substituted heterobicycle" formed by fusion of ring P and ring Q is preferably

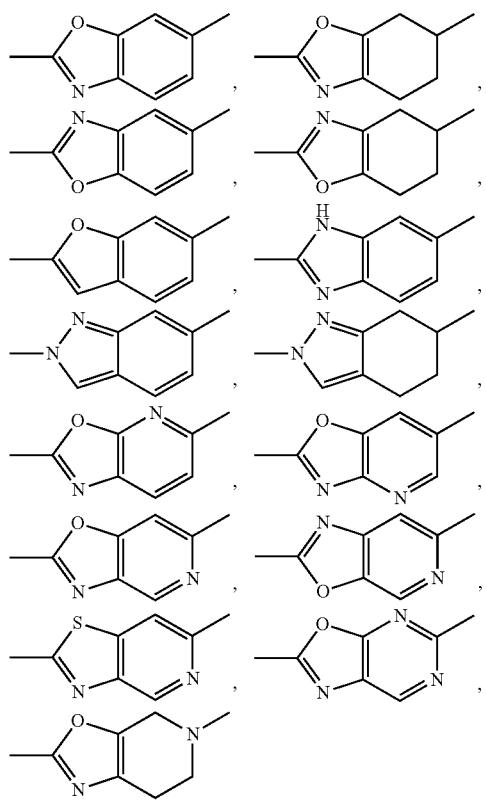

or the like.

The "heterobicycle" of the "optionally further substituted heterobicycle" formed by ring P and ring Q is more preferably

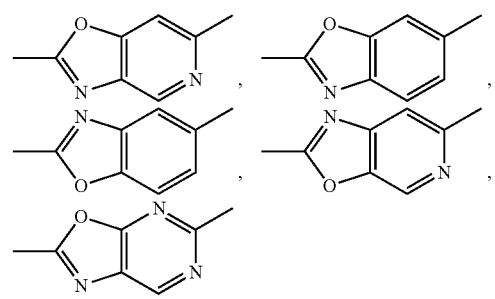

or the like.

In another embodiment, the "heterobicycle" of the "optionally further substituted heterobicycle" formed by fusion of ring P and ring Q is more preferably

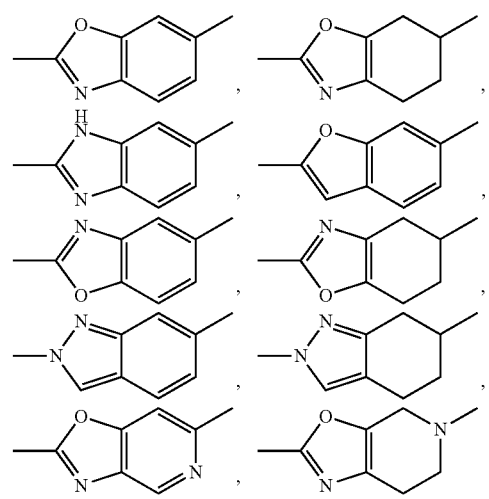

or the like.

The "heterobicycle" of the "optionally further substituted heterobicycle" formed by fusion of ring P and ring Q is still more preferably

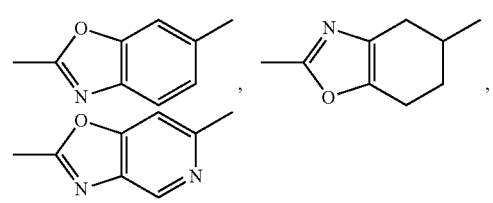

or the like.

The "heterobicycle" of the "optionally further substituted heterobicycle" formed by fusion of ring P and ring Q is particularly preferably

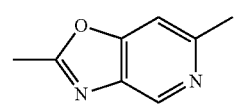

The "optionally further substituted heterobicycle" formed by fusion of ring P and ring Q is preferably

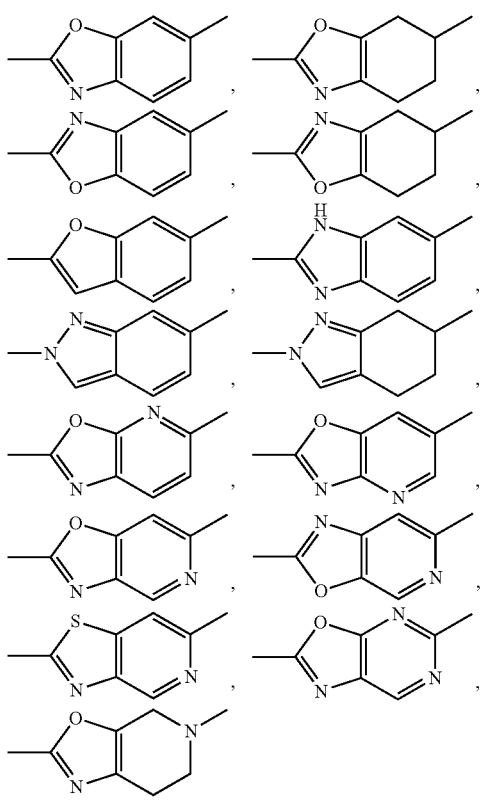

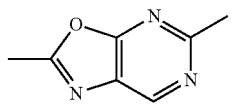

or the like).

In another embodiment, the "optionally further substituted heterobicycle" formed by fusion of ring P and ring Q is more preferably

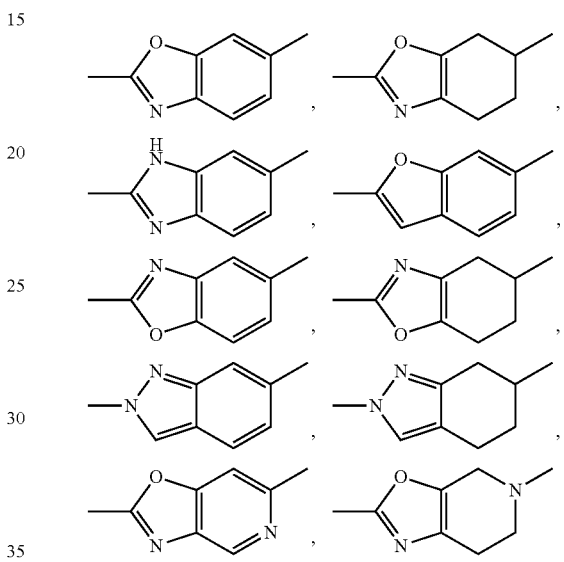

or the like, wherein each ring Q is optionally further substituted by 1 to 3 halogen atoms (e.g., a fluorine atom, a chlorine atom).

The "optionally further substituted heterobicycle" formed by ring P and ring Q is more preferably

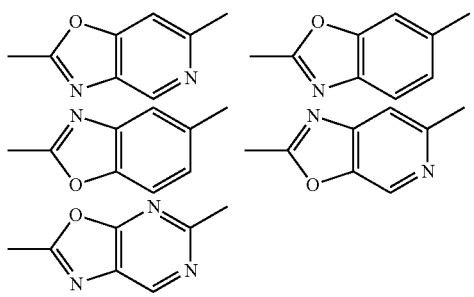

or the like, wherein each ring Q is optionally further substituted by 1 to 3 halogen atoms (e.g., a fluorine atom, a chlorine atom) (among them, the "optionally further substituted heterobicycle" formed by ring P and ring Q is preferably

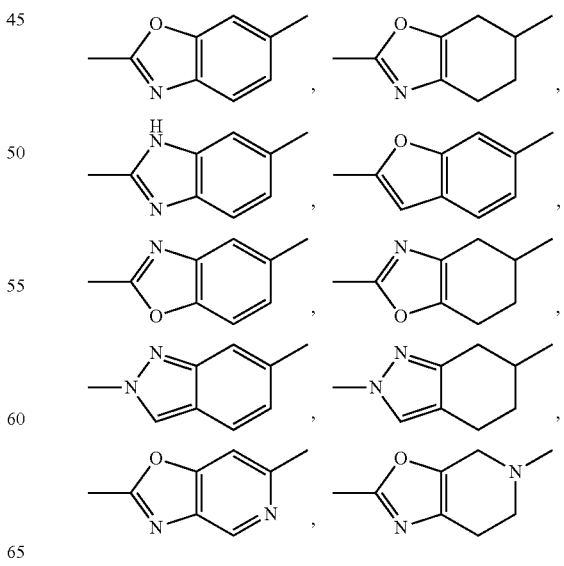

or the like, wherein each ring Q is optionally further substituted by 1 to 3 halogen atoms (e.g., a fluorine atom, a chlorine atom) (among them, the "optionally further substituted heterobicycle" formed by ring P and ring Q is preferably

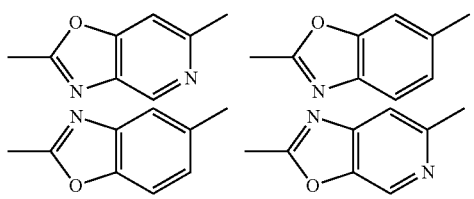

or the like).

The "optionally further substituted heterobicycle" formed by fusion of ring P and ring Q is still more preferably

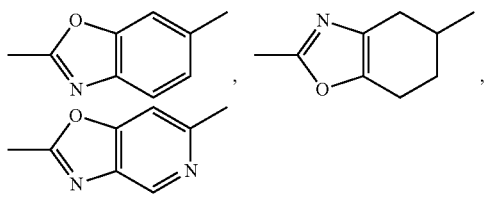

or the like, wherein each ring Q is optionally further substituted by 1 to 3 halogen atoms (e.g., a fluorine atom) (among them, the "optionally further substituted heterobicycle" formed by ring P and ring Q is preferably

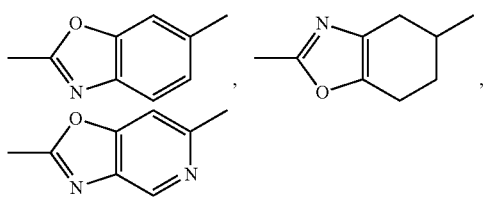

or the like).

The "optionally further substituted heterobicycle" formed by fusion of ring P and ring Q is particularly preferably [0181]

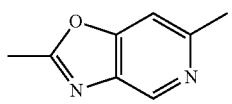

or the like, wherein each ring Q is optionally further substituted by 1 to 3 halogen atoms (e.g., a fluorine atom, a chlorine atom) (among them, the "optionally further substituted heterobicycle" formed by ring P and ring Q is preferably

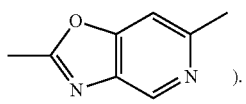

Ring A is an optionally further substituted 5- or 6-membered aromatic ring.

Examples of the "5- or 6-membered aromatic ring" of the "optionally further substituted 5- or 6-membered aromatic ring" for ring A include benzene, pyrrole, pyrazole, imidazole, triazole (1,2,3-triazole, 1,2,4-triazole, 1,3,4-triazole), tetrazole, oxazole, isoxazole, thiazole, isothiazole, oxadiazole, thiadiazole, furan, thiophene, pyridine, pyridazine, pyrimidine, pyrazine, triazine and the like. Among them, benzene, pyridine, isoxazole, thiophene, pyrimidine, pyridazine and pyrazine are preferable, benzene, pyridine and pyridazine are more preferable, and benzene and pyridine are still more preferable.

The "5- or 6-membered aromatic ring" of the "optionally further substituted 5- or 6-membered aromatic ring" for ring A optionally has 1 to 4 substituents at substitutable positions, in addition to group —C—R$^6$ and ring P. Examples of the substituent include those similar to the substituents that the $C_{3-10}$ cycloalkyl group and the like exemplified as the "hydrocarbon group" of the "optionally substituted hydrocarbon group", which is exemplified as the "substituent" for R$^2$, optionally has.

Additional substituent for the "5- or 6-membered aromatic ring" of the "optionally further substituted 5- or 6-membered aromatic ring" for ring A is preferably selected from (1) a halogen atom (e.g., a fluorine atom, a chlorine atom, a bromine atom),
(2) a $C_{1-6}$ alkyl group (e.g., methyl, ethyl) optionally substituted by 1 to 3 substituents selected from
   (a) a hydroxy group, and
   (b) a halogen atom (e.g., a fluorine atom),
(3) a $C_{1-6}$ alkoxy group (e.g., methoxy, ethoxy) optionally substituted by 1 to 3 halogen atoms (e.g., a fluorine atom),
(4) a cyano group, and
(5) a $C_{1-6}$ alkyl-carbonyl group (e.g., acetyl), more preferably selected from
(1) a halogen atom (e.g., a fluorine atom, a chlorine atom, a bromine atom),
(2) a $C_{1-6}$ alkyl group (e.g., methyl, ethyl), and
(3) a $C_{1-6}$ alkoxy group (e.g., methoxy, ethoxy) still more preferably selected from a halogen atom (e.g., a fluorine atom, a chlorine atom, a bromine atom) and a $C_{1-6}$ alkoxy group (e.g., methoxy, ethoxy).

Ring A is preferably a 5- or 6-membered aromatic ring (preferably benzene, pyridine, isoxazole, thiophene, pyrimidine, pyridazine or pyrazine, more preferably benzene, pyridine or pyridazine, particularly preferably benzene or pyridine) optionally further substituted by 1 to 4 substituents selected from
(1) a halogen atom (e.g., a fluorine atom, a chlorine atom, a bromine atom),
(2) a $C_{1-6}$ alkyl group (e.g., methyl, ethyl) optionally substituted by 1 to 3 substituents selected from
   (a) a hydroxy group, and
   (b) a halogen atom (e.g., a fluorine atom),
(3) a $C_{1-6}$ alkoxy group (e.g., methoxy, ethoxy) optionally substituted by 1 to 3 halogen atoms (e.g., a fluorine atom),
(4) a cyano group, and
(5) a $C_{1-6}$ alkyl-carbonyl group (e.g., acetyl).

Ring A is more preferably a 5- or 6-membered aromatic ring (preferably benzene, pyridine, isoxazole, thiophene, pyrimidine, pyridazine or pyrazine, more preferably benzene, pyridine or pyridazine, particularly preferably benzene or pyridine) optionally further substituted by 1 to 4 substituents selected from
(1) a halogen atom (e.g., a fluorine atom, a chlorine atom, a bromine atom),
(2) a $C_{1-6}$ alkyl group (e.g., methyl, ethyl), and
(3) a $C_{1-6}$ alkoxy group (e.g., methoxy, ethoxy).

Ring A is further more preferably benzene, pyridine, isoxazole, thiophene, pyrimidine, pyridazine or pyrazine, each of which is optionally further substituted by 1 to 4 substituents selected from
(1) a halogen atom (e.g., a fluorine atom, a chlorine atom, a bromine atom),
(2) a $C_{1-6}$ alkyl group (e.g., methyl, ethyl), and
(3) a $C_{1-6}$ alkoxy group (e.g., methoxy, ethoxy).

Ring A is still more preferably benzene, pyridine or pyridazine, each of which is optionally further substituted by 1 to 4 substituents selected from
(1) a halogen atom (e.g., a fluorine atom, a chlorine atom, a bromine atom),
(2) a $C_{1-6}$ alkyl group (e.g., methyl, ethyl), and
(3) a $C_{1-6}$ alkoxy group (e.g., methoxy, ethoxy).

Ring A is particularly preferably benzene or pyridine, each of which is optionally further substituted by 1 or 2 substituents selected from
  (1) a halogen atom (preferably a fluorine atom, a chlorine atom, a bromine atom), and
  (2) a $C_{1-6}$ alkoxy group (preferably methoxy, ethoxy).

Preferable examples of compound (I) include the following compounds.

[Compound A]
  Compound (I) wherein
  $R^1$ is
  (1) a group represented by —$COR^2$ wherein $R^2$ is an optionally substituted $C_{1-6}$ alkyl group, an optionally substituted $C_{1-6}$ alkoxy group or an optionally substituted amino group, or
  (2) an optionally substituted 5- or 6-membered aromatic ring group;
  $R^3$ is a $C_{1-6}$ alkyl group optionally substituted by 1 to 3 halogen atoms;
  $R^{4a}$ and $R^{4b}$ are both hydrogen atoms;
  $R^6$ is an optionally substituted $C_{1-6}$ alkyl group;
  X is preferably O, CO, $CR^{5a}R^{5b}$ wherein $R^{5a}$ and $R^{5b}$ are each independently a hydrogen atom or a halogen atom (e.g., a fluorine atom), $NR^{5c}$ wherein $R^{5c}$ is a hydrogen atom or a $C_{1-6}$ alkyl group, S, SO or $S(O)_2$;
  ring P is a 5-membered aromatic heterocycle;
  ring Q is an optionally further substituted 6-membered ring; and
  ring A is an optionally further substituted 5- or 6-membered aromatic ring.

[Compound A-1]
  Compound (I) wherein
  $R^1$ is
  (1) a group represented by —$COR^2$ wherein $R^2$ is an optionally substituted $C_{1-6}$ alkyl group, an optionally substituted $C_{1-6}$ alkoxy group, an optionally substituted amino group or an optionally substituted non-aromatic heterocyclic group, or
  (2) an optionally substituted 5- or 6-membered aromatic ring group;
  $R^3$ is a $C_{1-6}$ alkyl group optionally substituted by 1 to 3 halogen atoms;
  $R^{4a}$ and $R^{4b}$ are both hydrogen atoms;
  $R^6$ is an optionally substituted $C_{1-6}$ alkyl group;
  X is preferably O, CO, $CR^{5a}R^{5b}$ wherein $R^{5a}$ and $R^{5b}$ are each independently a hydrogen atom or a halogen atom (e.g., a fluorine atom), $NR^{5c}$ wherein $R^{5c}$ is a hydrogen atom or a $C_{1-6}$ alkyl group, S, SO or $S(O)_2$;
  ring P is a 5-membered aromatic heterocycle;
  ring Q is an optionally further substituted 6-membered ring; and
  ring A is an optionally further substituted 5- or 6-membered aromatic ring.

[Compound A-2]
  Compound (I) wherein
  $R^1$ is
  (1) a group represented by —$COR^2$ wherein $R^2$ is an optionally substituted $C_{1-6}$ alkyl group, an optionally substituted $C_{1-6}$ alkoxy group, an optionally substituted amino group, an optionally substituted non-aromatic heterocyclic group or an optionally substituted aromatic heterocyclic group, or
  (2) an optionally substituted 5- or 6-membered aromatic ring group;
  $R^3$ is a $C_{1-6}$ alkyl group optionally substituted by 1 to 3 halogen atoms;
  $R^{4a}$ and $R^{4b}$ are each independently a hydrogen atom or an optionally substituted $C_{1-6}$ alkyl group;
  $R^6$ is an optionally substituted $C_{1-6}$ alkyl group;
  X is preferably O, CO, $CR^{5a}R^{5b}$ wherein $R^{5a}$ and $R^{5b}$ are each independently a hydrogen atom or a halogen atom (e.g., a fluorine atom), $NR^{5c}$ wherein $R^{5c}$ is a hydrogen atom or a $C_{1-6}$ alkyl group, S, SO or $S(O)_2$;
  ring P is a 5-membered aromatic heterocycle;
  ring Q is an optionally further substituted 6-membered ring; and
  ring A is an optionally further substituted 5- or 6-membered aromatic ring.

[Compound B]
  Compound (I) wherein
  $R^1$ is
  (1) a group represented by —$COR^2$ wherein $R^2$ is a $C_{1-6}$ alkyl group (e.g., methyl), a $C_{1-6}$ alkoxy group (e.g., methoxy) or an amino group optionally mono- or di-substituted by $C_{1-6}$ alkyl group(s) (e.g., methyl), or
  (2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 $C_{1-6}$ alkyl groups (e.g., methyl);
  $R^3$ is a $C_{1-6}$ alkyl group (e.g., methyl);
  $R^{4a}$ and $R^{4b}$ are both hydrogen atoms;
  $R^6$ is a $C_{1-6}$ alkyl group (e.g., methyl, ethyl, propyl, isopropyl, isobutyl) optionally substituted by 1 to 3 substituents selected from
    (a) a $C_{3-6}$ cycloalkyl group (e.g., cyclopropyl) optionally substituted by 1 to 5 halogen atoms (e.g., a fluorine atom),
    (b) a halogen atom (e.g., a fluorine atom),
    (c) a hydroxy group, and
    (d) a $C_{6-14}$ aryl group (e.g., phenyl);
  X is O, CO, $CH_2$, NH, S, SO or $S(O)_2$;
  ring P is oxazole, thiazole, furan, pyrazole, imidazole or 1,2,3-triazole;
  ring Q is benzene, cyclohexane, cyclohexene, 2,4-cyclohexadiene, 2,5-cyclohexadiene, a 6-membered nitrogen-containing aromatic heterocycle (preferably pyridine, pyridazine, pyrimidine or pyrazine, particularly preferably pyridine) or a 6-membered nitrogen-containing non-aromatic heterocycle (preferably pyrrolidine, piperidine, piperazine, dihydropyrimidine or tetrahydropyridine, particularly preferably tetrahydropyridine), each of which is optionally further substituted by 1 to 3 halogen atoms (e.g., a fluorine atom, a chlorine atom); and ring A is benzene, pyridine or isoxazole, each of which is optionally further substituted by 1 to 4 substituents selected from
    (1) a halogen atom (e.g., a fluorine atom, a chlorine atom, a bromine atom),
    (2) a $C_{1-6}$ alkyl group (e.g., methyl), and
    (3) a $C_{1-6}$ alkoxy group (e.g., methoxy).

[Compound B-1]
  Compound (I) wherein
  $R^1$ is
  (1) a group represented by —$COR^2$ wherein $R^2$ is a $C_{1-6}$ alkyl group (e.g., methyl), a $C_{1-6}$ alkoxy group (e.g., methoxy), an amino group optionally mono- or di-substituted by $C_{1-6}$ alkyl group(s) (e.g., methyl) or a 4- to 7-membered monocyclic non-aromatic heterocyclic group (e.g., azetidinyl), or
  (2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 $C_{1-6}$ alkyl groups (e.g., methyl);
  $R^3$ is a $C_{1-6}$ alkyl group (e.g., methyl);
  $R^{4a}$ and $R^{4b}$ are both hydrogen atoms;
  $R^6$ is a $C_{1-6}$ alkyl group (e.g., methyl, ethyl, propyl, isopropyl, isobutyl) optionally substituted by 1 to 3 substituents selected from (a) a $C_{3-6}$ cycloalkyl group (e.g., cyclopropyl) optionally substituted by 1 to 5 halogen atoms (e.g., a fluorine atom),
(b) a halogen atom (e.g., a fluorine atom),
(c) a hydroxy group, and
(d) a $C_{6-14}$ aryl group (e.g., phenyl);
X is O, CO, $CH_2$, NH, S, SO or $S(O)_2$;
ring P is oxazole, thiazole, furan, pyrazole, imidazole or 1,2,3-triazole;
ring Q is benzene, cyclohexane, cyclohexene, 2,4-cyclohexadiene, 2,5-cyclohexadiene, a 6-membered nitrogen-containing aromatic heterocycle (preferably pyridine, pyridazine, pyrimidine or pyrazine, particularly preferably pyridine) or a 6-membered nitrogen-containing non-aromatic heterocycle (preferably pyrrolidine, piperidine, piperazine, dihydropyrimidine or tetrahydropyridine, particularly preferably tetrahydropyridine), each of which is optionally further substituted by 1 to 3 halogen atoms (e.g., a fluorine atom, a chlorine atom); and ring A is benzene, pyridine, isoxazole or thiophene, each of which is optionally further substituted by 1 to 4 substituents selected from
   (1) a halogen atom (e.g., a fluorine atom, a chlorine atom, a bromine atom),
   (2) a $C_{1-6}$ alkyl group (e.g., methyl), and
   (3) a $C_{1-6}$ alkoxy group (e.g., methoxy).

[Compound B-2]

Compound (I) wherein $R^1$ is (1) a group represented by —$COR^2$ wherein $R^2$ is a $C_{1-6}$ alkyl group (e.g., methyl), a $C_{1-6}$ alkoxy group (e.g., methoxy), an amino group optionally mono- or di-substituted by $C_{1-6}$ alkyl group(s) (e.g., methyl), a 4- to 7-membered monocyclic non-aromatic heterocyclic group (e.g., azetidinyl) or a 5- to 7-membered monocyclic aromatic heterocyclic group (e.g., pyrazolyl); or (2) a 5-membered aromatic heterocyclic group (e.g., pyrazolyl, oxazolyl, isoxazolyl, thiazolyl, isothiazolyl, thiadiazolyl, preferably isoxazolyl) optionally substituted by 1 to 3 $C_{1-6}$ alkyl groups (e.g., methyl);

$R^3$ is a $C_{1-6}$ alkyl group (e.g., methyl);
$R^{4a}$ and $R^{4b}$ are each independently a hydrogen atom or a $C_{1-6}$ alkyl group (e.g., methyl);
$R^6$ is a $C_{1-6}$ alkyl group (e.g., methyl, ethyl, propyl, isopropyl, butyl, isobutyl) optionally substituted by 1 to 3 substituents selected from
   (a) a $C_{3-6}$ cycloalkyl group (e.g., cyclopropyl, cyclobutyl) optionally substituted by 1 to 5 substituents selected from
      (i) a halogen atom (e.g., a fluorine atom), and
      (ii) a $C_{1-6}$ alkyl group (e.g., methyl),
   (b) a halogen atom (e.g., a fluorine atom),
   (c) a hydroxy group,
   (d) a $C_{6-14}$ aryl group (e.g., phenyl), and
   (e) a cyano group;
X is O, CO, $CH_2$, NH, S, SO or $S(O)_2$;
ring P is oxazole, thiazole, furan, pyrazole, imidazole or 1,2,3-triazole;
ring Q is benzene, cyclohexane, cyclohexene, 2,4-cyclohexadiene, 2,5-cyclohexadiene, a 6-membered nitrogen-containing aromatic heterocycle (preferably pyridine, pyridazine, pyrimidine or pyrazine, more preferably pyridine or pyrimidine, particularly preferably pyridine), or 6-membered nitrogen-containing non-aromatic heterocycle (preferably pyrrolidine, piperidine, piperazine, dihydropyrimidine or tetrahydropyridine, particularly preferably tetrahydropyridine), each of which is optionally further substituted by 1 to 3 halogen atoms (e.g., a fluorine atom, a chlorine atom); and ring A is a 5- or 6-membered aromatic ring (preferably benzene, pyridine, isoxazole, thiophene, pyrimidine, pyridazine or pyrazine, more preferably benzene, pyridine or pyridazine, particularly preferably benzene or pyridine) optionally further substituted by 1 to 4 substituents selected from
   (1) a halogen atom (e.g., a fluorine atom, a chlorine atom, a bromine atom),
   (2) a $C_{1-6}$ alkyl group (e.g., methyl, ethyl) optionally substituted by 1 to 3 substituents selected from
      (a) a hydroxy group, and
      (b) a halogen atom (e.g., a fluorine atom),
   (3) a $C_{1-6}$ alkoxy group (e.g., methoxy, ethoxy) optionally substituted by 1 to 3 halogen atoms (e.g., a fluorine atom),
   (4) a cyano group, and
   (5) a $C_{1-6}$ alkyl-carbonyl group (e.g., acetyl).

[Compound C]

Compound (I) wherein
$R^1$ is a group represented by —$COR^2$ wherein $R^2$ is a $C_{1-6}$ alkyl group (e.g., methyl), a $C_{1-6}$ alkoxy group (e.g., methoxy) or an amino group optionally mono- or di-substituted by $C_{1-6}$ alkyl group(s) (e.g., methyl);
$R^3$ is a $C_{1-6}$ alkyl group (e.g., methyl);
$R^{4a}$ and $R^{4b}$ are both hydrogen atoms;
$R^6$ is a $C_{1-6}$ alkyl group (e.g., methyl, ethyl, propyl, isopropyl, isobutyl) optionally substituted by 1 to 3 substituents selected from
   (a) a $C_{3-6}$ cycloalkyl group (e.g., cyclopropyl) optionally substituted by 1 to 5 halogen atoms (e.g., a fluorine atom),
   (b) a halogen atom (e.g., a fluorine atom),
   (c) a hydroxy group, and
   (d) a $C_{6-14}$ aryl group (e.g., phenyl);
X is O, CO or $CH_2$;
ring P is oxazole, furan, pyrazole or imidazole;
ring Q is benzene, pyridine, tetrahydropyridine, cyclohexane, cyclohexene or 2,4-cyclohexadiene, each of which is optionally further substituted by 1 to 3 halogen atoms (e.g., a fluorine atom, a chlorine atom);
(preferably ring P and ring Q form wherein each ring Q is optionally further substituted by 1 to 3 halogen atoms (e.g., a fluorine atom, a chlorine atom)); and
ring A is benzene, pyridine or isoxazole, each of which is optionally further substituted by 1 to 4 substituents selected from (1) a halogen atom (e.g., a fluorine atom, a chlorine atom, a bromine atom),
(2) a $C_{1-6}$ alkyl group (e.g., methyl), and
(3) a $C_{1-6}$ alkoxy group (e.g., methoxy).

[Compound C-1]

Compound (I) wherein
$R^1$ is a group represented by —$COR^2$ wherein $R^2$ is a $C_{1-6}$ alkyl group (e.g., methyl), a $C_{1-6}$ alkoxy group (e.g., methoxy), an amino group optionally mono- or di-substituted by $C_{1-6}$ alkyl group(s) (e.g., methyl) or a 4- to 7-membered monocyclic non-aromatic heterocyclic group (e.g., azetidinyl);
$R^3$ is a $C_{1-6}$ alkyl group (e.g., methyl);
$R^{4a}$ and $R^{4b}$ are both hydrogen atoms;
$R^6$ is a $C_{1-6}$ alkyl group (e.g., methyl, ethyl, propyl, isopropyl, isobutyl) optionally substituted by 1 to 3 substituents selected from
 (a) a $C_{3-6}$ cycloalkyl group (e.g., cyclopropyl) optionally substituted by 1 to 5 halogen atoms (e.g., a fluorine atom),
 (b) a halogen atom (e.g., a fluorine atom),
 (c) a hydroxy group, and
 (d) a $C_{6-14}$ aryl group (e.g., phenyl);
X is O, CO or $CH_2$;
ring P is oxazole, furan, pyrazole or imidazole;
ring Q is benzene, pyridine, tetrahydropyridine, cyclohexane, cyclohexene or 2,4-cyclohexadiene, each of which is optionally further substituted by 1 to 3 halogen atoms (e.g., a fluorine atom, a chlorine atom);
(preferably ring P and ring Q form

[Structures]

wherein each ring Q is optionally further substituted by 1 to 3 halogen atoms (e.g., a fluorine atom, a chlorine atom)); and
ring A is benzene, pyridine, isoxazole or thiophene, each of which is optionally further substituted by 1 to 4 substituents selected from
(1) a halogen atom (e.g., a fluorine atom, a chlorine atom, a bromine atom),
(2) a $C_{1-6}$ alkyl group (e.g., methyl), and
(3) a $C_{1-6}$ alkoxy group (e.g., methoxy).

[Compound C-2]

Compound (I) wherein
$R^1$ is a group represented by —$COR^2$ wherein $R^2$ is a $C_{1-6}$ alkyl group (e.g., methyl), a $C_{1-6}$ alkoxy group (e.g., methoxy), an amino group optionally mono- or di-substituted by $C_{1-6}$ alkyl group(s) (e.g., methyl), a 4- to 7-membered monocyclic non-aromatic heterocyclic group (e.g., azetidinyl) or a 5- to 7-membered monocyclic aromatic heterocyclic group (e.g., pyrazolyl);
$R^3$ is a $C_{1-6}$ alkyl group (e.g., methyl);
$R^{4a}$ and $R^{4b}$ are each independently a hydrogen atom or a $C_{1-6}$ alkyl group (e.g., methyl);
$R^6$ is a $C_{1-6}$ alkyl group (e.g., methyl, ethyl, propyl, isopropyl, butyl, isobutyl) optionally substituted by 1 to 3 substituents selected from
 (a) a $C_{3-6}$ cycloalkyl group (e.g., cyclopropyl, cyclobutyl) optionally substituted by 1 to 5 substituents selected from
  (i) a halogen atom (e.g., a fluorine atom), and
  (ii) a $C_{1-6}$ alkyl group (e.g., methyl),
 (b) a halogen atom (e.g., a fluorine atom),
 (c) a hydroxy group,
 (d) a $C_{6-14}$ aryl group (e.g., phenyl), and
 (e) a cyano group;
X is O, CO or $CH_2$;
ring P is oxazole, thiazole, furan, pyrazole or imidazole; ring Q is benzene, pyridine, pyrimidine, tetrahydropyridine, cyclohexane, cyclohexene or 2,4-cyclohexadiene, each of which is optionally further substituted by 1 to 3 halogen atoms (e.g., a fluorine atom, a chlorine atom);
(preferably ring P and ring Q form

[Structures]

wherein each ring Q is optionally further substituted by 1 to 3 halogen atoms (e.g., a fluorine atom, a chlorine atom)); and
ring A is a 5- or 6-membered aromatic ring (preferably benzene, pyridine, isoxazole, thiophene, pyrimidine, pyridazine or pyrazine, more preferably benzene, pyridine or pyridazine, particularly preferably benzene or pyridine) optionally further substituted by 1 to 4 substituents selected from
(1) a halogen atom (e.g., a fluorine atom, a chlorine atom, a bromine atom), (2) a $C_{1-6}$ alkyl group (e.g., methyl, ethyl) optionally substituted by 1 to 3 substituents selected from
  (a) a hydroxy group, and
  (b) a halogen atom (e.g., a fluorine atom),
(3) a $C_{1-6}$ alkoxy group (e.g., methoxy, ethoxy) optionally substituted by 1 to 3 halogen atoms (e.g., a fluorine atom),
(4) a cyano group, and
(5) a $C_{1-6}$ alkyl-carbonyl group (e.g., acetyl).

[Compound D-1]
Compound (I) wherein
$R^1$ is a group represented by —$COR^2$ wherein $R^2$ is a $C_{1-6}$ alkyl group (preferably methyl);
$R^3$ is a $C_{1-6}$ alkyl group (preferably methyl);
$R^{4a}$ and $R^{4b}$ are both hydrogen atoms;
$R^6$ is a $C_{1-6}$ alkyl group (preferably methyl) substituted by $C_{3-6}$ cycloalkyl group(s) (preferably cyclopropyl) optionally substituted by 1 to 3 halogen atoms (preferably a fluorine atom);
X is C;
ring P is oxazole;
ring Q is benzene, pyridine or cyclohexane, each of which is optionally further substituted by 1 to 3 halogen atoms (preferably a fluorine atom);
ring P and ring Q form

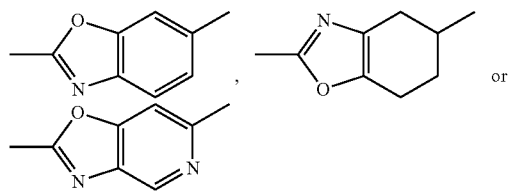

wherein each ring Q is optionally further substituted by 1 to 3 halogen atoms (e.g., a fluorine atom)), and
ring A is benzene or pyridine, each of which is optionally further substituted by 1 or 2 substituents selected from
  (1) a halogen atom (preferably a fluorine atom, a chlorine atom), and
  (2) a $C_{1-6}$ alkoxy group (preferably methoxy).

[Compound E-1]
The above-mentioned [Compound D-1] wherein
ring P and ring Q form

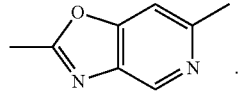

[Compound F]
Compound (I) wherein
$R^1$ is a group represented by —$COR^2$ wherein $R^2$ is a $C_{1-6}$ alkyl group (e.g., methyl), a $C_{1-6}$ alkoxy group (e.g., methoxy) or an amino group optionally mono- or di-substituted by $C_{1-6}$ alkyl group(s) (e.g., methyl);
$R^3$ is a $C_{1-6}$ alkyl group (e.g., methyl) optionally substituted by 1 to 3 halogen atoms;
$R^{4a}$ and $R^{4b}$ are both hydrogen atoms;
$R^6$ is a $C_{1-6}$ alkyl group (e.g., methyl, ethyl, propyl, isopropyl, butyl, isobutyl) optionally substituted by 1 to 3 substituents selected from
  (a) a $C_{3-6}$ cycloalkyl group (e.g., cyclopropyl) optionally substituted by 1 to 5 halogen atoms (e.g., a fluorine atom),
  (b) a halogen atom (e.g., a fluorine atom),
  (c) a hydroxy group, and
  (d) a $C_{6-14}$ aryl group (e.g., phenyl);
X is O, CO or $CH_2$;
ring P and ring Q form

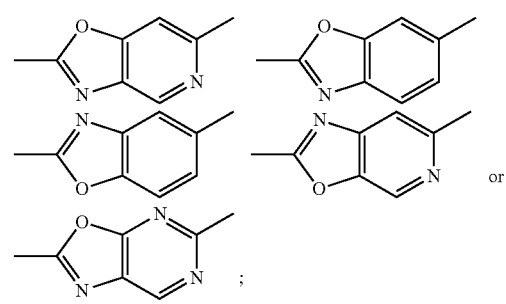

and
ring A is benzene, pyridine or pyridazine, each of which is optionally further substituted by 1 to 4 substituents selected from
  (1) a halogen atom (e.g., a fluorine atom, a chlorine atom, a bromine atom),
  (2) a $C_{1-6}$ alkyl group (e.g., methyl, ethyl), and
  (3) a $C_{1-6}$ alkoxy group (e.g., methoxy, ethoxy).

A salt of the compound represented by the formula (I) is preferably a pharmacologically acceptable salt. Examples of such salt include salts with inorganic base, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrogen chloride, hydrogen bromide, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Compound (I) may be used in the form of a prodrug.

A prodrug of compound (I) means a compound which is converted to compound (I) with a reaction due to an enzyme, an gastric acid, etc. under the physiological condition in the living body, that is, a compound which is converted to compound (I) by oxidation, reduction, hydrolysis, etc. due to an enzyme; a compound which is converted to compound (I) by hydrolysis etc. due to gastric acid, etc.

Examples of the prodrug of compound (I) include a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation);
a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation);
a compound obtained by subjecting a carboxy group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methyl amidation etc.)
and the like. These compounds can be produced from compound (I) according to a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

In the present specification, a prodrug may be in the form of a salt. Examples of the salt include those exemplified as the salt of the compound represented by the aforementioned formula (I).

Compound (I) may be labeled with an isotope (e.g., $^{3}H$, $^{13}C$, $^{14}C$, $^{18}F$, $^{35}S$, $^{125}I$) and the like.

Compound (I) labeled with or substituted by an isotope can be used, for example, as a tracer (PET tracer) in Positron Emission Tomography (PET), and useful in the field of medical diagnosis and the like. Compound (I) may be a hydrate or a non-hydrate, and a non-solvate or a solvate.

Compound (I) also encompasses a deuterium conversion form wherein $^{1}H$ is converted to $^{2}H(D)$.

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization known per se.

Compound (I) or a prodrug thereof (hereinafter sometimes to be abbreviated simply as the compound of the present invention) has low toxicity, and can be used as an agent for the prophylaxis or treatment of various diseases mentioned below in a mammal (e.g., human, mouse, rat, rabbit, dog, cat, bovine, horse, swine, monkey) directly or in the form of a pharmaceutical composition (hereinafter sometimes to be abbreviated as the medicament of the present invention) by admixing with a pharmacologically acceptable carrier and the like.

Here, examples of the pharmacologically acceptable carrier include various organic or inorganic carrier substances conventionally used as preparation materials, which are added as excipient, lubricant, binder or disintegrant for solid preparations; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological saline, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include paraoxybenzoates, chlorobutanol, benzyl alcohol, phenethyl alcohol, dehydroacetic acid and sorbic acid.

Preferable examples of the antioxidant include sulfites, ascorbates and the like.

Preferable examples of the colorant include aqueous food tar colors (e.g., food colors such as Food Red No. 2 and No. 3, Food Yellow No. 4 and No. 5, Food Blue No. 1 and No. 2, etc.), water insoluble lake dye (e.g., aluminum salt of the above-mentioned aqueous food tar color) and natural dye (e.g., β-carotene, chlorophyll, ferric oxide red).

Preferable examples of the sweetening agent include sodium saccharin, dipotassium glycyrrhizinate, aspartame and stevia.

Examples of the medicament of the present invention include tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, and they are orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

These preparations may be controlled-release preparations such as immediate-release preparations, sustained-release preparations and the like (e.g., sustained-release microcapsule).

The medicament of the present invention can be produced by a method conventionally used in the technical field of pharmaceutical preparation, for example, the method described in the Japanese Pharmacopoeia and the like.

While the content of the compound of the present invention in the medicament of the present invention varies depending on the dosage form, dose of the compound of the present invention, and the like, it is, for example, about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the water-soluble film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, ferric oxide and the like can be used.

The compound of the present invention shows low toxicity (e.g., acute toxicity, chronic toxicity, genetic toxicity, reproductive toxicity, pneumotoxicity, carcinogenicity and the like) and a few side effects. Therefore, it can be used as an agent for the prophylaxis or treatment or a diagnostic of various diseases in a mammal.

The compound of the present invention has a superior ACC (acetyl-CoA carboxylase) inhibitory action, and is useful for a acetyl-CoA carboxylase inhibitor. Examples of ACC include liver, adipose tissue, pancreas-specific isozyme (ACC1); and muscle-specific isozyme (ACC2). The compound of the present invention has a selective inhibitory action on ACC2.

The compound of the present invention is superior in the metabolism stability and has advantages such as long half-life of compound, difficult in vivo metabolism and the like.

Moreover, the compound of the present invention is superior in the in vivo kinetics (e.g., oral absorbability, bioavailability).

The compound of the present invention can be used as an agent for the prophylaxis or treatment of obesity, diabetes (e.g., type 1 diabetes, type 2 diabetes, gestational diabetes, obese diabetes), hyperlipidemia (e.g., hypertriglyceridemia, hypercholesterolemia, high LDL-cholesterolemia, hypo-HDL-emia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (pathology having three or more selected from hypertriglyceridemia (TG), low HDL cholesterol (HDL-C), hypertension, abdomen obesity and impaired glucose tolerance), sarcopenia, cancer and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 hr level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 hr level (glucose concentration of intravenous plasma) of less than 140 mg/dl" (normal type) is called a "borderline type".

In addition, ADA (American Diabetes Association) in 1997 and WHO (World Health Organization) in 1998 reported new diagnostic criteria of diabetes.

According to these reports, diabetes is a condition showing a fasting blood glucose level (glucose concentration of intravenous plasma) of not less than 126 mg/dl and a 75 g oral glucose tolerance test 2 hr level (glucose concentration of intravenous plasma) of not less than 200 mg/dl.

According to the above-mentioned reports, impaired glucose tolerance is a condition showing fasting blood sugar level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

Since the compound of the present invention has an activity of inhibiting body weight gain, it can be used as a body weight gain inhibitor to mammals. Target mammals may be any mammals of which body weight gain is to be avoided. The mammals may have a risk of body weight gain genetically or may be suffering from lifestyle-related diseases such as diabetes, hypertension and/or hyperlipidemia and the like. The body weight gain may be caused by excessive feeding or diet without nutrient balance, or may be derived from concomitant drug (e.g., agents for enhancing insulin sensitivity having PPARγ-agonistic activity such as troglitazone, rosiglitazone, englitazone, ciglitazone, pioglitazone and the like). In addition, body weight gain may be preliminary to obesity, or may be body weight gain of obesity patients. Here, obesity is defined that BMI (body mass index; body weight (kg)/[height (m)]$^2$) is not less than 25 for Japanese (criterion by Japan Society for the Study of Obesity), or not less than 30 for westerner (criterion by WHO).

The compound of the present invention is also useful as an agent for the prophylaxis or treatment of metabolic syndrome. Because patients with metabolic syndrome have an extreme high incidence of cardiovascular diseases as compared to patients with single lifestyle-related disease, the prophylaxis or treatment of metabolic syndrome is quite important to prevent cardiovascular diseases.

Criteria for diagnosis of metabolic syndrome are announced by WHO in 1999, and by NCEP in 2001. According to the criterion of WHO, patients with at least two of abdominal obesity, dyslipidemia (high TG or low HDL) and hypertension in addition to hyperinsulinemia or impaired glucose tolerance are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criterion of Adult Treatment Panel III of National Cholesterol Education Program, that is an indicator for managing ischemic heart diseases in America, patients with at least three of abdominal obesity, high triglycerides, low HDL cholesterol, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can also be used, for example, as an agent for the prophylaxis or treatment of osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, myocardial infarction, angina pectoris, cerebrovascular disorder (e.g., cerebral infarction, cerebral apoplexy), Alzheimer's disease, Parkinson's disease, anxiety, dementia, insulin resistance syndrome, syndrome X, hyperinsulinemia, sensory abnormality in hyperinsulinemia, irritable bowel syndrome, acute or chronic diarrhea, inflammatory disease (e.g., chronic rheumatoid arthritis, spondylitis deformans, osteoarthritis, lumbago, gout, postoperative or posttraumatic inflammation, swelling, neuralgia, pharyngolaryngitis, cystitis, hepatitis (including nonalcoholic steatohepatitis), pneumonia, pancreatitis, enteritis, inflammatory bowel disease (including inflammatory colitis), ulcerative colitis, stomach mucosal injury (including stomach mucosal injury caused by aspirin)), small intestine mucosal injury, malabsorption, testis dysfunction, visceral obesity syndrome or sarcopenia.

In addition, the compound of the present invention can also be used as an agent for the prophylaxis or treatment of various carcinomas (particularly breast cancer (e.g., invasive ductal carcinoma, ductal carcinoma in situ, inflammatory breast cancer and the like), prostate cancer (e.g., hormone-dependent prostate cancer, non-hormone dependent prostate cancer and the like), pancreatic cancer (e.g., pancreatic duct cancer and the like), gastric cancer (e.g., papillary adenocarcinoma, mucinous adenocarcinoma, adenosquamous carcinoma and the like), lung cancer (e.g., non-small cell lung cancer, small cell lung cancer, malignant mesothelioma and the like), colorectal cancer (e.g., gastrointestinal stromal tumor and the like), rectal cancer (e.g., gastrointestinal stromal tumor and the like), colorectal cancer (e.g., familial colorectal cancer, hereditary nonpolyposis colorectal cancer, gastrointestinal stromal tumor and the like), small intestinal cancer (e.g., non-Hodgkin lymphoma, gastrointestinal stromal tumor and the like), esophagus cancer, duodenal cancer, cancer of the tongue, pharyngeal cancer (e.g., nasopharyngeal cancer, mesopharyngeal cancer, hypopharyngeal cancer and the like), salivary gland cancer, brain tumor (e.g., pineal astrocytoma, pilocytic astrocytoma, diffuse astrocytoma, anaplastic astrocytoma and the like), schwannoma, liver cancer (e.g., primary liver cancer, Extrahepatic Bile Duct Cancer and the like), kidney cancer (e.g., renal cell carcinoma, transitional carcinoma of kidney pelvis and urinary duct, and the like), biliary tract cancer, endometrial carcinoma, cervical cancer, ovarian cancer (e.g., ovarian epithelial carcinoma, extragonadal germ cell tumor ovarian germ cell tumor ovarian low malignant potential tumor and the like), urinary bladder cancer, urinary tract cancer, skin cancer (e.g., intraocular (ocular) melanoma, Merkel cell carcinoma and the like), Hemangioma, malignant lymphoma, malignant melanoma, thyroid cancer (e.g., medullary thyroid carcinoma and the like), parathyroid cancer, nasal cavity cancer, paranasal sinus cancer, bone tumor (e.g., osteosarcoma, Ewing's sarcoma, uterus sarcoma, soft tissue sarcoma and the like), vascular fibroma, retinoblastoma, penile cancer, testis tumor solid cancer in childhood (e.g., Wilms' tumor, childhood kidney tumor and the like), Kaposi's sarcoma, Kaposi's sarcoma derived from AIDS, maxillary tumor, fibrous histiocytoma, leiomyosarcoma, rhabdomyosarcoma, leukemia (e.g., acute myeloid leukemia, acute lymphoblastic leukemia and the like) etc.).

The compound of the present invention can also be used for secondary prevention or suppression of progression of the above-mentioned various diseases (e.g., cardiovascular events such as myocardial infarction and the like).

While the dose of the compound of the present invention varies depending on the subject of administration, administration route, target disease, symptom and the like, for example, for oral administration to an adult obese patient, it is generally about 0.01 to 100 mg/kg body weight, preferably 0.05 to 30 mg/kg body weight, further preferably 0.5 to 10 mg/kg body weight for one dose, which is desirably administered once to 3 times a day.

With the aim of enhancing the action of the compound of the present invention or decreasing the dose of the compound and the like, the compound can be used in combination with medicaments such as therapeutic agents for diabetes, therapeutic agents for diabetic complications, therapeutic agents for hyperlipidemia, antihypertensive agents, antiobesity agents, diuretics, antithrombotic agents and the like (hereinafter to be abbreviated as concomitant drug). The time of administration of the compound of the present invention and that of the concomitant drug are not limited, and these concomitant drugs may be low-molecular-weight compounds or high-molecular-weight protein, polypeptide, antibody, vaccine and the like. They may be administered simultaneously or in a staggered manner to the administration subject. In addition, the compound of the present invention and the concomitant drug may be administered as two kinds of preparations containing respective active ingredients or a single preparation containing both active ingredients.

The dose of the concomitant drug can be appropriately determined based on the dose employed clinically. In addition, the mixing ratio of the compound of the present invention and the concomitant drug can be appropriately determined according to the administration subject, administration route, target disease, symptom, combination, and the like. For example, when the administration subject is a human, the concomitant drug may be used in an amount of 0.01 to 100 parts by weight per 1 part by weight of the compound of the present invention.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO 2007/013694, WO 2007/018314, WO 2008/093639 or WO 2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Alogliptin, Vildagliptin, Sitagliptin, Saxagliptin, BI356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compound described in WO 2004/041266, WO 2004/106276, WO 2005/063729, WO 2005/063725, WO 2005/087710, WO 2005/095338, WO 2007/013689 or WO 2008/001931), GLP-1 receptor agonists [e.g., GLP-1, GLP-1MR preparation, Liraglutide, Exenatide, AVE-0010, BIM-51077, Aib(8.35)hGLP-1(7.37)NH$_2$, CJC-1131, Albiglutide], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498), adiponectin or an agonist thereof, IKK inhibitors (e.g., AS-2868), leptin resistance improving drugs, somatostatin receptor agonists, glucokinase activators (e.g., Piragliatin, AZD1656, AZD6370, TTP-355, compound described in WO 2006/112549, WO 2007/028135, WO 2008/047821, WO 2008/050821, WO 2008/136428 or WO2008/156757), GIP (Glucose-dependent insulinotropic peptide) and the like.

Examples of the therapeutic agents for diabetic complications include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF, neutrophin production-secretion promoters thereof (e.g., 4-(4-chlorophenyl)-2-(2-methyl-1-imidazolyl)-5-[3-(2-methylphenoxy)propyl]oxazole) described in WO 01/14372, a compound described in WO 2004/039365), nerve regeneration promoters (e.g., Y-128), PKC inhibitors (e.g., ruboxistaurin mesylate), AGE inhibitors (e.g., ALT946, pyratoxanthine, N-phenacylthiazolium bromide (ALT766), ALT-711, EXO-226, Pyridorin, pyridoxamine), GABA receptor agonists (e.g., gabapentin, Pregabalin), serotonin-noradrenaline re-uptake inhibitors (e.g., duloxetine), sodium channel inhibitors (e.g., lacosamide), active oxygen scavengers (e.g., thioctic acid), cerebral vasodilators (e.g., tiapride, mexiletine), somatostatin receptor agonists (e.g., BIM23190), apoptosis signal regulating kinase-1 (ASK-1) inhibitors and the like.

Examples of the therapeutic agent for hyperlipidemia include statin compounds (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., a compound described in WO 97/10224, for example, N-[[(3R,5S)-1-(3-acetoxy-2,2-dimethylpropyl)-7-chloro-5-(2,3-dimethoxyphenyl)-2-oxo-1,2, 3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., cohlestyramine), probucol, nicotinic acid drugs (e.g., nicomol, niceritrol, niaspan), ethyl icosapentate, phytosterols (e.g., soysterol, γ-oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, efonidipine, nicardipine, amlodipine, cilnidipine and the like), β blockers (e.g., metoprolol, atenolol, propranolol, carvedilol, pindolol), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor GABA modulators (e.g., topiramate), MCH receptor antagonists (e.g., SB-568849; SNAP-7941; compound described in WO 01/82925 or WO 01/87834), neuropeptide Y antagonists (e.g., velneperit), cannabinoid receptor antagonists (e.g., rimonabant, taranabant), ghrelin antagonists, ghrelin receptor antagonists, ghrelinacylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFκ inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine and pig; human GLP-1 preparations genetically synthesized using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine and pig; human FGF21 preparations genetically synthesized using *Escherichia coli* or yeast; fragments or derivatives of FGF21)), combination drug of naltrexone hydrochloride sustained-release preparation and bupropion hydrochloride sustained-release preparation, anorexigenic agents (e.g., P-57) and the like.

Examples of the diuretics include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like.

Examples of the antithrombotic agent include heparins (e.g., heparin sodium, heparin calcium, enoxaparin sodium, dalteparin sodium), warfarins (e.g., warfarin potassium), anti-thrombin drugs (e.g., argatroban, dabigatran), thrombolytic agents (e.g., urokinase, tisokinase, alteplase, nateplase, monteplase, pamiteplase), platelet aggregation inhibitors (e.g., ticlopidine hydrochloride, clopidogrel, E5555, SHC530348, cilostazol, ethyl icosapentate, beraprost sodium, sarpogrelate hydrochloride, prasugrel, E5555, SHC530348), FXa inhibitors (e.g., rivaroxaban, apixaban, edoxaban, YM150, compound described in WO 02/06234, WO 2004/048363, WO 2005/030740, WO 2005/058823 or WO 2005/113504) and the like.

The administration time of the aforementioned concomitant drug is not limited, and the compound of the present invention and the concomitant drug may be administered to an administration subject simultaneously, or may be administered at different times. The dosage of the concomitant drug may be determined according to the dosage clinically used, and can be appropriately selected depending on the administration subject, administration route, diseases, combination thereof and the like.

The administration mode of the concomitant drug is not particularly limited, and the compound of the present invention and the concomitant drug only need to be combined on administration. Examples of such administration mode include the following:

(1) administration of a single preparation obtained by simultaneously processing the compound of the present invention and the concomitant drug,
(2) simultaneous administration of two kinds of preparations of the compound of the present invention and the concomitant drug, which have been separately produced, by the same administration route,
(3) administration of two kinds of preparations of the compound of the present invention and the concomitant drug, which have been separately produced, by the same administration route in a staggered manner,
(4) simultaneous administration of two kinds of preparations of the compound of the present invention and the concomitant drug, which have been separately produced, by different administration routes,
(5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug can be appropriately selected depending on the administration subject, administration route(s), diseases and the like.

The production method of the compound of the present invention is explained in the following.

As production methods of compounds (I), (I-1), (I-2), (I-3) and (I-4), the representative production methods are explained in the following, which are not to be construed as limitative. Compounds (I), (I-1), (I-3) and (I-4) can also be produced according to the method shown in the following Reaction Schemes 1, 2, 12, 13 and 15 or a method analogous thereto or the like. Compounds (I-1), (I-2), (I-3) and (I-4) are encompassed in compound (I).

In the following Reaction Schemes, starting compounds may be each in the form of a salt as long as it does not inhibit the reaction. Examples of the salt include those exemplified as the above-mentioned salt of the compound represented by formula (I).

When a specific production method is not described, the starting compound may be easily commercially available, or can also be produced according to a method known per se, or a method analogous thereto.

The product in each reaction can be used for the next reaction as the reaction mixture or as a crude product, or can also be isolated according to a conventional method from the reaction mixture, and can also be purified according to a separation means (e.g., recrystallization, distillation, chromatography, HPLC etc.). When the resultant product is a mixture of stereoisomers, it can be purified according to separation means such as diastereomer salt method, chromatography, HPLC or SFC (supercritical fluid chromatography) and the like, for example, the method described in Example, or a method analogous thereto or the like.

When alkylation reaction, hydrolysis reaction, amination reaction, esterification reaction, amidation reaction, etherification reaction, oxidation reaction, reduction reaction and the like are to be carried out in the following Reaction Schemes, these reactions are carried out according to a method known per se. Examples of such method include the methods described in ORGANIC FUNCTIONAL GROUP PREPARATIONS, 2nd ed., ACADEMIC PRESS, INC., 1989; Comprehensive Organic Transformations, VCH Publishers Inc., 1989 and the like, and the like.

The following are explanations of the solvents in generic terms, which are used for the following reactions.

Examples of the "nitrile solvents" include acetonitrile, propionitrile and the like.

Examples of the "amide solvents" include N,N-dimethylformamide (DMF), N,N-dimethylacetamide, N-methylpyrrolidone and the like.

Examples of the "halogenated hydrocarbon solvents" include dichloromethane, chloroform, 1,2-dichloroethane, carbon tetrachloride and the like.

Examples of the "ether solvents" include diethyl ether, diisopropyl ether, tert-butyl methyl ether, tetrahydrofuran (THF), 1,4-dioxane, 1,2-dimethoxyethane and the like.

Examples of the "aromatic solvents" include benzene, toluene, xylene, chlorobenzene, (trifluoromethyl)benzene, pyridine and the like.

Examples of the "aliphatic hydrocarbon solvents" include hexane, pentane, cyclohexane and the like.

Examples of the "sulfoxide solvents" include dimethyl sulfoxide (DMSO) and the like.

Examples of the "alcohol solvents" include methanol, ethanol, propanol, 2-propanol, butanol, isobutanol, tert-butanol and the like.

Examples of the "ester solvents" include methyl acetate, ethyl acetate, n-butyl acetate, tert-butyl acetate and the like.

Examples of the "ketone solvents" include acetone, methyl ethyl ketone and the like.

Examples of the "organic acid solvents" include formic acid, acetic acid, propionic acid, trifluoroacetic acid, methanesulfonic acid and the like.

The following are explanations of the bases in generic terms, which are used for the following reactions.

Examples of the "inorganic bases" include sodium hydroxide, potassium hydroxide, lithium hydroxide, barium hydroxide and the like.

Examples of the "basic salt" include sodium carbonate, potassium carbonate, cesium carbonate, sodium hydrogen carbonate, potassium hydrogen carbonate, tripotassium phosphate and the like.

Examples of the "aromatic amines" include pyridine, imidazole, 2,6-lutidine and the like.

Examples of the "tertiary amines" include triethylamine, diisopropylethylamine, N-methylmorpholine, 1,8-diazabicyclo[5.4.0]undec-7-ene (DBU), 1,5-diazabicyclo[4.3.0]non-5-ene (DBN) and the like.

Examples of the "hydrides of an alkali metal or alkaline earth metal" include lithium hydride, sodium hydride, potassium hydride, calcium hydride and the like.

Examples of the "metal amides" include lithium amide, sodium amide, lithium diisopropylamide, lithium dicyclohexylamide, lithium hexamethyldisilazide, sodium hexamethyldisilazide, potassium hexamethyldisilazide and the like.

Examples of the "alkyl metals" include n-butyllithium, sec-butyllithium, tert-butyllithium, methylmagnesium bromide and the like.

Examples of the "aryl metals" include phenyllithium, phenylmagnesium bromide and the like.

Examples of the "metal alkoxides" include sodium methoxide, sodium ethoxide, potassium tert-butoxide, sodium tert-butoxide and the like.

In the following production methods, when the starting compound has an amino group, a carboxyl group, a hydroxy group, a carbonyl group or a sulfanyl group as a substituent, a protecting group generally used in peptide chemistry and the like may be introduced into these groups. By removing the protecting group as necessary after the reaction, the object compound can be obtained.

Examples of the amino-protecting group or nitrogen atom-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, a 9-fluorenylmethoxycarbonyl group), a trityl group, a phthaloyl group, a N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl), a substituted $C_{7-10}$ aralkyl group (e.g., 2,4-dimethoxybenzyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group or a nitro group.

Examples of the protected carbonyl group include a cyclic acetal (e.g., 1,3-dioxane), a non-cyclic acetal (e.g., a di-$C_{1-6}$ alkylacetal) and the like.

Examples of the sulfanyl-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl), a 9-fluorenylmethoxycarbonyl group, a 2-tetrahydropyranyl group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The method for removing the protecting group can be carried out according to a method known per se, for example, the method described in Protective Groups in Organic Synthesis, John Wiley and Sons (1980) or the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like can be employed.

<Reaction Scheme 1>

[Structure (3): HO-(A)-(P)-(Q)-X-C(R^{4a})(R^{4b})-C(R^3)(H)-N(H)(R^1)]

[Structure (I): R^6-O-(A)-(P)-(Q)-X-C(R^{4a})(R^{4b})-C(R^3)(H)-N(H)(R^1)]

wherein $M^1$ is an amino-protecting group, and other symbols are as defined above.

Compound (1) can be produced, for example, according to the method described in Reaction Schemes 3, 9, 11, 13, 14, 17 and 21, a method known per se, or a method analogous thereto.

Compound (2) can be produced, for example, by subjecting compound (1) to a deprotection reaction. The deprotection reaction can be carried out according to a method known per se, for example, the method described in Protective Groups in Organic Synthesis, John Wiley and Sons (1980) or the like.

Compound (I-1) can be produced, for example, by subjecting compound (2) to an acylation reaction.

The above-mentioned "acylation reaction" encompasses, for example, synthesis reactions of an amide derivative, a carbamate derivative and a urea derivative, and the like. The production of the "amide derivative" is carried out according to the following "method using a dehydrating condensing agent" or the "method using a reactive derivative of carboxylic acid".

i) Method Using a Dehydrating Condensing Agent

This method is performed by reacting compound (2) with the carboxylic acid corresponding to $R^2$ in the presence of a dehydrating condensing agent, in an inert solvent. Where necessary, the reaction may be carried out in the presence of 1-hydroxybenzylotriazole (HOBt) in an amount of a catalytic amount to 5 equivalents, a base in an amount of a catalytic amount to 5 equivalents, and the like.

The amount of the above-mentioned "carboxylic acid" to be used is generally 0.5 to 5 equivalents, preferably 0.8 to 1.5 equivalents, relative to compound (2).

Examples of the above-mentioned "dehydrating condensing agent" include dicyclohexylcarbodiimide (DCC), 1-ethyl-3-(3-dimethylaminopropyl)carbodiimide hydrochloride (WSC), O-(7-azabenzotriazol-1-yl)-N,N,N',N'-tetramethyluronium hexafluorophosphate (HATU) and the like. Among them, HATU and WSC are preferable. The amount of the "dehydrating condensing agent" to be used is generally 1 to 10 equivalents, preferably 1 to 5 equivalents, relative to compound (2).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, amide solvents are preferable.

Examples of the above-mentioned "base" include "aromatic amines", "tertiary amines" and the like.

The reaction temperature is generally –70° C. to 150° C., preferably –20° C. to 100° C.

The reaction time is generally 0.1 hr to 100 hr, preferably 1 hr to 48 hr.

ii) Method Using a Reactive Derivative of Carboxylic Acid

This method is performed by reacting compound (2) with the reactive derivative of the carboxylic acid corresponding to $R^2$ in an amount of 0.5 to 5 equivalents (preferably 0.8 to 3 equivalents) in an inert solvent. Where necessary, the reaction may be carried out in the presence of a base in an amount of 1 to 10 equivalents, preferably 1 to 3 equivalents.

Examples of the above-mentioned "reactive derivative of the carboxylic acid" include acid halides (e.g., acid chlorides, acid bromides), mixed anhydrides (e.g., acid anhydrides with a $C_{1-6}$ alkyl-carboxylic acid, a $C_{6-10}$ aryl-carboxylic acid, a $C_{1-6}$ alkylcarbonic acid etc.), activated esters (e.g., esters with a phenol optionally having substituent(s), HOBt, N-hydroxysuccinimide etc.), activate amides (e.g., amides with imidazole, triazole etc.) and the like.

Examples of the above-mentioned "phenol optionally having substituent(s)" include phenol, pentachlorophenol, pentafluorophenol, p-nitrophenol and the like.

The above-mentioned "reactive derivative of the carboxylic acid" is preferably a mixed anhydride.

Examples of the above-mentioned "inert solvent" include ether solvents, halogenated hydrocarbon solvents, aromatic solvent, aliphatic hydrocarbon solvents, nitrile solvents, amide solvents, sulfoxide solvents and the like. These solvents may be used in a mixture of two or more kinds thereof in an appropriate ratio. Among them, pyridine, acetonitrile, THF, dichloromethane, chloroform and the like are preferable.

Examples of the above-mentioned "base" include "aromatic amines", "tertiary amines" and the like.

The reaction temperature is generally –20° C. to 100° C., preferably –20° C. to 50° C.

The reaction time is generally 5 min to 40 hr, preferably 30 min to 18 hr.

The production of the above-mentioned "carbamate derivative" is carried out by reacting compound (2) with a diester of dicarbonic acid or chloroformate corresponding to $R^2$ in an amount of 0.5 to 5 equivalents (preferably 0.8 to 3 equivalents) in an inert solvent. Where necessary, the reaction may be carried out in the presence of a base in an amount of a catalytic amount to 5 equivalents.

Examples of the above-mentioned "inert solvent" include ether solvents, halogenated hydrocarbon solvents, aromatic solvents, aliphatic hydrocarbon solvents, nitrile solvents, amide solvents and the like. These solvents may be used in a mixture of two or more kinds thereof in an appropriate ratio. Among them, pyridine, acetonitrile, THF, DMF, dichloromethane, chloroform and the like are preferable.

Examples of the above-mentioned "base" include "aromatic amines", "tertiary amines" and the like.

The reaction temperature is generally –20° C. to 100° C., preferably –20° C. to 50° C.

The reaction time is generally 5 min to 40 hr, preferably 30 min to 18 hr.

The production of the above-mentioned "urea derivative" is carried out by reacting compound (2) with an isocyanate or carbamoyl chloride derivative corresponding to $R^2$ in an amount of 0.5 to 5 equivalents (preferably 0.8 to 3 equivalents) in an inert solvent. Where necessary, the reaction may be carried out in the presence of a base in an amount of a catalytic amount to 5 equivalents.

Examples of the above-mentioned "inert solvent" include ether solvents, halogenated hydrocarbon solvents, aromatic solvents, aliphatic hydrocarbon solvents, nitrile solvents, amide solvents and the like. These solvents may be used in a mixture of two or more kinds thereof in an appropriate ratio. Among them, pyridine, acetonitrile, THF, DMF, dichloromethane, chloroform and the like are preferable.

Examples of the above-mentioned "base" include "aromatic amines", "tertiary amines" and the like.

The reaction temperature is generally −20° C. to 100° C., preferably −20° C. to 50° C.

The reaction time is generally 5 min to 40 hr, preferably 30 min to 18 hr.

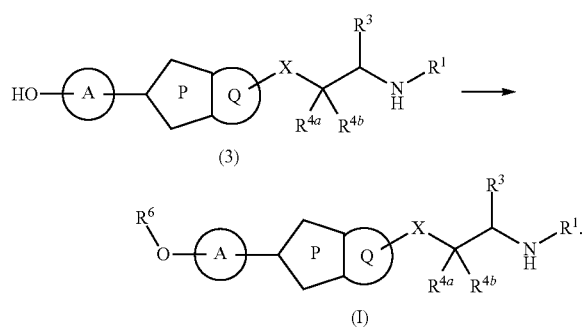

wherein each symbol is as defined above.

Compound (3) can be produced, for example, according to the method described in Reaction Scheme 7 or a method known per se or a method analogous thereto.

Compound (I) can be produced, for example, by subjecting to compound (3) to an alkylation reaction.

Examples of the alkylation reaction include the following "method using a base and an alkyl halide or sulfonate", "method employing the Mitsunobu reaction" and the like.

The "method using a base and an alkyl halide or sulfonate" can be performed according to a method known per se, for example, the method described in Journal of the Chemical Society (J. Chem. Soc.), pages 1530-1534, 1937, or the like, or a method analogous thereto.

This reaction is carried out by reacting compound (3) with an alkyl halide or sulfonate corresponding to $R^6$ in the presence of a base, in an inert solvent.

Examples of the above-mentioned "alkyl halide" include an optionally substituted $C_{1-6}$ alkyl halide or an optionally substituted $C_{3-6}$ cycloalkyl halide. The amount of the "alkyl halide" to be used is generally 1 to 10 equivalents, preferably 1 to 5 equivalents, relative to compound (3).

Examples of the above-mentioned "sulfonate" include an optionally substituted $C_{1-6}$ alkyl ester of sulfonic acid, or an optionally substituted $C_{3-6}$ cycloalkyl ester of sulfonic acid. Examples of the "sulfonic acid" include methylsulfonic acid, p-methylphenylsulfonic acid, trifluoromethylsulfonic acid and the like. The amount of the "sulfonate" to be used is generally 1 to 10 equivalents, preferably 1 to 5 equivalents, relative to compound (3).

Examples of the above-mentioned "base" include "inorganic bases", "basic salts", "aromatic amines", "tertiary amines", "hydrides of an alkali metal or alkaline earth metal", "alkylmetals", "arylmetals", "metal alkoxides" and the like. The amount of the "base" to be used is generally 1 to 10 equivalents, preferably 1 to 5 equivalents, relative to compound (3).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, THF, DMF and the like are preferable.

The reaction temperature is generally −100° C. to 150° C., preferably 0° C. to 100° C.

The reaction time is generally 5 min to 48 hr, preferably 30 min to 24 hr.

The "method employing the Mitsunobu reaction" can be performed according to a method known per se, for example, the method described in Tetrahedron Letters (Tetrahedron Lett.), pages 769-770, 1980, or the like, or a method analogous thereto.

This reaction is carried out by reacting compound (3) with compound $R^6OH$ in the presence of a hydroxy group-activator, in an inert solvent.

The amount of the above-mentioned "compound $R^6OH$" to be used is generally 1 to 10 equivalents, preferably 1 to 5 equivalents, relative to compound (3).

Examples of the above-mentioned "hydroxy group-activator" include cyanomethylenetri-n-butylphosphorane, a combination of diisopropyl azodicarboxylate and triphenylphosphine, and the like. The amount of the "hydroxy group-activator" to be used is generally 1 to 10 equivalents, preferably 1 to 5 equivalents, relative to compound (3).

Examples of the above-mentioned "inert solvent" include aromatic solvents, aliphatic hydrocarbon solvents, ether solvents, ester solvents, amide solvents and the like. These solvents may be used in a mixture of two or more kinds thereof in an appropriate ratio.

The reaction temperature is generally −70° C. to 150° C., preferably −20° C. to 100° C.

The reaction time is generally 0.1 hr to 100 hr, preferably 0.1 hr to 48 hr.

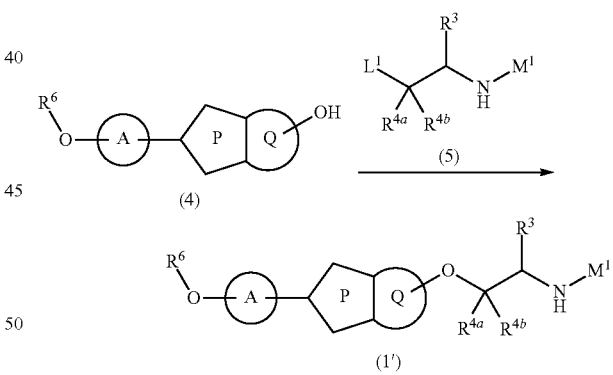

wherein $L^1$ is a hydroxyl group or a leaving group, and other symbols are as defined above.

Examples of the leaving group for $L^1$ include an optionally substituted $C_{1-6}$ alkylsulfonyloxy group, an optionally substituted $C_{6-12}$ arylsulfonyloxy group, a halogen atom and the like.

Examples of the "substituent" of the "optionally substituted $C_{1-6}$ alkylsulfonyloxy group" include a halogen atom and the like. Specific examples of the "optionally substituted $C_{1-6}$ alkylsulfonyloxy group" include methylsulfonyloxy, ethylsulfonyloxy, trifluoromethylsulfonyloxy and the like.

Examples of the "substituent" of the "optionally substituted $C_{6-10}$ arylsulfonyloxy group" include a $C_{1-6}$ alkyl group and the like. Specific examples of the "optionally substituted $C_{6-12}$ arylsulfonyloxy group" include phenylsulfonyloxy, p-methylphenylsulfonyloxy and the like.

Compound (4) can be produced, for example, according to the method described in Reaction Schemes 4 and 10 or a method known per se or a method analogous thereto.

Compound (1') can be produced, for example, by subjecting compound (4) to an etherification reaction with compound (5).

Examples of the above-mentioned "etherification reaction" include a "method employing the Mitsunobu reaction" and the like in the case of $L^1$ in compound (5) is a hydroxyl group, and a "method using a base" and the like in the case of $L^1$ in compound (5) is a leaving group.

The "method employing the Mitsunobu reaction" can be performed according to a method known per se, for example, the method described in Tetrahedron Letters (Tetrahedron Lett.), pages 769-770, 1980, or the like, or a method analogous thereto.

This reaction is carried out by reacting compound (4) with compound (5) wherein $L^1$ is a hydroxyl group in the presence of a hydroxy group-activator, in an inert solvent. The amount of compound (5) wherein $L^1$ is a hydroxyl group to be used is generally 1 to 10 equivalents, preferably 1 to 5 equivalents, relative to compound (4).

Examples of the above-mentioned "hydroxy group-activator" include cyanomethylenetri-n-butylphosphorane, a combination of diisopropyl azodicarboxylate and triphenylphosphine, and the like. The amount of the "hydroxy group-activator" to be used is generally 1 to 10 equivalents, preferably 1 to 5 equivalents, relative to compound (4).

Examples of the above-mentioned "inert solvent" include aromatic solvents, aliphatic hydrocarbon solvents, ether solvents, ester solvents, amide solvents and the like. These solvents may be used in a mixture of two or more kinds thereof in an appropriate ratio.

The reaction temperature is generally −70° C. to 150° C., preferably −20° C. to 100° C.

The reaction time is generally 0.1 hr to 100 hr, preferably 0.1 hr to 48 hr.

The "method using a base" can be performed according to a method known per se, for example, the method described in Journal of the Chemical Society (J. Chem. Soc.), pages 1530-1534, 1937, or the like, or a method analogous thereto.

This reaction is carried out by reacting compound (4) with compound (5) wherein $L^1$ is a leaving group in the presence of a base, in an inert solvent.

Examples of the above-mentioned "base" include "inorganic bases", "basic salts", "aromatic amines", "tertiary amines", "hydrides of an alkali metal or alkaline earth metal", "alkylmetals", "arylmetals", "metal alkoxides" and the like. The amount of the "base" to be used is generally 1 to 10 equivalents, preferably 1 to 5 equivalents, relative to compound (4).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, THF, DMF and the like are preferable.

The reaction temperature is generally −100° C. to 150° C., preferably 0° C. to 100° C.

The reaction time is generally 5 min to 48 hr, preferably 30 min to 24 hr.

<Reaction Scheme 4> wherein each symbol is as defined above.

Compound (6) may be easily commercially available, or can also be produced, for example, according to the method described in Reaction Schemes 18 and 19, or a method known per se or a method analogous thereto.

Compound (8) can be produced, for example, by subjecting compound (6) to an amidation reaction with compound (7).

The above-mentioned "amidation reaction" encompasses the following "method using a dehydrating condensing agent", "method using a reactive derivative of carboxylic acid" and the like.

i) Method Using a Dehydrating Condensing Agent

The above-mentioned "amidation reaction" is carried out by reacting compound (6) with compound (7) in the presence of a dehydrating condensing agent, in an inert solvent. Where necessary, the reaction may be carried out in the presence of 1-hydroxybenzotriazole (HOBt) in an amount of a catalytic amount to 5 equivalents, a base in an amount of a catalytic amount to 5 equivalents, and the like.

The amount of compound (7) to be used is generally 0.5 to 5 equivalents, preferably 0.8 to 1.5 equivalents, relative to compound (6).

Examples of the above-mentioned "dehydrating condensing agent" include dicyclohexylcarbodiimide (DCC), 1-ethyl-3-(3-dimethylaminopropyl)carbodiimide hydrochloride (WSC), O-(7-azabenzotriazol-1-yl)-N,N,N',N'-tetramethyluronium hexafluorophosphate (HATU) and the like. Among them, HATU is preferable. The amount of the "dehydrating condensing agent" to be used is generally 1 to 10 equivalents, preferably 1 to 5 equivalents, relative to compound (7).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, amide solvents are preferable.

Examples of the above-mentioned "base" include "aromatic amines", "tertiary amines" and the like.

The reaction temperature is generally −70° C. to 150° C., preferably −20° C. to 100° C.

The reaction time is generally 0.1 hr to 100 hr, preferably 1 hr to 48 hr.

ii) Method Using a Reactive Derivative of Carboxylic Acid

The above-mentioned "amidation reaction" is carried out by reacting the reactive derivative of compound (7) with compound (6) in an amount of 0.5 to 5 equivalents (preferably 0.8 to 3 equivalents) in an inert solvent. Where necessary, the reaction may be carried out in the presence of a base in an amount of 1 to a solvent amount, preferably 1 to 3 equivalents.

Examples of the "reactive derivative" of compound (7) include acid halides (e.g., acid chlorides, acid bromides), mixed anhydrides (e.g., acid anhydrides with a $C_{1-6}$ alkyl-carboxylic acid, a $C_{6-10}$ aryl-carboxylic acid, a $C_{1-6}$ alkylcarbonic acid etc.), activated esters (e.g., esters with a phenol optionally having substituent(s), HOBt, N-hydroxysuccinimide etc.) and the like.

Examples of the above-mentioned "phenol optionally having substituent(s)" include phenol, pentachlorophenol, pentafluorophenol, p-nitrophenol and the like.

The reactive derivative of compound (7) is preferably an acid halide.

Examples of the above-mentioned "inert solvent" include ether solvents, halogenated hydrocarbon solvents, aromatic solvents, aliphatic hydrocarbon solvents, nitrile solvents, amide solvents, ketone solvents, sulfoxide solvents, water and the like. These solvents may be used in a mixture of two or more kinds thereof in an appropriate ratio. Among them, acetonitrile, THF, dichloromethane, chloroform and the like are preferable.

Examples of the above-mentioned "base" include "aromatic amines", "tertiary amines" and the like.

The reaction temperature is generally −20 to 100° C., preferably −20° C. to 50° C.

The reaction time is generally 5 min to 40 hr, preferably 30 min to 18 hr.

Compound (4-1) can be produced, for example, by subjecting compound (8) to a ring-closing reaction.

The above-mentioned "ring-closing reaction" is carried out by reacting compound (8) in the presence of an activator, in an inert solvent.

Examples of the above-mentioned "activator" include p-toluenesulfonic acid, a combination of diisopropyl azodicarboxylate and triphenylphosphine, a combination of hexachloroethane, triphenylphosphine and a base, and the like. The amount of the "activator" to be used is generally 0.001 to 10 equivalents, preferably 0.01 to 8 equivalents, relative to compound (8).

Examples of the above-mentioned "inert solvent" include aromatic solvents, aliphatic hydrocarbon solvents, ether solvents, ester solvents, amide solvents, nitrile solvents, halogenated hydrocarbon solvents and the like. These solvents may be used in a mixture of two or more kinds thereof in an appropriate ratio.

Examples of the above-mentioned "base" include "aromatic amines", "tertiary amines" and the like.

The reaction temperature is generally −70° C. to 200° C., preferably −20° C. to 150° C.

The reaction time is generally 0.1 hr to 100 hr, preferably 0.1 hr to 40 hr.

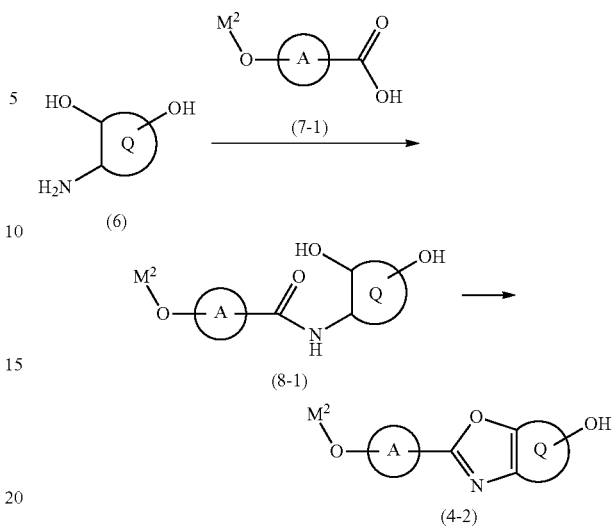

wherein $M^2$ is a phenolic hydroxyl-protecting group, and other symbols are as defined above.

Compound (8-1) can be produced, for example, by subjecting compound (6) to an amidation reaction with compound (7-1).

This reaction is carried out in the same manner as in the production method of compound (8) in Reaction Scheme 4.

Compound (4-2) can be produced, for example, by subjecting compound (8) to a ring-closing reaction.

This reaction is carried out in the same manner as in the production method of compound (4-1) in Reaction Scheme 4.

<Reaction Scheme 6>

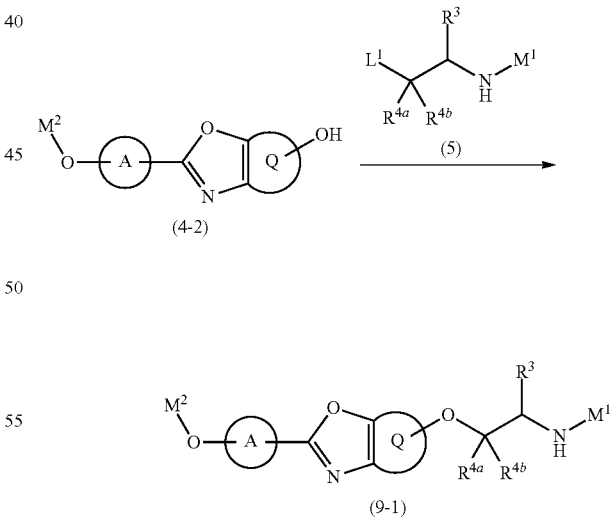

wherein each symbol is as defined above.

Compound (9-1) can be produced, for example, by subjecting compound (4-2) to an etherification reaction with compound (5).

This reaction is carried out in the same manner as in the production method of compound (1') in Reaction Scheme 3.

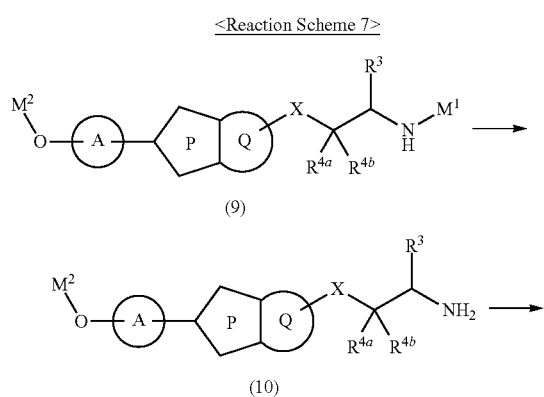

<Reaction Scheme 7>

(9)

(10)

Compound (10) can be produced, for example, by subjecting compound (9) to a deprotection reaction. The deprotection reaction can be carried out according to a method known per se, for example, the method described in Protective Groups in Organic Synthesis, John Wiley and Sons (1980), or the like.

Compound (11) can be produced, for example, by subjecting compound (10) to an acylation reaction.

This reaction is carried out in the same manner as in the production method of compound (I-1) in Reaction Scheme 1.

Compound (3-1) can be produced, for example, by subjecting compound (11) to a deprotection reaction. The deprotection reaction can be carried out according to a method known per se, for example, the method described in Protective Groups in Organic Synthesis, John Wiley and Sons (1980), or the like.

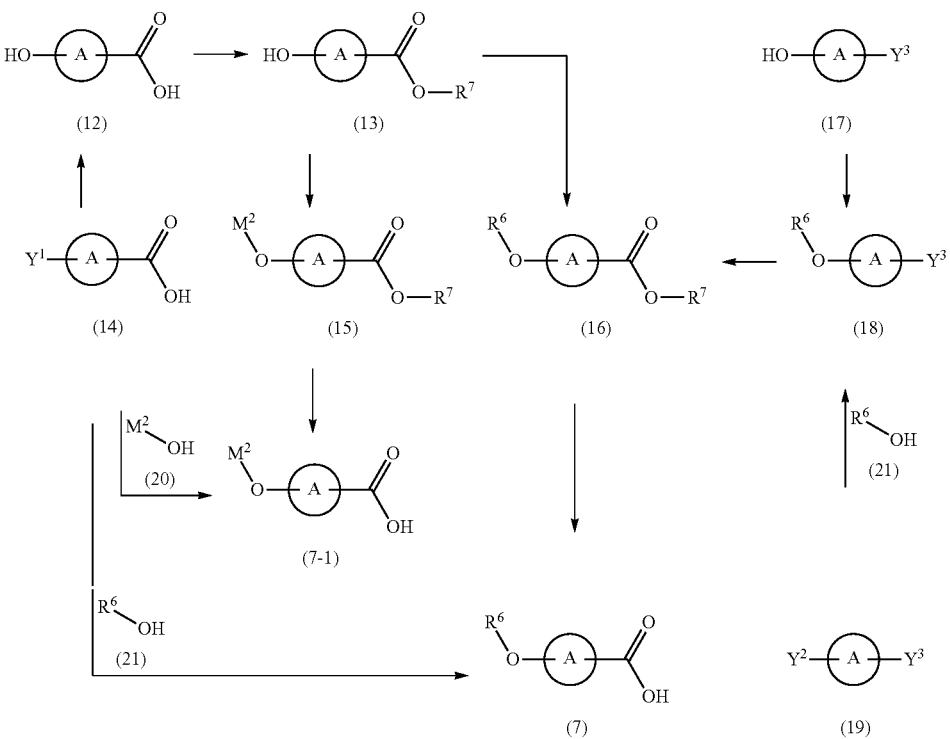

<Reaction Scheme 8>

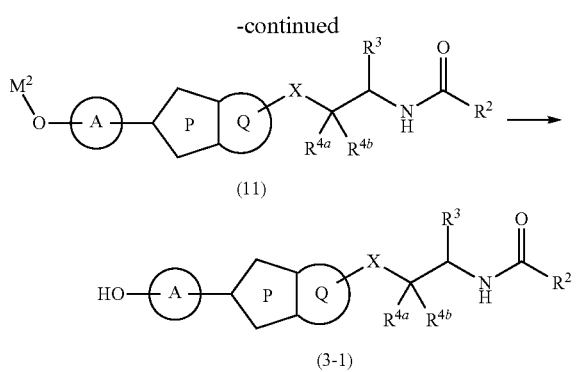

(11)

(3-1)

wherein each symbol is as defined above.

wherein $Y^1$, $Y^2$ and $Y^3$ are each independently a halogen atom, $R^7$ is a substituent, and other symbols are as defined above.

Compounds (12), (14), (17) and (19) may be easily commercially available, or can also be produced according to a method known per se or a method analogous thereto.

Compound (12) can be produced, for example, by subjecting compound (14) to a hydroxylation reaction. Where necessary, the reaction may be carried out under microwave irradiation.

The above-mentioned "hydroxylation reaction" is carried out by reacting compound (14) in the presence of water and a base, in an inert solvent.

The amount of the above-mentioned "water" to be used is 1 to 100 equivalents, preferably 10 to 50 equivalents, relative to compound (14).

Examples of the above-mentioned "base" include "alkylmetals", "metal amides", "inorganic bases", "basic salts", "arylmetals", "metal alkoxides" and the like. The amount of the "base" to be used is generally 1 equivalent to 10 equivalents, relative to compound (14).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, THF, DMF and the like are preferable.

The reaction temperature is generally −100° C. to 200° C., preferably 0° C. to 150° C.

The reaction time is generally 5 min to 48 hr, preferably 30 min to 24 hr.

Examples of the above-mentioned "inert solvent" include aliphatic hydrocarbon solvents, aromatic solvents, ether solvents and the like. These solvents may be used in a mixture of two or more kinds thereof in an appropriate ratio.

Compound (13) can be produced, for example, by subjecting compound (12) to an esterification reaction. The esterification can be carried out according to a method known per se, for example, the method described in Protective Groups in Organic Synthesis, John Wiley and Sons (1980), or the like.

Compound (15) can be produced, for example, by subjecting compound (13) to a protection reaction. The protection reaction can be carried out according to a method known per se, for example, the method described in Protective Groups in Organic Synthesis, John Wiley and Sons (1980), or the like.

Compound (7-1) can be produced, for example, by subjecting compound (14) to an etherification reaction with compound (20).

This reaction is carried out by reacting compound (14) with compound (20) in the presence of a base, in an inert solvent. Where necessary, the reaction may be carried out under microwave irradiation.

The amount of compound (20) to be used is generally 1 to 10 equivalents, preferably 1 to 5 equivalents, relative to compound (14).

Examples of the above-mentioned "base" include "inorganic bases", "basic salts", "aromatic amines", "tertiary amines", "hydrides of an alkali metal or alkaline earth metal", "alkylmetals", "arylmetals", "metal alkoxides" and the like. The amount of the "base" to be used is generally 1 to 10% equivalents, preferably 1 to 5 equivalents, relative to compound (14).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, THF, DMF and the like are preferable.

The reaction temperature is generally −100° C. to 200° C., preferably 0° C. to 150° C.

The reaction time is generally 5 min to 48 hr, preferably 30 min to 24 hr.

Compound (7-1) can also be produced, for example, by subjecting compound (15) to a hydrolysis reaction.

This reaction is carried out by reacting compound (15) with a base in an inert solvent.

Examples of the above-mentioned "base" include "inorganic bases" and the like. The amount of the "base" to be used is generally 1 to 10 equivalents, preferably 1 to 5 equivalents, relative to compound (15).

Examples of the above-mentioned "inert solvent" include alcohol solvents, ether solvents, amide solvents, halogenated hydrocarbon solvents and the like. These solvents are preferably used in a mixture with water in an appropriate ratio. Among them, aqueous alcohol solvents are preferable.

The reaction temperature is generally −78° C. to 150° C., preferably −20° C. to 100° C.

The reaction time is generally 5 min to 100 hr, preferably 30 min to 24 hr.

When $R^7$ in compound (15) is a carboxy-protecting group, compound (7-1) can be produced according to a method known per se, for example, the method described in Protective Groups in Organic Synthesis, John Wiley and Sons (1980), or the like.

Compound (18) can be produced, for example, by subjecting compound (17) to an alkylation reaction.

This reaction is carried out in the same manner as in the production method of compound (I) in Reaction Scheme 2.

Compound (18) can also be produced, for example, by subjecting compound (19) to an etherification reaction with compound (21).

This reaction is carried out by reacting compound (19) with compound (21) in the presence of a base, in an inert solvent. Where necessary, the reaction may be carried out under microwave irradiation.

The amount of compound (21) to be used is generally 1 to equivalents, preferably 1 to 5 equivalents, relative to compound (19).

Examples of the above-mentioned "base" include "inorganic bases", "basic salts", "aromatic amines", "tertiary amines", "hydrides of an alkali metal or alkaline earth metal", "alkylmetals", "arylmetals", "metal alkoxides" and the like. The amount of the "base" to be used is generally 1 to 10 equivalents, preferably 1 to 5 equivalents, relative to compound (19).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, THF, DMF and the like are preferable.

The reaction temperature is generally −100° C. to 200° C., preferably 0° C. to 150° C.

The reaction time is generally 5 min to 48 hr, preferably 30 min to 24 hr.

Compound (16) can also be produced, for example, by subjecting compound (13) to an alkylation reaction.

This reaction is carried out in the same manner as in the production method of compound (I) in Reaction Scheme 2.

Compound (16) can also be produced, for example, by subjecting compound (18) to a carbon monoxide insertion reaction.

The above-mentioned "carbon monoxide insertion reaction" is carried out by reacting compound (18) in the presence of a metal catalyst and a carbon monoxide source, in an inert solvent. Where necessary, the reaction may be carried out using a ligand and a base.

Examples of the above-mentioned "metal catalyst" include 1,1'-bis(diphenylphosphino)ferrocene-palladium(II) dichloride dichloromethane complex, and the like. The amount of the "metal catalyst" to be used is generally 0.001 to 100 equivalents, preferably 0.01 to 10 equivalents, relative to compound (18).

Examples of the above-mentioned "ligand" include 1,1'-bis(diphenylphosphino)ferrocene and the like. The amount of the "ligand" to be used is generally 0.001 to 100 equivalents, preferably 0.01 to 10 equivalents, relative to compound (18).

Examples of the above-mentioned "carbon monoxide source" include carbon monoxide gas and the like.

Examples of the above-mentioned "base" include "aromatic amines", "tertiary amines" and the like. The amount of the "base" to be used is generally 1 to 10 equivalents, preferably 1 to 5 equivalents, relative to compound (18).

Examples of the above-mentioned "inert solvent" include alcohol solvents, amide solvents, aromatic solvents, halogenated hydrocarbon solvents, ether solvents and the like. Among them, alcohol solvents are preferable. These solvents may be used in a mixture of two or more kinds thereof in an appropriate ratio.

The reaction temperature is generally −20° C. to 200° C., preferably 0° C. to 150° C.

The reaction time is generally 5 min to 40 hr, preferably 30 min to 24 hr.

Compound (7) can be produced, for example, by subjecting compound (14) to an etherification reaction with compound (21).

This reaction is carried out by reacting compound (14) with compound (21) in the presence of a base, in an inert solvent. Where necessary, the reaction may be carried out under microwave irradiation.

The amount of compound (21) to be used is generally 1 to 10 equivalents, preferably 1 to 5 equivalents, relative to compound (14).

Examples of the above-mentioned "base" include "inorganic bases", "basic salts", "aromatic amines", "tertiary amines", "hydrides of an alkali metal or alkaline earth metal", "alkylmetals", "arylmetals", "metal alkoxides" and the like. The amount of the "base" to be used is generally 1 to 10 equivalents, preferably 1 to 5 equivalents, relative to compound (14).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, THF, DMF and the like are preferable.

The reaction temperature is generally −100° C. to 200° C., preferably 0° C. to 150° C.

The reaction time is generally 5 min to 48 hr, preferably 30 min to 24 hr.

Compound (7) can also be produced, for example, by subjecting compound (16) to a hydrolysis reaction.

This reaction is carried out by reacting compound (16) with a base in an inert solvent.

Examples of the above-mentioned "base" include "inorganic bases" and the like. The amount of the "base" to be used is generally 1 to 10 equivalents, preferably 1 to 5 equivalents, relative to compound (16).

Examples of the above-mentioned "inert solvent" include alcohol solvents, ether solvents, amide solvents, halogenated hydrocarbon solvents and the like. These solvents are preferably used in a mixture with water in an appropriate ratio. Among them, aqueous alcohol solvents are preferable.

The reaction temperature is generally −78° C. to 150° C., preferably −20° C. to 100° C.

The reaction time is generally 5 min to 100 hr, preferably 30 min to 24 hr.

When $R^7$ in compound (16) is a carboxy-protecting group, compound (7-1) can be produced according to a method known per se, for example, the method described in Protective Groups in Organic Synthesis, John Wiley and Sons (1980), or the like.

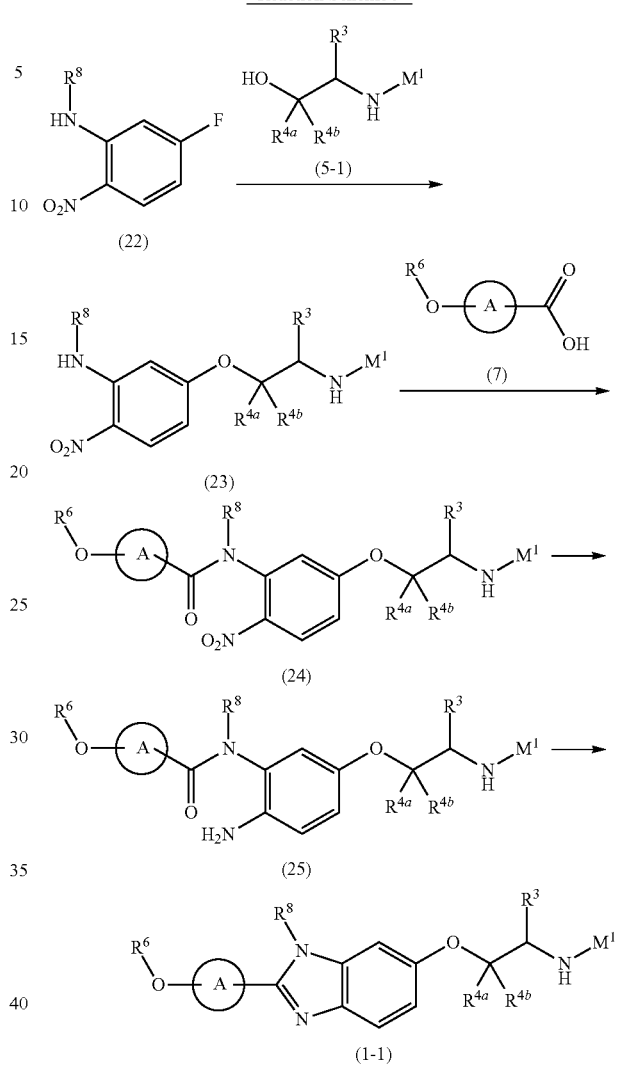

<Reaction Scheme 9> wherein each symbol is as defined above, and $R^8$ is a substituent.

Compound (22) may be easily commercially available, or can also be produced according to a method known per se or a method analogous thereto.

Compound (23) can be produced, for example, by subjecting compound (22) to an etherification reaction with compound (5-1).

This reaction is carried out by reacting compound (22) with compound (5-1) in the presence of a base, in an inert solvent.

The amount of compound (5-1) to be used is generally 1 to 10 equivalents, preferably 1 to 5 equivalents, relative to compound (22).

Examples of the above-mentioned "base" include "inorganic bases", "basic salts", "aromatic amines", "tertiary amines", "hydrides of an alkali metal or alkaline earth metal", "alkylmetals", "arylmetals", "metal alkoxides" and the like. The amount of the "base" to be used is generally 1 to 10 equivalents, preferably 1 to 5 equivalent, relative to compound (22).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, THF, DMF and the like are preferable.

The reaction temperature is generally −100° C. to 200° C., preferably 0° C. to 150° C.

The reaction time is generally 5 min to 48 hr, preferably 30 min to 24 hr.

Compound (24) can be produced for example, by subjecting compound (23) to an amidation reaction with compound (7).

This reaction is carried out in the same manner as in the production method of compound (8) in Reaction Scheme 4.

Compound (25) can be produced for example, by subjecting compound (24) to a reduction reaction.

This reaction is carried out by reacting compound (24) in the presence of a metal catalyst and a hydrogen source, in an inert solvent. Where necessary, the reaction may be carried out in the presence of an organic acid in an amount of a catalytic amount to a solvent amount or hydrogen chloride in an amount of 1 equivalent to 50 equivalents.

Examples of the above-mentioned "metal catalyst" include palladium-carbon, palladium black, palladium chloride, palladium hydroxide, rhodium-carbon, platinum oxide, platinum black, platinum-palladium, Raney-nickel, Raney-cobalt and the like. The amount of the "metal catalyst" to be used is generally 0.001 to 1000 equivalents, preferably 0.01 to 100 equivalents, relative to compound (24).

Examples of the above-mentioned "hydrogen source" include hydrogen gas and the like.

Examples of the above-mentioned "organic acid" include acetic acid and the like.

Examples of the above-mentioned "inert solvent" include alcohol solvents, nitrile solvents, aromatic solvents, aliphatic hydrocarbon solvents, ether solvents, amide solvents, halogenated hydrocarbon solvents and the like. These solvents may be used in a mixture of two or more kinds thereof in an appropriate ratio.

The reaction temperature is generally −70° C. to 150° C., preferably −20° C. to 100° C.

The reaction time is generally 0.1 hr to 100 hr, preferably 0.1 hr to 40 hr.

Compound (1-1) can be produced for example, by subjecting compound (25) to a cyclization reaction.

This reaction is carried out by reacting compound (25) in an inert solvent. Where necessary, the reaction may be carried out using an acid, an anhydride, a dehydrating agent, an activator or the like.

Examples of the above-mentioned "acid, anhydride, dehydrating agent or activator" include sulfuric acid, hydrochloric acid, methanesulfonic acid, pyridinium methanesulfonate, acetic acid, trifluoroacetic acid, acetic anhydride, polyphosphoric acid, diphosphorus pentoxide, phosphoryl chloride, triphenylphosphine, DIAD (diisopropyl azodicarboxylate) and the like. In addition, azido(trimethyl)silane may be added as an additive. The amount of the "acid, anhydride, dehydrating agent or activator" to be used is generally 0.01 to 20 equivalents, preferably 1 to 5 equivalents, relative to compound (25). An excess amount thereof may be used as a solvent.

Examples of the above-mentioned "inert solvent" include aromatic solvents, halogenated hydrocarbon solvents, nitrile solvents, alcohol solvents, ketone solvents aromatic solvents, aliphatic hydrocarbon solvents, ether solvents, ester solvents, amide solvents, and the like. These solvents may be used in a mixture of two or more kinds thereof in an appropriate ratio.

The reaction temperature is generally −70 to 250° C., preferably −20 to 200° C.

The reaction time is generally 0.1 to 100 hr, preferably 0.1 to 40 hr.

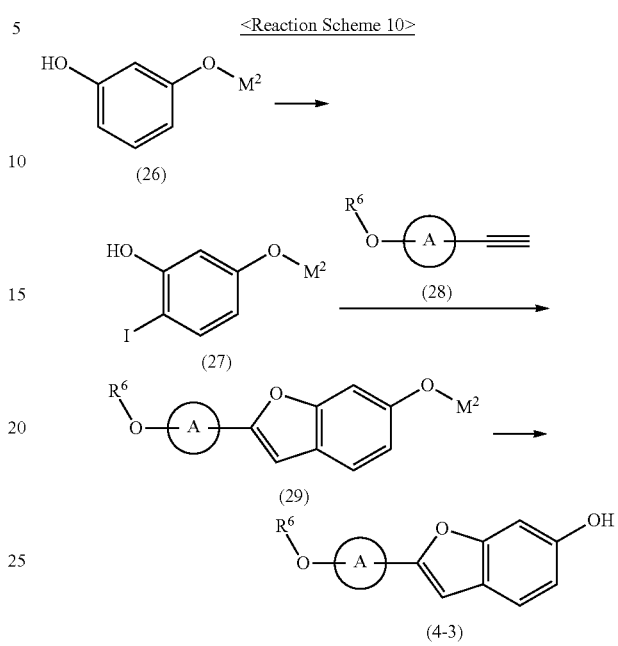

wherein each symbol is as defined above.

Compound (26) may be easily commercially available, or can also be produced according to a method known per se or a method analogous thereto.

Compound (27) can be produced, for example, by subjecting compound (26) to an iodination reaction.

This reaction is carried out by reacting compound (26) in the presence of an iodinating agent, in an inert solvent. This reaction may be carried out in the co-presence of a base or an additive.

Examples of the above-mentioned "iodinating agent" include N-iodosuccinimide, iodine and the like. The amount of the "iodinating agent" to be used is generally 1 to 20 equivalents, preferably 1 to 5 equivalents, relative to compound (26).

Examples of the above-mentioned "inert solvent" include nitrile solvents, amide solvents, ether solvents, aromatic solvents, aliphatic hydrocarbon solvents, water and the like. These solvents may be used in a mixture of two or more kinds thereof in an appropriate ratio.

Examples of the above-mentioned "base" include "basic salts", "aromatic amines", "tertiary amines", "hydrides of an alkali metal or alkaline earth metal", "metal amides", "alkylmetals", "arylmetals", "metal alkoxides" and the like. The amount of the "base" to be used is generally 0.1 to 20 equivalents, preferably 1 to 5 equivalents, relative to compound (26). The base may be used as a solvent.

Examples of the above-mentioned "additive" include silver trifluoroacetate. The amount of the "additive" to be used is generally 0.1 to 20 equivalents, preferably 1 to 5 equivalents, relative to compound (26).

The reaction temperature is generally −100 to 100° C., preferably 0 to 100° C.

The reaction time is generally 0.1 to 100 hr, preferably 0.1 to 8 hr.

Compound (29) can be produced, for example, by subjecting compound (27) to a coupling reaction with compound (28) and the subsequent cyclization reaction.

The above-mentioned "coupling reaction and the subsequent cyclization reaction" can be carried out according to a method known per se, for example, the method described in Synthesis, pages 749-751, 1986, or the like, or a method analogous thereto.

This reaction is carried out by reacting compound (27) with compound (28) in the presence of a transition metal catalyst and a base, in an inert solvent, under an inert gas atmosphere. Where necessary, the reaction may be carried out by addition of a ligand.

The amount of compound (28) to be used is generally 1 to 20 equivalents, preferably 1 to 5 equivalents, relative to compound (27).

Examples of the above-mentioned "transition metal catalyst" include palladium catalysts, nickel catalysts, iron catalysts, cobalt catalysts and the like. Examples of the palladium catalyst include dichlorobis(triphenylphosphine)palladium and the like. The amount of the "transition metal catalyst" to be used is generally 0.001 to 1 equivalents, preferably 0.01 to 0.1 equivalents, relative to compound (27). In addition, a copper catalyst and the like may be added as a co-catalyst. Examples of the copper catalyst include copper(I) iodide and the like. The amount of the "co-catalyst" to be used is generally 0.001 to 1 equivalents, preferably 0.01 to 0.1 equivalents, relative to compound (27).

Examples of the above-mentioned "ligand" include phosphine ligands. Examples of the phosphine ligand include triphenylphosphine and the like. The amount of the "ligand" to be used is generally 0 to 20 equivalents, preferably 0 to 1 equivalents, relative to compound (27).

Examples of the above-mentioned "base" include "aromatic amines", "tertiary amines" and the like. The amount of the "base" to be used is generally 0.1 to 20 equivalents, preferably 1 to 5 equivalents, relative to compound (27). The base may be used as a solvent.

Examples of the above-mentioned "inert solvent" include amide solvents, aromatic solvents, aliphatic hydrocarbon solvents, ether solvents, ester solvents and the like. These solvents may be used in a mixture of two or more kinds thereof in an appropriate ratio.

Examples of the above-mentioned "inert gas" include nitrogen, argon and the like.

The reaction temperature is generally −70 to 150° C., preferably −20 to 150° C.

The reaction time is generally 0.1 to 100 hr, preferably 0.1 to 40 hr.

Compound (4-3) can be produced for example, by subjecting compound (29) to a deprotection reaction. The deprotection reaction can be carried out according to a method known per se, for example, the method described in Protective Groups in Organic Synthesis, John Wiley and Sons (1980), or the like.

<Reaction Scheme 11>

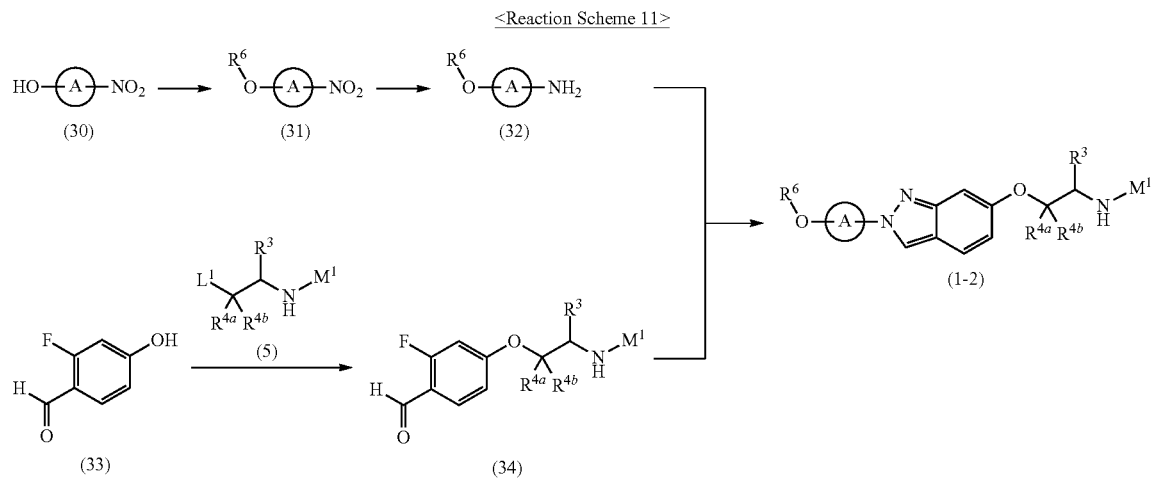

wherein each symbol is as defined above.

Compound (30) and compound (33) may be easily commercially available, or can also be produced according to a method known per se or a method analogous thereto.

Compound (31) can be produced, for example, by subjecting m compound (30) to an alkylation reaction.

This reaction is carried out in the same manner as in the production method of compound (I) in Reaction Scheme 2.

Compound (32) can be produced, for example, by subjecting compound (31) to a reduction reaction.

This reaction is carried out in the same manner as in the production method of compound (25) in Reaction Scheme 9.

Compound (34) can be produced, for example, by subjecting compound (33) to an etherification reaction with compound (5).

This reaction is carried out in the same manner as in the production method of compound (1') in Reaction Scheme 3.

Compound (1-2) can be produced, for example, by subjecting compound (32) and compound (34) to a dehydrating condensation reaction and the subsequent ring-closing reaction.

The above-mentioned "dehydrating condensation reaction" is carried out by reacting compound (32) and compound (34) in an inert solvent. Where necessary, a dehydrating agent may be used.

The amount of compound (32) to be used is generally 0.01 to 5 equivalents, relative to compound (34).

Examples of the above-mentioned "dehydrating agent" include magnesium sulfate and the like. The amount of the "dehydrating agent" to be used is generally 1 to 1000 equivalents, relative to compound (34).

Examples of the above-mentioned "inert solvent" include alcohol solvents, aromatic solvents, aliphatic hydrocarbon solvents, ether solvents, amide solvents, halogenated hydrocarbon solvents and the like. These solvents may be used in a mixture of two or more kinds thereof in an appropriate ratio.

The reaction temperature is generally −78° C. to 200° C., preferably 50° C. to 150° C.

The reaction time is generally 5 min to 48 hr, preferably 30 min to 24 hr.

The above-mentioned "ring-closing reaction" is carried out by reacting the obtained compound (obtained by subjecting compound (32) and compound (34) to the above-mentioned dehydrating condensation reaction) in the presence of an azidating agent.

Examples of the above-mentioned "azidating agent" include sodium azide and the like. The amount of the "azidating agent" to be used is generally 1 equivalent to an excess amount, relative to compound (34).

The reaction temperature is generally −78° C. to 200° C., preferably 50° C. to 150° C.

The reaction time is generally 5 min to 48 hr, preferably 30 min to 24 hr.

<Reaction Scheme 12>

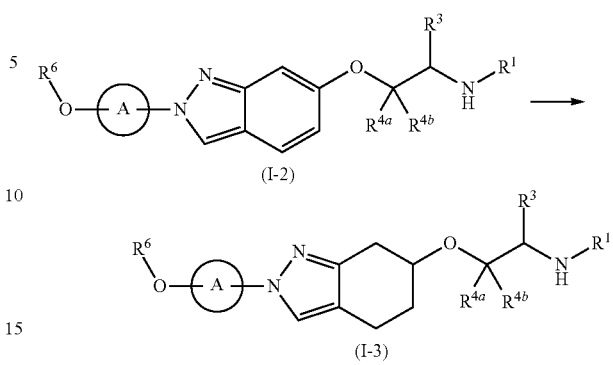

wherein each symbol is as defined above.

Compound (I-3) can be produced, for example, by subjecting compound (I-2) to a reduction reaction.

This reaction is carried out in the same manner as in the production method of compound (25) in Reaction Scheme 9.

<Reaction Scheme 13>

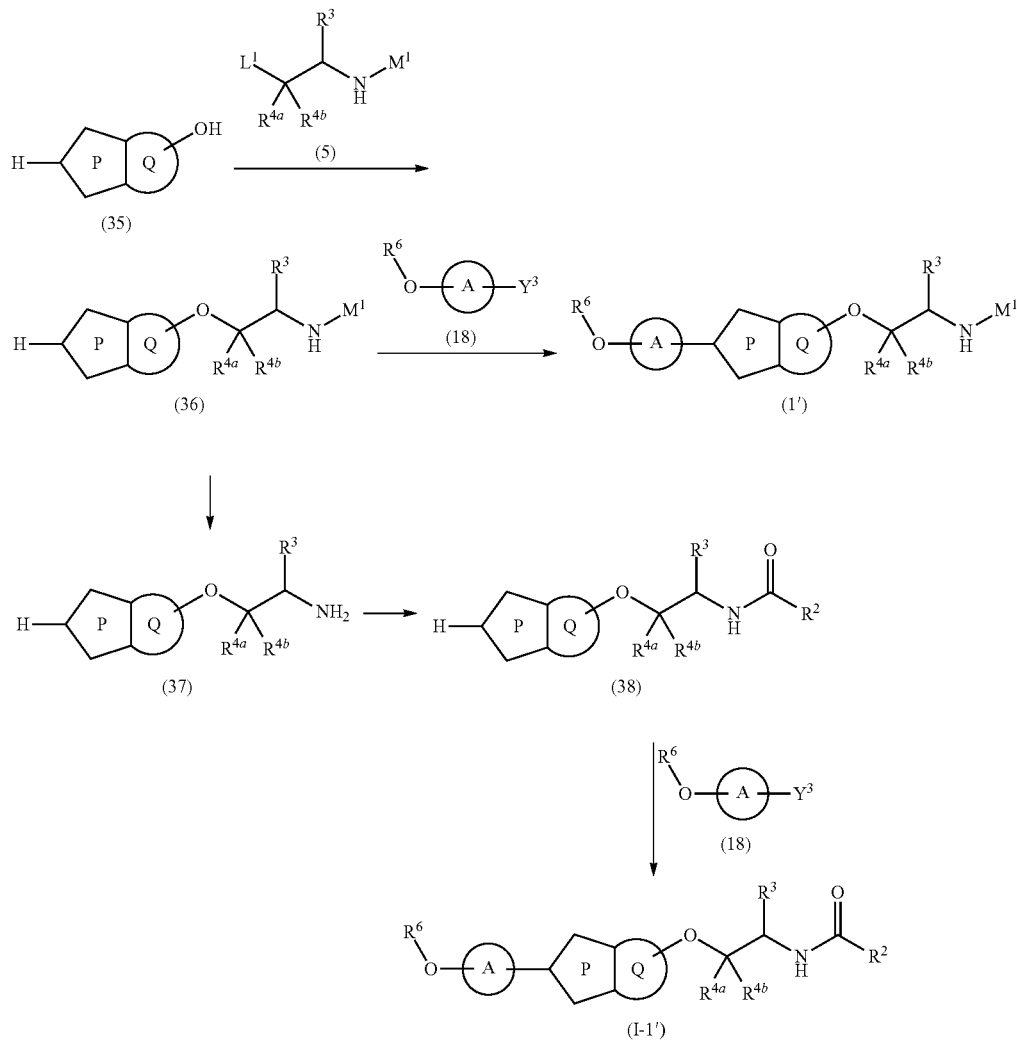

wherein each symbol is as defined above.

Compound (36) can be produced, for example, by subjecting compound (35) to an etherification reaction with compound (5).

This reaction is carried out in the same manner as in the production method of compound (1') in Reaction Scheme 3.

Compound (37) can be produced, for example, by subjecting compound (36) to a deprotection reaction. The deprotection reaction can be carried out according to a method known per se, for example, the method described in Protective Groups in Organic Synthesis, John Wiley and Sons (1980), or the like.

Compound (38) can be produced, for example, by subjecting compound (37) to an acylation reaction.

This reaction is carried out in the same manner as in the production method of compound (I-1) in Reaction Scheme 1.

Compound (1') can be produced, for example, by subjecting compound (36) to a coupling reaction with compound (18).

The above-mentioned "coupling reaction" is carried out by reacting compound (36) with compound (18) in the presence of a metal catalyst, a ligand and a base, in an inert solvent. This reaction is preferably carried out under an inert gas atmosphere.

The amount of compound (18) to be used is generally 0.5 to 5 equivalents, preferably 0.8 to 1.5 equivalents, relative to compound (36).

Examples of the above-mentioned "metal catalyst" include palladium(II) acetate, copper(I) iodide and the like. The amount of the "metal catalyst" to be used is generally 0.001 to 100 equivalents, preferably 0.01 to 10 equivalents, relative to compound (36).

Examples of the above-mentioned "ligand" include butyldi-(1-adamantyl)phosphine, (1R,2R)—N,N'-dimethyl-cyclohexane-1,2-diamine and the like. The amount of the "ligand" to be used is generally 0.001 to 100 equivalents, preferably 0.01 to 10 equivalents, relative to compound (36).

Examples of the above-mentioned "base" include "basic salts" and the like. Among them, tripotassium phosphate, cesium carbonate and the like are preferable. The amount of the "base" to be used is generally 1 to 10 equivalents, preferably 1 to 5 equivalents, relative to compound (36).

Examples of the above-mentioned "inert solvent" include amide solvents, aromatic solvents, halogenated hydrocarbon solvents and the like.

Examples of the above-mentioned "inert gas" include argon gas, nitrogen gas and the like.

The reaction temperature is generally −20° C. to 200° C., preferably 0° C. to 150° C.

The reaction time is generally 5 min to 40 hr, preferably 30 min to 24 hr.

Compound (I-1') can be produced, for example, by subjecting compound (38) to a coupling reaction with compound (18).

This reaction is carried out in the same manner as in the production method of compound (1') in Reaction Scheme 13.

<Reaction Scheme 14>

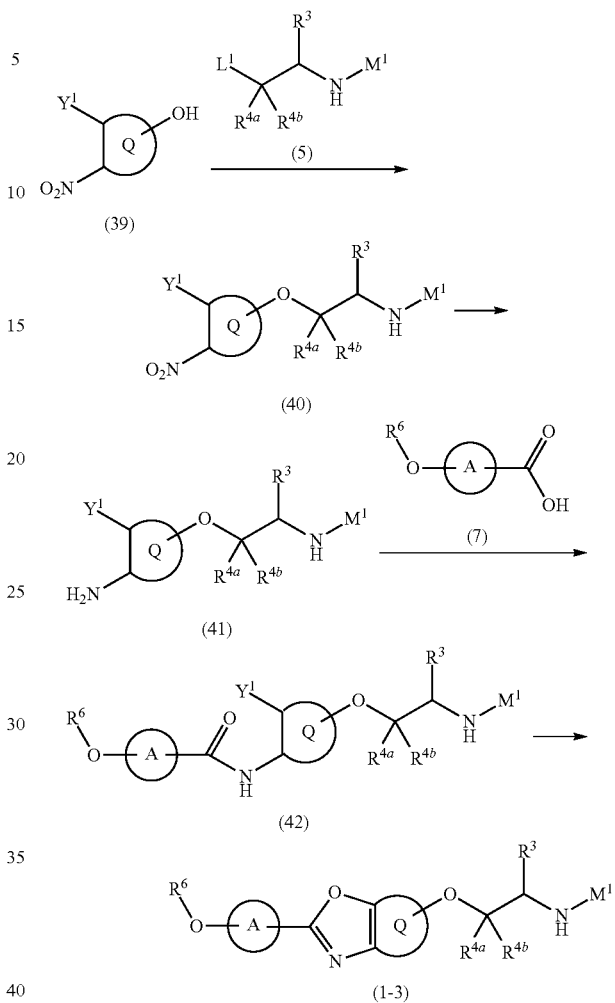

wherein each symbol is as defined above.

Compound (39) may be easily commercially available, or can also be produced according to a method known per se or a method analogous thereto.

Compound (40) can be produced, for example, by subjecting compound (39) to an etherification reaction with compound (5).

This reaction is carried out in the same manner as in the production method of compound (1') in Reaction Scheme 3.

Compound (41) can be produced, for example, by subjecting compound (40) to a reduction reaction.

This reaction is carried out by reacting compound (40) in the presence of a metal, in an inert solvent. Where necessary, the reaction may be carried out in the presence of a hydrogen source and an additive.

Examples of the above-mentioned "metal" include palladium-carbon, palladium black, palladium chloride, palladium hydroxide, rhodium-carbon, platinum oxide, platinum black, platinum-palladium, Raney-nickel, Raney-cobalt, reduced iron and the like. The amount of the "metal" to be used is generally 0.001 to 1000 equivalents, preferably 0.01 to 100 equivalents, relative to compound (40).

Examples of the above-mentioned "hydrogen source" include hydrogen gas, ammonium formate, ammonium chloride and the like.

Examples of the above-mentioned "additive" include organic acids in an amount of a catalytic amount to a solvent amount, hydrogen chloride in an amount of 1 equivalent to 50 equivalents, iron(III) chloride in an amount of 1 equivalent to 50 equivalents, and the like.

Examples of the above-mentioned "organic acid" include acetic acid and the like.

Examples of the above-mentioned "inert solvent" include alcohol solvents, nitrile solvents, aromatic solvents, aliphatic hydrocarbon solvents, ether solvents, amide solvents, halogenated hydrocarbon solvents, water and the like. These solvents may be used in a mixture of two or more kinds thereof in an appropriate ratio.

The reaction temperature is generally −70° C. to 150° C., preferably −20° C. to 100° C.

The reaction time is generally 0.1 hr to 100 hr, preferably 0.1 hr to 40 hr.

Compound (42) can be produced, for example, by subjecting compound (41) to an amidation reaction with compound (7).

This reaction is carried out in the same manner as in the production method of compound (8) in Reaction Scheme 4.

Compound (1-3) can be produced, for example, by subjecting compound (42) to a ring-closing reaction.

This reaction is carried out by reacting compound (42) in the presence of a base and a metal catalyst, in an inert solvent. Where necessary, the reaction may be carried out under microwave irradiation.

Examples of the above-mentioned "base" include "inorganic bases", "basic salts", "aromatic amines", "tertiary amines", "hydrides of an alkali metal or alkaline earth metal", "alkylmetals", "arylmetals" and the like. The amount of the "base" to be used is generally 1 to 10 equivalents, preferably 1 to 5 equivalents, relative to compound (42).

Examples of the above-mentioned "metal catalyst" include copper halides such as copper(I) chloride, copper(I) bromide, copper(I) iodide and the like, and the like. The amount of the "metal catalyst" to be used is generally 0.001 to 100 equivalents, preferably 0.01 to 10 equivalents, relative to compound (42).

Examples of the above-mentioned "inert solvent" include aromatic solvents, aliphatic hydrocarbon solvents, ether solvents, amide solvents, halogenated hydrocarbon solvents and the like. These solvents may be used in a mixture of two or more kinds thereof in an appropriate ratio. Among them, DMF, THF and the like are preferable.

The reaction temperature is generally −78° C. to 200° C., preferably −20° C. to 150° C.

The reaction time is generally 5 min to 48 hr, preferably 30 min to 24 hr.

<Reaction Scheme 15>

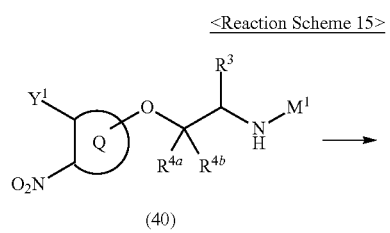

(40)

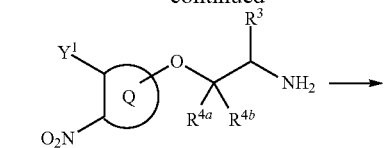

(43)

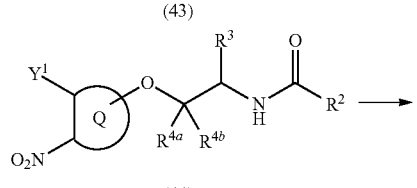

(44)

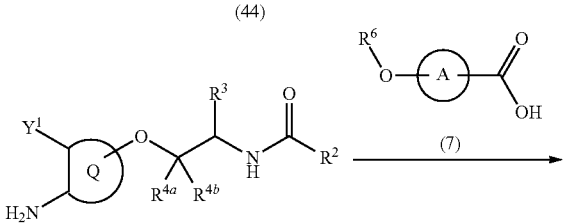

(45)

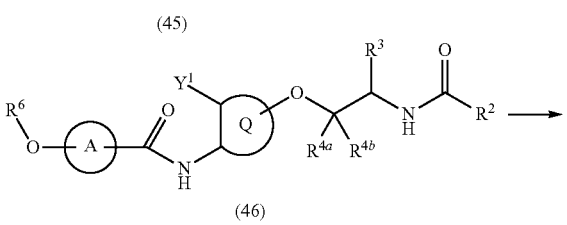

(46)

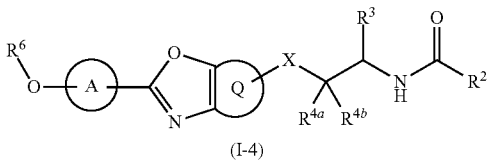

(I-4)

wherein each symbol is as defined above.

Compound (43) can be produced, for example, by subjecting compound (40) to a deprotection reaction. The deprotection reaction can be carried out according to a method known per se, for example, the method described in Protective Groups in Organic Synthesis, John Wiley and Sons (1980), or the like.

Compound (44) can be produced, for example, by subjecting compound (43) to an acylation reaction.

This reaction is carried out in the same manner as in the production method of compound (I-1) in Reaction Scheme 1.

Compound (45) can be produced, for example, by subjecting compound (44) to a reduction reaction.

This reaction is carried out in the same manner as in the production method of compound (41) in Reaction Scheme 14.

Compound (46) can be produced, for example, by subjecting compound (45) to an amidation reaction with compound (7).

This reaction is carried out in the same manner as in the production method of compound (8) in Reaction Scheme 4.

Compound (I-4) can be produced, for example, by subjecting compound (46) to a ring-closing reaction.

This reaction is carried out in the same manner as in the production method of compound (1-3) in Reaction Scheme 14.

<Reaction Scheme 16>

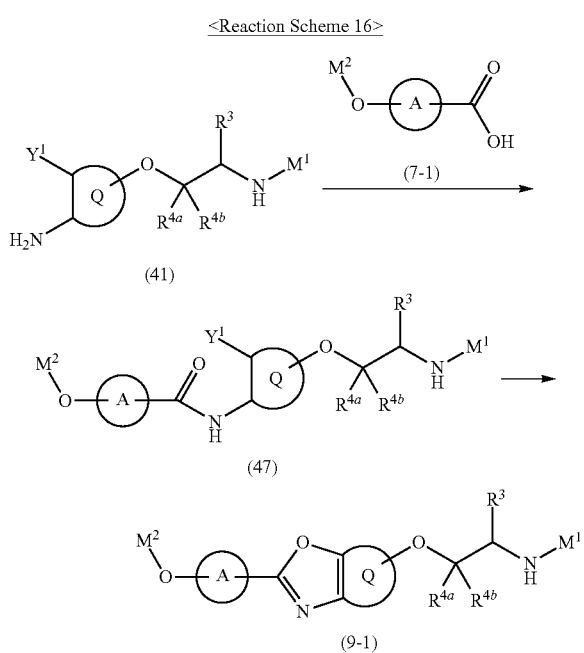

wherein each symbol is as defined above.

Compound (47) can be produced, for example, by subjecting compound (41) to an amidation reaction with compound (7-1).

This reaction is carried out in the same manner as in the production method of compound (8) in Reaction Scheme 4.

Compound (9-1) can be produced, for example, by subjecting compound (47) to a ring-closing reaction.

This reaction is carried out in the same manner as in the production method of compound (1-3) in Reaction Scheme 14.

<Reaction Scheme 17>

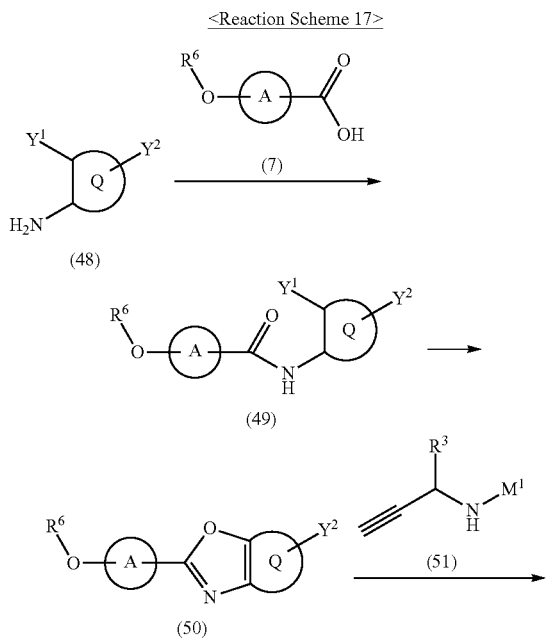

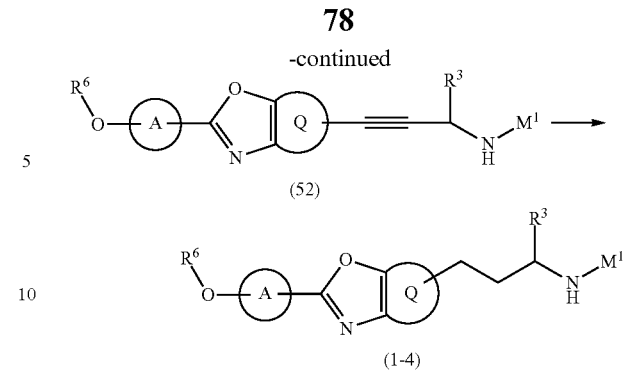

wherein each symbol is as defined above.

Compound (48) may be easily commercially available, or can also be produced according to a method known per se or a method analogous thereto.

Compound (49) can be produced, for example, by subjecting compound (48) to an amidation reaction with compound (7).

This reaction is carried out in the same manner as in the production method of compound (8) in Reaction Scheme 4.

Compound (50) can be produced, for example, by subjecting compound (49) to a ring-closing reaction.

This reaction is carried out in the same manner as in the production method of compound (1-3) in Reaction Scheme 14.

Compound (52) can be produced, for example, by subjecting compound (50) to a coupling reaction with compound (51).

This reaction is carried out by reacting compound (50) with compound (51) in the presence of a transition metal catalyst and a base, in an inert solvent, under an inert gas atmosphere. Where necessary, the reaction may be carried out by addition of a ligand.

The amount of compound (51) to be used is generally 1 to 20 equivalents, preferably 1 to 5 equivalents, relative to compound (50).

Examples of the above-mentioned "transition metal catalyst" include palladium catalysts, nickel catalysts, iron catalysts, cobalt catalysts and the like. Examples of the palladium catalyst include dichlorobis(triphenylphosphine)palladium and the like. The amount of the "transition metal catalyst" to be used is generally 0.001 to 1 equivalents, preferably 0.01 to 0.1 equivalents, relative to compound (50). In addition, a copper catalyst and the like may be added as a co-catalyst. Examples of the copper catalyst include copper(I) iodide and the like. The amount of the "co-catalyst" to be used is generally 0.001 to 1 equivalents, preferably 0.01 to 0.1 equivalents, relative to compound (50).

Examples of the above-mentioned "ligand" include phosphine ligands. Examples of the phosphine ligand include triphenylphosphine and the like. The amount of the "ligand" to be used is generally 0 to 20 equivalents, preferably 0 to 1 equivalents, relative to compound (50).

Examples of the above-mentioned "base" include "aromatic amines", "tertiary amines" and the like. The amount of the "base" to be used is generally 0.1 to 20 equivalents, preferably 1 to 5 equivalents, relative to compound (50). The base may be used as a solvent.

Examples of the above-mentioned "inert solvent" include amide solvents, aromatic solvents, aliphatic hydrocarbon solvents, ether solvents, ester solvents and the like. These solvents may be used in a mixture of two or more kinds thereof in an appropriate ratio.

Examples of the above-mentioned "inert gas" include nitrogen, argon and the like.

The reaction temperature is generally −70 to 150° C., preferably −20 to 150° C.

The reaction time is generally 0.1 to 100 hr, preferably 0.1 to 40 hr.

Compound (1-4) can be produced, for example, by subjecting compound (52) to a reduction reaction.

This reaction is carried out in the same manner as in the production method of compound (25) in Reaction Scheme 9.

used in a mixture of two or more kinds thereof in an appropriate ratio. Among them, THF, DMF and the like are preferable.

The reaction temperature is generally −100° C. to 200° C., preferably 0° C. to 150° C.

The reaction time is generally 5 min to 48 hr, preferably 30 min to 24 hr.

Compound (55) can be produced, for example, by subjecting compound (54) to a reduction reaction.

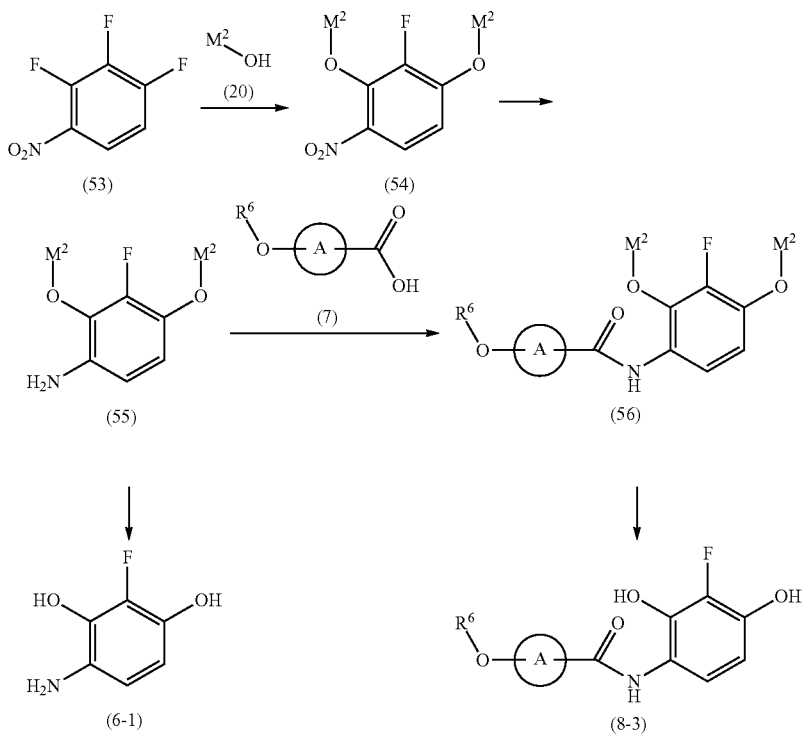

<Reaction Scheme 18> wherein each symbol is as defined above.

Compound (53) may be easily commercially available, or can also be produced according to a method known per se or a method analogous thereto.

Compound (54) can be produced, for example, by subjecting compound (53) to an etherification reaction with compound (20).

This reaction is carried out by reacting compound (53) with compound (20) in the presence of a base, in an inert solvent. Where necessary, the reaction may be carried out under microwave irradiation.

The amount of compound (20) to be used is generally 1 to 10 equivalents, preferably 2 to 5 equivalents, relative to compound (53).

Examples of the above-mentioned "base" include "inorganic bases", "basic salts", "aromatic amines", "tertiary amines", "hydrides of an alkali metal or alkaline earth metal", "alkylmetals", "arylmetals", "metal alkoxides" and the like. The amount of the "base" to be used is generally 1 to 10 equivalents, preferably 1 to 5 equivalents, relative to compound (53).

Examples of the above-mentioned "inert solvent" include nitrile solvents, amide solvents, halogenated hydrocarbon solvents, ether solvents and the like. These solvents may be This reaction is carried out in the same manner as in the production method of compound (25) in Reaction Scheme 9.

Compound (56) can be produced, for example, by subjecting compound (55) to an amidation reaction with compound (7).

This reaction is carried out in the same manner as in the production method of compound (8) in Reaction Scheme 4.

Compound (6-1) can be produced, for example, by subjecting compound (55) to a deprotection reaction. The deprotection reaction can be carried out according to a method known per se, for example, the method described in Protective Groups in Organic Synthesis, John Wiley and Sons (1980), or the like.

Compound (8-3) can be produced, for example, by subjecting compound (56) to a deprotection reaction. The deprotection reaction can be carried out according to a method known per se, for example, the method described in Protective Groups in Organic Synthesis, John Wiley and Sons (1980), or the like.

\<Reaction Scheme 19\>

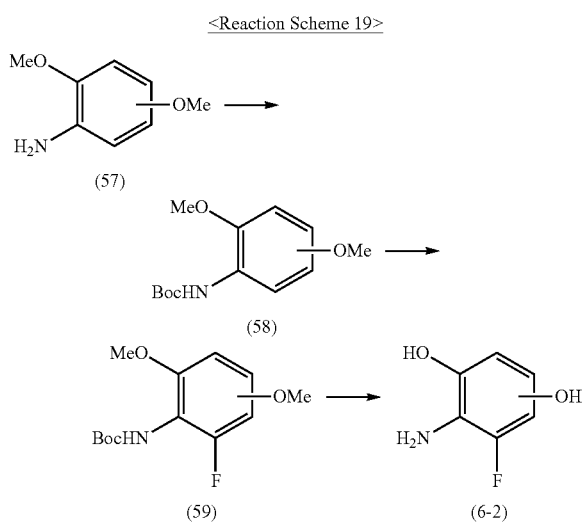

wherein each symbol is as defined above.

Compound (57) may be easily commercially available, or can also be produced according to a method known per se or a method analogous thereto.

Compound (58) can be produced, for example, by subjecting compound (57) to a tert-butoxycarbonylation reaction.

This reaction can be carried out according to a method known per se, for example, the method described in Synthesis, pages 2784-2788, 2006, or the like.

This reaction can also be carried out according to a method known per se, for example, the method described in Protective Groups in Organic Synthesis, John Wiley and Sons (1980), or the like.

Compound (59) can be produced, for example, by subjecting compound (58) to a fluorination reaction.

The above-mentioned "fluorination reaction" is carried out by reacting compound (58) in the presence of an organic metal reagent, in an inert solvent to convert the hydrogen atom to a metal atom, and reacting the resulting compound with a fluorinating agent.

Examples of the above-mentioned "organic metal reagent" include "alkylmetals", "metal amides" and the like. The amount of the "organic metal reagent" to be used is generally 2 equivalents to 10 equivalents, relative to compound (58).

Examples of the above-mentioned "fluorinating agent" include N-fluorobenzenesulfonimide and the like. The amount of the "fluorinating agent" to be used is generally 2 equivalents to 10 equivalents, relative to compound (58).

Examples of the above-mentioned "inert solvent" include aliphatic hydrocarbon solvents, aromatic solvents, ether solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

Compound (6-2) can be produced, for example, by subjecting compound (59) to a deprotection reaction. The deprotection reaction can be carried out according to a method known per se, for example, the method described in Protective Groups in Organic Synthesis, John Wiley and Sons (1980), or the like.

\<Reaction Scheme 20\>

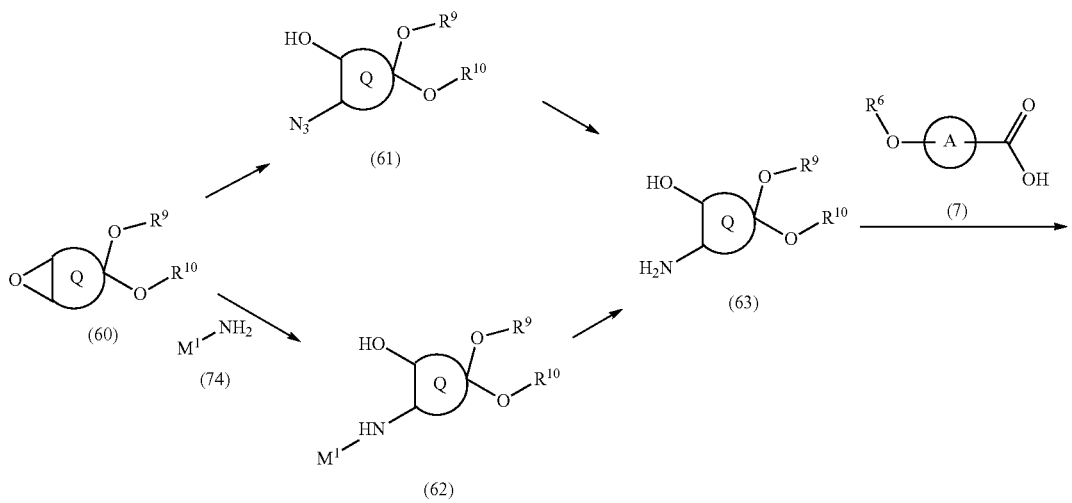

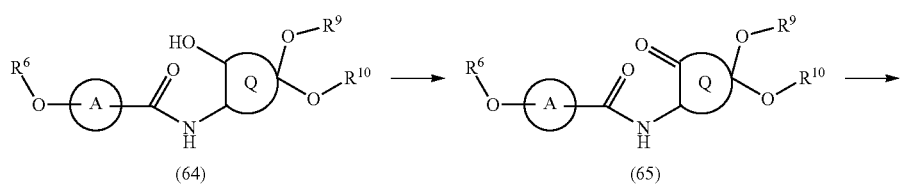

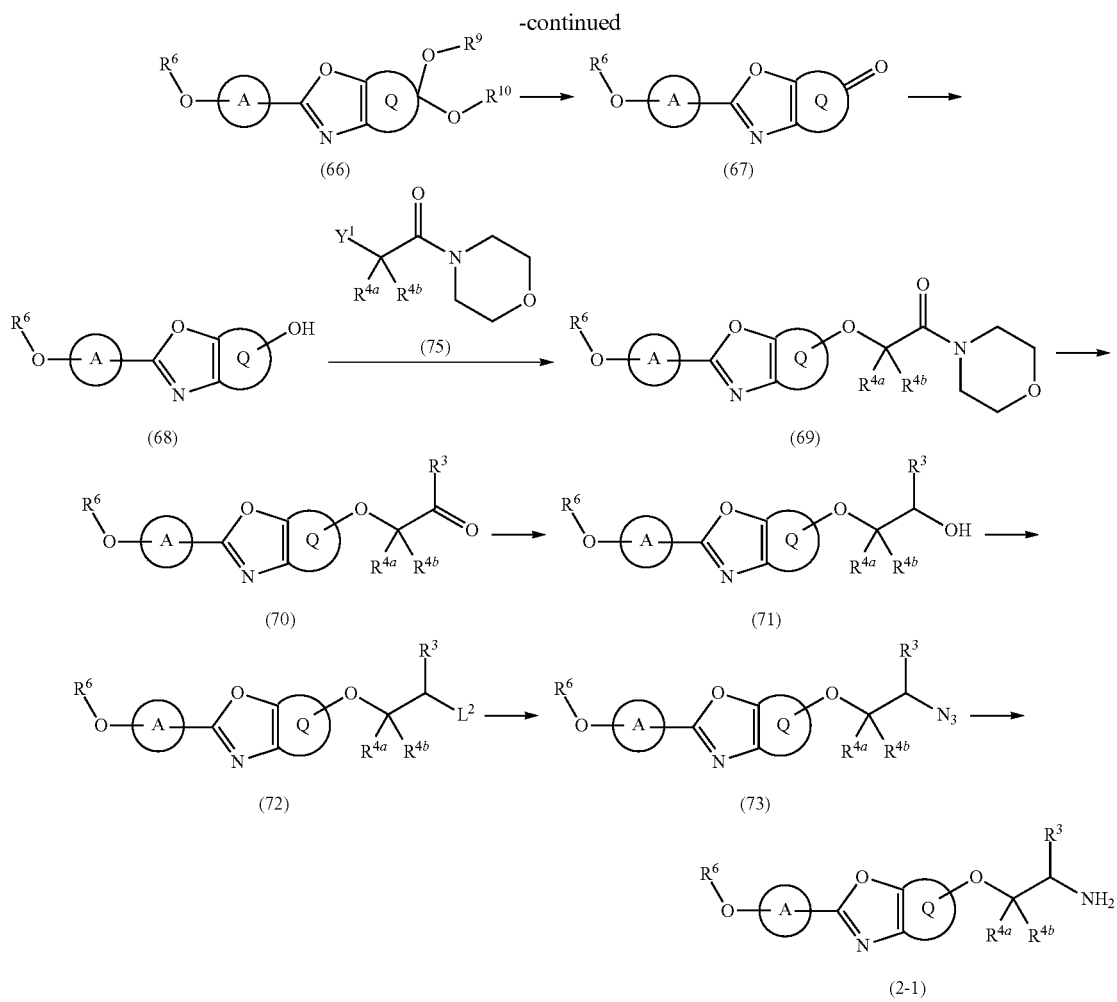

wherein $L^2$ is an optionally substituted $C_{1-6}$ alkylsulfonyloxy group, or an optionally substituted $C_{6-12}$ arylsulfonyloxy group, $R^9$ and $R^{10}$ are each a substituent, or $R^9$ and $R^{10}$ in combination optionally form a ring, and other symbols are as defined above.

Examples of the "optionally substituted $C_{1-6}$ alkylsulfonyloxy group" for $L^2$ include those similar to the "optionally substituted $C_{1-6}$ alkylsulfonyloxy group" exemplified as the "leaving group" for $L^1$.

Examples of the "optionally substituted $C_{6-10}$ arylsulfonyloxy group" for $L^2$ include those similar to the "optionally substituted $C_{6-10}$ arylsulfonyloxy group" exemplified as the "leaving group" for $L^1$.

Compound (61) can be produced, for example, by subjecting compound (60) to an epoxide ring-opening reaction.

This reaction is carried out by reacting compound (60) with an azidating agent in an inert solvent.

Examples of the above-mentioned "azidating agent" include sodium azide, lithium azide, trimethylsilyl azide and the like. The amount of the "azidating agent" to be used is generally 1 to 20 equivalents, preferably 1 to 10 equivalents, relative to compound (60).

Examples of the above-mentioned "inert solvent" include ether solvents, amide solvents, sulfoxide solvents and the like. These solvents may be used in a mixture of two or more kinds thereof in an appropriate ratio. Where necessary, the reaction may be carried out in the presence of water in an amount of a catalytic amount to a solvent amount.

The reaction temperature is generally −70 to 200° C., preferably 0 to 150° C.

The reaction time is generally 0.1 to 100 hr, preferably 0.1 to 48 hr.

Compound (62) can be produced, for example, by subjecting compound (60) to an epoxide ring-opening reaction.

This reaction is carried out by reacting compound (60) with compound (74) in an inert solvent.

The amount of compound (74) to be used is generally 1 to 20 equivalents, preferably 1 to 10 equivalents, relative to compound (60).

Examples of the above-mentioned "inert solvent" include ether solvents, amide solvents, sulfoxide solvents, alcohol solvents and the like. These solvents may be used in a mixture of two or more kinds thereof in an appropriate ratio. Where necessary, the reaction may be carried out in the presence of water in an amount of a catalytic amount to a solvent amount.

The reaction temperature is generally −70 to 200° C., preferably 0 to 150° C.

The reaction time is generally 0.1 to 100 hr, preferably 0.1 to 48 hr.

Compound (63) can be produced, for example, by subjecting compound (61) to a reduction reaction.

This reaction can be carried out by reacting compound (61) in the presence of a metal catalyst and a hydrogen source, in an inert solvent.

Examples of the above-mentioned "metal catalyst" include palladium-carbon, palladium black, palladium chloride, platinum oxide, platinum black, Raney-nickel, Raney-cobalt and the like. The amount of the "metal catalyst" to be used is generally 0.001 to 100 equivalents, preferably 0.01 to 10 equivalents, relative to compound (61).

Examples of the above-mentioned "hydrogen source" include hydrogen gas, formic acid, amine salt of formic acid, phosphinate, hydrazine and the like.

Examples of the above-mentioned "inert solvent" include alcohol solvents, ester solvents, ether solvents, amide solvents, halogenated hydrocarbon solvents and the like. These solvents are preferably used in a mixture with water in an appropriate ratio. Among them, alcohol solvents are preferable.

The reaction temperature is generally −70 to 150° C., preferably −20 to 100° C.

The reaction time is generally 0.1 to 100 hr, preferably 0.1 to 48 hr.

This reaction can also be carried out by reacting compound (61) with triphenylphosphine and water in an inert solvent.

The amount of the "triphenylphosphine" to be used is generally 1 to 20 equivalents, preferably 1 to 5 equivalents, relative to compound (61).

Examples of the above-mentioned "inert solvent" include aromatic solvents, aliphatic hydrocarbon solvents, ether solvents, amide solvents, sulfoxide solvents, halogenated hydrocarbon solvents and the like. These solvents are preferably used in a mixture with water in an appropriate ratio. Among them, ether solvents are preferable.

The reaction temperature is generally −70 to 150° C., preferably −20 to 100° C.

The reaction time is generally 0.1 to 100 hr, preferably 0.1 to 40 hr.

Compound (63) can also be produced, for example, by subjecting compound (62) to a deprotection reaction. The deprotection reaction can be carried out according to a method known per se, for example, the method described in Protective Groups in Organic Synthesis, John Wiley and Sons (1980), or the like.

Compound (64) can be produced, for example, by subjecting compound (63) to an amidation reaction with compound (7).

This reaction is carried out in the same manner as in the production method of compound (8) in Reaction Scheme 4.

Compound (65) can be produced, for example, by subjecting compound (64) to an oxidization reaction.

This reaction is carried out by reacting compound (64) with an oxidant in an inert solvent. Where necessary, the reaction may be carried out in the presence of a base in an amount of 1 to 10 equivalents.

Examples of the above-mentioned "oxidant" include tetrapropylammonium perruthenate, chromium trioxide, Dess-Martin reagent, sulfur trioxide pyridine complex and the like. The amount of the "oxidant" to be used is generally 1 to 10 equivalents, preferably 1 to 5 equivalents, relative to compound (64).

Examples of the above-mentioned "base" include "aromatic amines", "tertiary amines" and the like.

Examples of the above-mentioned "inert solvent" include alcohol solvents, nitrile solvents, amide solvents, halogenated hydrocarbon solvents, ether solvents, aromatic solvents, sulfoxide solvents and the like. These solvents may be used in a mixture of two or more kinds thereof in an appropriate ratio.

The reaction temperature is generally −100° C. to 50° C., preferably −78° C. to 0° C.

The reaction time is generally 5 min to 48 hr, preferably 30 min to 24 hr.

Compound (66) can be produced, for example, by subjecting compound (65) to a ring-closing reaction.

The above-mentioned "ring-closing reaction" is carried out by reacting compound (65) in the presence of an activator, in an inert solvent.

Examples of the above-mentioned "activator" include p-toluenesulfonic acid, a combination of diisopropyl azodicarboxylate and triphenylphosphine, a combination of hexachloroethane, triphenylphosphine and a base, (methoxycarbonylsulfamoyl)triethylammonium hydroxide inner salt (Burgess reagent) and the like. The amount of the "activator" to be used is generally 0.001 to 10 equivalents, preferably 0.01 to 8 equivalents, relative to compound (65).

Examples of the above-mentioned "inert solvent" include aromatic solvents, aliphatic hydrocarbon solvents, ether solvents, ester solvents, amide solvents, nitrile solvents, halogenated hydrocarbon solvents and the like. These solvents may be used in a mixture of two or more kinds thereof in an appropriate ratio.

Examples of the above-mentioned "base" include "aromatic amines", "tertiary amines" and the like.

The reaction temperature is generally −70° C. to 200° C., preferably −20° C. to 150° C.

The reaction time is generally 0.1 hr to 100 hr, preferably 0.1 hr to 40 hr.

Compound (67) can be produced, for example, by subjecting compound (66) to a deprotection reaction. The deprotection reaction can be carried out according to a method known per se, for example, the method described in Protective Groups in Organic Synthesis, John Wiley and Sons (1980), or the like.

Compound (68) can be produced, for example, by subjecting compound (67) to a reduction reaction.

This reaction is carried out by reacting compound (67) with a reducing agent in an inert solvent.

Examples of the above-mentioned "reducing agent" include metal hydrides (e.g., diisobutylaluminum hydride), metal hydride complex compounds (e.g., sodium borohydride, sodium cyanoborohydride, lithium aluminum hydride, sodium aluminium hydride, sodium bis(2-methoxyethoxy) aluminium hydride) and the like. The amount of the "reducing agent" to be used is generally 0.1 to 20 equivalents, preferably 1 to 5 equivalents, relative to compound (67).

Examples of the above-mentioned "inert solvent" include alcohol solvents, aromatic solvents, aliphatic hydrocarbon solvents, ether solvents, amide solvents, halogenated hydrocarbon solvents and the like. These solvents may be used in a mixture of two or more kinds thereof in an appropriate ratio. Among them, THF, ethanol, methanol and the like are preferable.

The reaction temperature is generally −78° C. to 150° C., preferably −20° C. to 100° C.

The reaction time is generally 5 min to 48 hr, preferably 30 min to 24 hr.

Compound (69) can be produced, for example, by reacting compound (68) with compound (75) in the presence of a base, in an inert solvent. Where necessary, the reaction may be carried out in the presence of a phase-transfer catalyst.

The amount of compound (75) to be used is generally 1 to 5 equivalents, preferably 1 to 3 equivalents, relative to compound (68).

Examples of the above-mentioned "base" include "inorganic bases", "basic salts", "aromatic amines", "tertiary amines", "hydrides of an alkali metal or alkaline earth metal", "metal alkoxides" and the like. The amount of the "base" to be used is generally 1 to 10 equivalents, preferably 1 to 5 equivalents, relative to compound (68).

Examples of the above-mentioned "phase-transfer catalyst" include quaternary ammonium salts (e.g., tetrabutylammonium bromide, benzyltrioctylammonium chloride, tetrabutylammonium hydrogensulfate) and the like. The amount of the "phase-transfer catalyst" to be used is generally 0.001 to 10 equivalents, preferably 0.01 to 1 equivalents, relative to compound (68).

Examples of the above-mentioned "inert solvent" include aromatic solvents, nitrile solvents, amide solvents, halogenated hydrocarbon solvents, ether solvents, alcohol solvents and the like. These solvents are preferably used in a mixture with water in an appropriate ratio. Among them, THF, DMF and the like are preferable.

The reaction temperature is generally $-100°$ C. to $200°$ C., preferably $0°$ C. to $150°$ C.

The reaction time is generally 5 min to 48 hr, preferably 30 min to 24 hr.

Compound (70) can be produced, for example, by reacting compound (69) with an organic metal reagent corresponding to $R^3$ in an inert solvent.

Examples of the above-mentioned "organic metal reagent" include organic Grignard reagents (e.g., methylmagnesium bromide, methylmagnesium chloride), organic lithium reagents (e.g., methyl lithium) and the like. The amount of the "organic metal reagent" to be used is generally 0.1 to 20 equivalents, preferably 1 to 5 equivalents, relative to compound (69).

Examples of the above-mentioned "inert solvent" include aromatic solvents, aliphatic hydrocarbon solvents, ether solvents and the like. These solvents may be used in a mixture of two or more kinds thereof in an appropriate ratio. Among them, THF and the like are preferable.

The reaction temperature is generally $-78°$ C. to $150°$ C., preferably $-20°$ C. to $100°$ C.

The reaction time is generally 5 min to 48 hr, preferably 30 min to 24 hr.

Compound (71) can be produced, for example, by subjecting compound (70) to a reduction reaction.

This reaction is carried out in the same manner as in the production method of compound (68) in Reaction Scheme 20.

Compound (72) can be produced, for example, by subjecting compound (71) to a sulfonylation reaction.

This reaction is carried out by reacting compound (71) with a sulfonylating agent in the presence of a base, in an inert solvent.

Examples of the above-mentioned "sulfonylating agent" include methanesulfonyl chloride, p-toluenesulfonyl chloride and the like. The amount of the "sulfonylating agent" to be used is generally 1 to 10 equivalents, preferably 1 to 1.5 equivalents, relative to compound (71).

Preferable examples of the above-mentioned "base" include "aromatic amines", "tertiary amines" and the like. The amount of the "base" to be used is generally 1 to 20 equivalents, preferably 1 to 10 equivalents, relative to compound (71).

Examples of the above-mentioned "inert solvent" include aromatic solvents, aliphatic hydrocarbon solvents, ether solvents, ester solvents, amide solvents and the like. These solvents may be used in a mixture of two or more kinds thereof in an appropriate ratio.

The reaction temperature is generally $-70$ to $150°$ C., preferably $-20$ to $100°$ C.

The reaction time is generally 0.1 to 100 hr, preferably 0.1 to 48 hr.

Compound (73) can be produced, for example, by subjecting compound (72) to an azidation reaction.

This reaction is carried out by reacting compound (72) with an azidating agent in an inert solvent.

Examples of the above-mentioned "azidating agent" include sodium azide, lithium azide, trimethylsilyl azide and the like. The amount of the "azidating agent" to be used is generally 1 to 20 equivalents, preferably 1 to 10 equivalents, relative to compound (72).

Examples of the above-mentioned "inert solvent" include ether solvents, amide solvents, sulfoxide solvents and the like. These solvents may be used in a mixture of two or more kinds thereof in an appropriate ratio.

The reaction temperature is generally $-70$ to $200°$ C., preferably 0 to $150°$ C.

The reaction time is generally 0.1 to 100 hr, preferably 0.1 to 48 hr.

Compound (2-1) can be produced, for example, by subjecting compound (73) to a reduction reaction.

This reaction can be carried out by reacting compound (73) in the presence of a metal catalyst and a hydrogen source, in an inert solvent.

Examples of the above-mentioned "metal catalyst" include palladium-carbon, palladium black, palladium chloride, platinum oxide, platinum black, Raney-nickel, Raney-cobalt and the like. The amount of the "metal catalyst" to be used is generally 0.001 to 100 equivalents, preferably 0.01 to 10 equivalents, relative to compound (73).

Examples of the above-mentioned "hydrogen source" include hydrogen gas, formic acid, amine salt of formic acid, phosphinate, hydrazine and the like.

Examples of the above-mentioned "inert solvent" include alcohol solvents, ester solvents, ether solvents, amide solvents, halogenated hydrocarbon solvents and the like. These solvents are preferably used in a mixture with water in an appropriate ratio. Among them, alcohol solvents are preferable:

The reaction temperature is generally $-70$ to $150°$ C., preferably $-20$ to $100°$ C.

The reaction time is generally 0.1 to 100 hr, preferably 0.1 to 48 hr.

This reaction can also be carried out by reacting compound (73) with triphenylphosphine and water in an inert solvent.

The amount of the "triphenylphosphine" to be used is generally 1 to 20 equivalents, preferably 1 to 5 equivalents, relative to compound (73).

Examples of the above-mentioned "inert solvent" include aromatic solvents, aliphatic hydrocarbon solvents, ether solvents, amide solvents, sulfoxide solvents, halogenated hydrocarbon solvents and the like. These solvents are preferably used in a mixture with water in an appropriate ratio. Among them, ether solvents are preferable.

The reaction temperature is generally $-70$ to $150°$ C., preferably $-20$ to $100°$ C.

The reaction time is generally 0.1 to 100 hr, preferably 0.1 to 40 hr.

Reaction Scheme 21

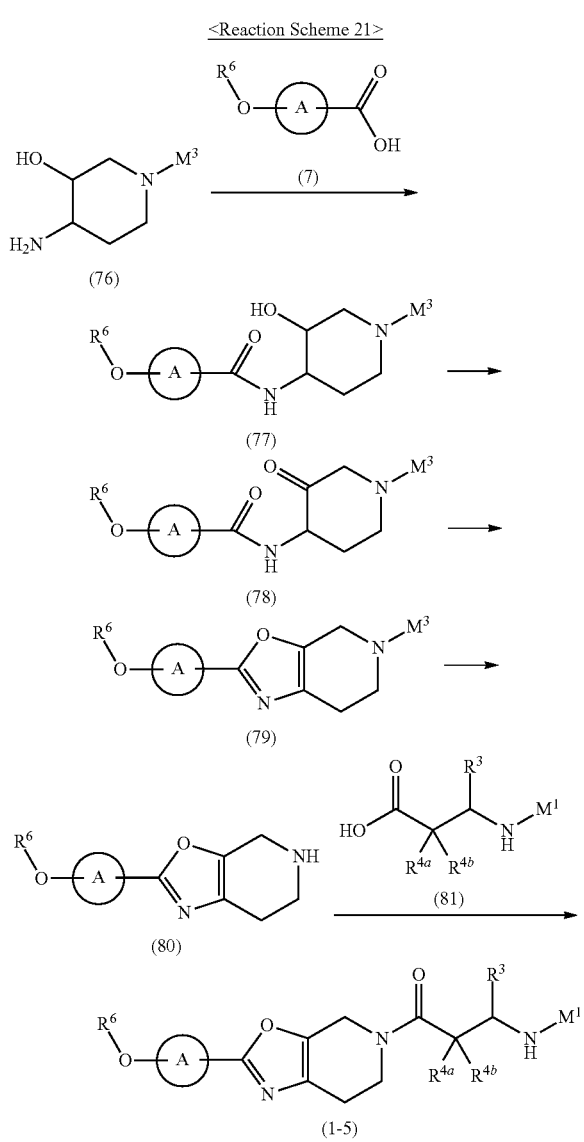

wherein $M^3$ is a nitrogen atom-protecting group, and other symbols are as defined above.

Compound (77) can be produced, for example, by subjecting compound (76) to an amidation reaction with compound (7).

This reaction is carried out in the same manner as in the production method of compound (8) in Reaction Scheme 4.

Compound (78) can be produced, for example, by subjecting compound (77) to an oxidization reaction.

This reaction is carried out in the same manner as in the production method of compound (65) in Reaction Scheme 20.

Compound (79) can be produced, for example, by subjecting compound (78) to a ring-closing reaction.

This reaction is carried out in the same manner as in the production method of compound (66) in Reaction Scheme 20.

Compound (80) can be produced, for example, by subjecting compound (79) to a deprotection reaction. The deprotection reaction can be carried out according to a method known per se, for example, the method described in Protective Groups in Organic Synthesis, John Wiley and Sons (1980), or the like.

Compound (1-5) can be produced, for example, by subjecting compound (80) to an amidation reaction with compound (81).

This reaction is carried out in the same manner as in the production method of compound (8) in Reaction Scheme 4.

Reaction Scheme 22

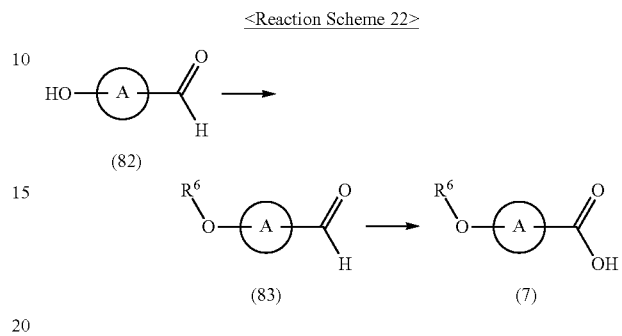

wherein each symbol is as defined above.

Compound (82) may be easily commercially available, or can also be produced according to a method known per se or a method analogous thereto.

Compound (83) can be produced, for example, by subjecting compound (82) to an alkylation reaction.

This reaction is carried out in the same manner as in the production method of compound (I) in Reaction Scheme 2.

Compound (7) can be produced, for example, by subjecting compound (83) to an oxidization reaction.

This reaction is carried out by reacting compound (83) with an oxidant in an inert solvent. Where necessary, an additive may be added.

Examples of the above-mentioned "oxidant" include sodium chlorite, potassium permanganate, chromic anhydride and the like. The amount of the "oxidant" to be used is generally 1 to 10 equivalents, preferably 1 to 5 equivalents, relative to compound (83).

Examples of the above-mentioned "inert solvent" include alcohol solvents, ether solvents, amide solvents, ketone solvents and the like. Where necessary, these solvents are preferably used in a mixture with water in an appropriate ratio.

Examples of the above-mentioned "additive" include sodium dihydrogen phosphate, 2-methyl-2-butene and the like. The amount of the "additive" to be used is generally 1 to an excess amount, relative to compound (83).

The reaction temperature is generally −78° C. to 150° C., preferably −20° C. to 100° C.

The reaction time is generally 5 min to 100 hr, preferably 30 min to 24 hr.

Reaction Scheme 23

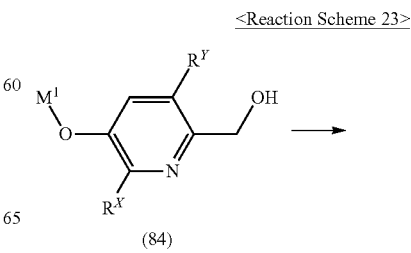

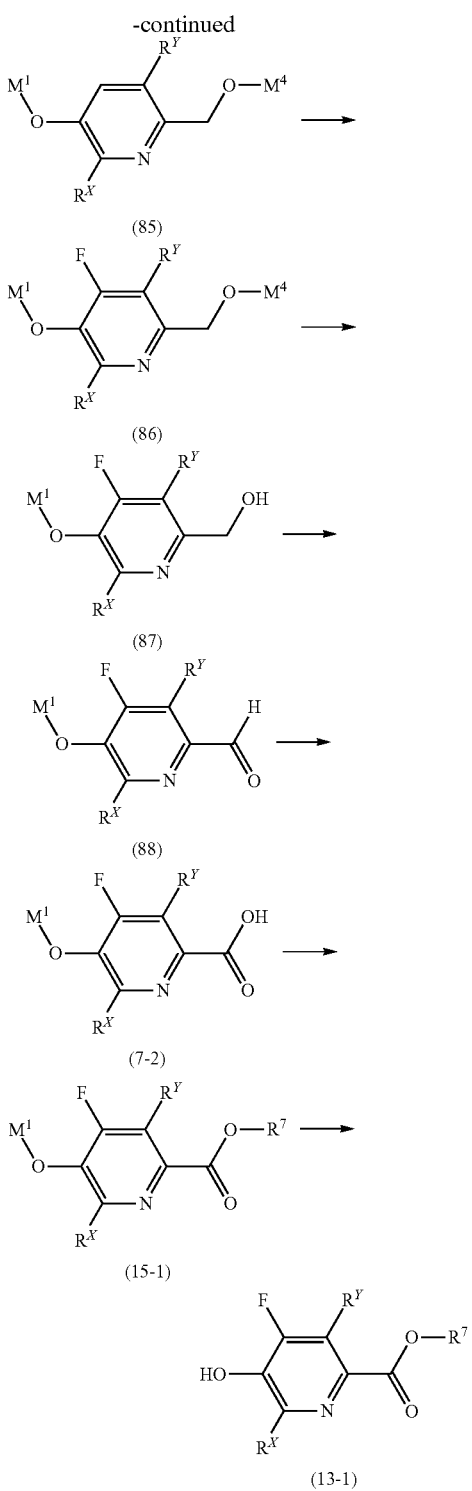

se, for example, the method described in Protective Groups in Organic Synthesis, John Wiley and Sons (1980), or the like.

Compound (86) can be produced, for example, by subjecting compound (85) to a fluorination reaction.

The above-mentioned "fluorination reaction" is carried out by reacting compound (85) with an alkylmetal in an inert solvent to convert the hydrogen atom to a metal atom, and reacting the resulting compound with a fluorinating agent.

Examples of the above-mentioned "alkylmetal" include alkyllithiums, alkylmagnesium halides and the like. The amount of the "alkylmetal" to be used is generally 1 equivalent to 10 equivalents, relative to compound (85).

Examples of the above-mentioned "fluorinating agent" include N-fluoro-N-(phenylsulfonyl)benzenesulfonamide and the like. The amount of the "fluorinating agent" to be used is generally 1 equivalent to 10 equivalents, relative to compound (85).

Examples of the above-mentioned "inert solvent" include aliphatic hydrocarbon solvents, aromatic solvents, ether solvents and the like. These solvents may be used in a mixture of two or more kinds thereof in an appropriate ratio.

The reaction temperature is generally −100° C. to 200° C., preferably −100° C. to 100° C.

The reaction time is generally 1 min to 48 hr, preferably 5 min to 24 hr.

Compound (87) can be produced, for example, by subjecting compound (86) to a deprotection reaction. The deprotection reaction can be carried out according to a method known per se, for example, the method described in Protective Groups in Organic Synthesis, John Wiley and Sons (1980), or the like.

Compound (88) can be produced, for example, by subjecting compound (87) to an oxidization reaction.

The oxidation reaction can be carried out according to a method known per se, for example, the method described in Journal of Medicinal Chemistry (J. Med. Chem.), pages 5282-5290, 2006, or the like, or a method analogous thereto.

This reaction is carried out by reacting compound (87) with an oxidant in an inert solvent.

Examples of the above-mentioned "oxidant" include manganese dioxide, tetrapropylammonium perruthenate, chromium trioxide, Dess-Martin reagent and the like. The amount of the "oxidant" to be used is generally 1 to 5 equivalents, preferably 1 to 1.5 equivalents, relative to compound (87).

Examples of the above-mentioned "inert solvent" include alcohol solvents, nitrile solvents, amide solvents, halogenated hydrocarbon solvents, ether solvents, aromatic solvents and the like. These solvents may be used in a mixture of two or more kinds thereof in an appropriate ratio. Among them, halogenated hydrocarbon solvents and the like are preferable.

The reaction temperature is generally −100° C. to 50° C., preferably −78° C. to 0° C.

The reaction time is generally 5 min to 48 hr, preferably 30 min to 24 hr.

Compound (7-2) can be produced, for example, by subjecting compound (88) to an oxidization reaction.

This reaction is carried out in the same manner as in the production method of compound (7) in Reaction Scheme 22.

Compound (7-2) is encompassed in compound (7).

Compound (15-1) can be produced, for example, by subjecting compound (7-2) to an esterification reaction. The esterification can be carried out according to a method known per se, for example, the method described in Protective Groups in Organic Synthesis, John Wiley and Sons (1980), or the like.

Compound (15-1) is encompassed in compound (15).

wherein $M^4$ is a hydroxyl-protecting group, $R^X$ and $R^Y$ are each hydrogen or a substituent, and the other symbols are as defined above.

Compound (84) may be easily commercially available, or can also be produced according to a method known per se or a method analogous thereto.

Compound (85) can be produced, for example, by subjecting compound (84) to a protection reaction. The protection reaction can be carried out according to a method known per Compound (13-1) can be produced, for example, by subjecting compound (15-1) to a deprotection reaction. The deprotection reaction can be carried out according to a method known per se, for example, the method described in Protective Groups in Organic Synthesis, John Wiley and Sons (1980), or the like.

Compound (13-1) is encompassed in compound (13).

<Reaction Scheme 24>

$$R^6\text{—OH} \xrightarrow{(90)} R^6\text{—O—S(=O)}_2\text{—}R^z$$

(89) (91)

wherein $R^z$ is an optionally substituted 5- or 6-membered aromatic heterocyclic group, or an optionally substituted hydrocarbon group, and other symbols are as defined above.

Examples of the "optionally substituted 5- or 6-membered aromatic heterocyclic group" for $R^z$ include heterocyclic groups, from among the groups exemplified as the "optionally substituted 5- or 6-membered aromatic ring group" for $R^1$.

Examples of the "optionally substituted hydrocarbon group" for $R^z$ include those similar to the groups exemplified as the "optionally substituted hydrocarbon group" in the "substituent" for $R^2$. Preferable examples of include a phenyl group substituted by nitro group(s); and a methyl group.

Compound (89) and compound (90) may be easily commercially available, or can also be produced according to a method known per se or a method analogous thereto.

Compound (91) can be produced, for example, by subjecting compound (90) to a sulfonylation reaction with compound (89).

This reaction is carried out by reacting compound (89) with compound (90) in the presence of a base, in an inert solvent.

The amount of compound (90) to be used is generally 1 to 10 equivalents, preferably 1 to 1.5 equivalents, relative to compound (89).

Preferable examples of the above-mentioned "base" include "aromatic amines", "tertiary amines" and the like. The amount of the "base" to be used is generally 1 to 20 equivalents, preferably 1 to 10 equivalents, relative to compound (89).

Examples of the above-mentioned "inert solvent" include aromatic solvents, aliphatic hydrocarbon solvents, ether solvents, ester solvents, amide solvents and the like. These solvents may be used in a mixture of two or more kinds thereof in an appropriate ratio.

The reaction temperature is generally −70 to 150° C., preferably −20 to 100° C.

The reaction time is generally 0.1 to 100 hr, preferably 0.1 to 48 hr.

<Reaction Scheme 25>

(92) → (93) → (94) → (95) → (4)

wherein each symbol is as defined above.

Compound (92) may be easily commercially available, or can be produced according to a method known per se or a method analogous thereto.

Compound (93) can be produced, for example, by subjecting compound (92) to a halogenation reaction.

The above-mentioned "halogenation reaction" is carried out by reacting compound (92) in the presence of a halogenating agent, in an inert solvent.

Examples of the above-mentioned "halogenating agent" include bromine, chlorine, iodine, N-chlorosuccinimide, N-bromosuccinimide, N-iodosuccinimide and the like. The amount of the "halogenating agent" to be used is generally 1 to 10 equivalents, preferably 1 to 5 equivalents, relative to compound (92).

Examples of the above-mentioned "inert solvent" include aliphatic hydrocarbon solvents, ether solvents, ester solvents, nitrile solvents, amide solvents, halogenated hydrocarbon solvents, acetic acid, water and the like. These solvents may be used in a mixture of two or more kinds thereof in an appropriate ratio.

The reaction temperature is generally −70° C. to 200° C., preferably −20° C. to 150° C.

The reaction time is generally 0.1 hr to 100 hr, preferably 0.1 hr to 40 hr.

Compound (94) can be produced, for example, by subjecting compound (93) to an amidation reaction with compound (7).

This reaction is carried out in the same manner as in the production method of compound (8) in Reaction Scheme 4.

Compound (95) can be produced, for example, by subjecting compound (94) to a ring-closing reaction.

This reaction is carried out in the same manner as in the production method of compound (4-1) in Reaction Scheme 4.

Compound (4) can be produced, for example, by subjecting compound (95) to a deprotection reaction. The deprotection reaction can be carried out according to a method known per se, for example, the method described in Protective Groups in Organic Synthesis, John Wiley and Sons (1980), or the like.

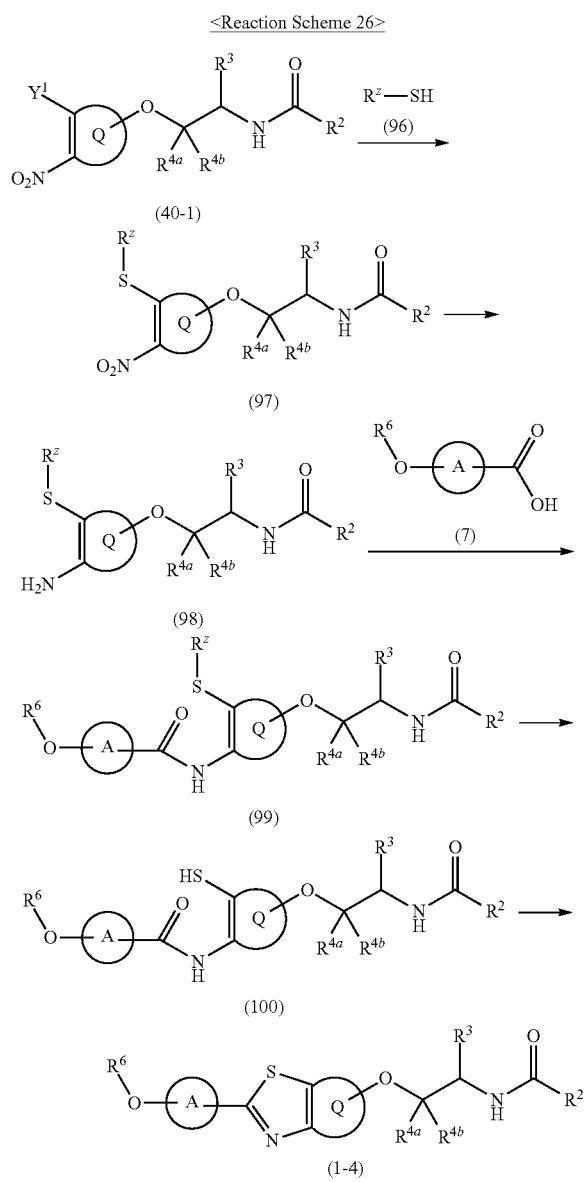

wherein each symbol is as defined above, and $R^z$ is a substituent.

Compound (40-1), for example, can be produced according to the method shown in Reaction Scheme 14 or a method known per se or a method analogous thereto.

Compound (97) can be produced, for example, by subjecting compound (40-1) to a substitution reaction with compound (96).

This reaction is carried out by reacting compound (40-1) with compound (96) in the presence of a base, in an inert solvent.

Examples of the above-mentioned "base" include "inorganic bases", "basic salts", "aromatic amines", "tertiary amines", "hydrides of an alkali metal or alkaline earth metal", "alkylmetals", "arylmetals", "metal alkoxides" and the like.

The amount of the "base" to be used is generally 1 to 10 equivalents, preferably 1 to 5 equivalents, relative to compound (40-1).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, THF, DMF and the like are preferable.

The reaction temperature is generally −100° C. to 150° C., preferably 0° C. to 100° C.

The reaction time is generally 5 min to 48 hr, preferably 30 min to 24 hr.

Compound (98) can be produced, for example, by subjecting compound (97) to a reduction reaction.

This reaction is carried out in the same manner as in the production method of compound (25) in Reaction Scheme 9.

Compound (99) can be produced, for example, by subjecting compound (98) to an amidation reaction with compound (7).

This reaction is carried out in the same manner as in the production method of compound (8) in Reaction Scheme 4.

Compound (100) can be produced, for example, by subjecting compound (99) to a deprotection reaction. The deprotection reaction can be carried out according to a method known per se, for example, the method described in Protective Groups in Organic Synthesis, John Wiley and Sons (1980), or the like.

Compound (I-4) can be produced, for example, by subjecting compound (100) to a ring-closing reaction.

This reaction is carried out by reacting compound (100) in the presence of an acid.

Examples of the above-mentioned "acid" include acetic acid, trifluoroacetic acid and the like. The amount of the "acid" to be used is generally 1 to an excess amount, relative to compound (100).

The reaction temperature is generally 0° C. to 150° C., preferably 0° C. to 100° C.

The reaction time is generally 5 min to 48 hr, preferably 30 min to 24 hr.

In compound (I) thus obtained, a functional group in a molecule can also be converted to a desired functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

Compound (I) obtained by the above-mentioned production methods can be isolated and purified according to a known means, for example, solvent extraction, pH control, phase transfer, crystallization, recrystallization, chromatography and the like.

When compound (I) contains an optical isomer, a stereoisomer, a regioisomer or a rotamer, these are also encompassed in compound (I), and can be obtained as a single product according to synthesis methods and separation methods known per se. For example, when compound (I) contains an optical isomer, an optical isomer resolved from this compound is also encompassed in compound (I).

The optical isomer can be produced according to a method known per se.

Compound (I) may be a crystal.

Crystals of compound (I) (hereinafter sometimes to be abbreviated as the crystals of the present invention) can be produced by crystallization according to crystallization methods known per se.

In the present specification, the melting point means that measured using, for example, a micromelting point apparatus (Yanako, MP-500D or Buchi, B-545), a DSC (differential scanning calorimetry) device (SEIKO, EXSTAR6000) or the like.

In general, the melting points vary depending on the measurement apparatuses, the measurement conditions and the like. The crystal in the present specification may show different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

EXAMPLE

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bonded silica gel. In HPLC (high performance liquid chromatography), C18 means use of octadecyl-bound silica gel. The ratios of elution solvents are volume mixing ratios, unless otherwise specified.

In the following Examples, the following abbreviations are used.
mp: melting point
THF: tetrahydrofuran
DMF: dimethylformamide
HATU: O-(7-azabenzotriazol-1-yl)-N,N,N',N'-tetramethyluronium hexafluorophosphate
$^1$H NMR (proton nuclear magnetic resonance spectrum) was measured by Fourier-transform type NMR. For the analysis, ACD/SpecManager (trade name) and the like were used. Peaks with very mild protons such as hydroxyl group, amino group and the like are not described.
Other abbreviations used in the specification mean the following.
s: singlet
d: doublet
t: triplet
q: quartet
m: multiplet
br: broad
J: coupling constant
Hz: Hertz
CDCl$_3$: deuterated chloroform
DMSO-d$_6$: d$_6$-dimethyl sulfoxide
$^1$H NMR: proton nuclear magnetic resonance
TFA: trifluoroacetic acid
MS (mass spectrum) was measured by LC/MS (liquid chromatography mass spectrometer). As the ionization method, ESI (ElectroSpray Ionization) method, or APCI (Atmospheric Pressure Chemical Ionization) method was used. As the ionization mode, either or both the positive mode (ESI+) and the negative mode (ESI−) was/were used, and the data of either of them is indicated. The data indicate those found. Generally, a molecular ion peak is observed. In the case of a compound having a tert-butoxycarbonyl group (-Boc), a peak after elimination of the tert-butoxycarbonyl group or tert-butyl group may be observed as a fragment ion. A peak after addition of sodium ion (+Na) may be observed as a fragment ion, depending on the kind of the compound. In the case of a compound having a hydroxyl group (—CH), a peak after elimination of H$_2$O may be observed as a fragment ion. In the case of a salt, a molecular ion peak or fragment ion peak of free form is generally observed.

The unit of reagent concentration (c) in optical rotation ($[\alpha]_D$) is g/100 mL.

The elemental analysis value (Anal.) shows Calculated (Calcd) and Found.

Example 1

N-((2S)-1-((2-(4-(cyclopropylmethoxy)-3-fluorophenyl)-1,3-benzoxazol-6-yl)oxy)propan-2-yl)acetamide A) 4-(cyclopropylmethoxy)-3-fluorobenzoic Acid To a solution of 3-fluoro-4-hydroxybenzoic acid (10.0 g) in methanol (200 mL) was added sulfuric acid (3.5 mL), and the mixture was heated under reflux for 1 day. To the reaction mixture was added saturated brine, and the mixture was extracted with ethyl acetate. The obtained organic layer was dried over anhydrous magnesium sulfate, and the solvent was evaporated under reduced pressure. To a solution of the obtained residue in DMF (100 mL) were added potassium carbonate (17.7 g) and (bromomethyl)cyclopropane (9.32 mL), and the mixture was stirred with heating at 70° C. for 1 hr. The reaction mixture was allowed to cool to room temperature, diluted with ethyl acetate, and washed with saturated brine. The obtained organic layer was subjected to silica gel column chromatography (NH, ethyl acetate), and the solvent was evaporated. To a solution of the obtained residue in a mixed solvent of THF (50 mL) and methanol (50 mL) was added 2 M aqueous sodium hydroxide solution (64 mL), and the mixture was stirred with heating at 50° C. for 2 hr. The reaction mixture was allowed to cool to room temperature, and neutralized with 6 M hydrochloric acid, and the mixture was extracted with ethyl acetate. The obtained organic layer was washed with saturated brine, and dried over anhydrous magnesium sulfate, and the solvent was evaporated under reduced pressure. The obtained solid was washed with ethyl acetate to give the title compound (12.7 g).

$^1$H NMR (300 MHz, DMSO-d$_6$) δ 0.32-0.39 (2H, m), 0.56-0.64 (2H, m), 1.17-1.36 (1H, m), 3.98 (2H, d, J=7.2 Hz), 7.23 (1H, t, J=8.5 Hz), 7.66 (1H, dd, J=11.9, 2.1 Hz), 7.70-7.76 (1H, m), 12.90 (1H, brs).

B) 2-(4-(cyclopropylmethoxy)-3-fluorophenyl)-1,3-benzoxazol-6-ol

To a solution of 4-aminoresorcinol hydrochloride (5.00 g), 4-(cyclopropylmethoxy)-3-fluorobenzoic acid (5.91 g) and diisopropylethylamine (7.37 mL) in DMF (50 mL) was added HATU (11.8 g), and the mixture was stirred at room temperature for 1 hr. The reaction mixture was diluted with ethyl acetate, washed with saturated brine, and dried over anhydrous magnesium sulfate. The solvent was evaporated under reduced pressure, and the obtained solid was washed with ethyl acetate. To a solution of the obtained solid, hexachloroethane (16.7 g) and triphenylphosphine (18.5 g) in acetonitrile (50 mL) was added triethylamine (11.8 mL), and the mixture was stirred at room temperature for 15 min, and then with heating at 80° C. for 2 hr. The reaction mixture was filtered, the solvent was evaporated under reduced pressure, and the residue was purified by silica gel column chromatography (hexane/ethyl acetate) to give the title compound (2.23 g).

$^1$H NMR (300 MHz, DMSO-$d_6$) δ 0.32-0.42 (2H, m), 0.56-0.68 (2H, m), 1.20-1.37 (1H, m), 4.01 (2H, d, J=7.2 Hz), 6.84 (1H, dd, J=8.7, 2.3 Hz), 7.07 (1H, d, J=1.9 Hz), 7.33 (1H, t, J=8.9 Hz), 7.54 (1H, d, J=8.7 Hz), 7.83-7.93 (2H, m), 9.84 (1H, s).

C) tert-butyl ((2S)-1-((2-(4-(cyclopropylmethoxy)-3-fluorophenyl)-1,3-benzoxazol-6-yl)oxy)propan-2-yl)carbamate To a solution of 2-(4-(cyclopropylmethoxy)-3-fluorophenyl)-1,3-benzoxazol-6-ol (1.00 g), tert-butyl ((2S)-1-hydroxypropan-2-yl)carbamate (0.878 g) and triphenylphosphine (1.32 g) in THF (10 mL) was added dropwise diisopropyl azodicarboxylate toluene solution (1.9 M, 2.64 mL), and the mixture was stirred at room temperature for 16 hr. The reaction mixture was concentrated under reduced pressure, and the residue was purified by silica gel column chromatography (NH, hexane/ethyl acetate) to give the title compound (0.744 g). $^1$H NMR (300 MHz, CDCl$_3$) δ 0.35-0.45 (2H, m), 0.63-0.76 (2H, m), 1.29-1.39 (4H, m), 1.46 (9H, s), 3.91-4.02 (4H, m), 4.04-4.18 (1H, m), 4.70-4.85 (1H, m), 6.95 (1H, dd, J=8.7, 2.3 Hz), 7.04 (1H, t, J=8.3 Hz), 7.10 (1H, d, J=2.3 Hz), 7.60 (1H, d, J=8.7 Hz), 7.84-8.01 (2H, m).

D) N-((2S)-1-((2-(4-(cyclopropylmethoxy)-3-fluorophenyl)-1,3-benzoxazol-6-yl)oxy)propan-2-yl)acetamide To tert-butyl ((2S)-1-((2-(4-(cyclopropylmethoxy)-3-fluorophenyl)-1,3-benzoxazol-6-yl)oxy)propan-2-yl)carbamate (774 mg) was added 4 M hydrogen chloride/ethyl acetate (10 mL), and the mixture was stirred at room temperature for 10 min, and concentrated. To the residue were added pyridine (10 mL) and acetic anhydride (10 mL), and the mixture was stirred at room temperature for 15 min. The reaction mixture was concentrated under reduced pressure, and the residue was purified by silica gel column chromatography (NH, hexane/ethyl acetate) to give the title compound (570 mg).

$^1$H NMR (300 MHz, CDCl$_3$) δ 0.36-0.46 (2H, m), 0.61-0.79 (2H, m), 1.22-1.46 (4H, m), 2.02 (3H, s), 3.96 (2H, d, J=7.2 Hz), 3.99-4.10 (2H, m), 4.32-4.54 (1H, m), 5.74 (1H, d, J=7.9 Hz), 6.95 (1H, dd, J=8.9, 2.4 Hz), 7.04 (1H, t, J=8.3 Hz), 7.11 (1H, d, J=2.3 Hz), 7.60 (1H, d, J=9.0 Hz), 7.84-7.97 (2H, m).

mp 174° C.

Anal. Calcd for $C_{22}H_{23}N_2O_4F$: C, 66.32; H, 5.82; N, 7.03. Found: C, 66.24; H, 5.92; N, 7.01.

Example 2

N-((2S)-1-((2-(4-(benzyloxy)-3-fluorophenyl)-1,3-benzoxazol-6-yl)oxy)propan-2-yl)acetamide

A) 4-(benzyloxy)-3-fluorobenzoic Acid

To a solution of 3-fluoro-4-hydroxybenzoic acid (25.0 g) in methanol (150 mL) was added sulfuric acid (20.0 mL), and the mixture was heated under reflux for 1 day. To the reaction mixture was added saturated brine, and the mixture was extracted with ethyl acetate. The obtained organic layer was dried over anhydrous magnesium sulfate, and the solvent was evaporated under reduced pressure. To a solution of the obtained residue in DMF (200 mL) were added potassium carbonate (33.2 g) and benzyl bromide (21.0 mL), and the mixture was stirred with heating at 70° C. for 30 min. The reaction mixture was allowed to cool to room temperature, diluted with ethyl acetate, and washed with saturated brine. The obtained organic layer was subjected to silica gel column chromatography (NH, ethyl acetate), and the solvent was evaporated. To a solution of the obtained residue in a mixed solvent of THF (100 mL) and methanol (100 mL) was added 2 M aqueous sodium hydroxide solution (160 mL), and the mixture was stirred with heating at 50° C. for 2 hr. The reaction mixture was allowed to cool to room temperature, and neutralized with 6 M hydrochloric acid, and the mixture was extracted with ethyl acetate. The obtained organic layer was washed with saturated brine, and dried over anhydrous magnesium sulfate, and the solvent was evaporated under reduced pressure. The obtained solid was washed with ethyl acetate to give the title compound (36.3 g).

$^1$H NMR (300 MHz, CDCl$_3$) δ 5.22 (2H, s), 7.05 (1H, t, J=8.5 Hz), 7.31-7.48 (5H, m), 7.77-7.88 (2H, m).

B) tert-butyl ((2S)-1-((2-(4-(benzyloxy)-3-fluorophenyl)-1,3-benzoxazol-6-yl)oxy)propan-2-yl)carbamate Using 4-(benzyloxy)-3-fluorobenzoic acid, and in the same manner as in Step B and Step C of Example 1, the title compound was obtained.

MS (ESI+): [M+H]$^+$ 511.2.

C) N-((2S)-1-((2-(4-(benzyloxy)-3-fluorophenyl)-1,3-benzoxazol-6-yl)oxy)propan-2-yl)acetamide Using tert-butyl ((2S)-1-((2-(4-(benzyloxy)-3-fluorophenyl)-1,3-benzoxazol-6-yl)oxy)propan-2-yl)carbamate, and in the same manner as in Step D of Example 1, the title compound was obtained.

Example 3

N-((2S)-1-((2-(4-(2,2-difluoropropoxy)-3-fluorophenyl)-1,3-benzoxazol-6-yl)oxy)propan-2-yl)acetamide

A) tert-butyl ((2S)-1-((2-(3-fluoro-4-(2-oxopropoxy)phenyl)-1,3-benzoxazol-6-yl)oxy)propan-2-yl)carbamate A mixture of tert-butyl ((2S)-1-((2-(4-(benzyloxy)-3-fluorophenyl)-1,3-benzoxazol-6-yl)oxy)propan-2-yl)carbamate (4.26 g), 10% palladium-carbon (containing water (50%), 0.920 g) and THF (40 mL) was stirred at room temperature for 1 hr and min under a hydrogen atmosphere. The catalyst was removed by filtration, and the obtained filtrate was concentrated under reduced pressure. The obtained residue was dissolved in ethyl acetate, and the solution was subjected to silica gel chromatography (ethyl acetate), and the solvent was evaporated. To a solution of the obtained residue in DMF (40 mL) were added potassium carbonate (1.32 g) and bromoacetone (0.888 mL), and the mixture was stirred overnight at 60° C. The reaction mixture was diluted with ethyl acetate, and washed with saturated brine, and the solvent was evaporated under reduced pressure. The residue was purified by silica gel column chromatography (hexane/ethyl acetate) to give the title compound (4.67 g).

MS (ESI+): [M+H]$^+$ 459.1.

B) tert-butyl ((2S)-1-((2-(4-(2,2-difluoropropoxy)-3-fluorophenyl)-1,3-benzoxazol-6-yl)oxy)propan-2-yl)carbamate A mixture of tert-butyl ((2S)-1-((2-(3-fluoro-4-(2-oxopropoxy)phenyl)-1,3-benzoxazol-6-yl)oxy)propan-2-yl)carbamate (4.67 g), bis(2-methoxyethyl)aminosulfur trifluoride (5.63 mL) and toluene (40 mL) was stirred at 80° C. for 1 hr. To the reaction mixture was added saturated aqueous sodium hydrogen carbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (550 mg).

MS (ESI+): [M+H]+ 481.3.

C) N-((2S)-1-((2-(4-(2,2-difluoropropoxy)-3-fluorophenyl)-1,3-benzoxazol-6-yl)oxy)propan-2-yl)acetamide Using tert-butyl ((2S)-1-((2-(4-(2,2-difluoropropoxy)-3-fluorophenyl)-1,3-benzoxazol-6-yl)oxy)propan-2-yl)carbamate, and in the same manner as in Step D of Example 1, the title compound was obtained.

Example 4

N-((2S)-1-((2-(4-(2-cyclopropylethoxy)-3-fluorophenyl)-1,3-benzoxazol-6-yl)oxy)propan-2-yl)acetamide

A) N-((2S)-1-((2-(3-fluoro-4-hydroxyphenyl)-1,3-benzoxazol-6-yl)oxy)propan-2-yl)acetamide A mixture of N-((2S)-1-((2-(4-(benzyloxy)-3-fluorophenyl)-1,3-benzoxazol-6-yl)oxy)propan-2-yl)acetamide (1.22 g), 10% palladium-carbon (containing water (50%), 1.00 g) and THF (20 mL) was stirred at room temperature for 20 min under a hydrogen atmosphere. The catalyst was removed by filtration, and the obtained filtrate was concentrated under reduced pressure. The obtained solid was washed with diethyl ether to give the title compound (850 mg).

MS (ESI+): [M+H]$^+$ 345.1.

B) N-((2S)-1-((2-(4-(2-cyclopropylethoxy)-3-fluorophenyl)-1,3-benzoxazol-6-yl)oxy)propan-2-yl)acetamide To a solution of 2-cyclopropylethanol (389 mg) in THF (10 mL) were added triethylamine (1.26 mL) and methanesulfonyl chloride (0.525 mL), and the mixture was stirred at room temperature for 10 min. To the reaction mixture was added saturated aqueous sodium hydrogen carbonate solution, and the mixture was extracted with ethyl acetate. The organic layer was dried over anhydrous magnesium sulfate, and concentrated under reduced pressure. A suspension of the obtained residue, N-((2S)-1-((2-(3-fluoro-4-hydroxyphenyl)-1,3-benzoxazol-6-yl)oxy)propan-2-yl)acetamide (77.8 mg) and potassium carbonate (625 mg) in DMF (5 mL) was stirred at 60° C. for 30 min. The reaction mixture was diluted with ethyl acetate, and washed with saturated brine, and the organic layer was subjected to silica gel column chromatography (NH, ethyl acetate), and the solvent was evaporated. The obtained solid was washed with diethyl ether to give the title compound (39.4 mg).

Example 5

N-((2S)-1-((2-(4-ethoxy-3-fluorophenyl)-1,3-benzoxazol-6-yl)oxy)propan-2-yl)acetamide A suspension of N-((2S)-1-((2-(3-fluoro-4-hydroxyphenyl)-1,3-benzoxazol-6-yl)oxy)propan-2-yl)acetamide (200 mg), potassium carbonate (161 mg) and ethyl iodide (181 mg) in DMF (5 mL) was stirred at 60° C. for 30 min. The reaction mixture was diluted with ethyl acetate, and washed with saturated brine, and the organic layer was subjected to silica gel column chromatography (NH, ethyl acetate), and the solvent was evaporated. The obtained solid was recrystallized from hexane/ethyl acetate to give the title compound (167 mg).

Example 6

N-((2S)-1-((2-(3-fluoro-4-methoxyphenyl)-1,3-benzoxazol-6-yl)oxy)propan-2-yl)acetamide Using N-((2S)-1-((2-(3-fluoro-4-hydroxyphenyl)-1,3-benzoxazol-6-yl)oxy)propan-2-yl)acetamide and methyl iodide, and in the same manner as in Example 5, the title compound was obtained.

Example 7

N-((2S)-1-((2-(3-fluoro-4-isopropoxyphenyl)-1,3-benzoxazol-6-yl)oxy)propan-2-yl)acetamide Using N-((2S)-1-((2-(3-fluoro-4-hydroxyphenyl)-1,3-benzoxazol-6-yl)oxy)propan-2-yl)acetamide and isopropyl iodide, and in the same manner as in Example 5, the title compound was obtained.

Example 8

N-((2S)-1-((2-(3-fluoro-4-(2-hydroxyethoxy)phenyl)-1,3-benzoxazol-6-yl)oxy)propan-2-yl)acetamide Using N-((2S)-1-((2-(3-fluoro-4-hydroxyphenyl)-1,3-benzoxazol-6-yl)oxy)propan-2-yl)acetamide and 2-bromoethanol, and in the same manner as in Example 5, the title compound was obtained.

Example 9

N-((2S)-1-((2-(3-fluoro-4-(2-hydroxy-2-methylpropoxy)phenyl)-1,3-benzoxazol-6-yl)oxy)propan-2-yl)acetamide Using N-((2S)-1-((2-(3-fluoro-4-hydroxyphenyl)-1,3-benzoxazol-6-yl)oxy)propan-2-yl)acetamide and 1,2-epoxy-2-methylpropane, and in the same manner as in Example 5, the title compound was obtained.

Example 10

3-((2S)-1-((2-(4-(cyclopropylmethoxy)-3-fluorophenyl)-1,3-benzoxazol-6-yl)oxy)propan-2-yl)-1,1-dimethylurea To tert-butyl ((2S)-1-((2-(4-(cyclopropylmethoxy)-3-fluorophenyl)-1,3-benzoxazol-6-yl)oxy)propan-2-yl)carbamate (300 mg) was added 4 M hydrogen chloride/ethyl acetate (10 mL), and the mixture was stirred at room temperature for 10 min, and concentrated. To the residue was added THF (10 mL), and then triethylamine (0.366 mL) and dimethylcarbamoyl chloride (0.0910 mL) were added thereto, and the mixture was stirred with heating at 60° C. for 2 hr. The reaction mixture was purified by silica gel column chromatography (hexane/ethyl acetate) to give the title compound (93.5 mg).

Example 11

1-((2S)-1-((2-(4-(cyclopropylmethoxy)-3-fluorophenyl)-1,3-benzoxazol-6-yl)oxy)propan-2-yl)-3-methylurea Using tert-butyl ((2S)-1-((2-(4-(cyclopropylmethoxy)-3-fluorophenyl)-1,3-benzoxazol-6-yl)oxy)propan-2-yl)carbamate and methyl isocyanate, and in the same manner as in Example 10, the title compound was obtained.

Example 12 methyl ((2S)-1-((2-(4-(cyclopropylmethoxy)-3-fluorophenyl)-1,3-benzoxazol-6-yl)oxy)propan-2-yl)carbamate Using tert-butyl ((2S)-1-((2-(4-(cyclopropylmethoxy)-3-fluorophenyl)-1,3-benzoxazol-6-yl)oxy)propan-2-yl)carbamate and methyl chloroformate, and in the same manner as in Example 10, the title compound was obtained.

Example 13

1-((2S)-1-((2-(4-(cyclopropylmethoxy)-3-fluorophenyl)-1,3-benzoxazol-6-yl)oxy)propan-2-yl)urea Using tert-butyl ((2S)-1-((2-(4-(cyclopropylmethoxy)-3-fluorophenyl)-1,3-benzoxazol-6-yl)oxy)propan-2-yl)carbamate and trimethylsilyl isocyanate, and in the same manner as in Example 10, the title compound was obtained.

Example 14

N-((2S)-1-((2-(4-(cyclopropylmethoxy)phenyl)-1H-benzimidazol-6-yl)oxy)propan-2-yl)acetamide A) tert-butyl ((2S)-1-(3-amino-4-nitrophenoxy)propan-2-yl)carbamate To a solution of 5-fluoro-2-nitroaniline (2.00 g) and tert-butyl ((2S)-1-hydroxypropan-2-yl)carbamate (2.25 g) in DMF (50 mL) was added sodium hydride (60% in oil, 0.564 g), and the mixture was stirred at room temperature for 10 min. The reaction mixture was diluted with ethyl acetate, and washed with saturated brine. The obtained organic layer was dried over anhydrous magnesium sulfate, and the solvent was evaporated under reduced pressure. The residue was purified by silica gel column chromatography (hexane/ethyl acetate) to give the title compound (1.75 g).
$^1$H NMR (300 MHz, CDCl$_3$) δ 1.28 (3H, d, J=6.4 Hz), 1.45 (9H, s), 3.88-4.07 (3H, m), 4.66 (1H, brs), 6.13-6.24 (3H, m), 6.29 (1H, dd, J=9.4, 2.6 Hz), 8.08 (1H, d, J=9.4 Hz).

B) tert-butyl ((2S)-1-(3-((4-(cyclopropylmethoxy)benzoyl)amino)-4-nitrophenoxy)propan-2-yl)carbamate To a solution of 4-(cyclopropylmethoxy)benzoic acid (1.62 g) in THF (30 mL) were added oxalyl dichloride (1.11 mL) and DMF (3 drops), and the mixture was stirred at room temperature for 30 min. The solvent was evaporated under reduced pressure, and to a solution of the obtained residue in pyridine (20 mL) was added a solution of tert-butyl ((2S)-1-(3-amino-4-nitrophenoxy)propan-2-yl)carbamate (1.75 g) in THF (3 mL), and the mixture was stirred at room temperature for 10 min, and then at 70° C. for 1 hr. The reaction mixture was subjected to silica gel column chromatography (NH, ethyl acetate), and the solvent was evaporated. The obtained solid was washed with diethyl ether to give the title compound (1.00 g).
$^1$H NMR (300 MHz, CDCl$_3$) δ 0.34-0.43 (2H, m), 0.61-0.75 (2H, m), 1.21-1.36 (4H, m), 1.46 (9H, s), 3.89 (2H, d, J=7.2 Hz), 4.03-4.19 (3H, m), 4.70 (1H, brs), 6.70 (1H, dd, J=9.5, 2.7 Hz), 7.01 (2H, d, J=8.7 Hz), 7.96 (2H, d, J=9.1 Hz), 8.27 (1H, d, J=9.5 Hz), 8.65 (1H, d, J=3.0 Hz), 11.71 (1H, s).

C) tert-butyl ((2S)-1-((2-(4-(cyclopropylmethoxy)phenyl)-1H-benzimidazol-6-yl)oxy)propan-2-yl)carbamate A mixture of tert-butyl ((2S)-1-(3-((4-(cyclopropylmethoxy)benzoyl)amino)-4-nitrophenoxy)propan-2-yl)carbamate (1.00 g), 10% palladium-carbon (containing water (50%), 1.00 g) and THF (10 mL) was stirred at room temperature for 30 min under a hydrogen atmosphere. The catalyst was removed by filtration, and the obtained filtrate was concentrated under reduced pressure. A solution of the obtained solid in acetic acid (20 mL) was stirred at 80° C. for 1 hr. The reaction mixture was neutralized with saturated aqueous sodium hydrogen carbonate solution, and the mixture was extracted with ethyl acetate. The organic layer was dried over anhydrous magnesium sulfate, the solvent was evaporated under reduced pressure, and the obtained residue was purified by silica gel column chromatography (NH, hexane/ethyl acetate) to give the title compound (901 mg).
MS (ESI+): [M+H]$^+$ 438.1.

D) N-((2S)-1-((2-(4-(cyclopropylmethoxy)phenyl)-1H-benzimidazol-6-yl)oxy)propan-2-yl)acetamide To tert-butyl ((2S)-1-((2-(4-(cyclopropylmethoxy)phenyl)-1H-benzimidazol-6-yl)oxy)propan-2-yl)carbamate (901 mg) was added 4 M hydrogen chloride/ethyl acetate (10 mL), and the mixture was stirred at room temperature for 20 min, and concentrated. To the residue were added pyridine (10 mL) and acetic anhydride (10 mL), and the mixture was stirred at room temperature for 15 min, and concentrated. The residue was dissolved in methanol (10 mL) and THF (10 mL), and saturated aqueous sodium hydrogen carbonate solution (10 mL) was added thereto, and the mixture was stirred at room temperature for 30 min. The reaction mixture was extracted with ethyl acetate, and the organic layer was dried over anhydrous magnesium sulfate. The solvent was evaporated under reduced pressure, and the obtained residue was purified by silica gel column chromatography (NH, hexane/ethyl acetate) to give the title compound (490 mg).

Example 15

N-((2S)-1-((2-(4-propoxyphenyl)-1-benzofuran-6-yl)oxy)propan-2-yl)acetamide

A) 5-(benzyloxy)-2-iodophenol

To a suspension of 3-(benzyloxy)phenol (5.00 g) and silver trifluoroacetate (5.52 g) in toluene (25 mL) was added dropwise a solution of iodine (6.35 g) in toluene (75 mL) over 30 min under ice-cooling. The reaction mixture was filtered, and to the organic layer were added saturated aqueous sodium hydrogen carbonate solution and saturated brine, and the mixture was extracted with ethyl acetate. The obtained organic layer was dried over anhydrous magnesium sulfate, and the solvent was evaporated under reduced pressure. The residue was purified by silica gel column chromatography (hexane/ethyl acetate) to give the title compound (7.26 g).

$^1$H NMR (300 MHz, CDCl$_3$) δ 5.03 (2H, s), 5.26 (1H, s), 6.34-6.45 (1H, m), 6.67 (1H, d, J=2.6 Hz), 7.29-7.43 (5H, m), 7.49 (1H, d, J=8.7 Hz).

B) 6-(benzyloxy)-2-(4-propoxyphenyl)-1-benzofuran

To a solution of 5-(benzyloxy)-2-iodophenol (2.65 g), 4-propoxyphenylacetylene (1.97 g) and 1,1,3,3-tetramethylguanidine (3.08 mL) in DMF (15 mL) were added bistriphenylphosphinedichloropalladium(II) (288 mg) and copper(I) iodide (156 mg) under a nitrogen atmosphere, and the mixture was stirred at 60° C. for 30 min. The reaction mixture was diluted with ethyl acetate, washed with water and saturated brine, and dried over anhydrous magnesium sulfate, and the solvent was evaporated under reduced pressure. The residue was purified by silica gel column chromatography (hexane/ethyl acetate) to give the title compound (1.35 g).

$^1$H NMR (300 MHz, CDCl$_3$) δ 1.05 (3H, t, J=7.5 Hz), 1.80-1.87 (2H, m), 3.97 (2H, t, J=6.4 Hz), 5.12 (2H, s), 6.80 (1H, s), 6.91-6.97 (3H, m), 7.12 (1H, s), 7.33-7.49 (6H, m), 7.72 (2H, d, J=8.7 Hz).

C) 2-(4-propoxyphenyl)-1-benzofuran-6-ol

Using 6-(benzyloxy)-2-(4-propoxyphenyl)-1-benzofuran, and in the same manner as in Step A of Example 4, the title compound was obtained.

$^1$H NMR (300 MHz, CDCl$_3$) δ 1.06 (3H, t, J=7.4 Hz), 1.74-1.94 (2H, m), 3.97 (2H, t, J=6.4 Hz), 4.74 (1H, s), 6.75 (1H, dd, J=8.3, 2.3 Hz), 6.79 (1H, s), 6.91-7.04 (3H, m), 7.37 (1H, d, J=8.3 Hz), 7.63-7.80 (2H, m).

D) tert-butyl ((2S)-1-((2-(4-propoxyphenyl)-1-benzofuran-6-yl)oxy)propan-2-yl)carbamate To a solution of 2-(4-propoxyphenyl)-1-benzofuran-6-ol (918 mg) in DMF (10 mL) was added sodium hydride (60% oil, 137 mg), and the mixture was stirred at room temperature for 10 min. To the reaction mixture was added (2S)-2-[(tert-butoxycarbonyl)amino]propyl 4-methylbenzenesulfonate (1.13 g), and the mixture was stirred at 60° C. for 1 hr. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (460 mg).

E) N-((2S)-1-((2-(4-propoxyphenyl)-1-benzofuran-6-yl)oxy)propan-2-yl)acetamide

Using tert-butyl ((2S)-1-((2-(4-propoxyphenyl)-1-benzofuran-6-yl)oxy)propan-2-yl)carbamate, and in the same manner as in Step D of Example 1, the title compound was obtained.

Example 16

N-((2S)-1-((2-(4-(cyclopropylmethoxy)phenyl)-1,3-benzoxazol-6-yl)oxy)propan-2-yl)acetamide Using 4-aminoresorcinol hydrochloride and 4-(cyclopropylmethoxy)benzoic acid, and in the same manner as in Step B of Example 1, Step D of Example 15 and Step D of Example 1, the title compound was obtained.

Example 17

N-((2S)-1-((2-(4-(cyclopropylmethoxy)phenyl)-1,3-benzoxazol-5-yl)oxy)propan-2-yl)acetamide Using 2-aminobenzene-1,4-diol hydrochloride and 4-(cyclopropylmethoxy)benzoic acid, and in the same manner as in Step B of Example 1, Step D of Example 15 and Step D of Example 1, the title compound was obtained.

Example 18

N-((2S)-1-((2-(4-(cyclopropylmethoxy)-3-fluorophenyl)-2H-indazol-6-yl)oxy)propan-2-yl)acetamide A) tert-butyl ((2S)-1-(3-fluoro-4-formylphenoxy)propan-2-yl)carbamate Using 2-fluoro-4-hydroxybenzaldehyde, and in the same manner as in Step C of Example 1, the title compound was obtained.

$^1$H NMR (300 MHz, CDCl$_3$) δ 1.30 (3H, d, J=7.2 Hz), 1.45 (9H, s), 3.88-4.11 (3H, m), 4.68 (1H, brs), 6.66 (1H, dd, J=12.5, 2.3 Hz), 6.80 (1H, dd, J=8.7, 1.5 Hz), 7.82 (1H, t, J=8.3 Hz), 10.21 (1H, s).

B) 1-(cyclopropylmethoxy)-2-fluoro-4-nitrobenzene

To a solution of 2-fluoro-4-nitrophenol (10.0 g) in DMF (100 mL) were added potassium carbonate (17.6 g) and (bromomethyl)cyclopropane (9.26 mL), and the mixture was stirred with heating at 70° C. for 30 min. The reaction mixture was allowed to cool to room temperature, diluted with ethyl acetate, and washed with saturated brine. The obtained organic layer was subjected to silica gel column chromatography (NH, ethyl acetate), and the solvent was evaporated to give the title compound (13.8 g).

$^1$H NMR (300 MHz, CDCl$_3$) δ 0.32-0.51 (2H, m), 0.62-0.81 (2H, m), 1.27-1.42 (1H, m), 3.99 (2H, d, J=7.2 Hz), 7.00 (1H, t, J=8.5 Hz), 7.95-8.08 (2H, m).

C) 4-(cyclopropylmethoxy)-3-fluoroaniline

A mixture of 1-(cyclopropylmethoxy)-2-fluoro-4-nitrobenzene (3.00 g), 10% palladium-carbon (containing water (50%), 3.00 g) and THF (30 mL) was stirred at room temperature for 1 hr under a hydrogen atmosphere. The catalyst was removed by filtration, and the obtained filtrate was concentrated under reduced pressure to give the title compound (2.57 g).

$^1$H NMR (300 MHz, CDCl$_3$) δ 0.26-0.35 (2H, m), 0.55-0.65 (2H, m), 1.16-1.33 (1H, m), 3.50 (2H, brs), 3.77 (2H, d, J=7.2 Hz), 6.30-6.38 (1H, m), 6.45 (1H, dd, J=12.8, 2.6 Hz), 6.80 (1H, t, J=8.9 Hz).

D) tert-butyl ((2S)-1-((2-(4-(cyclopropylmethoxy)-3-fluorophenyl)-2H-indazol-6-yl)oxy)propan-2-yl)carbamate A solution of 4-(cyclopropylmethoxy)-3-fluoroaniline (1.68 g) and tert-butyl ((2S)-1-(3-fluoro-4-formylphenoxy)propan-2-yl)carbamate (2.76 g) in ethanol (30 mL) was stirred with heating under reflux for 30 min. The mixture was allowed to cool to room temperature, and concentrated under reduced pressure. To a solution of the obtained residue in N,N-dimethylacetamide (40 mL) was added sodium azide (3.01 g), and the mixture was stirred overnight with heating at 150° C. The reaction mixture was allowed to cool to room temperature, diluted with ethyl acetate, and washed with saturated brine. The obtained organic layer was dried over anhydrous magnesium sulfate, and the solvent was evaporated under reduced pressure. The obtained residue was purified by silica gel column chromatography (hexane/ethyl acetate) to give the title compound (920 mg).
MS (ESI+): [M+H]$^+$ 456.0.

E) N-((2S)-1-((2-(4-(cyclopropylmethoxy)-3-fluorophenyl)-2H-indazol-6-yl)oxy)propan-2-yl)acetamide Using tert-butyl ((2S)-1-((2-(4-(cyclopropylmethoxy)-3-fluorophenyl)-2H-indazol-6-yl)oxy)propan-2-yl)carbamate, and in the same manner as in Step D of Example 1, the title compound was obtained.

Example 19

N-((2S)-1-((2-(4-(cyclopropylmethoxy)-3-fluorophenyl)-4,5,6,7-tetrahydro-2H-indazol-6-yl)oxy)propan-2-yl)acetamide Using N-((2S)-1-((2-(4-(cyclopropylmethoxy)-3-fluorophenyl)-2H-indazol-6-yl)oxy)propan-2-yl)acetamide, and in the same manner as in Step C of Example 18, the title compound was obtained.

Example 20

N-((2S)-1-((2-(4-(cyclopropylmethoxy)-2-fluorophenyl)-1,3-benzoxazol-6-yl)oxy)propan-2-yl)acetamide Using 4-aminoresorcinol hydrochloride and 4-(cyclopropylmethoxy)-2-fluorobenzoic acid, and in the same manner as in Step B of Example 1, Step D of Example 15 and Step D of Example 1, the title compound was obtained.

Example 21

N-((2S)-1-((2-(3-(cyclopropylmethoxy)phenyl)-1,3-benzoxazol-6-yl)oxy)propan-2-yl)acetamide A) 3-(cyclopropylmethoxy)benzoic Acid To a solution of ethyl 3-hydroxybenzoate (15.0 g) in DMF (150 mL) were added potassium carbonate (25.0 g) and (bromomethyl)cyclopropane (13.1 mL), and the mixture was stirred with heating at 70° C. for 3 hr. The reaction mixture was allowed to cool to room temperature, diluted with ethyl acetate, and washed with saturated brine. The obtained organic layer was subjected to silica gel column chromatography (NH, ethyl acetate), and the solvent was evaporated. To a solution of the obtained residue in a mixed solvent of THF (100 mL) and methanol (50 mL) was added 2 M aqueous sodium hydroxide solution (47 mL), and the mixture was stirred with heating at 60° C. for 40 min. The reaction mixture was allowed to cool to room temperature, and neutralized with 6 M hydrochloric acid, and the mixture was extracted with ethyl acetate. The obtained organic layer was washed with saturated brine, and dried over anhydrous magnesium sulfate, and the solvent was evaporated under reduced pressure. The obtained solid was washed with diethyl ether/hexane to give the title compound (13.4 g).
$^1$H NMR (300 MHz, DMSO-d$_6$) δ0.28-0.39 (2H, m), 0.51-0.63 (2H, m), 1.10-1.33 (1H, m), 3.86 (2H, d, J=6.8 Hz), 7.17 (1H, dd, J=8.0, 2.7 Hz), 7.33-7.46 (2H, m), 7.48-7.55 (1H, m), 12.95 (1H, s).

B) N-((2S)-1-((2-(3-(cyclopropylmethoxy)phenyl)-1,3-benzoxazol-6-yl)oxy)propan-2-yl)acetamide Using 4-aminoresorcinol hydrochloride and 3-(cyclopropylmethoxy)benzoic acid, and in the same manner as in Step B of Example 1, Step D of Example 15 and Step D of Example 1, the title compound was obtained.

Example 22

N-((2S)-1-((2-(5-(cyclopropylmethoxy)pyridin-2-yl)-1,3-benzoxazol-6-yl)oxy)propan-2-yl)acetamide A) tert-butyl ((2S)-1-(1,3-benzoxazol-6-yloxy)propan-2-yl)carbamate Using 1,3-benzoxazol-6-ol, and in the same manner as in Step C of Example 1, the title compound was obtained.
MS (ESI+): [M+H]$^+$ 293.3.

B) tert-butyl ((2S)-1-((2-(5-(cyclopropylmethoxy)pyridin-2-yl)-1,3-benzoxazol-6-yl)oxy)propan-2-yl)carbamate A mixture of tert-butyl ((2S)-1-(1,3-benzoxazol-6-yloxy)propan-2-yl)carbamate (516 mg), 2-bromo-5-(cyclopropylmethoxy)pyridine (604 mg), palladium(II) acetate (19.8 mg), butyldi(1-adamantyl)phosphine (63.3 mg), tripotassium phosphate (749 mg) and N-methylpyrrolidone (7 mL) was stirred at 125° C. for 15 hr under an argon atmosphere. The reaction mixture was allowed to cool to room temperature, and diluted with ethyl acetate and water, and the organic layer was separated. The organic layer was washed with saturated brine, and dried over anhydrous magnesium sulfate, and the solvent was evaporated under reduced pressure. The residue was purified by silica gel column chromatography (hexane/ethyl acetate) to give the title compound (369 mg).
MS (ESI+): [M+H]$^+$ 440.1.

C) N-((2S)-1-((2-(5-(cyclopropylmethoxy)pyridin-2-yl)-1,3-benzoxazol-6-yl)oxy)propan-2-yl)acetamide Using tert-butyl ((2S)-1-((2-(5-(cyclopropylmethoxy)pyridin-2-yl)-1,3-benzoxazol-6-yl)oxy)propan-2-yl)carbamate, and in the same manner as in Step D of Example 1, the title compound was obtained.

Example 23

N-((2S)-1-((2-(6-(cyclopropylmethoxy)pyridin-3-yl)-1,3-benzoxazol-6-yl)oxy)propan-2-yl)acetamide Using tert-butyl ((2S)-1-(1,3-benzoxazol-6-yloxy)propan-2-yl)carbamate and 5-bromo-2-(cyclopropylmethoxy)pyridine, and in the same manner as in Step B of Example 22 and Step D of Example 1, the title compound was obtained.

Example 24

N-((2S)-1-((2-(3-(cyclopropylmethoxy)-1,2-oxazol-5-yl)-1,3-benzoxazol-6-yl)oxy)propan-2-yl)acetamide Using methyl 3-hydroxy-1,2-oxazole-5-carboxylate, and in the same manner as in Step A of Example 21, and Step B, Step C and Step D of Example 1, the title compound was obtained.

Example 25

N-((2S)-1-((2-(4-(cyclopropylmethoxy)-3-methoxyphenyl)-1,3-benzoxazol-6-yl)oxy)propan-2-yl)acetamide Using ethyl 4-hydroxy-3-methoxybenzoate, and in the same manner as in Step A of Example 21, and Step B, Step C and Step D of Example 1, the title compound was obtained.

Example 26

N-((2S)-1-((2-(3-bromo-4-(cyclopropylmethoxy)phenyl)-1,3-benzoxazol-6-yl)oxy)propan-2-yl)acetamide Using 3-bromo-4-hydroxybenzoic acid, and in the same manner as in Step A, Step B, Step C and Step D of Example 1, the title compound was obtained.

Example 27

N-((2S)-1-((2-(4-(cyclopropylmethoxy)-3-methylphenyl)-1,3-benzoxazol-6-yl)oxy)propan-2-yl)acetamide Using 4-hydroxy-3-methylbenzoic acid, and in the same manner as in Step A, Step B, Step C and Step D of Example 1, the title compound was obtained.

Example 28

N-((2S)-1-((2-(6-(cyclopropylmethoxy)-5-fluoropyridin-3-yl)-1,3-benzoxazol-6-yl)oxy)propan-2-yl) acetamide A) 5-bromo-2-(cyclopropylmethoxy)-3-fluoropyridine To a solution of 5-bromo-3-fluoropyridin-2-ol (1.00 g) in DMF (10 mL) were added potassium carbonate (1.44 g) and (bromomethyl)cyclopropane (0.758 mL), and the mixture was stirred with heating at 70° C. for 30 min. The reaction mixture was allowed to cool to room temperature, and diluted with ethyl acetate and water, and the organic layer was separated. The organic layer was washed with saturated brine, and dried over anhydrous magnesium sulfate, and the solvent was evaporated under reduced pressure. The residue was purified by silica gel column chromatography (hexane/ethyl acetate) to give the title compound (491 mg).
$^1$H NMR (300 MHz, CDCl$_3$) δ 0.33-0.41 (2H, m), 0.59-0.68 (2H, m), 1.26-1.40 (1H, m), 4.20 (2H, d, J=7.2 Hz), 7.47 (1H, dd, J=9.3, 2.1 Hz), 7.95 (1H, d, J=1.9 Hz).

B) N-((2S)-1-(1,3-benzoxazol-6-yloxy)propan-2-yl) acetamide

Using tert-butyl ((2S)-1-(1,3-benzoxazol-6-yloxy)propan-2-yl)carbamate, and in the same manner as in Step D of Example 1, the title compound was obtained.
MS (ESI+): [M+H]$^+$ 235.1.

C) N-((2S)-1-((2-(6-(cyclopropylmethoxy)-5-fluoropyridin-3-yl)-1,3-benzoxazol-6-yl)oxy)propan-2-yl) acetamide Using N-((2S)-1-(1,3-benzoxazol-6-yloxy)propan-2-yl) acetamide and 5-bromo-2-(cyclopropylmethoxy)-3-fluoropyridine, and in the same manner as in Step B of Example 22, the title compound was obtained.

Example 29

N-((2S)-1-((2-(3-chloro-4-(cyclopropylmethoxy) phenyl)-1,3-benzoxazol-6-yl)oxy)propan-2-yl)acetamide A) 3-chloro-4-(cyclopropylmethoxy)benzoic Acid To a solution of methyl 3-chloro-4-hydroxybenzoate (10.0 g) in DMF (100 mL) were added potassium carbonate (14.8 g) and (bromomethyl)cyclopropane (7.80 mL), and the mixture was stirred with heating at 70° C. for 1 hr. The reaction mixture was allowed to cool to room temperature, diluted with ethyl acetate, and washed with saturated brine. The obtained organic layer was subjected to silica gel column chromatography (NH, ethyl acetate), and the solvent was evaporated. To a solution of the obtained residue in a mixed solvent of THF (50 mL) and methanol (50 mL) was added 2 M aqueous sodium hydroxide solution (54 mL), and the mixture was stirred with heating at 50° C. for 2 hr. The reaction mixture was allowed to cool to room temperature, and neutralized with 6 M hydrochloric acid, and the mixture was extracted with ethyl acetate. The obtained organic layer was washed with saturated brine, and dried over anhydrous magnesium sulfate, and the solvent was evaporated under reduced pressure. The obtained solid was washed with ethyl acetate to give the title compound (11.7 g).
$^1$H NMR (300 MHz, CDCl$_3$) δ 0.38-0.47 (2H, m), 0.64-0.75 (2H, m), 1.24-1.43 (1H, m), 3.97 (2H, d, J=6.8 Hz), 6.93 (1H, d, J=8.7 Hz), 7.97 (1H, dd, J=8.5, 2.1 Hz), 8.12 (1H, d, J=1.9 Hz).

B) 2-(3-chloro-4-(cyclopropylmethoxy)phenyl)-1,3-benzoxazol-6-ol

To a solution of 4-aminoresorcinol hydrochloride (5.00 g), 3-chloro-4-(cyclopropylmethoxy)benzoic acid (6.38 g) and diisopropylethylamine (7.37 mL) in DMF (50 mL) was added HATU (11.8 g), and the mixture was stirred at room temperature for 15 hr. The reaction mixture was diluted with ethyl acetate, washed with saturated brine, and dried over anhydrous magnesium sulfate. The solvent was evaporated under reduced pressure. To a suspension of the obtained residue, hexachloroethane (16.7 g) and triphenylphosphine (18.5 g) in acetonitrile (50 mL) was added triethylamine (11.8 mL), and the mixture was stirred at room temperature for 15 min, and then with heating at 80° C. for 2 hr. The reaction mixture was filtered, the solvent was evaporated under reduced pressure, and the residue was purified by silica gel column chromatography (hexane/ethyl acetate) to give the title compound (1.00 g).

$^1$H NMR (300 MHz, CDCl$_3$) δ 0.35-0.50 (2H, m), 0.61-0.80 (2H, m), 1.23-1.47 (1H, m), 3.97 (2H, d, J=6.8 Hz), 5.63 (1H, s), 6.86 (1H, dd, J=8.5, 2.5 Hz), 7.00 (1H, d, J=8.7 Hz), 7.06 (1H, d, J=2.3 Hz), 7.56 (1H, d, J=8.3 Hz), 8.04 (1H, dd, J=8.7, 2.3 Hz), 8.22 (1H, d, J=1.9 Hz).

C) tert-butyl ((2S)-1-((2-(3-chloro-4-(cyclopropylmethoxy)phenyl)-1,3-benzoxazol-6-yl)oxy)propan-2-yl)carbamate To a solution of 2-(3-chloro-4-(cyclopropylmethoxy)phenyl)-1,3-benzoxazol-6-ol (1.00 g), tert-butyl ((2S)-1-hydroxypropan-2-yl)carbamate (0.832 g) and triphenylphosphine (1.25 g) in THF (10 mL) was added dropwise diisopropyl azodicarboxylate toluene solution (1.9 M, 2.50 mL), and the mixture was stirred at room temperature for 16 hr. The reaction mixture was concentrated under reduced pressure, and the residue was purified by silica gel column chromatography (NH, hexane/ethyl acetate) to give the title compound (1.09 g). $^1$H NMR (300 MHz, CDCl$_3$) δ 0.39-0.48 (2H, m), 0.61-0.76 (2H, m), 1.14-1.37 (4H, m), 1.46 (9H, s), 3.90-4.04 (4H, m), 4.03-4.19 (1H, m), 4.77 (1H, brs), 6.95 (1H, dd, J=8.7, 2.3 Hz), 7.01 (1H, d, J=8.7 Hz), 7.10 (1H, d, J=2.3 Hz), 7.60 (1H, d, J=8.7 Hz), 8.04 (1H, dd, J=8.5, 2.1 Hz), 8.22 (1H, d, J=1.9 Hz).

D) N-((2S)-1-((2-(3-chloro-4-(cyclopropylmethoxy) phenyl)-1,3-benzoxazol-6-yl)oxy)propan-2-yl)acetamide To tert-butyl ((2S)-1-((2-(3-chloro-4-(cyclopropylmethoxy)phenyl)-1,3-benzoxazol-6-yl)oxy)propan-2-yl) carbamate (1.09 g) was added 4 M hydrogen chloride/ethyl acetate (10 mL), and the mixture was stirred at room temperature for 10 min, and concentrated. To the residue were added pyridine (10 mL) and acetic anhydride (10 mL), and the mixture was stirred at room temperature for 15 min. The reaction mixture was concentrated under reduced pressure, and the residue was purified by silica gel column chromatography (NH, hexane/ethyl acetate) to give the title compound (640 mg). $^1$H NMR (300 MHz, CDCl$_3$) δ 0.39-0.49 (2H, m), 0.63-0.75 (2H, m), 1.28-1.43 (4H, m), 2.02 (3H, s), 3.95-4.09 (4H, m), 4.36-4.50 (1H, m), 5.74 (1H, d, J=8.3 Hz), 6.95 (1H, dd, J=8.9, 2.5 Hz), 7.00 (1H, d, J=8.7 Hz), 7.11 (1H, d, J=2.3 Hz), 7.60 (1H, d, J=8.7 Hz), 8.04 (1H, dd, J=8.7, 1.9 Hz), 8.22 (1H, d, J=1.9 Hz).

mp 156-159° C.

Anal. Calcd for C$_{22}$H$_{23}$N$_2$O$_4$Cl: C, 63.69; H, 5.59; N, 6.75. Found: C, 63.68; H, 5.67; N, 6.69.

Example 30

N-((2S)-1-((2-(5-chloro-6-(cyclopropylmethoxy) pyridin-3-yl)-1,3-benzoxazol-6-yl)oxy)propan-2-yl) acetamide A) 5-bromo-3-chloro-2-(cyclopropylmethoxy)pyridine To a solution of cyclopropylmethanol (4.64 mL) in DMF (100 mL) was added sodium hydride (60% oil, 2.29 g), and the mixture was stirred at room temperature for 10 min. To the reaction mixture was added 5-bromo-2,3-dichloropyridine (10.0 g), and the mixture was stirred with heating at 70° C. for 30 min. The reaction mixture was allowed to cool to room temperature, and diluted with ethyl acetate and water, and the organic layer was separated. The organic layer was washed with saturated brine, and dried over anhydrous magnesium sulfate, and the solvent was evaporated under reduced pressure. The residue was purified by silica gel column chromatography (hexane/ethyl acetate) to give the title compound (8.11 g).

$^1$H NMR (300 MHz, CDCl$_3$) δ 0.31-0.42 (2H, m), 0.56-0.68 (2H, m), 1.20-1.41 (1H, m), 4.20 (2H, d, J=7.2 Hz), 7.75 (1H, d, J=2.3 Hz), 8.05 (1H, d, J=2.3 Hz).

B) N-((2S)-1-((2-(5-chloro-6-(cyclopropylmethoxy) pyridin-3-yl)-1,3-benzoxazol-6-yl)oxy)propan-2-yl) acetamide Using N-((2S)-1-(1,3-benzoxazol-6-yloxy)propan-2-yl) acetamide and 5-bromo-3-chloro-2-(cyclopropylmethoxy) pyridine, and in the same manner as in Step B of Example 22, the title compound was obtained.

Example 31

N-((2S)-1-((2-(4-(cyclopropylmethoxy)phenyl)[1,3] oxazolo[4,5-c]pyridin-6-yl)oxy)propan-2-yl)acetamide A) tert-butyl ((2S)-1-((4-chloro-5-nitropyridin-2-yl) oxy)propan-2-yl)carbamate To a solution of 4-chloro-5-nitropyridin-2-ol (1.00 g), tert-butyl ((2S)-1-hydroxypropan-2-yl)carbamate (1.51 g) and triphenylphosphine (2.25 g) in THF (10 mL) was added dropwise diisopropyl azodicarboxylate toluene solution (1.9 M, 4.52 mL), and the mixture was stirred at room temperature for 30 min. The reaction mixture was concentrated under reduced pressure, and the residue was purified by silica gel column chromatography (NH, hexane/ethyl acetate) to give the title compound (860 mg).

$^1$H NMR (300 MHz, CDCl$_3$) δ 1.21-1.27 (3H, m), 1.44 (9H, s), 4.03-4.17 (1H, m), 4.37 (2H, dd, J=4.9, 1.5 Hz), 4.62 (1H, brs), 6.92 (1H, s), 8.86 (1H, s).

B) tert-butyl ((2S)-1-((4-chloro-5-((4-(cyclopropylmethoxy)benzoyl)amino)pyridin-2-yl)oxy)propan-2-yl)carbamate To a solution of tert-butyl ((2S)-1-((4-chloro-5-nitropyridin-2-yl)oxy)propan-2-yl)carbamate (860 mg) in ethanol (10 mL) were added reduced iron (1.45 g) and iron(III) chloride (420 mg), and the mixture was stirred with heating under reflux for 1 hr. The reaction mixture was filtered, and the filtrate was diluted with ethyl acetate, washed with saturated brine, and dried over anhydrous magnesium sulfate. The solvent was evaporated under reduced pressure, and the obtained tert-butyl ((2S)-1-((5-amino-4-chloropyridin-2-yl)oxy)propan-2-yl)carbamate was used for the next reaction without further purification.

To a solution of 4-(cyclopropylmethoxy)benzoic acid (748 mg) in THF (15 mL) were added oxalyl dichloride (0.511 mL) and DMF (3 drops), and the mixture was stirred at room temperature for 30 min. The solvent was evaporated under reduced pressure, and to a solution of the obtained residue in pyridine (10 mL) was added a solution of tert-butyl ((2S)-1-((5-amino-4-chloropyridin-2-yl)oxy)propan-2-yl)carbamate (obtained in the above-mentioned reaction) in THF (2 mL), and the mixture was stirred at room temperature for 30 min.

The reaction mixture was subjected to silica gel column chromatography (NH, ethyl acetate), the solvent was evaporated, and the obtained solid was washed with diethyl ether to give the title compound (920 mg).

$^1$H NMR (300 MHz, DMSO-d$_6$) δ 0.30-0.39 (2H, m), 0.53-0.64 (2H, m), 1.10 (3H, d, J=6.8 Hz), 1.18-1.31 (1H, m), 1.38 (9H, s), 3.78-3.88 (1H, m), 3.91 (2H, d, J=6.8 Hz), 4.15 (2H, d, J=4.9 Hz), 6.87 (1H, d, J=7.9 Hz), 7.05 (2H, d, J=9.0 Hz), 7.08 (1H, s), 7.95 (2H, d, J=8.7 Hz), 8.19 (1H, s), 9.94 (1H, s).

C) tert-butyl ((2S)-1-((2-(4-(cyclopropylmethoxy) phenyl)[1,3]oxazolo[4,5-c]pyridin-6-yl)oxy)propan-2-yl)carbamate A suspension of tert-butyl ((2S)-1-((4-chloro-5-((4-(cyclopropylmethoxy)benzoyl)amino)pyridin-2-yl)oxy)propan-2-yl)carbamate (500 mg), potassium carbonate (290 mg) and copper(I) iodide (20.0 mg) in DMF (10 mL) was stirred at 160° C. for 5 hr and 30 min under microwave irradiation. To the reaction mixture was added water, and the obtained mixture was extracted with ethyl acetate. The extract was washed with saturated brine, and subjected to silica gel column chromatography (NH, ethyl acetate). The solvent was evaporated, and the obtained solid was washed with ethyl acetate/hexane to give the title compound (162 mg).

$^1$H NMR (300 MHz, CDCl$_3$) δ 0.31-0.45 (2H, m), 0.60-0.75 (2H, m), 1.21-1.40 (4H, m), 1.44 (9H, s), 3.90 (2H, d, J=7.2 Hz), 4.09 (1H, brs), 4.33 (2H, d, J=4.5 Hz), 4.88 (1H, brs), 6.88 (1H, d, J=0.8 Hz), 7.02 (2H, d, J=8.7 Hz), 8.14 (2H, d, J=9.1 Hz), 8.52 (1H, d, J=0.8 Hz).

D) N-((2S)-1-((2-(4-(cyclopropylmethoxy)phenyl)[1,3]oxazolo[4,5-c]pyridin-6-yl)oxy)propan-2-yl)acetamide To tert-butyl ((2S)-1-((2-(4-(cyclopropylmethoxy)phenyl)[1,3]oxazolo[4,5-c]pyridin-6-yl)oxy)propan-2-yl)carbamate (210 mg) was added 2 M hydrogen chloride/methanol (5 mL), and the mixture was stirred at room temperature for 10 min, and concentrated. To the residue were added pyridine (5 mL) and acetic anhydride (5 mL), and the mixture was stirred at room temperature for 15 min. The reaction mixture was concentrated under reduced pressure, and the residue was purified by silica gel column chromatography (NH, hexane/ethyl acetate) to give the title compound (46.5 mg). $^1$H NMR (300 MHz, CDCl$_3$) δ 0.29-0.46 (2H, m), 0.63-0.78 (2H, m), 1.22-1.40 (4H, m), 1.97 (3H, s), 3.90 (2H, d, J=7.2 Hz), 4.28-4.48 (3H, m), 6.07 (1H, brs), 6.90 (1H, s), 7.03 (2H, d, J==9.0 Hz), 8.14 (2H, d, J=9.0 Hz), 8.52 (1H, s).

Example 32

N-((2S)-1-((2-(4-(cyclopropylmethoxy)-3-fluorophenyl)[1,3]oxazolo[4,5-c]pyridin-6-yl)oxy)propan-2-yl)acetamide A) tert-butyl ((2S)-1-((4-chloro-5-((4-(cyclopropylmethoxy)-3-fluorobenzoyl)amino)pyridin-2-yl)oxy)propan-2-yl)carbamate To a solution of tert-butyl ((2S)-1-((4-chloro-5-nitropyridin-2-yl)oxy)propan-2-yl)carbamate (1.00 g) in ethanol (10 mL) were added reduced iron (1.68 g) and iron(III) chloride (489 mg), and the mixture was stirred with heating under reflux for 1 hr. The reaction mixture was filtered, and the filtrate was diluted with ethyl acetate, washed with saturated brine, and dried over anhydrous magnesium sulfate. The solvent was evaporated under reduced pressure, and the obtained tert-butyl ((2S)-1-((5-amino-4-chloropyridin-2-yl)oxy)propan-2-yl)carbamate was used for the next reaction without further purification.

To a solution of 4-(cyclopropylmethoxy)-3-fluorobenzoic acid (950 mg) in THF (15 mL) were added oxalyl dichloride (0.593 mL) and DMF (3 drops), and the mixture was stirred at room temperature for 30 min. The solvent was evaporated under reduced pressure, and to a solution of the obtained residue in pyridine (10 mL) was added a solution of tert-butyl ((2S)-1-((5-amino-4-chloropyridin-2-yl)oxy)propan-2-yl)carbamate (obtained in the above-mentioned reaction) in THF (2 mL), and the mixture was stirred at room temperature for 30 min. The reaction mixture was subjected to silica gel column chromatography (NH, ethyl acetate), the solvent was evaporated, and the obtained solid was washed with diethyl ether to give the title compound (1.09 g).

$^1$H NMR (300 MHz, DMSO-d$_6$) δ 0.31-0.41 (2H, m), 0.57-0.65 (2H, m), 1.10 (3H, d, J=6.8 Hz), 1.19-1.33 (1H, m), 1.38 (9H, s), 3.78-3.93 (1H, m), 4.00 (2H, d, J=7.2 Hz), 4.15 (2H, d, J=4.9 Hz), 6.87 (1H, d, J=7.9 Hz), 7.09 (1H, s), 7.29 (1H, t, J=8.5 Hz), 7.82 (2H, d, J=10.2 Hz), 8.19 (1H, s), 10.05 (1H, s).

B) tert-butyl ((2S)-1-((2-(4-(cyclopropylmethoxy)-3-fluorophenyl)[1,3]oxazolo[4,5-c]pyridin-6-yl)oxy) propan-2-yl)carbamate A suspension of tert-butyl ((2S)-1-((4-chloro-5-((4-(cyclopropylmethoxy)-3-fluorobenzoyl)amino)pyridin-2-yl)oxy) propan-2-yl)carbamate (990 mg), potassium carbonate (554 mg) and copper(I) iodide (38.2 mg) in DMF (10 mL) was stirred at 160° C. for 5 hr under microwave irradiation. To the reaction mixture was added water, and the obtained mixture was extracted with ethyl acetate. The extract was washed with saturated brine, and subjected to silica gel column chromatography (NH, ethyl acetate). The solvent was evaporated, and the obtained solid was washed with ethyl acetate/hexane to give the title compound (393 mg).

$^1$H NMR (300 MHz, CDCl$_3$) δ 0.37-0.47 (2H, m), 0.62-0.79 (2H, m), 1.28 (3H, d, J=7.2 Hz), 1.32-1.41 (1H, m), 1.44 (9H, s), 3.97 (2H, d, J=6.8 Hz), 4.11 (1H, brs), 4.33 (2H, d, J=4.5 Hz), 4.86 (1H, brs), 6.89 (1H, s), 7.06 (1H, t, J=8.7 Hz), 7.81-7.98 (2H, m), 8.53 (1H, s).

C) N-((2S)-1-((2-(4-(cyclopropylmethoxy)-3-fluorophenyl)[1,3]oxazolo[4,5-c]pyridin-6-yl)oxy)propan-2-yl)acetamide To tert-butyl ((2S)-1-((2-(4-(cyclopropylmethoxy)-3-fluorophenyl)[1,3]oxazolo[4,5-c]pyridin-6-yl)oxy)propan-2-yl)carbamate (423 mg) was added 2 M hydrogen chloride/methanol (5 mL), and the mixture was stirred at room temperature for 10 min, and concentrated. To the residue were added pyridine (5 mL) and acetic anhydride (5 mL), and the mixture was stirred at room temperature for 15 min. The reaction mixture was concentrated under reduced pressure, and the residue was purified by silica gel column chromatography (NH, hexane/ethyl acetate) to give the title compound (146 mg).

$^1$H NMR (300 MHz, CDCl$_3$) δ 0.35-0.46 (2H, m), 0.64-0.76 (2H, m), 1.24-1.44 (4H, m), 1.97 (3H, s), 3.98 (2H, d, J=6.8 Hz), 4.29-4.51 (3H, m), 6.02 (1H, d, J=6.4 Hz), 6.91 (1H, s), 7.06 (1H, t, J=8.5 Hz), 7.83-7.98 (2H, m), 8.53 (1H, s).

Example 33

N-((2S)-1-((2-(6-(cyclopropylmethoxy)-5-fluoropyridin-3-yl)[1,3]oxazolo[4,5-c]pyridin-6-yl)oxy)propan-2-yl)acetamide

A) methyl 6-(cyclopropylmethoxy)-5-fluoronicotinate

A mixture of 5-bromo-2-(cyclopropylmethoxy)-3-fluoropyridine (2.49 g), [1,1'-bis(diphenylphosphino)ferrocene]dichloropalladium(II) dichloromethane adduct (832 mg), triethylamine (2.82 mL), methanol (2 mL) and DMF (20 mL) was stirred overnight at 80° C. under a carbon monoxide atmosphere. To the reaction mixture was added water, and the mixture was extracted with ethyl acetate. The organic layer was washed with saturated brine, and dried over anhydrous magnesium sulfate, and the solvent was evaporated under reduced pressure. The residue was purified by silica gel column chromatography (hexane/ethyl acetate) to give the title compound (1.75 g).

$^1$H NMR (300 MHz, CDCl$_3$) δ 0.31-0.45 (2H, m), 0.57-0.70 (2H, m), 1.24-1.46 (1H, m), 3.92 (3H, s), 4.30 (2H, d, J=7.2 Hz), 7.88 (1H, dd, J=10.2, 1.9 Hz), 8.57 (1H, d, J=1.9 Hz).

B) 6-(cyclopropylmethoxy)-5-fluoronicotinic Acid

A mixture of methyl 6-(cyclopropylmethoxy)-5-fluoronicotinate (1.75 g), THF (15 mL), methanol (1.7 mL) and 2 M aqueous lithium hydroxide solution (7.8 mL) was stirred at room temperature for 20 min. The reaction mixture was neutralized with 1 M hydrochloric acid at 0° C., and the mixture was extracted with ethyl acetate. The organic layer was washed with saturated brine, and dried over anhydrous magnesium sulfate, and the solvent was evaporated under reduced pressure, and the obtained solid was washed with diethyl ether to give the title compound (1.21 g).

$^1$H NMR (300 MHz, DMSO-d$_6$) δ 0.32-0.42 (2H, m), 0.54-0.64 (2H, m), 1.21-1.38 (1H, m), 4.27 (2H, d, J=7.2 Hz), 8.00 (1H, dd, J=10.6, 1.9 Hz), 8.51 (1H, d, J=1.9 Hz), 13.32 (1H, brs).

C) N-((2S)-1-((4-chloro-5-nitropyridin-2-yl)oxy)propan-2-yl)acetamide

To tert-butyl ((2S)-1-((4-chloro-5-nitropyridin-2-yl)oxy)propan-2-yl)carbamate (1.53 g) was added 4 M hydrogen chloride/ethyl acetate (5 mL), and the mixture was stirred at room temperature for 10 min, and concentrated. To the residue were added pyridine (5 mL) and acetic anhydride (5 mL), and the mixture was stirred at room temperature for 15 min. The reaction mixture was concentrated under reduced pressure, and the residue was purified by silica gel column chromatography (hexane/ethyl acetate) to give the title compound (810 mg).

$^1$H NMR (300 MHz, CDCl$_3$) δ 1.27 (3H, d, J=6.4 Hz), 1.98 (3H, s), 4.33-4.51 (3H, m), 5.58 (1H, brs), 6.94 (1H, s), 8.86 (1H, s).

D) N-(6-((2S)-2-acetamidopropyl)oxy)-4-chloropyridin-3-yl)-6-(cyclopropylmethoxy)-5-fluoronicotinamide To a solution of N-((2S)-1-((4-chloro-5-nitropyridin-2-yl)oxy)propan-2-yl)acetamide (810 mg) in ethanol (10 mL) were added reduced iron (1.65 g) and iron(III) chloride (480 mg), and the mixture was stirred with heating under reflux for 1 hr. The reaction mixture was filtered, and the filtrate was diluted with ethyl acetate, washed with saturated brine, and dried over anhydrous magnesium sulfate. The solvent was evaporated under reduced pressure, and to a solution of the obtained residue, 6-(cyclopropylmethoxy)-5-fluoronicotinic acid (813 mg) and diisopropylethylamine (1.03 mL) in DMF (10 mL) was added HATU (1.46 g), and the mixture was stirred at room temperature overnight. The precipitated solid was washed with ethyl acetate to give the title compound (960 mg).

$^1$H NMR (300 MHz, DMSO-d$_6$) δ 0.35-0.44 (2H, m), 0.55-0.64 (2H, m), 1.13 (3H, d, J=6.8 Hz), 1.22-1.42 (1H, m), 1.80 (3H, s), 4.05-4.22 (3H, m), 4.29 (2H, d, J=7.2 Hz), 7.15 (1H, s), 7.88-7.98 (1H, m), 8.16 (1H, dd, J=11.1, 2.1 Hz), 8.23 (1H, s), 8.62 (1H, d, J=1.9 Hz), 10.23 (1H, s).

E) N-((2S)-1-((2-(6-(cyclopropylmethoxy)-5-fluoropyridin-3-yl)[1,3]oxazolo[4,5-c]pyridin-6-yl)oxy)propan-2-yl)acetamide A suspension of N-(6-(((2S)-2-acetamidopropyl)oxy)-4-chloropyridin-3-yl)-6-(cyclopropylmethoxy)-5-fluoronicotinamide (860 mg), potassium carbonate (544 mg) and copper (I) iodide (37.5 mg) in DMF (10 mL) was stirred at 160° C. for 3 hr under microwave irradiation. To the reaction mixture was added water, and the obtained mixture was extracted with ethyl acetate. The extract was washed with saturated brine, and subjected to silica gel column chromatography (NH, ethyl acetate). The solvent was evaporated, and the obtained solid was washed with ethyl acetate/hexane to give the title compound (39.8 mg).

$^1$H NMR (300 MHz, DMSO-d$_6$) δ 0.33-0.45 (2H, m), 0.53-0.68 (2H, m), 1.15 (3H, d, J=6.4 Hz), 1.25-1.41 (1H, m), 1.81 (3H, s), 4.06-4.25 (3H, m), 4.32 (2H, d, J=7.2 Hz), 7.22 (1H, s), 7.92 (1H, d, J=7.5 Hz), 8.21-8.38 (1H, m), 8.66 (1H, d. J=0.8 Hz), 8.74 (1H, d, J=2.3 Hz).

Example 34

N-((2S)-1-((2-(3-chloro-4-(cyclopropylmethoxy)phenyl)[1,3]oxazolo[4,5-c]pyridin-6-yl)oxy)propan-2-yl)acetamide

A) tert-butyl ((2S)-1-((4-chloro-5-((3-chloro-4-(cyclopropylmethoxy)benzoyl)amino)pyridin-2-yl)oxy)propan-2-yl)carbamate To a solution of tert-butyl ((2S)-1-((4-chloro-5-nitropyridin-2-yl)oxy)propan-2-yl)carbamate (1.23 g) in ethanol (10 mL) were added reduced iron (2.07 g) and iron(III) chloride (601 mg), and the mixture was stirred with heating under reflux for 30 min. The reaction mixture was filtered, and the filtrate was diluted with ethyl acetate, washed with saturated brine, and dried over anhydrous magnesium sulfate. The solvent was evaporated under reduced pressure, and the obtained tert-butyl ((2S)-1-((5-amino-4-chloropyridin-2-yl)oxy)propan-2-yl)carbamate was used for the next reaction without further purification.

To a solution of 3-chloro-4-(cyclopropylmethoxy)benzoic acid (1.26 g) in THF (15 mL) were added oxalyl dichloride (0.731 mL) and DMF (2 drops), and the mixture was stirred at room temperature for 30 min. The solvent was evaporated under reduced pressure, and to a solution of the obtained residue in pyridine (10 mL) was added a solution of tert-butyl ((2S)-1-((5-amino-4-chloropyridin-2-yl)oxy)propan-2-yl) carbamate (obtained in the above-mentioned reaction) in THF (2 mL), and the mixture was stirred at room temperature for 30 min. The reaction mixture was subjected to silica gel column chromatography (NH, ethyl acetate), the solvent was evaporated, and the obtained solid was washed with diethyl ether to give the title compound (1.02 g).

$^1$H NMR (300 MHz, CDCl$_3$) δ 0.35-0.49 (2H, m), 0.62-0.76 (2H, m), 1.25 (3H, d, J=6.8 Hz), 1.28-1.41 (1H, m), 1.45 (9H, s), 3.98 (2H, d, J=6.8 Hz), 4.06 (1H, brs), 4.28 (2H, d, J=4.9 Hz), 4.75 (1H, brs), 6.89 (1H, s), 6.98 (1H, d, J=8.7 Hz), 7.77 (1H, dd, J=8.3, 2.3 Hz), 7.85 (1H, s), 7.93 (1H, d, J=2.3 Hz), 9.03 (1H, s).

B) N-((2S)-1-((2-(3-chloro-4-(cyclopropylmethoxy) phenyl)[1,3]oxazolo[4,5-c]pyridin-6-yl)oxy)propan-2-yl)acetamide A suspension of tert-butyl ((2S)-1-((4-chloro-5-((3-chloro-4-(cyclopropylmethoxy)benzoyl)amino)pyridin-2-yl)oxy)propan-2-yl)carbamate (1.02 g), potassium carbonate (0.552 g) and copper(I) iodide (38.0 mg) in DMF (10 mL) was stirred at 160° C. for 5 hr under microwave irradiation. To the reaction mixture was added water, and the obtained mixture was extracted with ethyl acetate. The extract was washed with saturated brine, and subjected to silica gel column chromatography (NH, ethyl acetate). The solvent was evaporated, and to the obtained residue was added 2 M hydrogen chloride/methanol (5 mL), and the mixture was stirred at room temperature for 10 min, and concentrated. To the residue were added pyridine (5 mL) and acetic anhydride (5 mL), and the mixture was stirred at room temperature for 15 min. The reaction mixture was concentrated under reduced pressure, and the residue was purified by silica gel column chromatography (NH, hexane/ethyl acetate) to give the title compound (92.4 mg). $^1$H NMR (300 MHz, CDCl$_3$) δ 0.38-0.48 (2H, m), 0.64-0.77 (2H, m), 1.30 (3H, d, J=6.4 Hz), 1.33-1.44 (1H, m), 1.97 (3H, s), 3.99 (2H, d, J=6.8 Hz), 4.25-4.51 (3H, m), 6.01 (1H, d, J=6.0 Hz), 6.91 (1H, s), 7.02 (1H, d, J=8.7 Hz), 8.06 (1H, dd, J=8.7, 1.9 Hz), 8.24 (1H, d, J=2.3 Hz), 8.53 (1H, s).

Example 35

N-((2S)-1-((2-(5-chloro-6-(cyclopropylmethoxy) pyridin-3-yl)[1,3]oxazolo[4,5-c]pyridin-6-yl)oxy) propan-2-yl)acetamide A)
5-bromo-3-chloro-2-(cyclopropylmethoxy)pyridine To a solution of cyclopropylmethanol (4.64 mL) in DMF (100 mL) was added sodium hydride (60% oil, 2.29 g), and the mixture was stirred at room temperature for 10 min. To the reaction mixture was added 5-bromo-2,3-dichloropyridine (10.0 g), and the mixture was stirred with heating at 70° C. for 30 min. The reaction mixture was allowed to cool to room temperature, and diluted with ethyl acetate and water, and the organic layer was separated. The organic layer was washed with saturated brine, and dried over anhydrous magnesium sulfate, and the solvent was evaporated under reduced pressure. The residue was purified by silica gel column chromatography (hexane/ethyl acetate) to give the title compound (8.11 g).

$^1$H NMR (300 MHz, CDCl$_3$) δ 0.31-0.42 (2H, m), 0.56-0.68 (2H, m), 1.20-1.41 (1H, m), 4.20 (2H, d, J=7.2 Hz), 7.75 (1H, d, J=2.3 Hz), 8.05 (1H, d, J=2.3 Hz).

B) methyl
5-chloro-6-(cyclopropylmethoxy)nicotinate

A mixture of 5-bromo-3-chloro-2-(cyclopropylmethoxy) pyridine (3.00 g), [1,1'-bis(diphenylphosphino)ferrocene] dichloropalladium(II) dichloromethane adduct (470 mg), triethylamine (3.19 mL), methanol (3 mL) and DMF (30 mL) was stirred at 80° C. for 15 hr under a carbon monoxide atmosphere. To the reaction mixture was added water, and the mixture was extracted with ethyl acetate. The organic layer was washed with saturated brine, and dried over anhydrous magnesium sulfate, and the solvent was evaporated under reduced pressure. The residue was purified by silica gel column chromatography (hexane/ethyl acetate) to give the title compound (2.53 g).

$^1$H NMR (300 MHz, CDCl$_3$) δ 0.35-0.46 (2H, m), 0.58-0.69 (2H, m), 1.26-1.43 (1H, m), 3.91 (3H, s), 4.30 (2H, d, J=7.2 Hz), 8.21 (1H, d, J=2.3 Hz), 8.67 (1H, d, J=2.3 Hz).

C) 5-chloro-6-(cyclopropylmethoxy)nicotinic Acid

A mixture of methyl 5-chloro-6-(cyclopropylmethoxy) nicotinate (2.00 g), THF (15 mL), methanol (1.7 mL) and 2 M aqueous lithium hydroxide solution (8.3 mL) was stirred at room temperature for 20 min. The reaction mixture was neutralized with 1 M hydrochloric acid at 0° C., and the mixture was extracted with ethyl acetate. The organic layer was washed with saturated brine, and dried over anhydrous magnesium sulfate, and the solvent was evaporated under reduced pressure, and the obtained solid was washed with diethyl ether/hexane to give the title compound (1.68 g).

$^1$H NMR (300 MHz, CDCl$_3$) δ 0.37-0.47 (2H, m), 0.58-0.70 (2H, m), 1.25-1.46 (1H, m), 4.33 (2H, d, J=7.2 Hz), 8.26 (1H, d, J=1.9 Hz), 8.75 (1H, d, J=2.3 Hz).

D) N-((2S)-1-((4-chloro-5-nitropyridin-2-yl)oxy) propan-2-yl)acetamide

To tert-butyl ((2S)-1-((4-chloro-5-nitropyridin-2-yl)oxy) propan-2-yl)carbamate (1.35 g) was added 4 M hydrogen chloride/ethyl acetate (5 mL), and the mixture was stirred at room temperature for 10 min, and concentrated. To the residue were added pyridine (5 mL) and acetic anhydride (5 mL), and the mixture was stirred at room temperature for 15 min. The reaction mixture was concentrated under reduced pressure, and the residue was purified by silica gel column chromatography (hexane/ethyl acetate) to give the title compound (1.00 g). $^1$H NMR (300 MHz, CDCl$_3$) δ 1.27 (3H, d, J=6.4 Hz), 1.98 (3H, s), 4.33-4.55 (3H, m), 5.65 (1H, d, J=6.1 Hz), 6.94 (1H, s), 8.86 (1H, s).

E) N-(6-(((2S)-2-acetamidopropyl)oxy)-4-chloropyridin-3-yl)-5-chloro-6-(cyclopropylmethoxy)nicotinamide To a solution of N-((2S)-1-((4-chloro-5-nitropyridin-2-yl) oxy)propan-2-yl)acetamide (1.00 g) in ethanol (10 mL) were added reduced iron (2.04 g) and iron(III) chloride (593 mg), and the mixture was stirred with heating under reflux for 1 hr. The reaction mixture was filtered, and the filtrate was diluted with ethyl acetate, washed with saturated brine, and dried over anhydrous magnesium sulfate. The solvent was evaporated under reduced pressure, and to a solution of the obtained residue, 5-chloro-6-(cyclopropylmethoxy)nicotinic acid (1.08 g) and diisopropylethylamine (1.28 mL) in DMF (10 mL) was added HATU (1.80 g), and the mixture was stirred at room temperature overnight. The precipitated solid was collected by filtration, and washed with ethyl acetate to give the title compound (910 mg).

$^1$H NMR (300 MHz, CDCl$_3$) δ 0.38-0.46 (2H, m), 0.59-0.71 (2H, m), 1.26 (3H, d, J=6.8 Hz), 1.30-1.46 (1H, m), 1.97

(3H, s), 4.21-4.49 (5H, m), 5.95 (1H, d, J=7.5 Hz), 6.91 (1H, s), 7.95 (1H, s), 8.19 (1H, d, J=2.3 Hz), 8.58 (1H, d, J=2.3 Hz), 8.96 (1H, s).

F) N-((2S)-1-((2-(5-chloro-6-(cyclopropylmethoxy)pyridin-3-yl)[1,3]oxazolo[4,5-c]pyridin-6-yl)oxy)propan-2-yl)acetamide A suspension of N-(6-(((2S)-2-acetamidopropyl)oxy)-4-chloropyridin-3-yl)-5-chloro-6-(cyclopropylmethoxy)nicotinamide (910 mg), potassium carbonate (555 mg) and copper (I) iodide (38.2 mg) in DMF (10 mL) was stirred at 160° C. for 3 hr under microwave irradiation. To the reaction mixture was added water, and the obtained mixture was extracted with ethyl acetate. The extract was washed with saturated brine, and subjected to silica gel column chromatography (NH, ethyl acetate). The solvent was evaporated, and the obtained solid was washed with ethyl acetate/hexane to give the title compound (153 mg).

$^1$H NMR (300 MHz, DMSO-$d_6$) δ 0.34-0.46 (2H, m), 0.53-0.68 (2H, m), 1.15 (3H, d, J=6.4 Hz), 1.24-1.40 (1H, m), 1.81 (3H, s), 4.06-4.27 (3H, m), 4.32 (2H, d, J=6.8 Hz), 7.22 (1H, s), 7.93 (1H, d, J=7.2 Hz), 8.50 (1H, s), 8.66 (1H, s), 8.86 (1H, s).

Example 36

N-((2S)-4-(2-(4-(cyclopropylmethoxy)phenyl)[1,3]oxazolo[4,5-c]pyridin-6-yl)butan-2-yl)acetamide

A) 4-(cyclopropylmethoxy)-N-(4,6-dichloropyridin-3-yl)benzamide

To a solution of 4,6-dichloropyridin-3-amine (2.00 g) in pyridine (30 mL) was added a solution of 4-(cyclopropylmethoxy)benzoyl chloride (3.88 g) in THF (5 mL), and the mixture was stirred at room temperature for 10 min. The reaction mixture was subjected to silica gel column chromatography (NH, ethyl acetate), and the solvent was evaporated, and the obtained solid was washed with diethyl ether/hexane to give the title compound (1.50 g).

MS (ESI+): [M+H]$^+$ 337.1.

B) 6-chloro-2-(4-(cyclopropylmethoxy)phenyl)[1,3]oxazolo[4,5-c]pyridine

Using 4-(cyclopropylmethoxy)-N-(4,6-dichloropyridin-3-yl)benzamide, and in the same manner as in Step C of Example 31, the title compound was obtained.

MS (ESI+): [M+H]$^+$ 301.0.

C) tert-butyl ((2S)-4-(2-(4-(cyclopropylmethoxy)phenyl)[1,3]oxazolo[4,5-c]pyridin-6-yl)but-3-yn-2-yl)carbamate To a solution of 6-chloro-2-(4-(cyclopropylmethoxy)phenyl) [1,3]oxazolo[4,5-c]pyridine (700 mg), tert-butyl (2S)-but-3-yn-2-ylcarbamate (1.13 g) and triethylamine (0.649 g) in DMF (10 mL) were added bistriphenylphosphinedichloropalladium(II) (163 mg) and copper(I) iodide (88.7 mg), and the mixture was stirred at 100° C. for 2 hr under an argon atmosphere. The reaction mixture was allowed to cool to room temperature, water was added thereto, and the mixture was extracted with ethyl acetate. The extract was washed with saturated brine, and subjected to silica gel column chromatography (NH, ethyl acetate). The solvent was evaporated under reduced pressure, and the obtained solid was washed with ethyl acetate to give the title compound (132 mg).

MS (ESI+): [M+H]$^+$ 434.2.

D) N-((2S)-4-(2-(4-(cyclopropylmethoxy)phenyl)[1,3]oxazolo[4,5-c]pyridin-6-yl)butan-2-yl)acetamide Using tert-butyl ((2S)-4-(2-(4-(cyclopropylmethoxy)phenyl) [1,3]oxazolo[4,5-c]pyridin-6-yl)but-3-yn-2-yl)carbamate, and in the same manner as in Step A of Example 4 and Step D of Example 31, the title compound was obtained.

Example 37

N-((2S)-1-((2-(4-(cyclopropylmethoxy)-3-fluorophenyl)-7-fluoro-1,3-benzoxazol-6-yl)oxy)propan-2-yl)acetamide

A) 1,3-bis(benzyloxy)-2-fluoro-4-nitrobenzene

To a solution of benzyl alcohol (29.4 mL) in DMF (300 mL) was added sodium hydride (60% oil, 11.3 g), and the mixture was stirred at room temperature for 30 min. To the reaction mixture was added 1,2,3-trifluoro-4-nitrobenzene (20.0 g), and the mixture was stirred with heating at 80° C. for 30 min. The reaction mixture was allowed to cool to room temperature, and diluted with ethyl acetate and water, and the organic layer was separated. The organic layer was washed with saturated brine, and dried over anhydrous magnesium sulfate, and the solvent was evaporated under reduced pressure. The residue was purified by silica gel column chromatography (hexane/ethyl acetate) to give the title compound (33.1 g).

$^1$H NMR (300 MHz, CDCl$_3$) δ 5.22 (2H, s), 5.24 (2H, s), 6.78 (1H, dd, J=9.3, 7.4 Hz), 7.28-7.56 (10H, m), 7.68 (1H, dd, J=9.4, 2.3 Hz).

B) N-(2,4-bis(benzyloxy)-3-fluorophenyl)-4-(cyclopropylmethoxy)-3-fluorobenzamide To a solution of 1,3-bis(benzyloxy)-2-fluoro-4-nitrobenzene (20.0 g) in ethanol (75 mL) were added reduced iron (31.6 g) and iron(III) chloride (9.18 g), and the mixture was stirred with heating under reflux for 30 min. The reaction mixture was filtered, and the filtrate was diluted with ethyl acetate, washed with saturated brine, and dried over anhydrous magnesium sulfate. The solvent was evaporated under reduced pressure, and the obtained 2,4-bis(benzyloxy)-3-fluoroaniline was used for the next reaction without further purification.

To a solution of 4-(cyclopropylmethoxy)-3-fluorobenzoic acid (9.52 g) in THF (50 mL) were added oxalyl dichloride (5.95 mL) and DMF (2 drops), and the mixture was stirred at room temperature for 30 min. The solvent was evaporated under reduced pressure, and a solution of the obtained residue in THF (10 mL) was added to a solution of 2,4-bis(benzyloxy)-3-fluoroaniline (obtained in the above-mentioned reaction) in pyridine (100 mL), and the mixture was stirred at room temperature for 30 min. The reaction mixture was subjected to silica gel column chromatography (NH, ethyl acetate), the solvent was evaporated, and the obtained solid was washed with diethyl ether to give the title compound (12.3 g).

$^1$H NMR (300 MHz, CDCl$_3$) δ 0.36-0.44 (2H, m), 0.63-0.73 (2H, m), 1.19-1.40 (1H, m), 3.93 (2H, d, J=6.8 Hz), 5.15

(2H, s), 5.18 (2H, s), 6.79 (1H, t, J=8.9 Hz), 6.88 (1H, t, J=8.1 Hz), 7.27-7.52 (12H, m), 8.01 (1H, s), 8.09 (1H, dd, J=9.3, 2.5 Hz).

C) 2-(4-(cyclopropylmethoxy)-3-fluorophenyl)-7-fluoro-1,3-benzoxazol-6-ol

A mixture of N-(2,4-bis(benzyloxy)-3-fluorophenyl)-4-(cyclopropylmethoxy)-3-fluorobenzamide (12.3 g), 10% palladium-carbon (containing water (50%), 12.0 g) and THF (80 mL) was stirred at room temperature for 20 min under a hydrogen atmosphere. The catalyst was removed by filtration, and the obtained filtrate was concentrated under reduced pressure, and the solid was washed with diethyl ether. To a solution of the obtained solid, hexachloroethane (14.6 g) and triphenylphosphine (16.2 g) in acetonitrile (50 mL) was added triethylamine (10.3 mL) at 0° C., and the mixture was stirred at room temperature for 15 min, and then with heating at 80° C. for 2 hr. The reaction mixture was filtered, the solvent was evaporated under reduced pressure, and the residue was purified by silica gel column chromatography (hexane/ethyl acetate) to give the title compound (3.96 g).
$^1$H NMR (300 MHz, CDCl$_3$) δ 0.33-0.46 (2H, m), 0.64-0.75 (2H, m), 1.26-1.42 (1H, m), 3.97 (2H, d, J=7.2 Hz), 5.41 (1H, brs), 6.96-7.13 (2H, m), 7.38 (1H, dd, J=8.7, 1.1 Hz), 7.89-7.97 (2H, m).

D) N-((2S)-1-((2-(4-(cyclopropylmethoxy)-3-fluorophenyl)-7-fluoro-1,3-benzoxazol-6-yl)oxy)propan-2-yl)acetamide To a solution of 2-(4-(cyclopropylmethoxy)-3-fluorophenyl)-7-fluoro-1,3-benzoxazol-6-ol (3.96 g), tert-butyl ((2S)-1-hydroxypropan-2-yl)carbamate (3.28 g) and triphenylphosphine (4.91 g) in THF (50 mL) was added dropwise diisopropyl azodicarboxylate toluene solution (1.9 M, 9.85 mL) at 0° C., and the mixture was stirred at room temperature for 30 min. The reaction mixture was concentrated under reduced pressure, and the residue was purified by silica gel column chromatography (NH, hexane/ethyl acetate) to give a solid. To this solid was added 4 M hydrogen chloride/ethyl acetate (50 mL), and the mixture was stirred at room temperature for 10 min, and concentrated. To the residue were added pyridine (50 mL) and acetic anhydride (50 mL), and the mixture was stirred at room temperature for 15 min. The reaction mixture was concentrated under reduced pressure, and the obtained solid was dissolved in ethyl acetate/methanol, and the solution was subjected to silica gel column chromatography (NH, ethyl acetate), and concentrated. The obtained solid was recrystallized (hexane/ethyl acetate) to give the title compound as white crystals (2.80 g).
$^1$H NMR (300 MHz, CDCl$_3$) δ 0.36-0.46 (2H, m), 0.64-0.75 (2H, m), 1.25-1.43 (4H, m), 2.02 (3H, s), 3.97 (2H, d, J=6.8 Hz), 4.04-4.18 (2H, m), 4.34-4.48 (1H, m), 5.79 (1H, d, J=7.2 Hz), 6.94-7.11 (2H, m), 7.40 (1H, dd, J=8.7, 1.5 Hz), 7.89-7.99 (2H, m).
mp 163-164° C.
Anal. Calcd for C$_{22}$H$_{22}$N$_2$O$_4$F$_2$: C, 63.45; H, 5.33; N, 6.73. Found: C, 63.46; H, 5.40; N, 6.69.

Example 38

N-((2S)-1-((2-(4-(cyclopropylmethoxy)-2,3-difluorophenyl)-7-fluoro-1,3-benzoxazol-6-yl)oxy)propan-2-yl)acetamide A) 4-(cyclopropylmethoxy)-2,3-difluorobenzoic Acid To a solution of 2,3-difluoro-4-hydroxybenzoic acid (10.0 g) in methanol (150 mL) was added sulfuric acid (5.63 g), and the mixture was heated under reflux for 1 day. To the reaction mixture was added saturated brine, and the mixture was extracted with ethyl acetate. The obtained organic layer was dried over anhydrous magnesium sulfate, and the solvent was evaporated under reduced pressure. To a solution of the obtained residue in DMF (100 mL) were added potassium carbonate (15.9 g) and (bromomethyl)cyclopropane (8.36 mL), and the mixture was stirred with heating at 70° C. for 1 hr. The reaction mixture was allowed to cool to room temperature, diluted with ethyl acetate, and washed with saturated brine. The obtained organic layer was subjected to silica gel column chromatography (NH, ethyl acetate), and the solvent was evaporated. To a solution of the obtained residue in a mixed solvent of THF (100 mL) and methanol (100 mL) was added 2 M aqueous sodium hydroxide solution (57 mL), and the mixture was stirred with heating at 60° C. for 40 min. The reaction mixture was allowed to cool to room temperature, and neutralized with 6 M hydrochloric acid, and the mixture was extracted with ethyl acetate. The obtained organic layer was washed with saturated brine, and dried over anhydrous magnesium sulfate, and the solvent was evaporated under reduced pressure. The obtained solid was washed with ethyl acetate to give the title compound (4.78 g).
$^1$H NMR (300 MHz, CDCl$_3$) δ 0.29-0.50 (2H, m), 0.61-0.80 (2H, m), 1.16-1.47 (1H, m), 3.98 (2H, d, J=7.2 Hz), 6.63-6.85 (1H, m), 7.64-7.83 (1H, m).

B) N-(2,4-bis(benzyloxy)-3-fluorophenyl)-4-(cyclopropylmethoxy)-2,3-difluorobenzamide To a solution of 1,3-bis(benzyloxy)-2-fluoro-4-nitrobenzene (5.00 g) in ethanol (75 mL) were added reduced iron (7.90 g) and iron(III) chloride (2.30 g), and the mixture was stirred with heating under reflux for 30 min. The reaction mixture was filtered, and the filtrate was diluted with ethyl acetate, washed with saturated brine, and dried over anhydrous magnesium sulfate. The solvent was evaporated under reduced pressure, and the obtained 2,4-bis(benzyloxy)-3-fluoroaniline was used for the next reaction without further purification.
To a solution of 4-(cyclopropylmethoxy)-2,3-difluorobenzoic acid (3.55 g) in THF (50 mL) were added oxalyl dichloride (2.04 mL) and DMF (2 drops), and the mixture was stirred at room temperature for 30 min. The solvent was evaporated under reduced pressure, and a solution of the obtained residue in THF (10 mL) was added to a solution of 2,4-bis(benzyloxy)-3-fluoroaniline (obtained in the above-mentioned reaction) in pyridine (10 mL), and the mixture was stirred at room temperature for 30 min. The reaction mixture was subjected to silica gel column chromatography (NH, ethyl acetate), the solvent was evaporated, and the obtained solid was washed with diethyl ether to give the title compound (4.40 g).
$^1$H NMR (300 MHz, CDCl$_3$) δ 0.33-0.45 (2H, m), 0.63-0.79 (2H, m), 1.22-1.46 (1H, m), 3.96 (2H, d, J=7.2 Hz), 5.14 (2H, s), 5.20 (2H, s), 6.71-6.92 (2H, m), 7.28-7.50 (10H, m), 7.77 (1H, td, J=8.9, 2.3 Hz), 8.12 (1H, dd, J=9.3, 2.1 Hz).

C) 2-(4-(cyclopropylmethoxy)-2,3-difluorophenyl)-7-fluoro-1,3-benzoxazol-6-ol

A mixture of N-(2,4-bis(benzyloxy)-3-fluorophenyl)-4-(cyclopropylmethoxy)-2,3-difluorobenzamide (4.40 g), 10% palladium-carbon (containing water (50%), 3.50 g) and THF (10 mL) was stirred at room temperature for 30 min under a hydrogen atmosphere. The catalyst was removed by filtration, and the obtained filtrate was concentrated under reduced pressure, and the solid was washed with diethyl ether. To a suspension of the obtained solid, hexachloroethane (4.88 g) and triphenylphosphine (5.41 g) in acetonitrile (40 mL) was added triethylamine (3.45 mL) at 0° C., and the mixture was stirred at room temperature for 15 min, and then with heating at 80° C. for 2 hr. The reaction mixture was filtered, the solvent was evaporated under reduced pressure, and the residue was purified by silica gel column chromatography (hexane/ethyl acetate) to give the title compound (1.37 g).

$^1$H NMR (300 MHz, CDCl$_3$) δ 0.26-0.51 (2H, m), 0.59-0.78 (2H, m), 1.29-1.46 (4H, m), 3.99 (2H, d, J=7.2 Hz), 5.56 (1H, d, J=2.3 Hz), 6.85 (1H, ddd, J=9.1, 7.2, 1.9 Hz), 7.04 (1H, dd, J=8.7, 7.9 Hz), 7.44 (1H, dd, J=8.7, 1.5 Hz), 7.77-7.93 (1H, m).

D) tert-butyl ((2S)-1-((2-(4-(cyclopropylmethoxy)-2,3-difluorophenyl)-7-fluoro-1,3-benzoxazol-6-yl)oxy)propan-2-yl)carbamate To a solution of 2-(4-(cyclopropylmethoxy)-2,3-difluorophenyl)-7-fluoro-1,3-benzoxazol-6-ol (1.37 g), tert-butyl ((2S)-1-hydroxypropan-2-yl)carbamate (1.07 g) and triphenylphosphine (1.61 g) in THF (15 mL) was added dropwise diisopropyl azodicarboxylate toluene solution (1.9 M, 3.23 mL) at 0° C., and the mixture was stirred at room temperature for 30 min. The reaction mixture was concentrated under reduced pressure, and the residue was purified by silica gel column chromatography (NH, hexane/ethyl acetate) to give the title compound (1.18 g).

$^1$H NMR (300 MHz, CDCl$_3$) δ 0.35-0.47 (2H, m), 0.62-0.78 (2H, m), 1.29-1.41 (1H, m), 1.56 (9H, s), 3.99 (2H, d, J=6.8 Hz), 4.03-4.18 (3H, m), 4.73-4.86 (1H, m), 6.79-6.90 (1H, m), 7.05 (1H, dd, J=8.9, 7.4 Hz), 7.47 (1H, dd, J=8.7, 1.5 Hz), 7.84-7.94 (1H, m).

E) N-((2S)-1-((2-(4-(cyclopropylmethoxy)-2,3-difluorophenyl)-7-fluoro-1,3-benzoxazol-6-yl)oxy)propan-2-yl)acetamide To tert-butyl ((2S)-1-((2-(4-(cyclopropylmethoxy)-2,3-difluorophenyl)-7-fluoro-1,3-benzoxazol-6-yl)oxy)propan-2-yl)carbamate (1.18 g) was added 4 M hydrogen chloride/ethyl acetate (10 mL), and the mixture was stirred at room temperature for 10 min, and concentrated. To the residue were added pyridine (10 mL) and acetic anhydride (10 mL), and the mixture was stirred at room temperature for 15 min. The reaction mixture was concentrated under reduced pressure, and the residue was purified by silica gel column chromatography (NH, hexane/ethyl acetate) to give the title compound (902 mg). $^1$H NMR (300 MHz, CDCl$_3$) δ 0.35-0.46 (2H, m), 0.66-0.77 (2H, m), 1.24-1.41 (4H, m), 2.02 (3H, s), 4.00 (2H, d, J=6.8 Hz), 4.05-4.18 (2H, m), 4.34-4.49 (1H, m), 5.86 (1H, d, J=7.9 Hz), 6.86 (1H, ddd, J=9.1, 7.2, 1.9 Hz), 7.05 (1H, dd, J=8.7, 7.2 Hz), 7.48 (1H, dd, J=8.7, 1.1 Hz), 7.89 (1H, td, J=8.1, 2.3 Hz).

mp 168° C.

Example 39

N-((2S)-1-((2-(4-(cyclopropylmethoxy)-2,5-difluorophenyl)-7-fluoro-1,3-benzoxazol-6-yl)oxy)propan-2-yl)acetamide A) 4-(cyclopropylmethoxy)-2,5-difluorobenzoic Acid A suspension of 2,4,5-trifluorobenzoic acid (25.0 g), sodium hydroxide (22.5 g) and water (125 mL) was stirred at 160° C. for 10 min under microwave irradiation. The reaction mixture was neutralized with 1 M hydrochloric acid, and the mixture was extracted with ethyl acetate. The extract was dried over anhydrous magnesium sulfate, and the solvent was evaporated under reduced pressure. To a solution of the obtained residue in DMF (100 mL) were added potassium carbonate (41.2 g) and (bromomethyl)cyclopropane (28.9 mL), and the mixture was stirred with heating at 70° C. for 1 hr. The reaction mixture was allowed to cool to room temperature, diluted with ethyl acetate, and washed with saturated brine. The obtained organic layer was subjected to silica gel column chromatography (NH, ethyl acetate), and then the solvent was evaporated. To a solution of the obtained residue in a mixed solvent of THF (100 mL) and methanol (50 mL) was added 2 M aqueous sodium hydroxide solution (142 mL), and the mixture was stirred with heating at 60° C. for 40 min. The reaction mixture was allowed to cool to room temperature, and neutralized with 6 M hydrochloric acid, and the mixture was extracted with ethyl acetate. The obtained organic layer was washed with saturated brine, and dried over anhydrous magnesium sulfate, and the solvent was evaporated under reduced pressure. The obtained solid was washed with ethyl acetate to give the title compound (3.77 g).

$^1$H NMR (300 MHz, CDCl$_3$) δ 0.36-0.45 (2H, m), 0.62-0.79 (2H, m), 1.22-1.42 (1H, m), 3.92 (2H, d, J=7.2 Hz), 6.70 (1H, dd, J=11.7, 6.8 Hz), 7.72 (1H, dd, J=11.1, 7.0 Hz).

B) N-(2,4-bis(benzyloxy)-3-fluorophenyl)-4-(cyclopropylmethoxy)-2,5-difluorobenzamide To a solution of 1,3-bis(benzyloxy)-2-fluoro-4-nitrobenzene (4.00 g) in ethanol (75 mL) were added reduced iron (6.32 g) and iron(III) chloride (1.84 g), and the mixture was stirred with heating under reflux for 30 min. The reaction mixture was filtered, and the filtrate was diluted with ethyl acetate, washed with saturated brine, and dried over anhydrous magnesium sulfate. The solvent was evaporated under reduced pressure, and the obtained 2,4-bis(benzyloxy)-3-fluoroaniline was used for the next reaction without further purification.

To a solution of 4-(cyclopropylmethoxy)-2,5-difluorobenzoic acid (1.35 g) in THF (50 mL) were added oxalyl dichloride (0.777 mL) and DMF (2 drops), and the mixture was stirred at room temperature for 30 min. The solvent was evaporated under reduced pressure, and a solution of the obtained residue in THF (10 mL) was added to a solution of 2,4-bis(benzyloxy)-3-fluoroaniline (obtained in the above-mentioned reaction) in pyridine (10 mL), and the mixture was stirred at room temperature for 30 min. The reaction mixture was subjected to silica gel column chromatography (NH, ethyl acetate), the solvent was evaporated, and the obtained solid was washed with diethyl ether to give the title compound (2.50 g).

$^1$H NMR (300 MHz, CDCl$_3$) δ 0.37-0.45 (2H, m), 0.67-0.75 (2H, m), 1.20-1.42 (1H, m), 3.91 (2H, d, J=7.2 Hz), 5.14 (2H, s), 5.18 (2H, s), 6.64 (1H, dd, J=13.0, 6.6 Hz), 6.77 (1H, t, J=8.9 Hz), 7.28-7.49 (10H, m), 7.80 (1H, dd, J=11.7, 7.5 Hz), 8.13 (1H, dd, J=9.0, 2.3 Hz), 8.87 (1H, d, J=15.4 Hz).

C) 2-(4-(cyclopropylmethoxy)-2,5-difluorophenyl)-7-fluoro-1,3-benzoxazol-6-ol

A mixture of N-(2,4-bis(benzyloxy)-3-fluorophenyl)-4-(cyclopropylmethoxy)-2,5-difluorobenzamide (2.50 g), 10% palladium-carbon (containing water (50%), 2.00 g) and THF (20 mL) was stirred at room temperature for 30 min under a hydrogen atmosphere. The catalyst was removed by filtration, and the obtained filtrate was concentrated under reduced pressure, and the solid was washed with diethyl ether. To a suspension of the obtained solid, hexachloroethane (2.78 g) and triphenylphosphine (3.08 g) in acetonitrile (20 mL) was added triethylamine (1.96 mL) at 0° C., and the mixture was stirred at room temperature for 15 min, and then with heating at 80° C. for 2 hr. The reaction mixture was filtered, the solvent was evaporated under reduced pressure, and the residue was purified by silica gel column chromatography (hexane/ethyl acetate) to give the title compound (1.34 g).

$^1$H NMR (300 MHz, CDCl$_3$) δ 0.38-0.45 (2H, m), 0.66-0.77 (2H, m), 1.28-1.41 (1H, m), 3.95 (2H, d, J=6.8 Hz), 5.33 (1H, brs), 6.83 (1H, dd, J=12.1, 6.8 Hz), 6.99-7.08 (1H, m), 7.44 (1H, dd, J=8.7, 1.1 Hz), 7.90 (1H, dd, J=11.3, 6.8 Hz).

D) N-((2S)-1-((2-(4-(cyclopropylmethoxy)-2,5-difluorophenyl)-7-fluoro-1,3-benzoxazol-6-yl)oxy)propan-2-yl)acetamide To a solution of 2-(4-(cyclopropylmethoxy)-2,5-difluorophenyl)-7-fluoro-1,3-benzoxazol-6-ol (1.34 g), tert-butyl ((2S)-1-hydroxypropan-2-yl)carbamate (1.05 g) and triphenylphosphine (1.57 g) in THF (50 mL) was added dropwise diisopropyl azodicarboxylate toluene solution (1.9 M, 3.16 mL) at 0° C., and the mixture was stirred at room temperature for 30 min. The reaction mixture was concentrated under reduced pressure, and the residue was purified by silica gel column chromatography (NH, hexane/ethyl acetate). To the obtained solid was added 4 M hydrogen chloride/ethyl acetate (10 mL), and the mixture was stirred at room temperature for 10 min, and concentrated. To the residue were added pyridine (10 mL) and acetic anhydride (10 mL), and the mixture was stirred at room temperature for 15 min. The reaction mixture was concentrated under reduced pressure, and the residue was purified by silica gel column chromatography (NH, hexane/ethyl acetate) to give the title compound (704 mg).

$^1$H NMR (300 MHz, CDCl$_3$) δ 0.34-0.47 (2H, m), 0.63-0.78 (2H, m), 1.29-1.45 (4H, m), 2.02 (3H, s), 3.95 (2H, d, J=7.2 Hz), 4.11 (2H, qd, J=9.4, 3.8 Hz), 4.33-4.54 (1H, m), 5.80 (1H, d, J=7.9 Hz), 6.83 (1H, dd, J=11.7, 6.8 Hz), 7.04 (1H, dd, J=8.7, 7.2 Hz), 7.47 (1H, dd, J=8.9, 1.3 Hz), 7.91 (1H, dd, J=11.3, 6.8 Hz).

mp 153° C.

Example 40

N-((2S)-1-((2-(4-(cyclopropylmethoxy)-3,5-difluorophenyl)-7-fluoro-1,3-benzoxazol-6-yl)oxy)propan-2-yl)acetamide

A) 4-(cyclopropylmethoxy)-3,5-difluorobenzoic Acid

To a solution of cyclopropylmethanol (5.62 mL) in DMF (30 mL) was added sodium hydride (60% oil, 2.84 g), and the mixture was stirred at room temperature for 15 min. To the reaction mixture was added 3,4,5-trifluorobenzoic acid (5.00 g), and the mixture was stirred at room temperature for 30 min. The reaction mixture was neutralized with 6 M hydrochloric acid, and the mixture was extracted with ethyl acetate. The obtained organic layer was washed with saturated brine, and dried over anhydrous magnesium sulfate, and the solvent was evaporated under reduced pressure. To a solution of the obtained residue in DMF (20 mL) were added potassium carbonate (3.92 g) and methyl iodide (1.77 mL), and the mixture was stirred with heating at 60° C. for 40 min. The reaction mixture was allowed to cool to room temperature, diluted with ethyl acetate, washed with saturated brine, and dried over anhydrous magnesium sulfate. The solvent was evaporated under reduced pressure, and the obtained residue was purified by silica gel column chromatography (hexane/ethyl acetate). To a solution of the obtained oil in a mixed solvent of THF (20 mL) and methanol (20 mL) was added 2 M aqueous sodium hydroxide solution (28.8 mL), and the mixture was stirred with heating at 60° C. for 40 min. The reaction mixture was allowed to cool to room temperature, and neutralized with 6 M hydrochloric acid, and the mixture was extracted with ethyl acetate. The obtained organic layer was washed with saturated brine, and dried over anhydrous magnesium sulfate, and the solvent was evaporated under reduced pressure. The obtained solid was washed with hexane to give the title compound (5.32 g).

$^1$H NMR (300 MHz, CDCl$_3$) δ 0.26-0.38 (2H, m), 0.56-0.67 (2H, m), 1.17-1.40 (1H, m), 4.11 (2H, d, J=7.2 Hz), 7.55-7.72 (2H, m).

B) N-(2,4-bis(benzyloxy)-3-fluorophenyl)-4-(cyclopropylmethoxy)-3,5-difluorobenzamide To a solution of 1,3-bis(benzyloxy)-2-fluoro-4-nitrobenzene (10.0 g) in ethanol (75 mL) were added reduced iron (15.8 g) and iron(III) chloride (4.59 g), and the mixture was stirred with heating under reflux for 30 min. The reaction mixture was filtered, and the filtrate was diluted with ethyl acetate, washed with saturated brine, and dried over anhydrous magnesium sulfate. The solvent was evaporated under reduced pressure, and the obtained 2,4-bis(benzyloxy)-3-fluoroaniline was used for the next reaction without further purification.

To a solution of 4-(cyclopropylmethoxy)-3,5-difluorobenzoic acid (1.26 g) in THF (20 mL) were added oxalyl dichloride (0.725 mL) and DMF (2 drops), and the mixture was stirred at room temperature for 30 min. The solvent was evaporated under reduced pressure, and a solution of the obtained residue in THF (10 mL) was added to a solution of 2,4-bis(benzyloxy)-3-fluoroaniline (obtained in the above-mentioned reaction) in pyridine (10 mL), and the mixture was stirred at room temperature for 30 min. The reaction mixture was subjected to silica gel column chromatography (NH, ethyl acetate), the solvent was evaporated, and the obtained solid was washed with diethyl ether to give the title compound (1.55 g).

$^1$H NMR (300 MHz, CDCl$_3$) δ 0.26-0.36 (2H, m), 0.56-0.70 (2H, m), 1.11-1.37 (1H, m), 4.05 (2H, d, J=7.2 Hz), 5.10-5.17 (2H, m), 5.19 (2H, s), 6.79 (1H, t, J=8.9 Hz), 6.95-7.12 (2H, m), 7.28-7.56 (10H, m), 7.93 (1H, s), 8.05 (1H, dd, J=9.4, 2.3 Hz).

C) tert-butyl ((2S)-1-((2-(4-(cyclopropylmethoxy)-3,5-difluorophenyl)-7-fluoro-1,3-benzoxazol-6-yl)oxy)propan-2-yl)carbamate A mixture of N-(2,4-bis(benzyloxy)-3-fluorophenyl)-4-(cyclopropylmethoxy)-3,5-difluorobenzamide (1.55 g), 10% palladium-carbon (containing water (50%), 1.50 g) and THF (20 mL) was stirred at room temperature for 30 min under a hydrogen atmosphere. The catalyst was removed by filtration, and the obtained filtrate was concentrated under reduced pressure, and the solid was washed with diethyl ether. To a suspension of the obtained solid, hexachloroethane (1.54 g) and triphenylphosphine (1.71 g) in acetonitrile (20 mL) was added triethylamine (1.09 mL) at 0° C., and the mixture was stirred at room temperature for 15 min, and then with heating at 80° C. for 2 hr. The reaction mixture was filtered, the solvent was evaporated under reduced pressure, and the residue was purified by silica gel column chromatography (hexane/ethyl acetate). To a solution of the obtained solid, tert-butyl ((2S)-1-hydroxypropan-2-yl)carbamate (683 mg) and triphenylphosphine (1.02 g) in THF (20 mL) was added dropwise diisopropyl azodicarboxylate toluene solution (1.9 M, 2.05 mL) at 0° C., and the mixture was stirred at room temperature for 30 min. The reaction mixture was concentrated under reduced pressure, and the residue was purified by silica gel column chromatography (NH, hexane/ethyl acetate) to give the title compound (1.28 g). $^1$H NMR (300 MHz, CDCl$_3$) δ 0.30-0.40 (2H, m), 0.56-0.66 (2H, m), 1.27 (1H, d, J=6.0 Hz), 1.31-1.38 (3H, m), 1.46 (9H, s), 4.02-4.16 (4H, m), 4.70-4.86 (1H, m), 6.17-6.41 (1H, m), 7.05 (1H, dd, J=8.7, 7.2 Hz), 7.42 (1H, dd, J=8.7, 1.1 Hz), 7.78 (2H, d, J=8.7 Hz).

D) N-((2S)-1-((2-(4-(cyclopropylmethoxy)-3,5-difluorophenyl)-7-fluoro-1,3-benzoxazol-6-yl)oxy)propan-2-yl)acetamide To tert-butyl ((2S)-1-((2-(4-(cyclopropylmethoxy)-3,5-difluorophenyl)-7-fluoro-1,3-benzoxazol-6-yl)oxy)propan-2-yl)carbamate (1.28 g) was added 4 M hydrogen chloride/ethyl acetate (10 mL), and the mixture was stirred at room temperature for 10 min, and concentrated. To the residue were added pyridine (10 mL) and acetic anhydride (10 mL), and the mixture was stirred at room temperature for 15 min. The reaction mixture was concentrated under reduced pressure, and the residue was dissolved in ethyl acetate/methanol, and the solution was subjected to silica gel column chromatography (NH, ethyl acetate). The solvent was evaporated, and the obtained solid was recrystallized (hexane/ethyl acetate) to give the title compound as white crystals (477 mg).
$^1$H NMR (300 MHz, CDCl$_3$) δ 0.25-0.39 (2H, m), 0.55-0.68 (2H, m), 1.20-1.33 (1H, m), 1.37 (3H, d, J=7.2 Hz), 2.02 (3H, s), 4.04-4.19 (4H, m), 4.33-4.51 (1H, m), 5.79 (1H, d, J=7.6 Hz), 7.05 (1H, dd, J=8.7, 7.6 Hz), 7.43 (1H, dd, J=8.7, 1.5 Hz), 7.71-7.83 (2H, m).
mp 146-147° C.

Example 41

N-((2S)-1-((2-(4-(benzyloxy)-3-fluorophenyl)-7-fluoro-1,3-benzoxazol-6-yl)oxy)propan-2-yl)acetamide A) 4-(benzyloxy)-3-fluoro-N-(3-fluoro-2,4-dihydroxyphenyl)benzamide A mixture of 1,3-bis(benzyloxy)-2-fluoro-4-nitrobenzene (4.00 g), 10% palladium-carbon (containing water (50%), 4.00 g) and ethanol (30 mL) was stirred at room temperature for 1 hr under a hydrogen atmosphere. The catalyst was removed by filtration, and the filtrate was concentrated under reduced pressure. The obtained 4-amino-2-fluorobenzene-1,3-diol was used for the next reaction without further purification.
To a solution of 4-(benzyloxy)-3-fluorobenzoic acid (1.89 g) in THF (30 mL) were added oxalyl dichloride (0.670 mL) and DMF (2 drops), and the mixture was stirred at room temperature for 15 min. The solvent was evaporated under reduced pressure, and the obtained residue was added to a mixture of 4-amino-2-fluorobenzene-1,3-diol (obtained in the above-mentioned reaction) in a mixed solvent of THF (30 mL) and saturated aqueous sodium hydrogen carbonate solution (15 mL). The reaction mixture was extracted with ethyl acetate, the organic layer was dried over anhydrous magnesium sulfate, and the solvent was evaporated under reduced pressure. The obtained solid was washed with diethyl ether to give the title compound (2.27 g).
$^1$H NMR (300 MHz, DMSO-d$_6$) δ 5.28 (2H, s), 6.42 (1H, t, J=8.9 Hz), 6.94 (1H, dd, J=9.1, 1.9 Hz), 7.30-7.54 (6H, m), 7.73-7.92 (2H, m), 9.48-9.73 (3H, m).

B) 2-(4-(benzyloxy)-3-fluorophenyl)-7-fluoro-1,3-benzoxazol-6-ol

To a suspension of 4-(benzyloxy)-3-fluoro-N-(3-fluoro-2,4-dihydroxyphenyl)benzamide (2.27 g), hexachloroethane (3.62 g) and triphenylphosphine (4.01 g) in acetonitrile (30 mL) was added triethylamine (2.56 mL) at 0° C., and the mixture was stirred at room temperature for 15 min, and then at 80° C. for 2 hr. The solvent was evaporated under reduced pressure, and the residue was purified by silica gel column chromatography (hexane/ethyl acetate) to give the title compound (1.13 g).
$^1$H NMR (300 MHz, CDCl$_3$) δ 5.14 (1H, d, J=3.4 Hz), 5.24 (2H, s), 7.02 (1H, t, J=8.1 Hz), 7.12 (1H, t, J=8.5 Hz), 7.33-7.51 (6H, m), 7.87-8.01 (2H, m).

C) N-((2S)-1-((2-(4-(benzyloxy)-3-fluorophenyl)-7-fluoro-1,3-benzoxazol-6-yl)oxy)propan-2-yl)acetamide To a solution of 2-(4-(benzyloxy)-3-fluorophenyl)-7-fluoro-1,3-benzoxazol-6-ol (1.13 g), tert-butyl ((2S)-1-hydroxypropan-2-yl)carbamate (0.841 g) and triphenylphosphine (1.26 g) in THF (20 mL) was added dropwise diisopropyl azodicarboxylate toluene solution (1.9 M, 2.52 mL) at 0° C., and the mixture was stirred at room temperature for 30 min. The reaction mixture was concentrated under reduced pressure, and the residue was purified by silica gel column chromatography (NH, hexane/ethyl acetate) to give a white solid. To the obtained solid was added 4 M hydrogen chloride/ethyl acetate (10 mL), and the mixture was stirred at room temperature for 10 min, and concentrated. To the residue were added pyridine (10 mL) and acetic anhydride (10 mL), and the mixture was stirred at room temperature for 15 min. The reaction mixture was concentrated under reduced pressure, and the residue was dissolved in ethyl acetate/methanol, and the solution was subjected to silica gel column chromatography (NH, ethyl acetate). The solvent was evaporated, and the obtained solid was recrystallized (hexane/ethyl acetate) to give the title compound as white crystals (1.08 g).
$^1$H NMR (300 MHz, CDCl$_3$) δ 1.37 (3H, d, J=7.2 Hz), 2.02 (3H, s), 4.01-4.19 (2H, m), 4.35-4.49 (1H, m), 5.24 (2H, s), 5.79 (1H, d, J=7.5 Hz), 7.02 (1H, dd, J=8.7, 7.2 Hz), 7.12 (1H, t, J=8.5 Hz), 7.31-7.52 (6H, m), 7.90-8.01 (2H, m).

Example 42

N-((2S)-1-((2-(4-((2,2-difluorocyclopropyl)methoxy)-3-fluorophenyl)-7-fluoro-1,3-benzoxazol-6-yl)oxy)propan-2-yl)acetamide A) N-((2S)-1-((7-fluoro-2-(3-fluoro-4-hydroxyphenyl)-1,3-benzoxazol-6-yl)oxy)propan-2-yl)acetamide A mixture of N-((2S)-1-((2-(4-(benzyloxy)-3-fluorophenyl)-7-fluoro-1,3-benzoxazol-6-yl)oxy)propan-2-yl)acetamide (1.05 g), 10% palladium-carbon (containing water (50%), 1.00 g) and THF (10 mL) was stirred at room temperature for 30 min under a hydrogen atmosphere. The catalyst was removed by filtration, and the obtained filtrate was concentrated under reduced pressure to give the title compound (810 mg).

$^1$H NMR (300 MHz, CDCl$_3$) δ 1.37 (3H, d, J=6.8 Hz), 2.02 (3H, s), 4.11 (2H, qd, J=9.3, 3.8 Hz), 4.30-4.49 (1H, m), 5.68-5.83 (1H, m), 6.95-7.06 (1H, m), 7.14 (1H, t, J=8.7 Hz), 7.41 (1H, dd, J=9.1, 1.1 Hz), 7.88-8.01 (2H, m).

B) N-((2S)-1-((2-(4-((2,2-difluorocyclopropyl)methoxy)-3-fluorophenyl)-7-fluoro-1,3-benzoxazol-6-yl)oxy)propan-2-yl)acetamide A suspension of N-((2S)-1-((7-fluoro-2-(3-fluoro-4-hydroxyphenyl)-1,3-benzoxazol-6-yl)oxy)propan-2-yl)acetamide (810 mg), 1-bromomethyl-2,2-difluorocyclopropane (573 mg) and potassium carbonate (463 mg) in DMF (10 mL) was stirred at 70° C. for 1 hr and 30 min. The reaction mixture was diluted with ethyl acetate, and washed with saturated brine, and the organic layer was subjected to silica gel column chromatography (NH, ethyl acetate), and the solvent was evaporated. The obtained solid was washed with diethyl ether to give the title compound (880 mg).

$^1$H NMR (300 MHz, CDCl$_3$) δ 1.26-1.44 (4H, m), 1.57-1.74 (1H, m), 2.02 (3H, s), 2.07-2.24 (1H, m), 4.01-4.31 (4H, m), 4.35-4.48 (1H, m), 5.78 (1H, d, J=8.7 Hz), 6.99-7.13 (2H, m), 7.41 (1H, dd, J=8.9, 1.3 Hz), 7.92-8.02 (2H, m).

Example 43

N-((2S)-1-((2-(4-(cyclopropylmethoxy)-3-fluorophenyl)-4-fluoro-1,3-benzoxazol-6-yl)oxy)propan-2-yl)acetamide A) tert-butyl (2,4-dimethoxyphenyl)carbamate To a solution of tribromoindium (116 mg) and di-tert-butyl dicarbonate (7.12 g) in THF (50 mL) was added 2,4-dimethoxyaniline (5.0 g). The reaction mixture was stirred at room temperature for 30 min, diluted with ethyl acetate, washed with saturated brine, dried over anhydrous magnesium sulfate, and concentrated under reduced pressure. The residue was purified by silica gel column chromatography (hexane/ethyl acetate) to give the title compound (7.09 g).

$^1$H NMR (300 MHz, CDCl$_3$) δ 1.51 (9H, s), 3.78 (3H, s), 3.83 (3H, s), 6.42-6.49 (2H, m), 7.91 (1H, d, J=8.3 Hz).

B) tert-butyl (2-fluoro-4,6-dimethoxyphenyl)carbamate

To a solution of tert-butyl (2,4-dimethoxyphenyl)carbamate (7.09 g) and tetramethylenediamine (12.7 mL) in THF (70 mL) was added 1.6 M n-butyllithium hexane solution (52.5 mL) at −78° C., and the mixture was stirred at the same temperature for 20 min, and then at room temperature for 45 min. To the reaction mixture was added a solution of N-fluoro-N-(phenylsulfonyl)benzenesulfonamide (12.8 g) in THF (30 mL) at −78° C., and the mixture was allowed to warm to room temperature, and stirred overnight. To the reaction mixture was added saturated aqueous ammonium chloride solution, and the mixture was extracted with ethyl acetate. The extract was washed with saturated brine, dried over anhydrous magnesium sulfate, and concentrated under reduced pressure. The residue was purified by silica gel column chromatography (hexane/ethyl acetate) to give the title compound (2.90 g).

$^1$H NMR (300 MHz, CDCl$_3$) δ 1.52 (9H, s), 3.85 (3H, s), 3.98 (3H, d, J=1.9 Hz), 6.63 (1H, t, J=9.1 Hz), 6.85 (1H, brs), 7.73 (1H, d, J=7.9 Hz).

C) 4-(cyclopropylmethoxy)-3-fluoro-N-(2-fluoro-4,6-dihydroxyphenyl)benzamide

To a solution of 4-(cyclopropylmethoxy)-3-fluorobenzoic acid (1.57 g) in THF (50 mL) were added oxalyl dichloride (0.982 mL) and DMF (2 drops), and the mixture was stirred at room temperature for 30 min. The solvent was evaporated under reduced pressure to give 4-(cyclopropylmethoxy)-3-fluorobenzoyl chloride. This compound was used for the next reaction without further purification.

To a solution of tert-butyl (2-fluoro-4,6-dimethoxyphenyl)carbamate (2.90 g) in toluene (50 mL) was added tribromoborane (3.15 mL) at 0° C., and the mixture was stirred at room temperature for 15 hr. To the reaction mixture were added water, saturated aqueous sodium hydrogen carbonate solution (50 mL) and THF (50 mL), and then a solution of 4-(cyclopropylmethoxy)-3-fluorobenzoyl chloride (obtained in the above-mentioned reaction) in THF (3 mL) was added thereto, and the mixture was stirred at room temperature for 30 min. The reaction mixture was extracted with ethyl acetate, the organic layer was dried over anhydrous magnesium sulfate, and the solvent was evaporated under reduced pressure. The obtained solid was washed with diethyl ether to give the title compound (2.29 g).

$^1$H NMR (300 MHz, DMSO-d$_6$) δ 0.32-0.41 (2H, m), 0.54-0.66 (2H, m), 1.20-1.36 (1H, m), 3.99 (2H, d, J=7.2 Hz), 6.42 (1H, t, J=8.7 Hz), 6.94 (1H, dd, J=8.9, 2.1 Hz), 7.26 (1H, t, J=8.9 Hz), 7.76-7.88 (2H, m), 9.51-9.74 (3H, m).

D) 2-(4-(cyclopropylmethoxy)-3-fluorophenyl)-4-fluoro-1,3-benzoxazol-6-ol

To a solution of 4-(cyclopropylmethoxy)-3-fluoro-N-(2-fluoro-4,6-dihydroxyphenyl)benzamide (2.29 g), hexachloroethane (4.04 g) and triphenylphosphine (4.48 g) in acetonitrile (50 mL) was added triethylamine (2.86 mL) at 0° C., and the mixture was stirred at room temperature for 15 min, and then with heating at 80° C. for 1 hr. The reaction mixture was filtered, the solvent was evaporated under reduced pressure, and the residue was purified by silica gel column chromatography (hexane/ethyl acetate) to give the title compound (110 mg). $^1$H NMR (300 MHz, CDCl$_3$) δ 0.37-0.45 (2H, m), 0.65-0.74 (2H, m), 1.24-1.44 (1H, m), 3.97 (2H, d, J=7.2 Hz), 5.26 (1H, d, J=3.4 Hz), 6.97-7.10 (2H, m), 7.38 (1H, dd, J=8.5, 1.3 Hz), 7.87-7.98 (2H, m).

E) tert-butyl ((2S)-1-((2-(4-(cyclopropylmethoxy)-3-fluorophenyl)-4-fluoro-1,3-benzoxazol-6-yl)oxy)propan-2-yl)carbamate To a solution of 2-(4-(cyclopropylmethoxy)-3-fluorophenyl)-4-fluoro-1,3-benzoxazol-6-ol (110 mg), tert-butyl ((2S)-1-hydroxypropan-2-yl)carbamate (91.0 mg) and triphenylphosphine (136 mg) in THF (5 mL) was added dropwise diisopropyl azodicarboxylate toluene solution (1.9 M, 0.274 mL) at 0° C., and the mixture was stirred at room temperature for 30 min. The reaction mixture was concentrated under reduced pressure, and the residue was purified by silica gel column chromatography (NH, hexane/ethyl acetate) to give the title compound (159 mg).

$^1$H NMR (300 MHz, CDCl$_3$) δ 0.40 (2H, q, J=4.9 Hz), 0.64-0.75 (2H, m), 1.29-1.40 (4H, m), 1.46 (9H, s), 3.97 (2H, d, J=6.8 Hz), 4.03-4.15 (3H, m), 4.78 (1H, td, J=11.5, 6.0 Hz), 6.98-7.10 (2H, m), 7.40 (1H, dd, J=8.7, 1.5 Hz), 7.91-7.99 (2H, m).

F) N-((2S)-1-((2-(4-(cyclopropylmethoxy)-3-fluorophenyl)-4-fluoro-1,3-benzoxazol-6-yl)oxy)propan-2-yl)acetamide To tert-butyl ((2S)-1-((2-(4-(cyclopropylmethoxy)-3-fluorophenyl)-4-fluoro-1,3-benzoxazol-6-yl)oxy)propan-2-yl)carbamate (159 mg) was added 4 M hydrogen chloride/ethyl acetate (10 mL), and the mixture was stirred at room temperature for 10 min, and concentrated. To the residue were added pyridine (10 mL) and acetic anhydride (10 mL), and the mixture was stirred at room temperature for 15 min. The reaction mixture was concentrated under reduced pressure, and the residue was dissolved in ethyl acetate/methanol, and the solution was subjected to silica gel column chromatography (NH, ethyl acetate). The solvent was evaporated, and the obtained solid was recrystallized (hexane/ethyl acetate) to give the title compound as white crystals (73.5 mg).
$^1$H NMR (300 MHz, CDCl$_3$) δ 0.33-0.44 (2H, m), 0.59-0.75 (2H, m), 1.24-1.41 (4H, m), 2.02 (3H, s), 3.97 (2H, d, J=7.2 Hz), 4.05-4.18 (2H, m), 4.31-4.47 (1H, m), 5.69-5.86 (1H, m), 6.95-7.09 (2H, m), 7.41 (1H, dd, J=8.7, 1.1 Hz), 7.84-8.02 (2H, m).

Example 44

N-((2S)-1-((2-(4-(cyclopropylmethoxy)-3,5-difluorophenyl)-1,3-benzoxazol-6-yl)oxy)propan-2-yl)acetamide

A) 4-(cyclopropylmethoxy)-N-(2,4-dihydroxyphenyl)-3,5-difluorobenzamide

To a solution of 4-(cyclopropylmethoxy)-3,5-difluorobenzoic acid (2.77 g) in THF (20 mL) were added oxalyl dichloride (1.59 mL) and DMF (2 drops), and the mixture was stirred at room temperature for 30 min. The solvent was evaporated under reduced pressure, and the obtained residue was added to a mixture of 4-aminoresorcinol hydrochloride (2.45 g) in a mixed solvent of THF (50 mL) and saturated aqueous sodium hydrogen carbonate solution (50 mL). The reaction mixture was extracted with ethyl acetate, the organic layer was dried over anhydrous magnesium sulfate, and the solvent was evaporated under reduced pressure. The obtained solid was washed with diethyl ether to give the title compound (3.78 g).
$^1$H NMR (300 MHz, DMSO-d$_6$) δ 0.20-0.36 (2H, m), 0.48-0.62 (2H, m), 1.14-1.28 (1H, m), 4.05 (2H, d, J=7.2 Hz), 6.23 (1H, dd, J=8.7, 2.6 Hz), 6.36 (1H, d, J=2.6 Hz), 7.14 (1H, d, J=8.3 Hz), 7.63-7.81 (2H, m), 9.23 (1H, s), 9.38 (1H, s), 9.48 (1H, s).

B) 2-(4-(cyclopropylmethoxy)-3,5-difluorophenyl)-1,3-benzoxazol-6-ol

To a solution of 4-(cyclopropylmethoxy)-N-(2,4-dihydroxyphenyl)-3,5-difluorobenzamide (3.78 g), hexachloroethane (6.67 g) and triphenylphosphine (7.39 g) in acetonitrile (50 mL) was added triethylamine (3.42 mL), and the mixture was stirred at room temperature for 15 min, and then with heating at 80° C. for 1 hr. The reaction mixture was filtered, the solvent was evaporated under reduced pressure, and the residue was purified by silica gel column chromatography (hexane/ethyl acetate) to give the title compound (1.92 g).
$^1$H NMR (300 MHz, CDCl$_3$) δ 0.27-0.41 (2H, m), 0.55-0.67 (2H, m), 1.18-1.37 (1H, m), 4.08 (2H, d, J=7.2 Hz), 5.07-5.37 (1H, m), 6.87 (1H, dd, J=8.5, 2.5 Hz), 7.06 (1H, d, J=2.6 Hz), 7.59 (1H, d, J=8.7 Hz), 7.63-7.83 (2H, m).

C) tert-butyl ((2S)-1-((2-(4-(cyclopropylmethoxy)-3,5-difluorophenyl)-1,3-benzoxazol-6-yl)oxy)propan-2-yl)carbamate To a solution of 2-(4-(cyclopropylmethoxy)-3,5-difluorophenyl)-1,3-benzoxazol-6-ol (1.92 g), tert-butyl ((2S)-1-hydroxypropan-2-yl)carbamate (1.59 g) and triphenylphosphine (2.38 g) in THF (15 mL) was added dropwise diisopropyl azodicarboxylate toluene solution (1.9 M, 4.78 mL), and the mixture was stirred at room temperature for 16 hr. The reaction mixture was concentrated under reduced pressure, and the residue was purified by silica gel column chromatography (NH, hexane/ethyl acetate) to give the title compound (2.60 g). $^1$H NMR (300 MHz, CDCl$_3$) δ 0.29-0.37 (2H, m), 0.56-0.67 (2H, m), 1.17-1.36 (4H, m), 1.46 (9H, s), 3.94-4.19 (5H, m), 4.67-4.82 (1H, m), 6.97 (1H, dd, J=8.7, 2.3 Hz), 7.10 (1H, d, J=2.3 Hz), 7.62 (1H, d, J=8.7 Hz), 7.68-7.81 (2H, m).

D) N-((2S)-1-((2-(4-(cyclopropylmethoxy)-3,5-difluorophenyl)-1,3-benzoxazol-6-yl)oxy)propan-2-yl)acetamide To tert-butyl ((2S)-1-((2-(4-(cyclopropylmethoxy)-3,5-difluorophenyl)-1,3-benzoxazol-6-yl)oxy)propan-2-yl)carbamate (2.60 g) was added 4 M hydrogen chloride/ethyl acetate (10 mL), and the mixture was stirred at room temperature for 10 min, and concentrated. To the residue were added pyridine (10 mL) and acetic anhydride (10 mL), and the mixture was stirred at room temperature for 15 min. The reaction mixture was concentrated under reduced pressure, and the residue was dissolved in ethyl acetate/methanol, and the solution was subjected to silica gel column chromatography (NH, ethyl acetate). The solvent was evaporated, and the obtained solid was washed with diethyl ether to give the title compound (1.39 g).
$^1$H NMR (300 MHz, CDCl$_3$) δ 0.27-0.39 (2H, m), 0.55-0.68 (2H, m), 1.19-1.33 (1H, m), 1.35 (3H, d, J=6.8 Hz), 2.02 (3H, s), 3.95-4.06 (2H, m), 4.08 (2H, d, J=7.2 Hz), 4.34-4.52 (1H, m), 5.72 (1H, d, J=7.6 Hz), 6.98 (1H, dd, J=8.7, 2.3 Hz), 7.12 (1H, d, J=2.3 Hz), 7.62 (1H, d, J=8.7 Hz), 7.68-7.82 (2H, m).

Example 45

N-((2S)-1-((2-(4-((2,2-difluorocyclopropyl)methoxy)-3-fluorophenyl)-1,3-benzoxazol-6-yl)oxy)propan-2-yl)acetamide A suspension of N-((2S)-1-((2-(3-fluoro-4-hydroxyphenyl)-1,3-benzoxazol-6-yl)oxy)propan-2-yl)acetamide (290 mg), 1-bromomethyl-2,2-difluorocyclopropane (288 mg) and potassium carbonate (175 mg) in DMF (10 mL) was stirred at 70° C. for 1 hr and 30 min. The reaction mixture was diluted with ethyl acetate, and washed with saturated brine, and the organic layer was subjected to silica gel column chromatography (NH, ethyl acetate), and the solvent was evaporated. The obtained solid was washed with diethyl ether to give the title compound (279 mg).
$^1$H NMR (300 MHz, CDCl$_3$) δ 1.26-1.42 (4H, m), 1.57-1.73 (1H, m), 2.01 (3H, s), 2.07-2.24 (1H, m), 3.96-4.08 (2H, m), 4.09-4.19 (1H, m), 4.21-4.31 (1H, m), 4.37-4.50 (1H, m), 5.70 (1H, d, J=7.2 Hz), 6.96 (1H, dd, J=8.9, 2.5 Hz), 7.07 (1H, t, J=8.3 Hz), 7.12 (1H, d, J=2.3 Hz), 7.61 (1H, d, J=8.7 Hz), 7.89-7.98 (2H, m).

Example 46

N-((2S)-1-((2-(4-((2,2-difluorocyclopropyl)methoxy)-3,5-difluorophenyl)-7-fluoro-1,3-benzoxazol-6-yl)oxy)propan-2-yl)acetamide A) 4-(benzyloxy)-3,5-difluorobenzoic Acid To a solution of benzyl alcohol (22.0 mL) in DMF (100 mL) was added sodium hydride (60% oil, 8.52 g), and the mixture was stirred at room temperature for 15 min. To the reaction mixture was added 3,4,5-trifluorobenzoic acid (15.0 g), and the mixture was stirred at room temperature for 1 hr. The reaction mixture was neutralized with 6 M hydrochloric acid, and the mixture was extracted with ethyl acetate. The obtained organic layer was washed with saturated brine, and dried over anhydrous magnesium sulfate, and the solvent was evaporated under reduced pressure. To a solution of the obtained residue in DMF (100 mL) were added potassium carbonate (11.8 g) and methyl iodide (5.30 mL), and the mixture was stirred with heating at 60° C. for 15 min. The reaction mixture was allowed to cool to room temperature, diluted with ethyl acetate, washed with saturated brine, and dried over anhydrous magnesium sulfate. The solvent was evaporated under reduced pressure, and the obtained residue was purified by silica gel column chromatography (hexane/ethyl acetate). To a solution of the obtained oil in a mixed solvent of THF (100 mL) and methanol (50 mL) was added 2 M aqueous sodium hydroxide solution (85 mL), and the mixture was stirred with heating at 60° C. for 40 min. The reaction mixture was allowed to cool to room temperature, and neutralized with 6 M hydrochloric acid, and the mixture was extracted with ethyl acetate. The obtained organic layer was washed with saturated brine, and dried over anhydrous magnesium sulfate, and the solvent was evaporated under reduced pressure. The obtained solid was washed with diethyl ether/hexane to give the title compound (18.2 g).
$^1$H NMR (300 MHz, CDCl$_3$) δ 5.31 (2H, s), 7.29-7.48 (5H, m), 7.55-7.70 (2H, m).

B) N-((2S)-1-((2-(4-(benzyloxy)-3,5-difluorophenyl)-1,3-benzoxazol-6-yl)oxy)propan-2-yl)acetamide Using 4-(benzyloxy)-3,5-difluorobenzoic acid, and in the same manner as in Step B, Step C and Step D of Example 1, the title compound was obtained.
MS (ESI+): [M+H]$^+$ 453.1.

C) N-((2S)-1-((2-(4-((2,2-difluorocyclopropyl)methoxy)-3,5-difluorophenyl)-7-fluoro-1,3-benzoxazol-6-yl)oxy)propan-2-yl)acetamide Using N-((2S)-1-((2-(4-(benzyloxy)-3,5-difluorophenyl)-1,3-benzoxazol-6-yl)oxy)propan-2-yl)acetamide, and in the same manner as in Step A of Example 4 and Step B of Example 42, the title compound was obtained.

Example 47

N-((2S)-1-((2-(4-(cyclopropylmethoxy)-3,5-difluorophenyl)[1,3]oxazolo[4,5-c]pyridin-6-yl)oxy)propan-2-yl)acetamide A) tert-butyl ((2S)-1-((4-chloro-5-((4-(cyclopropylmethoxy)-3,5-difluorobenzoyl)amino)pyridin-2-yl)oxy)propan-2-yl)carbamate To a solution of tert-butyl ((2S)-1-((4-chloro-5-nitropyridin-2-yl)oxy)propan-2-yl)carbamate (8.96 g) in ethanol (50 mL) were added reduced iron (15.1 g) and iron(III) chloride (4.38 g), and the mixture was stirred with heating under reflux for 1 hr. The reaction mixture was filtered, and the filtrate was diluted with ethyl acetate, washed with saturated brine, and dried over anhydrous magnesium sulfate. The solvent was evaporated under reduced pressure, and the obtained tert-butyl ((2S)-1-((5-amino-4-chloropyridin-2-yl)oxy)propan-2-yl)carbamate was used for the next reaction without further purification.

To a solution of 4-(cyclopropylmethoxy)-3,5-difluorobenzoic acid (3.00 g) in THF (20 mL) were added oxalyl dichloride (1.73 mL) and DMF (2 drops), and the mixture was stirred at room temperature for 30 min. The solvent was evaporated under reduced pressure, and to a solution of the obtained residue in pyridine (30 mL) was added a solution of tert-butyl ((2S)-1-((5-amino-4-chloropyridin-2-yl)oxy)propan-2-yl)carbamate (obtained in the above-mentioned reaction) in THF (2 mL), and the mixture was stirred at room temperature for 30 min. The reaction mixture was subjected to silica gel column chromatography (NH, ethyl acetate), the solvent was evaporated, and the obtained solid was washed with diethyl ether to give the title compound (4.40 g).
$^1$H NMR (300 MHz, CDCl$_3$) δ 0.29-0.37 (2H, m), 0.57-0.67 (2H, m), 1.19-1.34 (4H, m), 1.44 (9H, s), 3.98-4.13 (3H, m), 4.28 (2H, d, J=4.9 Hz), 4.66-4.85 (1H, m), 6.89 (1H, s), 7.38-7.53 (2H, m), 7.85 (1H, s), 8.99 (1H, s).

B) tert-butyl ((2S)-1-((2-(4-(cyclopropylmethoxy)-3,5-difluorophenyl) [1,3]oxazolo[4,5-c]pyridin-6-yl)oxy)propan-2-yl)carbamate A suspension of tert-butyl ((2S)-1-((4-chloro-5-((4-(cyclopropylmethoxy)-3,5-difluorobenzoyl)amino)pyridin-2-yl)oxy)propan-2-yl)carbamate (4.40 g), potassium carbonate (2.38 g) and copper(I) iodide (164 mg) in DMF (20 mL) was stirred at 160° C. for 4 hr under microwave irradiation. To the reaction mixture was added water, and the obtained mixture was extracted with ethyl acetate. The extract was washed with saturated brine, and subjected to silica gel column chromatography (NH, ethyl acetate). The solvent was evaporated, and the obtained residue was purified by silica gel column chromatography (hexane/ethyl acetate) to give the title compound (1.42 g).
$^1$H NMR (300 MHz, CDCl$_3$) δ 0.26-0.44 (2H, m), 0.54-0.68 (2H, m), 1.18-1.36 (4H, m), 1.44 (9H, s), 3.99-4.17 (3H, m), 4.34 (2H, d, J=4.9 Hz), 4.74-4.90 (1H, m), 6.90 (1H, s), 7.68-7.83 (2H, m), 8.56 (1H, s)

C) N-((2S)-1-((2-(4-(cyclopropylmethoxy)-3,5-difluorophenyl)[1,3]oxazolo[4,5-c]pyridin-6-yl)oxy)propan-2-yl)acetamide To tert-butyl ((2S)-1-((2-(4-(cyclopropylmethoxy)-3,5-difluorophenyl)[1,3]oxazolo[4,5-c]pyridin-6-yl)oxy)propan-2-yl)carbamate (1.42 g) was added 4M hydrogen chloride/ ethyl acetate (5 mL), and the mixture was stirred at room temperature for 10 min, and concentrated. To the residue were added pyridine (5 mL) and acetic anhydride (5 mL), and the mixture was stirred at room temperature for 15 min. The reaction mixture was concentrated under reduced pressure, and the residue was purified by silica gel column chromatography (NH, hexane/ethyl acetate) to give the title compound (701 mg).

$^1$H NMR (300 MHz, CDCl$_3$) δ 0.28-0.38 (2H, m), 0.55-0.68 (2H, m), 1.13-1.38 (4H, m), 1.97 (3H, s), 4.11 (2H, d, J=7.2 Hz), 4.27-4.52 (3H, m), 5.96 (1H, d, J=6.8 Hz), 6.91 (1H, d, J=0.8 Hz), 7.68-7.83 (2H, m), 8.56 (1H, d, J=1.1 Hz).

Example 48

N-((2S)-1-((2-(4-(cyclopropylmethoxy)-2,5-difluorophenyl)[1,3]oxazolo[4,5-c]pyridin-6-yl)oxy)propan-2-yl)acetamide A) tert-butyl ((2S)-1-((4-chloro-5-((4-(cyclopropylmethoxy)-2,5-difluorobenzoyl)amino)pyridin-2-yl)oxy)propan-2-yl)carbamate To a solution of tert-butyl ((2S)-1-((4-chloro-5-nitropyridin-2-yl)oxy)propan-2-yl)carbamate (5.00 g) in ethanol (50 mL) were added reduced iron (8.42 g) and iron(III) chloride (2.45 g), and the mixture was stirred with heating under reflux for 1 hr. The reaction mixture was filtered, and the filtrate was diluted with ethyl acetate, washed with saturated brine, and dried over anhydrous magnesium sulfate. The solvent was evaporated under reduced pressure, and the obtained tert-butyl ((2S)-1-((5-amino-4-chloropyridin-2-yl)oxy)propan-2-yl)carbamate was used for the next reaction without further purification.

To a solution of 4-(cyclopropylmethoxy)-2,5-difluorobenzoic acid (3.77 g) in THF (20 mL) were added oxalyl dichloride (2.17 mL) and DMF (2 drops), and the mixture was stirred at room temperature for 30 min. The solvent was evaporated under reduced pressure, and to a solution of obtained residue in pyridine (10 mL) was added a solution of tert-butyl ((2S)-1-((5-amino-4-chloropyridin-2-yl)oxy)propan-2-yl)carbamate (obtained in the above-mentioned reaction) in THF (2 mL), and the mixture was stirred at room temperature for 30 min. The reaction mixture was subjected to silica gel column chromatography (NH, ethyl acetate), then the solvent was evaporated, and the obtained solid was washed with diethyl ether to give the title compound (5.39 g).

$^1$H NMR (300 MHz, CDCl$_3$) δ 0.36-0.46 (2H, m), 0.64-0.82 (2H, m), 1.25 (3H, d, J=6.8 Hz), 1.28-1.40 (1H, m), 1.44 (9H, s), 3.94 (2H, d, J=6.8 Hz), 3.98-4.15 (1H, m), 4.28 (2H, d, J=4.9 Hz), 4.66-4.90 (1H, m), 6.74 (1H, dd, J=13.6, 6.4 Hz), 6.89 (1H, s), 7.91 (1H, dd, J=11.5, 7.4 Hz), 8.68 (1H, d, J=17.4 Hz), 9.12 (1H, s).

Anal. Calcd for C$_{21}$H$_{21}$N$_3$O$_4$F$_2$: C, 60.43; H, 5.07; N, 10.07. Found: C, 60.28; H, 5.16; N, 9.92.

mp 199.8-199.9° C.

B) tert-butyl ((2S)-1-((2-(4-(cyclopropylmethoxy)-2,5-difluorophenyl)[1,3]oxazolo[4,5-c]pyridin-6-yl)oxy)propan-2-yl)carbamate A suspension of tert-butyl ((2S)-1-((4-chloro-5-((4-(cyclopropylmethoxy)-2,5-difluorobenzoyl)amino)pyridin-2-yl)oxy)propan-2-yl)carbamate (5.39 g), potassium carbonate (2.91 g) and copper(I) iodide (201 mg) in DMF (30 mL) was stirred at 160° C. for 4 hr under microwave irradiation. To the reaction mixture was added water, and the obtained mixture was extracted with ethyl acetate. The extract was washed with saturated brine, and subjected to silica gel column chromatography (NH, ethyl acetate). The solvent was evaporated, and the obtained residue was purified by silica gel column chromatography (hexane/ethyl acetate) to give the title compound (1.64 g).

$^1$H NMR (300 MHz, CDCl$_3$) δ 0.37-0.47 (2H, m), 0.66-0.78 (2H, m), 1.28 (3H, d, J=6.8 Hz), 1.31-1.39 (1H, m), 1.44 (9H, s), 3.95 (2H, d, J=6.8 Hz), 4.02-4.18 (1H, m), 4.34 (2H, d, J=4.9% Hz), 4.71-4.92 (1H, m), 6.83 (1H, dd, J=11.9, 6.6 Hz), 6.91 (1H, d, J=0.8 Hz), 7.88 (1H, dd, J=11.3, 6.8 Hz), 8.59 (1H, d, J=0.8 Hz).

C) N-((2S)-1-((2-(4-(cyclopropylmethoxy)-2,5-difluorophenyl)[1,3]oxazolo[4,5-c]pyridin-6-yl)oxy)propan-2-yl)acetamide To tert-butyl ((2S)-1-((2-(4-(cyclopropylmethoxy)-2,5-difluorophenyl)[1,3]oxazolo[4,5-c]pyridin-6-yl)oxy)propan-2-yl)carbamate (1.64 g) was added 4M hydrogen chloride/ethyl acetate (5 mL), and the mixture was stirred at room temperature for 10 min, and concentrated. To the residue were added pyridine (5 mL) and acetic anhydride (5 mL), and the mixture was stirred at room temperature for 15 min. The reaction mixture was concentrated under reduced pressure, and the residue was purified by silica gel column chromatography (NH, hexane/ethyl acetate) to give the title compound (411 mg).

$^1$H NMR (300 MHz, CDCl$_3$) δ 0.35-0.47 (2H, m), 0.66-0.78 (2H, m), 1.26-1.43 (4H, m), 1.97 (3H, s), 3.95 (2H, d, J=6.8 Hz), 4.31-4.48 (3H, m), 6.00 (1H, d, J=6.0 Hz), 6.83 (1H, dd, J=12.1, 6.8 Hz), 6.92 (1H, d, J=0.8 Hz), 7.88 (1H, dd, J=11.3, 6.8 Hz), 8.59 (1H, d, J=0.8 Hz).

Example 49

N-((2S)-1-((2-(4-((2,2-difluorocyclopropyl)methoxy)-3-fluorophenyl)[1,3]oxazolo[4,5-c]pyridin-6-yl)oxy)propan-2-yl)acetamide A) tert-butyl ((2S)-1-((5-((4-(benzyloxy)-3-fluorobenzoyl)amino)-4-chloropyridin-2-yl)oxy)propan-2-yl)carbamate To a solution of tert-butyl ((2S)-1-((4-chloro-5-nitropyridin-2-yl)oxy)propan-2-yl)carbamate (5.00 g) in ethanol (50 mL) were added reduced iron (8.42 g) and iron(III) chloride (2.45 g), and the mixture was stirred with heating under reflux for 1 hr. The reaction mixture was filtered, and the filtrate was diluted with ethyl acetate, washed with saturated brine, and dried over anhydrous magnesium sulfate. The solvent was evaporated under reduced pressure, and the obtained tert-butyl ((2S)-1-((5-amino-4-chloropyridin-2-yl)oxy)propan-2-yl)carbamate was used for the next reaction without further purification.

To a solution of 4-(benzyloxy)-3-fluorobenzoic acid (3.71 g) in THF (20 mL) were added oxalyl dichloride (1.98 mL) and DMF (2 drops), and the mixture was stirred at room temperature for 30 min. The solvent was evaporated under reduced pressure, and to a solution of the obtained residue in pyridine (30 mL) was added a solution of tert-butyl ((2S)-1-((5-amino-4-chloropyridin-2-yl)oxy)propan-2-yl)carbamate (obtained in the above-mentioned reaction) in THF (2 mL), and the mixture was stirred at room temperature for 30 min. The reaction mixture was subjected to silica gel column chromatography (NH, ethyl acetate), the solvent was evaporated, and the obtained solid was washed with diethyl ether to give the title compound (6.28 g).

¹H NMR (300 MHz, CDCl₃) δ 1.20-1.35 (3H, m), 1.44 (9H, s), 3.95-4.14 (1H, m), 4.28 (2H, d, J=4.5 Hz), 4.68-4.85 (1H, m), 5.23 (2H, s), 6.88 (1H, d, J=1.9 Hz), 7.08 (1H, t, J=8.3 Hz), 7.30-7.49 (5H, m), 7.61 (1H, d, J=8.7 Hz), 7.68 (1H, dd, J=11.5, 2.1 Hz), 7.87 (1H, d, J=6.8 Hz), 9.03 (1H, d, J=6.8 Hz).

B) tert-butyl ((2S)-1-((2-(4-(benzyloxy)-3-fluorophenyl)[1,3]oxazolo[4,5-c]pyridin-6-yl)oxy)propan-2-yl)carbamate A suspension of tert-butyl ((2S)-1-((5-((4-(benzyloxy)-3-fluorobenzoyl)amino)-4-chloropyridin-2-yl)oxy)propan-2-yl)carbamate (6.28 g), potassium carbonate (3.28 g) and copper(I) iodide (226 mg) in DMF (40 mL) was stirred at 160° C. for 3 hr under microwave irradiation. To the reaction mixture was added water, and the obtained mixture was extracted with ethyl acetate. The extract was washed with saturated brine, and subjected to silica gel column chromatography (NH, ethyl acetate). The solvent was evaporated, and the obtained residue was purified by silica gel column chromatography (hexane/ethyl acetate) to give the title compound (1.72 g).

¹H NMR (300 MHz, DMSO-d₆) δ 1.13 (3H, d, J=6.8 Hz), 1.38 (9H, s), 3.79-3.97 (1H, m), 4.20 (2H, d, J=5.7 Hz), 5.32 (2H, s), 6.87 (1H, d, J=8.3 Hz), 7.17 (1H, s), 7.30-7.60 (6H, m), 7.87-8.06 (2H, m), 8.62 (1H, s).

C) N-((2S)-1-((2-(4-(benzyloxy)-3-fluorophenyl)[1,3]oxazolo[4,5-c]pyridin-6-yl)oxy)propan-2-yl)acetamide To tert-butyl ((2S)-1-((2-(4-(benzyloxy)-3-fluorophenyl)[1,3]oxazolo[4,5-c]pyridin-6-yl)oxy)propan-2-yl)carbamate (1.72 g) was added 4 M hydrogen chloride/ethyl acetate (5 mL), and the mixture was stirred at room temperature for 10 min, and concentrated. To the residue were added pyridine (5 mL) and acetic anhydride (5 mL), and the mixture was stirred at room temperature for 15 min. The reaction mixture was concentrated under reduced pressure, and the residue was purified by silica gel column chromatography (NH, hexane/ethyl acetate) to give the title compound (1.21 g).

¹H NMR (300 MHz, DMSO-d₆) δ 1.15 (3H, d, J=6.4 Hz), 1.81 (3H, s), 4.00-4.30 (3H, m), 5.32 (2H, s), 7.20 (1H, s), 7.33-7.59 (6H, m), 7.84-8.08 (3H, m), 8.63 (1H, s).

D) N-((2S)-1-((2-(4-((2,2-difluorocyclopropyl)methoxy)-3-fluorophenyl)[1,3]oxazolo[4,5-c]pyridin-6-yl)oxy)propan-2-yl)acetamide A mixture of N-((2S)-1-((2-(4-(benzyloxy)-3-fluorophenyl)[1,3]oxazolo[4,5-c]pyridin-6-yl)oxy)propan-2-yl)acetamide (1.21 g), 10% palladium-carbon (containing water (50%), 1.00 g) and THF (40 mL) was stirred at room temperature for 1 hr and 30 min under a hydrogen atmosphere. The catalyst was removed by filtration, and the obtained filtrate was concentrated under reduced pressure. A suspension of the obtained solid, 1-bromomethyl-2,2-difluorocyclopropane (631 mg) and potassium carbonate (510 mg) in DMF (10 mL) was stirred at 70° C. for 1 hr 30 min. The reaction mixture was diluted with ethyl acetate, and washed with saturated brine, and the organic layer was subjected to silica gel column chromatography (NH, ethyl acetate), and the solvent was evaporated. The obtained solid was washed with diethyl ether to give the title compound (428 mg).

¹H NMR (300 MHz, DMSO-d₆) δ 1.15 (3H, d, J=6.8 Hz), 1.46-1.63 (1H, m), 1.70-1.88 (4H, m), 2.17-2.44 (1H, m), 4.02-4.28 (4H, m), 4.28-4.41 (1H, m), 7.20 (1H, s), 7.45 (1H, t, J=8.7 Hz), 7.85-8.04 (3H, m), 8.63 (1H, s).

Example 50

N-(1-((2-(4-(cyclopropylmethoxy)-3-fluorophenyl)-4,5,6,7-tetrahydro-1,3-benzoxazol-5-yl)oxy)propan-2-yl)acetamide A) 7-(benzylamino)-1,4-dioxaspiro[4.5]decan-8-ol To a solution of spiro[1,3-dioxolan-2,3'-[7]oxabicyclo[4.1.0]heptane] (16.7 g) in 2-propanol (150 mL) was added benzylamine (17.5 mL), and the mixture was stirred overnight with heating at 90° C. The solvent was evaporated under reduced pressure, and the obtained residue was purified by silica gel column chromatography (hexane/ethyl acetate/methanol) to give the title compound (24.8 g).

¹H NMR (300 MHz, CDCl₃) δ 1.39 (1H, t, J=12.2 Hz), 1.49-1.67 (2H, m), 1.71-1.86 (1H, m), 1.88-2.02 (1H, m), 2.17 (1H, dd, J=16.2, 3.8 Hz), 2.59-2.71 (1H, m), 3.18-3.39 (1H, m), 3.71 (1H, d, J=12.8 Hz), 3.84-4.01 (5H, m), 7.21-7.36 (5H, m).

B) 4-(cyclopropylmethoxy)-3-fluoro-N-(8-hydroxy-1,4-dioxaspiro[4.5]dec-7-yl)benzamide A mixture of 7-(benzylamino)-1,4-dioxaspiro[4.5]decan-8-ol (24.8 g), 10% palladium-carbon (containing water (50%), 12.0 g) and ethanol (100 mL) was stirred at room temperature for 2 hr under a hydrogen atmosphere (5 atm). The catalyst was removed by filtration, and the obtained filtrate was concentrated under reduced pressure. The obtained 7-amino-1,4-dioxaspiro[4.5]decan-8-ol was used for the next reaction without further purification.

To a solution of 4-(cyclopropylmethoxy)-3-fluorobenzoic acid (22.3 g) in THF (150 mL) were added oxalyl dichloride (13.9 mL) and DMF (2 drops), and the mixture was stirred at room temperature for 30 min. The solvent was evaporated under reduced pressure, and to a mixture of the obtained residue, THF (100 mL) and saturated aqueous sodium hydrogen carbonate solution (50 mL) was added a solution of 7-amino-1,4-dioxaspiro[4.5]decan-8-ol (obtained in the above-mentioned reaction) in THF (5 mL). The precipitated solid was collected by filtration, and dissolved in THF-methanol. The filtrate was extracted with ethyl acetate, and the extract was combined with the above-mentioned THF-methanol solution, and subjected to silica gel column chromatography (NH, ethyl acetate). The solvent was evaporated, and the obtained solid was washed with diethyl ether/hexane to give the title compound (14.2 g).

¹H NMR (300 MHz, CDCl₃) δ 0.30-0.44 (2H, m), 0.61-0.74 (2H, m), 1.17-1.41 (1H, m), 1.52-2.00 (5H, m), 2.30 (1H, dd, J=13.8, 4.3 Hz), 2.87-3.05 (1H, m), 3.86 (1H, brs), 3.92 (2H, d, J=7.2 Hz), 3.97-4.06 (4H, m), 4.24-4.36 (1H, m), 6.85-7.01 (1H, m), 7.20 (1H, d, J=7.2 Hz), 7.40-7.57 (2H, m).

C) 2-(4-(cyclopropylmethoxy)-3-fluorophenyl)-6,7-dihydro-4H-spiro[1,3-benzoxazole-5,2'-[1,3]dioxolane]

To a solution of 4-(cyclopropylmethoxy)-3-fluoro-N-(8-hydroxy-1,4-dioxaspiro[4.5]dec-7-yl)benzamide (14.2 g) in dimethyl sulfoxide (100 mL) were added triethylamine (16.3 mL) and sulfur trioxide-pyridine complex (18.6 g), and the mixture was stirred for 1 hr under a nitrogen stream. To the reaction mixture was added water, and the mixture was extracted with ethyl acetate. The organic layer was washed with saturated brine, and dried over anhydrous magnesium sulfate, and the solvent was evaporated under reduced pressure. To a solution of the obtained residue in THF (100 mL) was added (methoxycarbonylsulfamoyl)triethylammonium hydroxide inner salt (14.0 g), and the mixture was stirred at 60° C. for 1 hr. To the reaction mixture was added saturated brine, and the mixture was extracted with ethyl acetate. The organic layer was dried over anhydrous magnesium sulfate, and subjected to silica gel column chromatography (NH, ethyl acetate). The solvent was evaporated, and the obtained solid was washed with diethyl ether to give the title compound (6.00 g).

$^1$H NMR (300 MHz, CDCl$_3$) δ 0.32-0.42 (2H, m), 0.58-0.75 (2H, m), 1.14-1.43 (1H, m), 2.05 (2H, t, J=6.6 Hz), 2.74-2.93 (4H, m), 3.92 (2H, d, J=6.8 Hz), 3.97-4.15 (4H, m), 6.89-7.01 (1H, m), 7.59-7.76 (2H, m).

D) 2-(4-(cyclopropylmethoxy)-3-fluorophenyl)-4,5,6,7-tetrahydro-1,3-benzoxazol-5-ol To 2-(4-(cyclopropylmethoxy)-3-fluorophenyl)-6,7-dihydro-4H-spiro[1,3-benzoxazole-5,2'-[1,3]dioxolane] (6.00 g) in a mixed solvent of THF (40 mL)-methanol (20 mL)-water (20 mL) was added 6 M hydrochloric acid (17.4 mL), and the mixture was stirred at 70° C. for 1 hr. The reaction mixture was neutralized with saturated aqueous sodium hydrogen carbonate solution, and the mixture was extracted with ethyl acetate. To the organic layer was added sodium tetrahydroborate (657 mg), and the mixture was stirred at room temperature for 20 min. To the reaction mixture was added saturated aqueous ammonium chloride solution, and the mixture was extracted with ethyl acetate. The organic layer was dried over anhydrous magnesium sulfate, and the solvent was evaporated under reduced pressure. The obtained residue was purified by silica gel column chromatography (hexane/ethyl acetate) to give the title compound (2.93 g).

$^1$H NMR (300 MHz, CDCl$_3$) δ 0.28-0.45 (2H, m), 0.58-0.72 (2H, m), 1.25-1.39 (1H, m), 1.95-2.15 (2H, m), 2.50-3.04 (4H, m), 3.92 (2H, d, J=7.2 Hz), 4.22-4.36 (1H, m), 6.82-7.03 (1H, m), 7.61-7.79 (2H, m).

E) 2-((2-(4-(cyclopropylmethoxy)-3-fluorophenyl)-4,5,6,7-tetrahydro-1,3-benzoxazol-5-yl)oxy)-1-(morpholin-4-yl)ethanone To a solution of 2-(4-(cyclopropylmethoxy)-3-fluorophenyl)-4,5,6,7-tetrahydro-1,3-benzoxazol-5-ol (3.44 g) and 4-(chloroacetyl)morpholine (2.95 mL) in THF (30 mL) was added potassium tert-butoxide (2.55 g), and the mixture was stirred for 1 hr under a nitrogen stream. To the reaction mixture was added saturated aqueous ammonium chloride solution, and the mixture was extracted with ethyl acetate. The organic layer was dried over anhydrous magnesium sulfate, and the solvent was evaporated under reduced pressure. The obtained residue was purified by silica gel column chromatography (hexane/ethyl acetate/methanol) to give the title compound (4.36 g).

$^1$H NMR (300 MHz, CDCl$_3$) δ 0.31-0.42 (2H, m), 0.61-0.72 (2H, m), 1.29-1.41 (1H, m), 2.05-2.17 (2H, m), 2.60-2.98 (4H, m), 3.46-3.74 (8H, m), 3.92 (2H, d, J=7.2 Hz), 3.95-4.03 (1H, m), 4.17-4.30 (2H, m), 6.93-7.02 (1H, m), 7.65-7.74 (2H, m).

F) 1-((2-(4-(cyclopropylmethoxy)-3-fluorophenyl)-4,5,6,7-tetrahydro-1,3-benzoxazol-5-yl)oxy)propan-2-ol To 2-((2-(4-(cyclopropylmethoxy)-3-fluorophenyl)-4,5,6,7-tetrahydro-1,3-benzoxazol-5-yl)oxy)-1-(morpholin-4-yl)ethanone (4.36 g) in THF (25 mL) was added methylmagnesium bromide (1 M THF solution, 15.2 mL), and the reaction mixture was stirred at room temperature for 10 min. To the reaction mixture was added saturated aqueous ammonium chloride solution, and the mixture was extracted with ethyl acetate. The organic layer was dried over anhydrous magnesium sulfate, and the solvent was evaporated under reduced pressure. To a solution of the obtained residue in a mixed solvent of THF (10 mL)-methanol (10 mL) was added sodium tetrahydroborate (383 mg), and the mixture was stirred at room temperature for 10 min. To the reaction mixture was added saturated aqueous ammonium chloride solution, and the mixture was extracted with ethyl acetate. The organic layer was dried over anhydrous magnesium sulfate, and the solvent was evaporated under reduced pressure. The obtained residue was purified by silica gel column chromatography (hexane/ethyl acetate) to give the title compound (3.48 g).

$^1$H NMR (300 MHz, CDCl$_3$) δ 0.32-0.43 (2H, m), 0.62-0.73 (2H, m), 1.16 (3H, d, J=6.4 Hz), 1.29-1.41 (1H, m), 2.04-2.14 (1H, m), 2.36 (1H, dd, J=10.9, 3.0 Hz), 2.58-3.00 (4H, m), 3.31 (1H, q, J=8.3 Hz), 3.51-3.59 (1H, m), 3.82-4.01 (4H, m), 6.93-7.05 (1H, m), 7.65-7.75 (2H, m).

G) 5-(2-azidopropoxy)-2-(4-(cyclopropylmethoxy)-3-fluorophenyl)-4,5,6,7-tetrahydro-1,3-benzoxazole To a solution of 1-((2-(4-(cyclopropylmethoxy)-3-fluorophenyl)-4,5,6,7-tetrahydro-1,3-benzoxazol-5-yl)oxy)propan-2-ol (3.48 g) and triethylamine (2.68 mL) in THF (30 mL) was added methanesulfonyl chloride (1.12 mL) at room temperature, and the mixture was stirred for 10 min. To the reaction mixture was added saturated aqueous sodium hydrogen carbonate solution, and the mixture was extracted with ethyl acetate. The organic layer was dried over anhydrous magnesium sulfate, and concentrated under reduced pressure. The obtained residue was dissolved in DMF (30 mL), sodium azide (3.13 g) was added thereto, and the mixture was stirred at 100° C. for 2 hr. To the reaction mixture was added water, and the mixture was extracted with ethyl acetate. The organic layer was washed with saturated brine, dried over anhydrous magnesium sulfate, and concentrated under reduced pressure. The obtained residue was purified by silica gel column chromatography (hexane/ethyl acetate) to give the title compound (3.08 g).

$^1$H NMR (300 MHz, CDCl$_3$) δ 0.26-0.44 (2H, m), 0.59-0.73 (2H, m), 1.19 (3H, t, J=6.2 Hz), 1.29-1.42 (1H, m), 2.05-2.14 (2H, m), 2.60-2.97 (4H, m), 3.38-3.71 (3H, m), 3.83-3.95 (3H, m), 6.88-7.02 (1H, m), 7.63-7.74 (2H, m).

H) N-(1-((2-(4-(cyclopropylmethoxy)-3-fluorophenyl)-4,5,6,7-tetrahydro-1,3-benzoxazol-5-yl)oxy)propan-2-yl)acetamide A mixture of 5-(2-azidopropoxy)-2-(4-(cyclopropylmethoxy)-3-fluorophenyl)-4,5,6,7-tetrahydro-1,3-benzoxazole (3.08 g), 10% palladium-carbon (containing water (50%), 500 mg) and THF (10 mL) was stirred at room temperature for 10 min under a hydrogen atmosphere. The catalyst was removed by filtration, and the obtained filtrate was concentrated under reduced pressure. To the obtained residue were added pyridine (10 mL) and acetic anhydride (10 mL), and the mixture was stirred at room temperature for 10 min. The reaction mixture was concentrated under reduced pressure, and the residue was purified by silica gel column chromatography (hexane/ethyl acetate/methanol) to give the title compound (2.80 g).

$^1$H NMR (300 MHz, CDCl$_3$) δ 0.33-0.42 (2H, m), 0.62-0.72 (2H, m), 1.17 (3H, dd, J=6.8, 2.6 Hz), 1.29-1.39 (1H, m), 1.95 (3H, d, J=4.2 Hz), 2.01-2.10 (2H, m), 2.56-2.96 (4H, m), 3.40-3.61 (2H, m), 3.76-3.88 (1H, m), 3.92 (2H, d, J=6.8 Hz), 4.14-4.23 (1H, m), 5.60 (1H, d, J=7.6 Hz), 6.90-7.02 (1H, m), 7.64-7.76 (2H, m).

Example 51a

Optically Active Form of N-(1-((2-(4-(cyclopropyl-methoxy)-3-fluorophenyl)-4,5,6,7-tetrahydro-1,3-benzoxazol-5-yl)oxy)propan-2-yl)acetamide A diastereomer mixture (1.00 g) of N-(1-((2-(4-(cyclopropylmethoxy)-3-fluorophenyl)-4,5,6,7-tetrahydro-1,3-benzoxazol-5-yl)oxy)propan-2-yl)acetamide was resolved by preparative HPLC (column: CHIRALPAK IC (trade name), 50 mmID×500 mL, DAICEL CHEMICAL INDUSTRIES, LTD., mobile phase:hexane/ethanol=50:50), and the compound having the shortest retention time was resolved by HPLC (column: CHIRALPAK AD (trade name), 50 mmID×500 mL, DAICEL CHEMICAL INDUSTRIES, LTD., mobile phase:hexane/ethanol=80:20) to give the compound having a longer retention time as the title compound (182 mg).

$^1$H NMR (300 MHz, CDCl$_3$) δ 0.22-0.47 (2H, m), 0.59-0.81 (2H, m), 1.17 (3H, d, J=6.8 Hz), 1.26-1.43 (1H, m), 1.87-2.15 (5H, m), 2.54-3.01 (4H, m), 3.34-3.63 (2H, m), 3.75-3.88 (1H, m), 3.92 (2H, d, J=6.8 Hz), 4.07-4.28 (1H, m), 5.55-5.93 (1H, m), 6.97 (1H, t, J=8.1 Hz), 7.56-7.84 (2H, m).

retention time (IC) 30.25 min.
retention time (AD) 25.45 min.

Example 51b

Optically Active Form N-(1-((2-(4-(cyclopropyl-methoxy)-3-fluorophenyl)-4,5,6,7-tetrahydro-1,3-benzoxazol-5-yl)oxy)propan-2-yl)acetamide A diastereomer mixture (1.00 g) of N-(1-((2-(4-(cyclopropylmethoxy)-3-fluorophenyl)-4,5,6,7-tetrahydro-1,3-benzoxazol-5-yl)oxy)propan-2-yl)acetamide was resolved by HPLC (column: CHIRALPAK IC (trade name), 50 mmID×500 mL, DAICEL CHEMICAL INDUSTRIES, LTD., mobile phase:hexane/ethanol=50:50), and the compound having the shortest retention time was resolved by HPLC (column: CHIRALPAK AD (trade name), 50 mmID×500 mL, DAICEL CHEMICAL INDUSTRIES, LTD., mobile phase:hexane/ethanol=80:20) to give the compound having a shorter retention time as the title compound (179 mg).

$^1$H NMR (300 MHz, CDCl$_3$) δ 0.30-0.43 (2H, m), 0.59-0.74 (2H, m), 1.18 (3H, d, J=6.8 Hz), 1.25-1.40 (1H, m), 1.94 (3H, s), 2.00-2.12 (2H, m), 2.55-2.97 (4H, m), 3.41-3.59 (2H, m), 3.84 (1H, dt, J=9.9, 5.1 Hz), 3.92 (2H, d, J=6.8 Hz), 4.08-4.24 (1H, m), 5.64 (1H, d, J=7.2 Hz), 6.91-7.05 (1H, m), 7.62-7.75 (2H, m).

retention time (IC) 30.25 min.
retention time (AD) 18.58 min.

Example 51c

Optically Active Form of N-(1-((2-(4-(cyclopropyl-methoxy)-3-fluorophenyl)-4,5,6,7-tetrahydro-1,3-benzoxazol-5-yl)oxy)propan-2-yl)acetamide A diastereomer mixture (1.00 g) of N-(1-((2-(4-(cyclopropylmethoxy)-3-fluorophenyl)-4,5,6,7-tetrahydro-1,3-benzoxazol-5-yl)oxy)propan-2-yl)acetamide was resolved by HPLC (column: CHIRALPAK IC (trade name), 50 mmID×500 mL, DAICEL CHEMICAL INDUSTRIES, LTD., mobile phase:hexane/ethanol=50:50) to give the compound having the second longest retention time as the title compound (179 mg).

$^1$H NMR (300 MHz, CDCl$_3$) δ 0.15-0.50 (2H, m), 0.57-0.82 (2H, m), 1.04-1.45 (4H, m), 1.81-2.22 (5H, m), 2.50-3.06 (4H, m), 3.37-3.69 (2H, m), 3.74-4.02 (3H, m), 4.05-4.30 (1H, m), 5.50-5.85 (1H, m), 6.90-7.14 (1H, m), 7.58-7.90 (2H, m).

retention time 37.06 min.

Example 51d

Optically Active Form of N-(1-((2-(4-(cyclopropyl-methoxy)-3-fluorophenyl)-4,5,6,7-tetrahydro-1,3-benzoxazol-5-yl)oxy)propan-2-yl)acetamide A diastereomer mixture (1.00 g) of N-(1-((2-(4-(cyclopropylmethoxy)-3-fluorophenyl)-4,5,6,7-tetrahydro-1,3-benzoxazol-5-yl)oxy)propan-2-yl)acetamide was resolved by HPLC (column: CHIRALPAK IC (trade name), 50 mmID×500 mL, DAICEL CHEMICAL INDUSTRIES, LTD., mobile phase:hexane/ethanol=50:50) to give the compound having the longest retention time as the title compound (204 mg).

$^1$H NMR (300 MHz, CDCl$_3$) δ 0.25-0.50 (2H, m), 0.55-0.78 (2H, m), 1.17 (3H, d, J=6.8 Hz), 1.22-1.42 (1H, m), 1.96 (3H, s), 2.04 (2H, q, J=6.0 Hz), 2.57-2.96 (4H, m), 3.40-3.50 (1H, m), 3.52-3.61 (1H, m), 3.85 (1H, quin, J=5.1 Hz), 3.92 (2H, d, J=6.8 Hz), 4.10-4.24 (1H, m), 5.60 (1H, d, J=7.6 Hz), 6.93-7.04 (1H, m), 7.64-7.74 (2H, m).

retention time 53.16 min.

Example 52

N-(1-((2-(4-(cyclopropylmethoxy)-3-fluorophenyl)-4,5,6,7-tetrahydro-1,3-benzoxazol-6-yl)oxy)propan-2-yl)acetamide A) 8-azido-1,4-dioxaspiro[4.5]decan-7-ol To a solution of spiro[1,3-dioxolan-2,3'-[7]oxabicyclo[4.1.0]heptane] (22.6 g) in a mixed solvent of DMF (200 mL)-water (50 mL) was added sodium azide (18.8 g), and the mixture was stirred overnight with heating at 70° C. The reaction mixture was diluted with ethyl acetate, and washed with saturated brine, and the organic layer was dried over anhydrous magnesium sulfate. The solvent was evaporated under reduced pressure, and the obtained residue was purified by silica gel column chromatography (hexane/ethyl acetate) to give the title compound (14.3 g).

$^1$H NMR (300 MHz, CDCl$_3$) δ 1.58-1.85 (4H, m), 1.93-2.20 (2H, m), 2.79 (1H, d, J=4.9 Hz), 3.36-3.54 (1H, m), 3.65-3.82 (1H, m), 3.89-4.03 (4H, m).

B) 4-(cyclopropylmethoxy)-3-fluoro-N-(7-hydroxy-1,4-dioxaspiro[4.5]dec-8-yl)benzamide A mixture of 8-azido-1,4-dioxaspiro[4.5]decan-7-ol (4.00 g), 10% palladium-carbon (containing water (50%), 4.00 g)

and THF (100 mL) was stirred at room temperature for 30 min under a hydrogen atmosphere. The catalyst was removed by filtration, and the obtained filtrate was concentrated under reduced pressure. The obtained 8-amino-1,4-dioxaspiro[4.5]decan-7-ol was used for the next reaction without further purification.

To a solution of 4-(cyclopropylmethoxy)-3-fluorobenzoic acid (6.33 g) in THF (100 mL) were added oxalyl dichloride (3.95 mL) and DMF (10 drops), and the mixture was stirred at room temperature for 30 min. The solvent was evaporated under reduced pressure, and to the obtained residue in a mixed solvent of THF (100 mL)-saturated aqueous sodium hydrogen carbonate solution (30 mL) was added a solution of 8-amino-1,4-dioxaspiro[4.5]decan-7-ol (obtained in the above-mentioned reaction) in THF (5 mL). The reaction mixture was extracted with ethyl acetate, and the organic layer was dried over anhydrous magnesium sulfate. The solvent was evaporated under reduced pressure, and the obtained residue was purified by silica gel column chromatography (hexane/ethyl acetate) to give the title compound (4.53 g).
$^1$H NMR (300 MHz, CDCl$_3$) δ 0.33-0.43 (2H, m), 0.61-0.76 (2H, m), 1.25-1.38 (1H, m), 1.59-1.82 (4H, m), 1.98-2.10 (1H, m), 2.13-2.23 (1H, m), 3.36 (1H, brs), 3.64-3.79 (1H, m), 3.86-4.03 (6H, m), 6.02 (1H, d, J=6.4 Hz), 6.88-7.01 (1H, m), 7.45-7.57 (2H, m).

C) 2-(4-(cyclopropylmethoxy)-3-fluorophenyl)-4,7-dihydro-5H-spiro[1,3-benzoxazole-6,2'-[1,3]dioxolane]

To a solution of 4-(cyclopropylmethoxy)-3-fluoro-N-(7-hydroxy-1,4-dioxaspiro[4.5]dec-8-yl)benzamide (4.53 g) in dimethyl sulfoxide (40 mL) were added triethylamine (5.18 mL) and sulfur trioxide-pyridine complex (5.92 g), and the mixture was stirred for 1 hr under a nitrogen stream. To the reaction mixture was added water, and the mixture was extracted with ethyl acetate. The organic layer was washed with saturated brine, and dried over anhydrous magnesium sulfate, and the solvent was evaporated under reduced pressure. To a solution of the obtained residue in THF (30 mL) was added (methoxycarbonylsulfamoyl)triethylammonium hydroxide inner salt (4.66 g), and the mixture was stirred at 60° C. for 30 min. To the reaction mixture was added saturated brine, and the mixture was extracted with ethyl acetate. The organic layer was dried over anhydrous magnesium sulfate, the solvent was evaporated, and the obtained residue was purified by silica gel column chromatography (hexane/ethyl acetate) to give the title compound (3.18 g).
$^1$H NMR (300 MHz, CDCl$_3$) δ 0.33-0.43 (2H, m), 0.61-0.72 (2H, m), 1.17-1.40 (1H, m), 2.00 (2H, t, J=6.4 Hz), 2.65-2.76 (2H, m), 2.90-3.01 (2H, m), 3.92 (2H, d, J=6.8 Hz), 4.01-4.09 (4H, m), 6.93-7.01 (1H, m), 7.63-7.73 (2H, m).

D) 2-(4-(cyclopropylmethoxy)-3-fluorophenyl)-4,5,6,7-tetrahydro-1,3-benzoxazol-6-ol To 2-(4-(cyclopropylmethoxy)-3-fluorophenyl)-4,7-dihydro-5H-spiro[1,3-benzoxazole-6,2'-[1,3]dioxolane] (3.75 g) in a mixed solvent of THF (25 mL)-methanol (12.5 mL)-water (12.5 mL) was added 6 M hydrochloric acid (10.8 mL), and the mixture was stirred at 70° C. for 1 hr. The reaction mixture was neutralized with saturated aqueous sodium hydrogen carbonate solution, and the mixture was extracted with ethyl acetate. To the organic layer was added sodium tetrahydroborate (411 mg), and the mixture was stirred at room temperature for 20 min. To the reaction mixture was added saturated aqueous ammonium chloride solution, and the mixture was extracted with ethyl acetate. The organic layer was dried over anhydrous magnesium sulfate, and the solvent was evaporated under reduced pressure. The obtained residue was purified by silica gel column chromatography (hexane/ethyl acetate) to give the title compound (1.58 g).
$^1$H NMR (300 MHz, CDCl$_3$) δ 0.31-0.43 (2H, m), 0.61-0.73 (2H, m), 1.16-1.42 (1H, m), 1.71 (1H, d, J=5.3 Hz), 1.90-2.10 (2H, m), 2.49-2.82 (3H, m), 2.99-3.14 (1H, m), 3.92 (2H, d, J=7.2 Hz), 4.25-4.39 (1H, m), 6.88-7.03 (1H, m), 7.65-7.74 (2H, m).

E) 2-((2-(4-(cyclopropylmethoxy)-3-fluorophenyl)-4,5,6,7-tetrahydro-1,3-benzoxazol-6-yl)oxy)-1-(morpholin-4-yl)ethanone To a solution of 2-(4-(cyclopropylmethoxy)-3-fluorophenyl)-4,5,6,7-tetrahydro-1,3-benzoxazol-6-ol (1.58 g) and 4-(chloroacetyl)morpholine (1.36 mL) in THF (30 mL) was added potassium tert-butoxide (1.17 g), and the mixture was stirred for 1 hr under a nitrogen stream. To the reaction mixture was added saturated aqueous ammonium chloride solution, and the mixture was extracted with ethyl acetate. The organic layer was dried over anhydrous magnesium sulfate, and the solvent was evaporated under reduced pressure. The obtained residue was purified by silica gel column chromatography (hexane/ethyl acetate/methanol) to give the title compound (1.68 g).
$^1$H NMR (300 MHz, CDCl$_3$) δ 0.33-0.42 (2H, m), 0.63-0.71 (2H, m), 1.26-1.40 (1H, m), 1.95-2.13 (2H, m), 2.52-2.87 (3H, m), 2.97-3.16 (1H, m), 3.44-3.76 (8H, m), 3.92 (2H, d, J=7.2 Hz), 3.97-4.07 (1H, m), 4.17-4.33 (2H, m), 6.86-7.06 (1H, m), 7.58-7.75 (2H, m).

F) 1-((2-(4-(cyclopropylmethoxy)-3-fluorophenyl)-4,5,6,7-tetrahydro-1,3-benzoxazol-6-yl)oxy)propan-2-ol To a solution of 2-((2-(4-(cyclopropylmethoxy)-3-fluorophenyl)-4,5,6,7-tetrahydro-1,3-benzoxazol-6-yl)oxy)-1-(morpholin-4-yl)ethanone (1.68 g) in THF (25 mL) was added methylmagnesium bromide (1 M THF solution, 5.85 mL). To the reaction mixture was added saturated aqueous ammonium chloride solution, and the mixture was extracted with ethyl acetate. The organic layer was dried over anhydrous magnesium sulfate, and the solvent was evaporated under reduced pressure. To the obtained residue in a mixed solvent of THF (10 mL)-methanol (10 mL) was added sodium tetrahydroborate (148 mg), and the mixture was stirred at room temperature for 10 min. To the reaction mixture was added saturated aqueous ammonium chloride solution, and the mixture was extracted with ethyl acetate. The organic layer was dried over anhydrous magnesium sulfate, and the solvent was evaporated under reduced pressure. The obtained residue was purified by silica gel column chromatography (hexane/ethyl acetate) to give the title compound (920 mg).
$^1$H NMR (300 MHz, CDCl$_3$) δ 0.33-0.45 (2H, m), 0.61-0.71 (2H, m), 1.17 (3H, d, J=6.4 Hz), 1.25-1.42 (1H, m), 1.88-2.10 (2H, m), 2.32 (1H, brs), 2.48-2.85 (3H, m), 2.93-3.14 (1H, m), 3.26-3.38 (1H, m), 3.46-3.64 (1H, m), 3.81-4.04 (4H, m), 6.87-7.06 (1H, m), 7.61-7.81 (2H, m).

G) 6-(2-azidopropoxy)-2-(4-(cyclopropylmethoxy)-3-fluorophenyl)-4,5,6,7-tetrahydro-1,3-benzoxazole To a solution of 1-((2-(4-(cyclopropylmethoxy)-3-fluorophenyl)-4,5,6,7-tetrahydro-1,3-benzoxazol-6-yl)oxy)propan-2-ol (920 mg) and triethylamine (0.710 mL) in THF (30 mL) was added methanesulfonyl chloride (0.296 mL) at room temperature, and the mixture was stirred for 10 min. To the reaction mixture was added saturated aqueous sodium hydrogen carbonate solution, and the mixture was extracted with ethyl acetate. The organic layer was dried over anhydrous magnesium sulfate, and concentrated under reduced pressure. The obtained residue was dissolved in DMF (30 mL), sodium azide (829 mg) was added thereto, and the mixture was stirred at 100° C. for 2 hr. To the reaction mixture was added water, and the mixture was extracted with ethyl acetate. The organic layer was washed with saturated brine, dried over anhydrous magnesium sulfate, and concentrated under reduced pressure. The obtained residue was purified by silica gel column chromatography (hexane/ethyl acetate) to give the title compound (870 mg).

$^1$H NMR (300 MHz, CDCl$_3$) δ 0.27-0.43 (2H, m), 0.58-0.76 (2H, m), 1.20 (3H, dd, J=6.6, 1.3 Hz), 1.29-1.39 (1H, m), 1.95-2.10 (2H, m), 2.47-2.86 (3H, m), 2.94-3.12 (1H, m), 3.41-3.72 (3H, m), 3.83-3.99 (3H, m), 6.91-7.03 (1H, m), 7.62-7.78 (2H, m).

H) N-(1-((2-(4-(cyclopropylmethoxy)-3-fluorophenyl)-4,5,6,7-tetrahydro-1,3-benzoxazol-6-yl)oxy)propan-2-yl)acetamide A mixture of 6-(2-azidopropoxy)-2-(4-(cyclopropylmethoxy)-3-fluorophenyl)-4,5,6,7-tetrahydro-1,3-benzoxazole (870 mg), 10% palladium-carbon (containing water (50%), 800 mg) and THF (10 mL) was stirred at room temperature for 10 min. The catalyst was removed by filtration, and the obtained filtrate was concentrated under reduced pressure. To the obtained residue were added pyridine (10 mL) and acetic anhydride (10 mL), and the mixture was stirred at room temperature for 10 min. The reaction mixture was concentrated under reduced pressure, and the residue was purified by silica gel column chromatography (hexane/ethyl acetate/methanol) to give the title compound (725 mg).

$^1$H NMR (300 MHz, CDCl$_3$) δ 0.32-0.43 (2H, m), 0.60-0.72 (2H, m), 1.18 (3H, dd, J=6.8, 1.5 Hz), 1.29-1.38 (1H, m), 1.87-2.03 (5H, m), 2.49-2.85 (3H, m), 2.92-3.09 (1H, m), 3.39-3.63 (2H, m), 3.79-3.98 (3H, m), 4.14-4.24 (1H, m), 5.47-5.70 (1H, m), 6.89-7.05 (1H, m), 7.60-7.75 (2H, m).

Example 53a

Optically Active Form of N-(1-((2-(4-(cyclopropylmethoxy)-3-fluorophenyl)-4,5,6,7-tetrahydro-1,3-benzoxazol-6-yl)oxy)propan-2-yl)acetamide A diastereomer mixture (700 mg) of N-(1-((2-(4-(cyclopropylmethoxy)-3-fluorophenyl)-4,5,6,7-tetrahydro-1,3-benzoxazol-6-yl)oxy)propan-2-yl)acetamide was resolved by HPLC (column: CHIRALPAK CD (trade name), 50 mmID×500 mL, DAICEL CHEMICAL INDUSTRIES, LTD., mobile phase:hexane/ethanol=50:50), and the compound having the shortest retention time was resolved by HPLC (column: CHIRALPAK AD (trade name), 50 mmID×500 mL, DAICEL CHEMICAL INDUSTRIES, LTD., mobile phase:hexane/ethanol=70:30) to give the compound having a longer retention time as the title compound (136 mg).

$^1$H NMR (300 MHz, CDCl$_3$) δ 0.30-0.45 (2H, m), 0.59-0.73 (2H, m), 1.18 (3H, d, J=6.8 Hz), 1.24-1.45 (1H, m), 1.87-2.08 (5H, m), 2.47-2.81 (3H, m), 2.94-3.11 (1H, m), 3.40-3.50 (1H, m), 3.53-3.61 (1H, m), 3.79-4.00 (3H, m), 4.07-4.27 (1H, m), 5.60 (1H, d, J=8.7 Hz), 6.85-7.06 (1H, m), 7.61-7.77 (2H, m).

retention time (OD) 13.59 min.
retention time (AD) 31.29 min.

Example 53b

Optically Active Form of N-(1-((2-(4-(cyclopropylmethoxy)-3-fluorophenyl)-4,5,6,7-tetrahydro-1,3-benzoxazol-6-yl)oxy)propan-2-yl)acetamide A diastereomer mixture (700 mg) of N-(1-((2-(4-(cyclopropylmethoxy)-3-fluorophenyl)-4,5,6,7-benzoxazol-6-yl)oxy)propan-2-yl)acetamide was resolved by HPLC (column: CHIRALPAK CD (trade name), 50 mmID×500 mL, DAICEL CHEMICAL INDUSTRIES, LTD., mobile phase:hexane/ethanol=50:50), and the compound having the shortest retention time was resolved by HPLC (column: CHIRALPAK AD (trade name), 50 mmID×500 mL, DAICEL CHEMICAL INDUSTRIES, LTD., mobile phase:hexane/ethanol=70:30) to give the compound having a shorter retention time as the title compound (140 mg).

$^1$H NMR (300 MHz, CDCl$_3$) δ 0.31-0.42 (2H, m), 0.59-0.72 (2H, m), 1.18 (3H, d, J=6.8 Hz), 1.25-1.41 (1H, m), 1.90-1.96 (3H, m), 1.96-2.07 (2H, m), 2.41-2.82 (3H, m), 2.95-3.08 (1H, m), 3.43-3.61 (2H, m), 3.82-3.96 (3H, m), 4.05-4.27 (1H, m), 5.57 (1H, d, J=8.7 Hz), 6.91-7.05 (1H, m), 7.63-7.78 (2H, m).

retention time (OD) 13.59 min.
retention time (AD) 25.28 min.

Example 53c

Optically Active Form of N-(1-((2-(4-(cyclopropylmethoxy)-3-fluorophenyl)-4,5,6,7-tetrahydro-1,3-benzoxazol-6-yl)oxy)propan-2-yl)acetamide A diastereomer mixture (700 mg) of N-(1-((2-(4-(cyclopropylmethoxy)-3-fluorophenyl)-4,5,6,7-tetrahydro-1,3-benzoxazol-6-yl)oxy)propan-2-yl)acetamide was resolved by HPLC (column: CHIRALPAK CD (trade name), 50 mmID×500 mL, DAICEL CHEMICAL INDUSTRIES, LTD., mobile phase:hexane/ethanol=50:50) to give the compound having the second longest retention time as the title compound (134 mg).

$^1$H NMR (300 MHz, CDCl$_3$) δ 0.30-0.45 (2H, m), 0.59-0.73 (2H, m), 1.18 (3H, d, J=6.8 Hz), 1.24-1.45 (1H, m), 1.87-2.08 (5H, m), 2.47-2.81 (3H, m), 2.94-3.11 (1H, m), 3.40-3.50 (1H, m), 3.53-3.61 (1H, m), 3.79-4.00 (3H, m), 4.07-4.27 (1H, m), 5.60 (1H, d, J=8.7 Hz), 6.85-7.06 (1H, m), 7.61-7.77 (2H, m).

retention time (OD) 18.07 min.

Example 53d

Optically Active Form of N-(1-((2-(4-(cyclopropylmethoxy)-3-fluorophenyl)-4,5,6,7-tetrahydro-1,3-benzoxazol-6-yl)oxy)propan-2-yl)acetamide A diastereomer mixture (700 mg) of N-(1-((2-(4-(cyclopropylmethoxy)-3-fluorophenyl)-4,5,6,7-tetrahydro-1,3-benzoxazol-6-yl)oxy)propan-2-yl)acetamide was resolved by HPLC (column: CHIRALPAK CD (trade name), 50 mmID×500 mL, DAICEL CHEMICAL INDUSTRIES, LTD., mobile phase:hexane/ethanol=50:50) to give the compound having the longest retention time as the title compound (129 mg).

¹H NMR (300 MHz, CDCl₃) δ 0.29-0.44 (2H, m), 0.56-0.75 (2H, m), 1.18 (3H, d, J=6.8 Hz), 1.24-1.40 (1H, m), 1.91-1.95 (3H, m), 1.96-2.07 (2H, m), 2.50-2.79 (3H, m), 2.93-3.10 (1H, m), 3.39-3.62 (2H, m), 3.81-3.97 (3H, m), 4.06-4.24 (1H, m), 5.58 (1H, d, J=7.6 Hz), 6.89-7.03 (1H, m), 7.55-7.78 (2H, m).

retention time (OD) δ9.06 min.

Example 54

N-(1-((2-(3-chloro-4-(cyclopropylmethoxy)phenyl)-4,5,6,7-tetrahydro-1,3-benzoxazol-5-yl)oxy)propan-2-yl)acetamide A) 3-chloro-4-(cyclopropylmethoxy)-N-(8-hydroxy-1,4-dioxaspiro[4.5]dec-7-yl)benzamide A mixture of 7-(benzylamino)-1,4-dioxaspiro[4.5]decan-8-ol (23.2 g), 10% palladium-carbon (containing water (50%), 8.00 g) and ethanol (100 mL) was stirred at room temperature for 2 hr under a hydrogen atmosphere (5 atm). The catalyst was removed by filtration, and the obtained filtrate was concentrated under reduced pressure. The obtained 7-amino-1,4-dioxaspiro[4.5]decan-8-ol was used for the next reaction without further purification.

To a solution of 3-chloro-4-(cyclopropylmethoxy)benzoic acid (13.9 g) in THF (150 mL) were added oxalyl dichloride (8.07 mL) and DMF (2 drops), and the mixture was stirred at room temperature for 30 min. The solvent was evaporated under reduced pressure, and to the obtained residue in THF (100 mL)-saturated aqueous sodium hydrogen carbonate solution (20 mL) was added a solution of 7-amino-1,4-dioxaspiro[4.5]decan-8-ol (obtained in the above-mentioned reaction) in THF (5 mL). The precipitated solid was collected by filtration, and washed with ethyl acetate. The filtrate was extracted with ethyl acetate, and the extract was dried over anhydrous magnesium sulfate, and concentrated under reduced pressure. The obtained solid was washed with diethyl ether/hexane, and combined with the above-mentioned collected solid to give the title compound (19.4 g). ¹H NMR (300 MHz, CDCl₃) δ 0.32-0.46 (2H, m), 0.62-0.72 (2H, m), 1.20-1.39 (1H, m), 1.53-2.00 (6H, m), 2.29 (1H, dd, J=13.6, 4.5 Hz), 3.80-3.87 (1H, m), 3.93 (2H, d, J=6.8 Hz), 4.01 (4H, s), 4.28 (1H, quin, J=5.9 Hz), 6.91 (1H, d, J=8.3 Hz), 7.16 (1H, d, J=7.2 Hz), 7.64 (1H, dd, J=8.3, 2.3 Hz), 7.78 (1H, d, J=2.3 Hz).

B) 2-(3-chloro-4-(cyclopropylmethoxy)phenyl)-6,7-dihydro-4H-spiro[1,3-benzoxazole-5,2'-[1,3]dioxolane]

To a solution of 3-chloro-4-(cyclopropylmethoxy)-N-(8-hydroxy-1,4-dioxaspiro[4.5]dec-7-yl)benzamide (19.4 g) in dimethyl sulfoxide (100 mL) were added triethylamine (22.2 mL) and sulfur trioxide-pyridine complex (25.4 g), and the mixture was stirred for 1 hr under a nitrogen stream. To the reaction mixture was added water, and the mixture was extracted with ethyl acetate. The organic layer was washed with saturated brine, and dried over anhydrous magnesium sulfate, and the solvent was evaporated under reduced pressure. To a solution of the obtained residue in THF (100 mL) was added (methoxycarbonylsulfamoyl)triethylammonium hydroxide inner salt (19.0 g), and the mixture was stirred at 60° C. for 1 hr. To the reaction mixture was added saturated brine, and the mixture was extracted with ethyl acetate. The organic layer was dried over anhydrous magnesium sulfate, and subjected to silica gel column chromatography (NH, ethyl acetate). The solvent was evaporated, and the obtained residue was purified by silica gel column chromatography (hexane/ethyl acetate) to give the title compound (12.5 g).

¹H NMR (300 MHz, CDCl₃) δ 0.36-0.44 (2H, m), 0.62-0.71 (2H, m), 1.29-1.40 (1H, m), 1.98-2.09 (2H, m), 2.80-2.89 (4H, m), 3.93 (2H, d, J=6.8 Hz), 3.99-4.07 (4H, m), 6.93 (1H, d, J=8.3 Hz), 7.81 (1H, dd, J=8.5, 2.1 Hz), 8.00 (1H, d, J=1.9 Hz).

C) 2-(3-chloro-4-(cyclopropylmethoxy)phenyl)-4,5,6,7-tetrahydro-1,3-benzoxazol-5-ol To 2-(3-chloro-4-(cyclopropylmethoxy)phenyl)-6,7-dihydro-4H-spiro[1,3-benzoxazole-5,2'-[1,3]dioxolane] (12.5 g) in a mixed solvent of THF (60 mL)-methanol (30 mL)-water (30 mL) was added 6 M hydrochloric acid (34.5 mL), and the mixture was stirred at 70° C. for 1 hr. The reaction mixture was neutralized with saturated aqueous sodium hydrogen carbonate solution, and the mixture was extracted with ethyl acetate. To the organic layer was added sodium tetrahydroborate (1.31 g), and the mixture was stirred at room temperature for 20 min. To the reaction mixture was added saturated aqueous ammonium chloride solution, and the mixture was extracted with ethyl acetate. The organic layer was dried over anhydrous magnesium sulfate, and the solvent was evaporated under reduced pressure. The obtained residue was purified by silica gel column chromatography (hexane/ethyl acetate) to give the title compound (5.63 g).

¹H NMR (300 MHz, CDCl₃) δ 0.35-0.45 (2H, m), 0.59-0.75 (2H, m), 1.29-1.39 (1H, m), 1.96-2.13 (2H, m), 2.54-3.06 (4H, m), 3.93 (2H, d, J=6.8 Hz), 4.21-4.33 (1H, m), 6.93 (1H, d, J=8.7 Hz), 7.81 (1H, dd, J=8.7, 2.3 Hz), 8.00 (1H, d, J=2.3 Hz).

D) 2-((2-(3-chloro-4-(cyclopropylmethoxy)phenyl)-4,5,6,7-tetrahydro-1,3-benzoxazol-5-yl)oxy)-1-(morpholin-4-yl)ethanone To a solution of 2-(3-chloro-4-(cyclopropylmethoxy)phenyl)-4,5,6,7-tetrahydro-1,3-benzoxazol-5-ol (5.63 g) and 4-(chloroacetyl)morpholine (4.58 mL) in THF (50 mL) was added potassium tert-butoxide (3.95 g), and the mixture was stirred for 1 hr under a nitrogen stream. To the reaction mixture was added saturated aqueous ammonium chloride solution, and the mixture was extracted with ethyl acetate. The organic layer was dried over anhydrous magnesium sulfate, and the solvent was evaporated under reduced pressure. The obtained residue was purified by silica gel column chromatography (hexane/ethyl acetate/methanol) to give the title compound (6.22 g).

¹H NMR (300 MHz, CDCl₃) δ 0.35-0.46 (2H, m), 0.60-0.72 (2H, m), 1.30-1.43 (1H, m), 2.06-2.18 (2H, m), 2.57-3.02 (4H, m), 3.46-3.74 (8H, m), 3.88-4.03 (3H, m), 4.18-4.32 (2H, m), 6.94 (1H, d, J=8.7 Hz), 7.81 (1H, dd, J=8.7, 2.3 Hz), 8.00 (1H, d, J=2.3 Hz).

E) 1-((2-(3-chloro-4-(cyclopropylmethoxy)phenyl)-4,5,6,7-tetrahydro-1,3-benzoxazol-5-yl)oxy)propan-2-ol To a solution of 2-((2-(3-chloro-4-(cyclopropylmethoxy)phenyl)-4,5,6,7-tetrahydro-1,3-benzoxazol-5-yl)oxy)-1-(morpholin-4-yl)ethanone (6.22 g) in THF (25 mL) was added methylmagnesium bromide (1 M THF solution, 20.9 mL). To the reaction mixture was added saturated aqueous ammonium chloride solution, and the mixture was extracted with ethyl acetate. The organic layer was dried over anhydrous magnesium sulfate, and the solvent was evaporated under reduced pressure. To the obtained residue in a mixed solvent of THF (10 mL)-methanol (10 mL) was added sodium tetrahydroborate (527 mg), and the mixture was stirred at room temperature for 10 min. To the reaction mixture was added saturated aqueous ammonium chloride solution, and the mixture was extracted with ethyl acetate. The organic layer was dried over anhydrous magnesium sulfate, and the solvent was evaporated under reduced pressure. The obtained residue was purified by silica gel column chromatography (hexane/ethyl acetate) to give the title compound (3.82 g).

$^1$H NMR (300 MHz, CDCl$_3$) δ 0.34-0.44 (2H, m), 0.61-0.74 (2H, m), 1.16 (3H, d, J=6.0 Hz), 1.29-1.41 (1H, m), 2.04-2.13 (2H, m), 2.37 (1H, dd, J=10.8, 2.8 Hz), 2.58-3.00 (4H, m), 3.22-3.37 (1H, m), 3.46-3.60 (1H, m), 3.82-4.01 (4H, m), 6.93 (1H, d, J=8.7 Hz), 7.82 (1H, dd, J=8.7, 2.3 Hz), 8.01 (1H, d, J=2.3 Hz).

F) 5-(2-azidopropoxy)-2-(3-chloro-4-(cyclopropylmethoxy)phenyl)-4,5,6,7-tetrahydro-1,3-benzoxazole To a solution of 1-((2-(3-chloro-4-(cyclopropylmethoxy)phenyl)-4,5,6,7-tetrahydro-1,3-benzoxazol-5-yl)oxy)propan-2-ol (3.82 g) and triethylamine (2.82 mL) in THF (30 mL) was added methanesulfonyl chloride (1.17 mL) at room temperature, and the mixture was stirred for 10 min. To the reaction mixture was added saturated aqueous sodium hydrogen carbonate solution, and the mixture was extracted with ethyl acetate. The organic layer was dried over anhydrous magnesium sulfate, and concentrated under reduced pressure. The obtained residue was dissolved in DMF (30 mL), sodium azide (3.29 g) was added thereto, and the mixture was stirred at 100° C. for 1 hr. To the reaction mixture was added water, and the mixture was extracted with ethyl acetate. The organic layer was washed with saturated brine, dried over anhydrous magnesium sulfate, and concentrated under reduced pressure. The obtained residue was purified by silica gel column chromatography (hexane/ethyl acetate) to give the title compound (3.40 g).

$^1$H NMR (300 MHz, CDCl$_3$) δ 0.36-0.45 (2H, m), 0.60-0.72 (2H, m), 1.19 (3H, t, J=6.2 Hz), 1.29-1.42 (1H, m), 2.05-2.13 (2H, m), 2.61-2.96 (4H, m), 3.38-3.71 (3H, m), 3.82-3.98 (3H, m), 6.93 (1H, d, J=8.7 Hz), 7.82 (1H, dd, J=8.7, 2.3 Hz), 8.01 (1H, d, J=1.9 Hz).

G) N-(1-((2-(3-chloro-4-(cyclopropylmethoxy)phenyl)-4,5,6,7-tetrahydro-1,3-benzoxazol-5-yl)oxy)propan-2-yl)acetamide To a solution of 5-(2-azidopropoxy)-2-(3-chloro-4-(cyclopropylmethoxy)phenyl)-4,5,6,7-tetrahydro-1,3-benzoxazole (3.40 g) in THF (30 mL) were added triphenylphosphine (2.66 g) and water (5 mL), and the mixture was stirred overnight at 60° C. The solvent was evaporated under reduced pressure, and the obtained residue was purified by silica gel column chromatography (NH, hexane/ethyl acetate). To the obtained oil were added pyridine (10 mL) and acetic anhydride (10 mL), and the mixture was stirred at room temperature for 10 min. The reaction mixture was concentrated under reduced pressure, and the residue was purified by silica gel column chromatography (hexane/ethyl acetate/methanol) to give the title compound (3.02 g).

$^1$H NMR (300 MHz, CDCl$_3$) δ 0.36-0.46 (2H, m), 0.63-0.73 (2H, m), 1.17 (3H, dd, J=6.6, 2.8 Hz), 1.27-1.41 (1H, m), 1.95 (3H, d, J=4.5 Hz), 2.00-2.11 (2H, m), 2.59-2.95 (4H, m), 3.40-3.62 (2H, m), 3.85 (1H, quin, J=5.1 Hz), 3.94 (2H, d, J=6.8 Hz), 4.09-4.24 (1H, m), 5.61 (1H, d, J=7.6 Hz), 6.94 (1H, d, J=8.7 Hz), 7.82 (1H, dd, J=8.7, 2.3 Hz), 8.01 (1H, d, J=2.3 Hz).

Example 55a

Optically Active Form of N-(1-((2-(3-chloro-4-(cyclopropylmethoxy)phenyl)-4,5,6,7-tetrahydro-1,3-benzoxazol-5-yl)oxy)propan-2-yl)acetamide A diastereomer mixture (1.00 g) of N-(1-((2-(3-chloro-4-(cyclopropylmethoxy)phenyl)-4,5,6,7-tetrahydro-1,3-benzoxazol-5-yl)oxy)propan-2-yl)acetamide was resolved by HPLC (column: CHIRALPAK IC (trade name), 50 mmID×500 mL, DAICEL CHEMICAL INDUSTRIES, LTD., mobile phase:hexane/ethanol=75:25), and a mixture of the compound having the shortest retention time and the compound having the second shortest retention time was resolved by HPLC (column: CHIRALPAK AD (trade name), 50 mmID×500 mL, DAICEL CHEMICAL INDUSTRIES, LTD., mobile phase:hexane/ethanol=87:13) to give the compound having a longer retention time as the title compound (243 mg).

$^1$H NMR (300 MHz, CDCl$_3$) δ 0.35-0.46 (2H, m), 0.63-0.71 (2H, m), 1.17 (3H, d, J=6.8 Hz), 1.24-1.43 (1H, m), 1.96 (3H, s), 2.00-2.11 (2H, m), 2.51-2.97 (4H, m), 3.38-3.49 (1H, m), 3.52-3.62 (1H, m), 3.78-3.89 (1H, m), 3.94 (2H, d, J=6.4 Hz), 4.08-4.27 (1H, m), 5.61 (1H, d, J=7.6 Hz), 6.94 (1H, d, J=8.7 Hz), 7.82 (1H, dd, J=8.7, 2.3 Hz), 8.01 (1H, d, J=2.3 Hz).

retention time (IC) 55.53 min. and 1 hr and 3 min
retention time (AD) 47.45 min.

Example 55b

Optically Active Form of N-(1-((2-(3-chloro-4-(cyclopropylmethoxy)phenyl)-4,5,6,7-tetrahydro-1,3-benzoxazol-5-yl)oxy)propan-2-yl)acetamide A diastereomer mixture (1.00 g) of N-(1-((2-(3-chloro-4-(cyclopropylmethoxy)phenyl)-4,5,6,7-tetrahydro-1,3-benzoxazol-5-yl)oxy)propan-2-yl)acetamide was resolved by HPLC (column: CHIRALPAK IC (trade name), 50 mmID×500 mL, DAICEL CHEMICAL INDUSTRIES, LTD., mobile phase:hexane/ethanol=75:25), and a mixture of the compound having the shortest retention time and the compound having the second shortest retention time was resolved by HPLC (column: CHIRALPAK AD (trade name), 50 mmID×500 mmL, DAICEL CHEMICAL INDUSTRIES, LTD., mobile phase:hexane/ethanol=87:13) to give the compound having a shorter retention time as the title compound (229 mg).

$^1$H NMR (300 MHz, CDCl$_3$) δ 0.35-0.46 (2H, m), 0.59-0.73 (2H, m), 1.18 (3H, d, J=6.8 Hz), 1.25-1.43 (1H, m), 1.94 (3H, s), 1.98-2.13 (2H, m), 2.57-2.96 (4H, m), 3.42-3.59 (2H, m), 3.77-3.89 (1H, m), 3.94 (2H, d, J=6.8 Hz), 4.06-4.26 (1H, m), 5.59 (1H, d, J=7.9 Hz), 6.94 (1H, d, J=8.7 Hz), 7.82 (1H, dd, J=8.5, 2.1 Hz), 8.01 (1H, d, J=2.3 Hz).

retention time (IC) 55.53 min. and 1 hr and 3 min
retention time (AD) 31.21 min.

Example 55c

Optically Active Form N-(1-((2-(3-chloro-4-(cyclopropylmethoxy)phenyl)-4,5,6,7-tetrahydro-1,3-benzoxazol-5-yl)oxy)propan-2-yl)acetamide A diastereomer mixture (1.00 g) of N-(1-((2-(3-chloro-4-(cyclopropylmethoxy)phenyl)-4,5,6,7-tetrahydro-1,3-benzoxazol-5-yl)oxy)propan-2-yl)acetamide was resolved by HPLC (column: CHIRALPAK IC (trade name), 50 mmID× 500 mL, DAICEL CHEMICAL INDUSTRIES, LTD., mobile phase:hexane/ethanol=75:25) to give the compound having the second longest retention time as the title compound (229 mg).

$^1$H NMR (300 MHz, CDCl$_3$) δ 0.36-0.45 (2H, m), 0.62-0.72 (2H, m), 1.18 (3H, d, J=6.8 Hz), 1.25-1.42 (1H, m), 1.94 (3H, s), 2.00-2.11 (2H, m), 2.54-2.95 (4H, m), 3.43-3.59 (2H, m), 3.84 (1H, dt, J=9.9, 5.1 Hz), 3.94 (2H, d, J=6.8 Hz), 4.06-4.23 (1H, m), 5.59 (1H, d, J=7.9 Hz), 6.94 (1H, d, J=8.7 Hz), 7.82 (1H, dd, J=8.7, 2.3 Hz), 8.01 (1H, d, J=2.3 Hz).

retention time (IC) 1 hr and 14 min

Example 55d

Optically Active Form N-(1-((2-(3-chloro-4-(cyclopropylmethoxy)phenyl)-4,5,6,7-tetrahydro-1,3-benzoxazol-5-yl)oxy)propan-2-yl)acetamide A diastereomer mixture (1.00 g) of N-(1-((2-(3-chloro-4-(cyclopropylmethoxy)phenyl)-4,5,6,7-tetrahydro-1,3-benzoxazol-5-yl)oxy)propan-2-yl)acetamide was resolved by HPLC (column: CHIRALPAK IC (trade name), 50 mmID× 500 mL, DAICEL CHEMICAL INDUSTRIES, LTD., mobile phase:hexane/ethanol=75:25) to give the compound having the longest retention time as the title compound (219 mg).

$^1$H NMR (300 MHz, CDCl$_3$) δ 0.32-0.46 (2H, m), 0.59-0.73 (2H, m), 1.17 (3H, d, J=6.8 Hz), 1.25-1.45 (1H, m), 1.96 (3H, s), 2.00-2.11 (2H, m), 2.50-2.99 (4H, m), 3.39-3.49 (1H, m), 3.53-3.64 (1H, m), 3.78-3.89 (1H, m), 3.94 (2H, d, J=6.8 Hz), 4.09-4.27 (1H, m), 5.59 (1H, d, J=7.6 Hz), 6.94 (1H, d, J=8.7 Hz), 7.82 (1H, dd, J=8.5, 2.1 Hz), 8.01 (1H, d, J=1.9 Hz).

retention time (IC) 1 hr and 39 min.

Example 56

N-(1-((2-(3-chloro-4-(cyclopropylmethoxy)phenyl)-4,5,6,7-tetrahydro-1,3-benzoxazol-6-yl)oxy)propan-2-yl)acetamide A) 3-chloro-4-(cyclopropylmethoxy)-N-(7-hydroxy-1,4-dioxaspiro[4.5]dec-8-yl)benzamide A mixture of 8-azido-1,4-dioxaspiro[4.5]decan-7-ol (16.8 g), 10% palladium-carbon (containing water (50%), 16.0 g) and ethanol (100 mL) was stirred at room temperature for 2 hr under a hydrogen atmosphere. The catalyst was removed by filtration, and the obtained filtrate was concentrated under reduced pressure. The obtained 8-amino-1,4-dioxaspiro[4.5]decan-7-ol was used for the next reaction without further purification.

To a solution of 3-chloro-4-(cyclopropylmethoxy)benzoic acid (14.0 g) in THF (150 mL) were added oxalyl dichloride (8.11 mL) and DMF (2 drops), and the mixture was stirred at room temperature for 30 min. The solvent was evaporated under reduced pressure, and to the obtained residue in THF (100 mL)-saturated aqueous sodium hydrogen carbonate solution (30 mL) was added a solution of 8-amino-1,4-dioxaspiro[4.5]decan-7-ol (obtained in the above-mentioned reaction) in THF (5 mL). The reaction mixture was extracted with ethyl acetate, and the organic layer was dried over anhydrous magnesium sulfate. The solvent was evaporated under reduced pressure, and the obtained solid was washed with diethyl ether to give the title compound (20.8 g).

$^1$H NMR (300 MHz, CDCl$_3$) δ 0.31-0.48 (2H, m), 0.58-0.76 (2H, m), 1.21-1.44 (3H, m), 1.55-1.84 (3H, m), 2.00-2.09 (1H, m), 2.17 (1H, dd, J=13.0, 4.3 Hz), 3.35-3.51 (1H, m), 3.72 (1H, t, J=10.0 Hz), 3.84-4.05 (6H, m), 6.02-6.24 (1H, m), 6.90 (1H, dd, J=8.7, 2.6 Hz), 7.64 (1H, dd, J=8.7, 2.3 Hz), 7.78 (1H, d, J=1.9 Hz).

B) 2-(3-chloro-4-(cyclopropylmethoxy)phenyl)-4,7-dihydro-5H-spiro[1,3-benzoxazole-6,2'-[1,3]dioxolane]

To a solution of 3-chloro-4-(cyclopropylmethoxy)-N-(7-hydroxy-1,4-dioxaspiro[4.5]dec-8-yl)benzamide (20.8 g) in dimethyl sulfoxide (80 mL) were added triethylamine (22.8 mL) and sulfur trioxide-pyridine complex (26.0 g), and the mixture was stirred for 1 hr under a nitrogen stream. To the reaction mixture was added water, and the mixture was extracted with ethyl acetate. The organic layer was washed with saturated brine, and dried over anhydrous magnesium sulfate, and the solvent was evaporated under reduced pressure. To a solution of the obtained residue in THF (80 mL) was added (methoxycarbonylsulfamoyl)triethylammonium hydroxide inner salt (21.4 g), and the mixture was stirred at 60° C. for 30 min. To the reaction mixture was added saturated brine, and the mixture was extracted with ethyl acetate. The organic layer was dried over anhydrous magnesium sulfate, the solvent was evaporated, and the obtained residue was purified by silica gel column chromatography (hexane/ethyl acetate) to give the title compound (10.0 g).

$^1$H NMR (300 MHz, CDCl$_3$) δ 0.36-0.46 (2H, m), 0.61-0.72 (2H, m), 1.30-1.40 (1H, m), 2.00 (2H, t, J=6.4 Hz), 2.66-2.76 (2H, m), 2.95 (2H, s), 3.93 (2H, d, J=6.8 Hz), 3.99-4.08 (4H, m), 6.93 (1H, d, J=8.7 Hz), 7.81 (1H, dd, J=8.7, 2.3 Hz), 8.00 (1H, d, J=1.9 Hz).

C) 2-(3-chloro-4-(cyclopropylmethoxy)phenyl)-4,5,6,7-tetrahydro-1,3-benzoxazol-6-ol To 2-(3-chloro-4-(cyclopropylmethoxy)phenyl)-4,7-dihydro-5H-spiro[1,3-benzoxazole-6,2'-[1,3]dioxolane] (10.0 g) in a mixed solvent of THF (50 mL)-methanol (25 mL)-water (25 mL) was added 6 M hydrochloric acid (27.6 mL), and the mixture was stirred at 70° C. for 1 hr. The reaction mixture was neutralized with saturated aqueous sodium hydrogen carbonate solution, and the mixture was extracted with ethyl acetate. To the organic layer was added sodium tetrahydroborate (1.05 g), and the mixture was stirred at room temperature for 20 min. To the reaction mixture was added saturated aqueous ammonium chloride solution, and the mixture was extracted with ethyl acetate. The organic layer was dried over anhydrous magnesium sulfate, and the solvent was evaporated under reduced pressure. The obtained residue was purified by silica gel column chromatography (hexane/ethyl acetate) to give the title compound (6.61 g).

$^1$H NMR (300 MHz, CDCl$_3$) δ 0.31-0.43 (2H, m), 0.60-0.74 (2H, m), 1.20-1.43 (1H, m), 1.81 (1H, d, J=5.3 Hz), 1.89-2.11 (2H, m), 2.53-2.82 (3H, m), 2.99-3.16 (1H, m), 3.94 (2H, d, J=6.8 Hz), 4.25-4.41 (1H, m), 6.93 (1H, d, J=8.7 Hz), 7.82 (1H, dd, J=8.7, 2.3 Hz), 8.01 (1H, d, J=2.3 Hz).

D) 2-((2-(3-chloro-4-(cyclopropylmethoxy)phenyl)-4,5,6,7-tetrahydro-1,3-benzoxazol-6-yl)oxy)-1-(morpholin-4-yl)ethanone To a solution of 2-(3-chloro-4-(cyclopropylmethoxy)phenyl)-4,5,6,7-tetrahydro-1,3-benzoxazol-6-ol (6.61 g) and 4-(chloroacetyl)morpholine (5.38 mL) in THF (50 mL) was added potassium tert-butoxide (4.64 g), and the mixture was stirred for 1 hr under a nitrogen stream. To the reaction mixture was added saturated aqueous ammonium chloride solution, and the mixture was extracted with ethyl acetate. The organic layer was dried over anhydrous magnesium sulfate, and the solvent was evaporated under reduced pressure. The obtained residue was purified by silica gel column chromatography (hexane/ethyl acetate/methanol) to give the title compound (9.24 g).

$^1$H NMR (300 MHz, CDCl$_3$) δ 0.41 (2H, q, J=4.9 Hz), 0.59-0.76 (2H, m), 1.30-1.43 (1H, m), 1.90-2.13 (2H, m), 2.47-2.90 (3H, m), 3.06 (1H, dd, J=16.2, 4.9 Hz), 3.46-3.75 (8H, m), 3.94 (2H, d, J=6.8 Hz), 4.02 (1H, quin, J=5.3 Hz), 4.18-4.33 (2H, m), 6.94 (1H, d, J=8.7 Hz), 7.81 (1H, dd, J=8.7, 2.3 Hz), 8.01 (1H, d, J=1.9 Hz).

E) 1-((2-(3-chloro-4-(cyclopropylmethoxy)phenyl)-4,5,6,7-tetrahydro-1,3-benzoxazol-6-yl)oxy)propan-2-ol To a solution of 2-((2-(3-chloro-4-(cyclopropylmethoxy)phenyl)-4,5,6,7-tetrahydro-1,3-benzoxazol-6-yl)oxy)-1-(morpholin-4-yl)ethanone (9.24 g) in THF (25 mL) was added methylmagnesium bromide (1 M THF solution, 31.0 mL). To the reaction mixture was added saturated aqueous ammonium chloride solution, and the mixture was extracted with ethyl acetate. The organic layer was dried over anhydrous magnesium sulfate, and the solvent was evaporated under reduced pressure. To the obtained residue in a mixed solvent of THF (10 mL)-methanol (10 mL) was added sodium tetrahydroborate (782 mg), and the mixture was stirred at room temperature for 10 min. the reaction mixture was added saturated aqueous ammonium chloride solution, and the mixture was extracted with ethyl acetate. The organic layer was dried over anhydrous magnesium sulfate, and the solvent was evaporated under reduced pressure. The obtained residue was purified by silica gel column chromatography (hexane/ethyl acetate) to give the title compound (6.51 g).

$^1$H NMR (300 MHz, CDCl$_3$) δ 0.35-0.45 (2H, m), 0.61-0.73 (2H, m), 1.17 (3H, d, J=6.4 Hz), 1.29-1.40 (1H, m), 1.96-2.07 (2H, m), 2.35 (1H, t, J=3.0 Hz), 2.50-2.89 (3H, m), 2.95-3.13 (1H, m), 3.26-3.38 (1H, m), 3.50-3.62 (1H, m), 3.86-4.02 (4H, m), 6.94 (1H, d, J=8.7 Hz), 7.82 (1H, dd, J=8.7, 2.3 Hz), 8.01 (1H, d, J=2.3 Hz).

F) 6-(2-azidopropoxy)-2-(3-chloro-4-(cyclopropylmethoxy)phenyl)-4,5,6,7-tetrahydro-1,3-benzoxazole To a solution of 1-((2-(3-chloro-4-(cyclopropylmethoxy)phenyl)-4,5,6,7-tetrahydro-1,3-benzoxazol-6-yl)oxy)propan-2-ol (6.51 g) and triethylamine (4.80 mL) in THF (30 mL) was added methanesulfonyl chloride (2.00 mL) at room temperature, and the mixture was stirred for 10 min. To the reaction mixture was added saturated aqueous sodium hydrogen carbonate solution, and the mixture was extracted with ethyl acetate. The organic layer was dried over anhydrous magnesium sulfate, and concentrated under reduced pressure. The obtained residue was dissolved in DMF (30 mL), sodium azide (5.60 g) was added thereto, and the mixture was stirred at 100° C. for 1 hr. To the reaction mixture was added water, and the mixture was extracted with ethyl acetate. The organic layer was washed with saturated brine, dried over anhydrous magnesium sulfate, and concentrated under reduced pressure. The obtained residue was purified by silica gel column chromatography (hexane/ethyl acetate) to give the title compound (6.08 g).

$^1$H NMR (300 MHz, CDCl$_3$) δ 0.35-0.44 (2H, m), 0.59-0.74 (2H, m), 1.20 (3H, dd, J=6.4, 1.1 Hz), 1.29-1.39 (1H, m), 1.94-2.07 (2H, m), 2.48-2.84 (3H, m), 2.95-3.13 (1H, m), 3.41-3.56 (1H, m), 3.55-3.73 (2H, m), 3.84-3.98 (3H, m), 6.93 (1H, d, J=8.7 Hz), 7.82 (1H, dd, J=8.5, 2.1 Hz), 8.01 (1H, d, J=2.3 Hz).

G) N-(1-((2-(3-chloro-4-(cyclopropylmethoxy)phenyl)-4,5,6,7-tetrahydro-1,3-benzoxazol-6-yl)oxy)propan-2-yl)acetamide To a solution of 6-(2-azidopropoxy)-2-(3-chloro-4-(cyclopropylmethoxy)phenyl)-4,5,6,7-tetrahydro-1,3-benzoxazole (6.08 g) in THF (30 mL) were added triphenylphosphine (4.75 g) and water (5 mL), and the mixture was stirred overnight at 60° C. The solvent was evaporated under reduced pressure, and the obtained residue was purified by silica gel column chromatography (NH, hexane/ethyl acetate). To the obtained oil were added pyridine (10 mL) and acetic anhydride (10 mL), and the mixture was stirred at room temperature for 10 min. The reaction mixture was concentrated under reduced pressure, and the residue was purified by silica gel column chromatography (hexane/ethyl acetate/methanol) to give the title compound (3.02 g).

$^1$H NMR (300 MHz, CDCl$_3$) δ 0.35-0.45 (2H, m), 0.62-0.72 (2H, m), 1.18 (3H, dd, J=6.8, 1.5 Hz), 1.29-1.40 (1H, m), 1.88-2.03 (5H, m), 2.46-2.79 (3H, m), 2.93-3.09 (1H, m), 3.39-3.61 (2H, m), 3.80-4.01 (3H, m), 4.14-4.26 (1H, m), 5.49-5.72 (1H, m), 6.94 (1H, d, J=8.7 Hz), 7.82 (1H, dd, J=8.7, 1.9 Hz), 8.01 (1H, d, J=2.3 Hz).

Example 57a

Optically Active Form of N-(1-((2-(3-chloro-4-(cyclopropylmethoxy)phenyl)-4,5,6,7-tetrahydro-1,3-benzoxazol-6-yl)oxy)propan-2-yl)acetamide A diastereomer mixture (1.00 g) of N-(1-((2-(3-chloro-4-(cyclopropylmethoxy)phenyl)-4,5,6,7-tetrahydro-1,3-benzoxazol-6-yl)oxy)propan-2-yl)acetamide was resolved by HPLC (column: CHIRALPAK CD (trade name), 50 mmID×500 mL, DAICEL CHEMICAL INDUSTRIES, LTD., mobile phase:hexane/ethanol=70:30), and the compound having the shortest retention time was resolved by HPLC (column: CHIRALPAK AD (trade name), 50 mmID×500 mL, DAICEL CHEMICAL INDUSTRIES, LTD., mobile phase:hexane/ethanol=85:15) to give the compound having a longer retention time as the title compound (238 mg).

$^1$H NMR (300 MHz, CDCl$_3$) δ 0.35-0.44 (2H, m), 0.61-0.73 (2H, m), 1.18 (3H, d, J=6.8 Hz), 1.24-1.40 (1H, m), 1.92-1.96 (3H, m), 1.96-2.06 (2H, m), 2.49-2.84 (3H, m), 3.01 (1H, dd, J=16.4, 5.1 Hz), 3.42-3.62 (2H, m), 3.82-4.00 (3H, m), 4.10-4.31 (1H, m), 5.58 (1H, d, J=7.2 Hz), 6.94 (1H, d, J=8.7 Hz), 7.82 (1H, dd, J=8.7, 1.9 Hz), 8.01 (1H, d, J=1.9 Hz).

retention time (OD) 15.49 min.
retention time (AD) 34.31 min.

Example 57b

Optically Active Form of N-(1-((2-(3-chloro-4-(cyclopropylmethoxy)phenyl)-4,5,6,7-tetrahydro-1,3-benzoxazol-6-yl)oxy)propan-2-yl)acetamide A diastereomer mixture (1.00 g) of N-(1-((2-(3-chloro-4-(cyclopropylmethoxy)phenyl)-4,5,6,7-tetrahydro-1,3-benzoxazol-6-yl)oxy)propan-2-yl)acetamide was resolved by HPLC (column: CHIRALPAK CD (trade name), 50 mmID× 500 mL, DAICEL CHEMICAL INDUSTRIES, LTD., mobile phase:hexane/ethanol=70:30), and the compound having the shortest retention time was resolved by HPLC (column: CHIRALPAK AD (trade name), 50 mmID×500 mL, DAICEL CHEMICAL INDUSTRIES, LTD., mobile phase:hexane/ethanol=85:15) to give the compound having a shorter retention time as the title compound (231 mg).

$^1$H NMR (300 MHz, CDCl$_3$) δ 0.34-0.47 (2H, m), 0.58-0.72 (2H, m), 1.18 (3H, d, J=6.8 Hz), 1.24-1.45 (1H, m), 1.90-2.08 (5H, m), 2.49-2.83 (3H, m), 2.94-3.10 (1H, m), 3.40-3.63 (2H, m), 3.83-3.96 (3H, m), 4.04-4.28 (1H, m), 5.61 (1H, d, J=6.4 Hz), 6.94 (1H, d, J=8.7 Hz), 7.82 (1H, dd, J=8.5, 2.1 Hz), 8.01 (1H, d, J=2.3 Hz).

retention time (OD) 15.49 min.

retention time (AD) 28.04 min.

Example 57c

Optically Active Form of N-(1-((2-(3-chloro-4-(cyclopropylmethoxy)phenyl)-4,5,6,7-tetrahydro-1,3-benzoxazol-6-yl)oxy)propan-2-yl)acetamide A diastereomer mixture (1.00 g) of N-(1-((2-(3-chloro-4-(cyclopropylmethoxy)phenyl)-4,5,6,7-tetrahydro-1,3-benzoxazol-6-yl)oxy)propan-2-yl)acetamide was resolved by HPLC (column: CHIRALPAK CD (trade name), 50 mmID× 500 mL, DAICEL CHEMICAL INDUSTRIES, LTD., mobile phase:hexane/ethanol=70:30) to give the compound having the second longest retention time as the title compound (252 mg).

$^1$H NMR (300 MHz, CDCl$_3$) δ 0.35-0.46 (2H, m), 0.59-0.71 (2H, m), 1.18 (3H, d, J=6.8 Hz), 1.23-1.45 (1H, m), 1.89-2.07 (5H, m), 2.46-2.80 (3H, m), 2.94-3.09 (1H, m), 3.39-3.60 (2H, m), 3.83-4.00 (3H, m), 4.09-4.25 (1H, m), 5.60 (1H, d, J=9.1 Hz), 6.94 (1H, d, J=8.7 Hz), 7.82 (1H, dd, J=8.5, 2.1 Hz), 8.01 (1H, d, J=2.3 Hz).

retention time (OD) 22.55 min.

Example 57d

Optically Active Form of N-(1-((2-(3-chloro-4-(cyclopropylmethoxy)phenyl)-4,5,6,7-tetrahydro-1,3-benzoxazol-6-yl)oxy)propan-2-yl)acetamide A diastereomer mixture (1.00 g) of N-(1-((2-(3-chloro-4-(cyclopropylmethoxy)phenyl)-4,5,6,7-tetrahydro-1,3-benzoxazol-6-yl)oxy)propan-2-yl)acetamide was resolved by HPLC (column: CHIRALPAK CD (trade name), 50 mmID× 500 mL, DAICEL CHEMICAL INDUSTRIES, LTD., mobile phase:hexane/ethanol=70:30) to give the compound having the longest retention time as the title compound (258 mg).

$^1$H NMR (300 MHz, CDCl$_3$) δ 0.35-0.44 (2H, m), 0.61-0.73 (2H, m), 1.18 (3H, d, J=6.8 Hz), 1.24-1.40 (1H, m), 1.92-1.96 (3H, m), 1.96-2.06 (2H, m), 2.49-2.84 (3H, m), 3.01 (1H, dd, J=16.4, 5.1 Hz), 3.42-3.62 (2H, m), 3.82-4.00 (3H, m), 4.10-4.31 (1H, m), 5.58 (1H, d, J=7.2 Hz), 6.94 (1H, d, J=8.7 Hz), 7.82 (1H, dd, J=8.7, 1.9 Hz), 8.01 (1H, d, J=1.9 Hz).

retention time (OD) 46.35 min.

Example 58

N-(4-(2-(4-(cyclopropylmethoxy)phenyl)-6,7-dihydro[1,3]oxazolo[5,4-c]pyridin-5(4H)-yl)-4-oxobutan-2-yl)acetamide A) tert-butyl 4-((4-(cyclopropylmethoxy)benzoyl)amino)-3-hydroxypiperidine-1-carboxylate To a solution of 4-(cyclopropylmethoxy)benzoic acid (11.3 g) in THF (100 mL) were added oxalyl dichloride (7.72 mL) and DMF (2 drops), and the mixture was stirred at room temperature for 30 min. The solvent was evaporated under reduced pressure, and the obtained 4-(cyclopropylmethoxy)benzoyl chloride was used for the next reaction without further purification.

To a solution of tert-butyl 4-azido-3-hydroxypiperidine-1-carboxylate (14.24 g) in THF (100 mL) were added triphenylphosphine (18.5 g) and water (25 mL), and the mixture was stirred at 70° C. for 4 hr. The solvent was evaporated under reduced pressure, and the obtained residue was dissolved in 1 M hydrochloric acid, and the solution was washed with ethyl acetate. The aqueous layer was neutralized with saturated aqueous sodium hydrogen carbonate solution, THF (100 mL) was added thereto, and then 4-(cyclopropylmethoxy)benzoyl chloride (obtained in the above-mentioned reaction) was added thereto, and the mixture was stirred at room temperature for 30 min. The reaction mixture was extracted with ethyl acetate, and the organic layer was dried over anhydrous magnesium sulfate. The solvent was evaporated under reduced pressure, and the obtained residue was purified by silica gel column chromatography (hexane/ethyl acetate) to give the title compound (20.1 g).

MS (ESI+): [M+H]$^+$ 335.1.

B) tert-butyl 2-(4-(cyclopropylmethoxy)phenyl)-6,7-dihydro[1,3]oxazolo[5,4-c]pyridine-5(4H)-carboxylate Using tert-butyl 4-((4-(cyclopropylmethoxy)benzoyl)amino)-3-hydroxypiperidine-1-carboxylate, and in the same manner as in Step C of Example 50, the title compound was obtained.

MS (ESI+): [M+H]$^+$ 371.1.

C) tert-butyl (4-(2-(4-(cyclopropylmethoxy)phenyl)-6,7-dihydro[1,3]oxazolo[5,4-c]pyridin-5(4H)-yl)-4-oxobutan-2-yl)carbamate To tert-butyl 2-(4-(cyclopropylmethoxy)phenyl)-6,7-dihydro[1,3]oxazolo[5,4-c]pyridine-5(4H)-carboxylate (1.00 g) was added 4 M hydrogen chloride/ethyl acetate (10 mL), and the mixture was stirred at room temperature for 30 min, and concentrated. To a solution of the residue, 3-((tert-butoxycarbonyl)amino)butanoic acid (658 mg) and diisopropylethylamine (0.707 mL) in DMF (10 mL) was added HATU (1.23 g), and the mixture was stirred at room temperature for 4 hr. The reaction mixture was diluted with ethyl acetate, washed with saturated brine, and dried over anhydrous magnesium sulfate. The solvent was evaporated under reduced pressure, and the obtained residue was purified by silica gel column chromatography (hexane/ethyl acetate) to give the title compound (370 mg).

MS (ESI+): [M+H]$^+$ 400.1.

D) N-(4-(2-(4-(cyclopropylmethoxy)phenyl)-6,7-dihydro[1,3]oxazolo[5,4-c]pyridin-5(4H)-yl)-4-oxobutan-2-yl)acetamide Using tert-butyl (4-(2-(4-(cyclopropylmethoxy)phenyl)-6,7-dihydro[1,3]oxazolo[5,4-c]pyridin-5(4H)-yl)-4-oxobutan-2-yl)carbamate, and in the same manner as in Step D of Example 1, the title compound was obtained.

Example 59

1-((2S)-1-((2-(4-(cyclopropylmethoxy)-3,5-difluorophenyl)[1,3]oxazolo[4,5-c]pyridin-6-yl)oxy)propan-2-yl)urea To tert-butyl ((2S)-1-((2-(4-(cyclopropylmethoxy)-3,5-difluorophenyl)[1,3]oxazolo[4,5-c]pyridin-6-yl)oxy)propan-2-yl)carbamate (0.920 g) was added 4 M hydrogen chloride/dioxane (10 mL), and the mixture was stirred at room temperature for 10 min, and concentrated. To the residue were added THF (5 mL) and triethylamine (2.16 mL), and then phenyl chloroformate (0.364 mL) was added thereto, and the mixture was stirred at room temperature for 30 min. To the reaction mixture was added 28% aqueous ammonia (20 mL), and the mixture was stirred overnight at 40° C. The reaction mixture was allowed to cool to room temperature, and the mixture was extracted with ethyl acetate. The obtained organic layer was subjected to silica gel chromatography (NH, ethyl acetate), the solvent was evaporated, and the obtained solid was washed with diethyl ether to give the title compound (0.580 g).

Example 60

N-((2S)-1-((2-(3-fluoro-4-(3,3,3-trifluoropropoxy)phenyl)-1,3-benzoxazol-6-yl)oxy)propan-2-yl)acetamide Using N-((2S)-1-((2-(3-fluoro-4-hydroxyphenyl)-1,3-benzoxazol-6-yl)oxy)propan-2-yl)acetamide and 1,1,1-trifluoro-3-iodopropane, and in the same manner as in Example 5, the title compound was obtained.

Example 61

N-((2S)-1-((2-(4-((2,2-difluorocyclopropyl)methoxy)-2,5-difluorophenyl) [1,3]oxazolo[4,5-c]pyridin-6-yl)oxy)propan-2-yl)acetamide

A) 4-(benzyloxy)-2,5-difluorobenzoic Acid

Using 2,4,5-trifluorobenzoic acid and benzyl bromide, and in the same manner as in Step A of Example 39, the title compound was obtained.
$^1$H NMR (300 MHz, CDCl$_3$) δ 6.78 (1H, dd, J=11.7, 6.6 Hz), 7.32-7.52 (5H, m), 7.74 (1H, dd, J=11.2, 6.8 Hz).

B) N-((2S)-1-((2-(4-(benzyloxy)-2,5-difluorophenyl)[1,3]oxazolo[4,5-c]pyridin-6-yl)oxy)propan-2-yl)acetamide Using 4-(benzyloxy)-2,5-difluorobenzoic acid and tert-butyl ((2S)-1-((4-chloro-5-nitropyridin-2-yl)oxy)propan-2-yl)carbamate, and in the same manner as in Step B, Step C and Step D of Example 31, the title compound was obtained.
MS (ESI+): [M+H]$^+$ 454.1.

C) N-((2S)-1-((2-(4-((2,2-difluorocyclopropyl)methoxy)-2,5-difluorophenyl)[1,3]oxazolo[4,5-c]pyridin-6-yl)oxy)propan-2-yl)acetamide Using N-((2S)-1-((2-(4-(benzyloxy)-2,5-difluorophenyl)[1,3]oxazolo[4,5-c]pyridin-6-yl)oxy)propan-2-yl)acetamide and (2,2-difluorocyclopropyl)methanol, and in the same manner as in Step A and Step B of Example 4, the title compound was obtained.

Example 62

N-((2S)-1-((2-(4-(cyclopropylmethoxy)-3-fluoro-5-methoxyphenyl) [1,3]oxazolo[4,5-c]pyridin-6-yl)oxy)propan-2-yl)acetamide

A) 4-(cyclopropylmethoxy)-3-fluoro-5-methoxybenzaldehyde

To a solution of 3-fluoro-4-hydroxy-5-methoxybenzaldehyde (5.00 g) in DMF (50 mL) were added potassium carbonate (6.09 g) and (bromomethyl)cyclopropane (3.42 mL), and the mixture was stirred with heating at 70° C. for 1 hr. The reaction mixture was allowed to cool to room temperature, diluted with ethyl acetate, and washed with saturated brine. The obtained organic layer was dried over anhydrous magnesium sulfate, and the solvent was evaporated under reduced pressure. The residue was purified by silica gel column chromatography (hexane/ethyl acetate) to give the title compound (6.59 g).
$^1$H NMR (300 MHz, CDCl$_3$) δ 0.27-0.34 (2H, m), 0.54-0.63 (2H, m), 1.29-1.36 (1H, m), 3.94 (3H, s), 4.03 (2H, d, J=7.8 Hz), 7.22-7.29 (2H, m), 9.84 (1H, d, J=1.2 Hz).

B) 4-(cyclopropylmethoxy)-3-fluoro-5-methoxybenzoic Acid

To a mixture of 4-(cyclopropylmethoxy)-3-fluoro-5-methoxybenzaldehyde (1.00 g), sodium dihydrogen phosphate (1.61 g), 2-methyl-2-butene (2.49 mL), water (2 mL) and tert-butanol (10 mL) was added sodium chlorite (0.756 g), and the mixture was stirred at room temperature for 2.5 hr. The reaction mixture was acidified with 1N hydrochloric acid, and the mixture was extracted with ethyl acetate. The obtained organic layer was washed with saturated brine, and dried over anhydrous magnesium sulfate, and the solvent was evaporated under reduced pressure. The obtained solid was washed with diethyl ether/hexane to give the title compound (0.890 g).
$^1$H NMR (300 MHz, DMSO-d$_6$) δ 0.18-0.28 (2H, m), 0.40-0.58 (2H, m), 0.98-1.27 (1H, m), 3.87 (3H, s), 3.91 (2H, d, J=7.2 Hz), 7.31-7.42 (2H, m).

C) tert-butyl ((2S)-1-((4-chloro-5-((4-(cyclopropylmethoxy)-3-fluoro-5-methoxybenzoyl)amino)pyridin-2-yl)oxy)propan-2-yl)carbamate To a solution of tert-butyl ((2S)-1-((4-chloro-5-nitropyridin-2-yl)oxy)propan-2-yl)carbamate (5.00 g) in ethanol (50 mL) were added reduced iron (8.42 g) and iron(III) chloride (2.45 g), and the mixture was stirred with heating under reflux for 1 hr. The reaction mixture was filtered, and the filtrate was diluted with ethyl acetate, washed with saturated brine, and dried over anhydrous magnesium sulfate. The solvent was evaporated under reduced pressure, and the obtained tert-butyl ((2S)-1-((5-amino-4-chloropyridin-2-yl)oxy)propan-2-yl)carbamate was used for the next reaction without further purification.

To a solution of 4-(cyclopropylmethoxy)-3-fluoro-5-methoxybenzoic acid (3.62 g) in THF (20 mL) were added oxalyl dichloride (1.98 mL) and DMF (3 drops), and the mixture was stirred at room temperature for 30 min. The solvent was evaporated under reduced pressure, and to a solution of the obtained residue in pyridine (30 mL) was added a solution of tert-butyl ((2S)-1-((5-amino-4-chloropyridin-2-yl)oxy)propan-2-yl)carbamate (obtained in the above-mentioned reaction) in THF (10 mL), and the mixture was stirred at room temperature for 30 min. The reaction mixture was subjected to silica gel chromatography (NH, ethyl acetate), the solvent was evaporated, and the obtained solid was washed with diethyl ether to give the title compound (5.87 g).

MS (ESI+): [M+H]$^+$ 524.1.

D) tert-butyl ((2S)-1-((2-(4-(cyclopropylmethoxy)-3-fluoro-5-methoxyphenyl)[1,3]oxazolo[4,5-c]pyridin-6-yl)oxy)propan-2-yl)carbamate A suspension of tert-butyl ((2S)-1-((4-chloro-5-((4-(cyclopropylmethoxy)-3-fluoro-5-methoxybenzoyl)amino)pyridin-2-yl)oxy)propan-2-yl)carbamate (5.87 g), potassium carbonate (3.10 g) and copper(I) iodide (213 mg) in DMF. (40 mL) was stirred at 150° C. for 1 hr, and then at 160° C. for 3 hr. The reaction mixture was subjected to silica gel chromatography (NH, ethyl acetate), and washed with saturated brine, and dried over anhydrous magnesium sulfate. The solvent was evaporated, and the obtained residue was purified by silica gel column chromatography (hexane/ethyl acetate) to give the title compound (1.35 g).

$^1$H NMR (300 MHz, CDCl$_3$) δ 0.25-0.34 (2H, m), 0.54-0.64 (2H, m), 1.21-1.36 (4H, m), 1.45 (9H, s), 3.96-4.04 (5H, m), 4.05-4.19 (1H, m), 4.34 (2H, d, J=4.8 Hz), 4.74-4.92 (1H, m), 6.90 (1H, d, J=0.8 Hz), 7.51-7.67 (2H, m), 8.56 (1H, d, J=0.8 Hz).

E) N-((2S)-1-((2-(4-(cyclopropylmethoxy)-3-fluoro-5-methoxyphenyl)[1,3]oxazolo[4,5-c]pyridin-6-yl)oxy)propan-2-yl)acetamide To tert-butyl ((2S)-1-((2-(4-(cyclopropylmethoxy)-3-fluoro-5-methoxyphenyl) [1,3]oxazolo[4,5-c]pyridin-6-yl)oxy)propan-2-yl)carbamate (1.35 g) was added 4 M hydrogen chloride/ethyl acetate (10 mL), and the reaction mixture was stirred at room temperature for 10 min, and concentrated. To the residue were added pyridine (10 mL) and acetic anhydride (10 mL), and the mixture was stirred at room temperature for 15 min. The reaction mixture was concentrated under reduced pressure, and the residue was dissolved in THF and methanol, and the solution was subjected to NH silica gel column chromatography (ethyl acetate). The solvent was evaporated, and the obtained solid was washed with ethyl acetate to give the title compound (995 mg).

$^1$H NMR (300 MHz, CDCl$_3$) δ 0.26-0.35 (2H, m), 0.53-0.65 (2H, m), 1.23-1.36 (4H, m), 1.97 (3H, s), 3.94-4.05 (5H, m), 4.31-4.48 (3H, m), 5.99 (1H, d, J=6.4 Hz), 6.92 (1H, d, J=0.8 Hz), 7.48-7.64 (2H, m), 8.56 (1H, d, J=0.8 Hz).

Anal. Calcd for C$_{22}$H$_{24}$N$_3$O$_5$F: C, 61.53; H, 5.63; N, 9.78. Found: C, 61.57; H, 5.64; N, 9.74.

mp 162.9-163.0° C.

Example 63

N-((2S)-1-((2-(4-(cyclopropylmethoxy)-3,5-difluorophenyl)[1,3]oxazolo[4,5-c]pyridin-6-yl)oxy)propan-2-yl)azetidine-1-carboxamide Using tert-butyl ((2S)-1-((2-(4-(cyclopropylmethoxy)-3,5-difluorophenyl)[1,3]oxazolo[4,5-c]pyridin-6-yl)oxy)propan-2-yl)carbamate and azetidine, and in the same manner as in Example 59, the title compound was obtained.

Example 64

N-((2S)-1-((2-(4-(cyclopropylmethoxy)-2,5-difluorophenyl)-1,3-benzoxazol-6-yl)oxy)propan-2-yl) acetamide Using 4-(cyclopropylmethoxy)-2,5-difluorobenzoic acid, and in the same manner as in Step B, Step C and Step D of Example 1, the title compound was obtained.

Example 65

N-((2S)-1-((2-(5-(cyclopropylmethoxy)-4-fluoropyridin-2-yl)[1,3]oxazolo[4,5-c]pyridin-6-yl)oxy)propan-2-yl)acetamide A) 2-(((tert-butyl(dimethyl)silyl)oxy)methyl)-5-(methoxymethoxy)pyridine To a mixture of (5-(methoxymethoxy)pyridin-2-yl)methanol (8.12 g), imidazole (4.90 g) and DMF (50 mL) was added tert-butyldimethylchlorosilane (8.68 g), and the mixture was stirred at room temperature for 30 min. The reaction mixture was diluted with ethyl acetate, washed with saturated brine, and dried over anhydrous magnesium sulfate, and the solvent was evaporated under reduced pressure. The residue was purified by silica gel column chromatography (hexane/ethyl acetate) to give the title compound (13.6 g).

$^1$H NMR (300 MHz, CDCl$_3$) δ 0.12 (6H, s), 0.96 (9H, s), 3.49 (3H, s), 4.79 (2H, s), 5.19 (2H, s), 7.35-7.47 (2H, m), 8.31 (1H, dd, J=2.5, 0.9 Hz).

B) 2-(((tert-butyl(dimethyl)silyl)oxy)methyl)-4-fluoro-5-(methoxymethoxy)pyridine To a solution of 2-(((tert-butyl(dimethyl)silyl)oxy)methyl)-5-(methoxymethoxy)pyridine (13.5 g) in THF (100 mL) was added 1.6 M n-butyllithium hexane solution (38.6 mL) at −78° C., and the mixture was stirred at the same temperature for 1 hr. To the reaction mixture was added N-fluoro-N-(phenylsulfonyl)benzenesulfonamide (19.5 g) at −78° C., and the mixture was allowed to warm to room temperature, and stirred for 30 min. To the reaction mixture was added saturated brine, and the mixture was extracted with ethyl acetate. The extract was dried over anhydrous magnesium sulfate, and concentrated under reduced pressure. The residue was purified by silica gel chromatography (hexane/ethyl acetate) to give the title compound (7.49 g).

$^1$H NMR (300 MHz, CDCl$_3$) δ 0.13 (6H, s), 0.96 (9H, s), 3.55 (3H, s), 4.76 (2H, s), 5.22 (2H, s), 7.28 (1H, d, J=11.6 Hz), 8.40 (1H, d, J=10.0 Hz).

C) (4-fluoro-5-(methoxymethoxy)pyridin-2-yl)methanol

To a solution of 2-(((tert-butyl(dimethyl)silyl)oxy)methyl)-4-fluoro-5-(methoxymethoxy)pyridine (8.04 g) in THF (60 mL) was added 1 M tetrabutylammonium fluoride THF solution (34.7 mL), and the mixture was stirred at room temperature for 30 min. To the reaction mixture was added saturated aqueous ammonium chloride solution, and the mixture was extracted with ethyl acetate. The extract was dried over anhydrous magnesium sulfate, and concentrated under reduced pressure. The residue was purified by silica gel chromatography (hexane/ethyl acetate/methanol) to give the title compound (3.59 g).

$^1$H NMR (300 MHz, CDCl$_3$) δ 3.55 (3H, s), 4.70 (2H, s), 5.23 (2H, s), 7.06 (1H, d, J=10.9 Hz), 8.46 (1H, d, J=9.7 Hz).

D) 4-fluoro-5-(methoxymethoxy)pyridine-2-carbaldehyde

To a solution of (4-fluoro-5-(methoxymethoxy)pyridin-2-yl)methanol (3.59 g) and triethylamine (8.02 mL) in DMSO (30 mL) was added sulfur trioxide pyridine complex (9.16 g), and the mixture was stirred at room temperature for 30 min. To the reaction mixture was added water, and the mixture was extracted with ethyl acetate. The organic layer was washed with saturated brine, dried over anhydrous magnesium sulfate, and concentrated under reduced pressure. The obtained residue was purified by silica gel chromatography (hexane/ethyl acetate) to give the title compound (2.43 g).

$^1$H NMR (300 MHz, CDCl$_3$) δ 3.56 (3H, s), 5.37 (2H, s), 7.73 (1H, d, J=10.3 Hz), 8.68 (1H, d, J=9.2 Hz), 9.97 (1H, d, J=3.3 Hz).

E) methyl 4-fluoro-5-(methoxymethoxy)pyridine-2-carboxylate

To a mixture of 4-fluoro-5-(methoxymethoxy)pyridine-2-carbaldehyde (2.43 g), sodium dihydrogen phosphate (4.72 g), 2-methyl-2-butene (7.32 mL), water (4 mL) and tert-butanol (20 mL) was added sodium chlorite (2.23 g), and the mixture was stirred at room temperature for 2.5 hr. The reaction mixture was acidified with 1N hydrochloric acid, and the mixture was extracted with ethyl acetate. The obtained organic layer was washed with saturated brine, and dried over anhydrous magnesium sulfate, and the solvent was evaporated under reduced pressure. The obtained residue was dissolved in DMF (30 mL), potassium carbonate (1.81 g) and methyl iodide (0.820 mL) were added thereto, and the mixture was stirred at 70° C. for 20 min. To the reaction mixture was added water, and the obtained mixture was extracted with ethyl acetate. The extract was washed with saturated brine, dried over anhydrous magnesium sulfate, and concentrated under reduced pressure. The obtained residue was purified by silica gel chromatography (hexane/ethyl acetate) to give the title compound (1.80 g).

$^1$H NMR (300 MHz, CDCl$_3$) δ 3.54 (3H, s), 4.00 (3H, s), 5.34 (2H, s), 7.91 (1H, d, J=10.9 Hz), 8.62 (1H, d, J=9.5 Hz).

F) methyl 5-(cyclopropylmethoxy)-4-fluoropyridine-2-carboxylate

To a solution of methyl 4-fluoro-5-(methoxymethoxy)pyridine-2-carboxylate (1.80 g) in THF (20 mL) was added 6 N hydrochloric acid (5 mL), and the mixture was stirred at 70° C. for 20 min. To the reaction mixture was added saturated brine, and the mixture was extracted with ethyl acetate. The extract was dried over anhydrous magnesium sulfate, and concentrated under reduced pressure. The residue was dissolved in DMF (20 mL), potassium carbonate (2.31 g) and (bromomethyl)cyclopropane (1.22 mL) were added thereto, and the mixture was stirred with heating at 70° C. for 1 hr. The reaction mixture was allowed to cool to room temperature, diluted with ethyl acetate, washed with saturated brine, and dried over anhydrous magnesium sulfate, and the solvent was evaporated under reduced pressure. The residue was purified by silica gel column chromatography (hexane/ethyl acetate) to give the title compound (1.07 g).

$^1$H NMR (300 MHz, CDCl$_3$) δ 0.35-0.46 (2H, m), 0.65-0.76 (2H, m), 1.27-1.42 (1H, m), 3.99 (3H, s), 4.06 (2H, d, J=7.1 Hz), 7.89 (1H, d, J=11.1 Hz), 8.39 (1H, d, J=9.7 Hz).

G) 5-(cyclopropylmethoxy)-4-fluoropyridine-2-carboxylic Acid

To a solution of methyl 5-(cyclopropylmethoxy)-4-fluoropyridine-2-carboxylate (1.07 g) in a mixed solvent of THF (10 mL) and methanol (1.1 mL) was added 2 M lithium hydroxide aqueous solution (4.75 mL), and the mixture was stirred at room temperature for 20 min. The reaction mixture was allowed to cool to room temperature, and neutralized with 1 M hydrochloric acid, and the mixture was extracted with ethyl acetate. The obtained organic layer was washed with saturated brine, and dried over anhydrous magnesium sulfate, and the solvent was evaporated under reduced pressure. The obtained solid was washed with diethyl ether/hexane to give the title compound (0.950 g).

$^1$H NMR (300 MHz, DMSO-d$_6$) δ 0.33-0.44 (2H, m), 0.55-0.67 (2H, m), 1.17-1.38 (1H, m), 4.14 (2H, d, J=7.2 Hz), 7.89 (1H, d, J==11.6 Hz), 8.54 (1H, d, J=10.1 Hz).

H) N-(6-(((2S)-2-acetamidopropyl)oxy)-4-chloropyridin-3-yl)-5-(cyclopropylmethoxy)-4-fluoropyridine-2-carboxamide To a solution of N-((2S)-1-((4-chloro-5-nitropyridin-2-yl)oxy)propan-2-yl)acetamide (1.23 g) in ethanol (20 mL) were added reduced iron (1.25 g) and iron(III) chloride (0.730 g), and the mixture was stirred with heating under reflux for 1 hr. The reaction mixture was filtered, and the filtrate was diluted with ethyl acetate, washed with saturated brine, and dried over anhydrous magnesium sulfate. The solvent was evaporated under reduced pressure, and to a solution of the obtained residue, 5-(cyclopropylmethoxy)-4-fluoropyridine-2-carboxylic acid (0.950 g) and diisopropylethylamine (1.53 mL) in DMF (10 mL) was added HATU (1.97 g), and the mixture was stirred at room temperature for 30 min. The precipitated solid was washed with ethyl acetate, the obtained solid was dissolved in THF, and the solution was subjected to silica gel chromatography (NH, ethyl acetate). The solvent was washed with saturated brine, and subjected to silica gel chromatography (NH, ethyl acetate). The solvent was evaporated, and the obtained solid was washed with ethyl acetate to give the title compound (1.35 g).

$^1$H NMR (300 MHz, CDCl$_3$) δ 0.37-0.48 (2H, m), 0.65-0.78 (2H, m), 1.20-1.45 (4H, m), 1.97 (3H, s), 4.07 (2H, d, J=7.1 Hz), 4.20-4.46 (3H, m), 5.83-6.07 (1H, m), 6.91 (1H, s), 8.01 (1H, d, J=11.0 Hz), 8.32 (1H, d, J=9.3 Hz), 9.22 (1H, s), 10.10 (1H, s).

I) N-((2S)-1-((2-(5-(cyclopropylmethoxy)-4-fluoropyridin-2-yl) [1,3]oxazolo[4,5-c]pyridin-6-yl)oxy)propan-2-yl)acetamide A suspension of N-(6-(((2S)-2-acetamidopropyl)oxy)-4-chloropyridin-3-yl)-5-(cyclopropylmethoxy)-4-fluoropyridine-2-carboxamide (1.05 g), potassium carbonate (664 mg) and copper(I) iodide (46.0 mg) in DMF (10 mL) was stirred at 160° C. for 1.5 hr. To the reaction mixture was added water, and the obtained mixture was extracted with ethyl acetate. The extract was washed with saturated brine, and subjected to silica gel chromatography (NH, ethyl acetate). The solvent was evaporated, and the obtained residue was purified by silica gel column chromatography (hexane/ethyl acetate) to give the title compound (56.9 mg).

$^1$H NMR (300 MHz, CDCl$_3$) δ 0.39-0.48 (2H, m), 0.68-0.78 (2H, m), 1.23-1.46 (4H, m), 1.98 (3H, s), 4.10 (2H, d, J=7.0 Hz), 4.26-4.51 (3H, m), 5.97 (1H, d, J=6.3 Hz), 6.97 (1H, d, J=0.8 Hz), 8.07 (1H, d, J=11.0 Hz), 8.47 (1H, d, J=9.6 Hz), 8.61 (1H, d, J=0.8 Hz).

Anal. Calcd for C$_{20}$H$_{21}$N$_4$O$_4$F: C, 59.99; H, 5.29; N, 13.99. Found: C, 59.86; H, 5.34; N, 13.78.

mp 183.3-183.4° C.

Example 66

N-((2S)-1-((2-(6-(2,2-difluorocyclopropylmethoxy)pyridin-3-yl)[1,3]oxazolo[4,5-c]pyridin-6-yl)oxy)propan-2-yl)acetamide A) 6-((2,2-difluorocyclopropyl)methoxy)nicotinic Acid Using 6-chloronicotinic acid and 2,2-difluorocyclopropanemethanol, and in the same manner as in Step A of Example 40, the title compound was obtained.

$^1$H NMR (300 MHz, CDCl$_3$) δ 1.19-1.38 (1H, m), 1.46-1.67 (1H, m), 2.02-2.27 (1H, m), 4.37-4.46 (1H, m), 4.49-4.60 (1H, m), 6.83 (1H, dd, J=8.7, 0.5 Hz), 8.23 (1H, dd, J=8.7, 2.4 Hz), 8.90 (1H, d, J=1.9 Hz).

B) N-((2S)-1-((2-(6-(2,2-difluorocyclopropylmethoxy)pyridin-3-yl)[1,3]oxazolo[4,5-c]pyridin-6-yl)oxy)propan-2-yl)acetamide Using 6-((2,2-difluorocyclopropyl)methoxy)nicotinic acid, and in the same manner as in Step E and Step F of Example 35, the title compound was obtained.

Example 67

N-((2S)-1-((2-(5-(cyclopropylmethoxy)-2-thienyl)[1,3]oxazolo[4,5-c]pyridin-6-yl)oxy)propan-2-yl)acetamide A) cyclopropylmethyl 5-chlorothiophene-2-carboxylate To a solution of 5-chlorothiophene-2-carboxylic acid (5.00 g) in DMF (50 mL) were added potassium carbonate (6.38 g) and (bromomethyl)cyclopropane (4.47 mL), and the mixture was stirred with heating at 70° C. for 30 min. The reaction mixture was allowed to cool to room temperature, and diluted with ethyl acetate and water, and the organic layer was separated. The organic layer was washed with saturated brine, and dried over anhydrous magnesium sulfate, and the solvent was evaporated under reduced pressure. The residue was purified by silica gel column chromatography (hexane/ethyl acetate) to give the title compound (2.54 g).

$^1$H NMR (300 MHz, CDCl$_3$) δ 0.31-0.40 (2H, m), 0.55-0.66 (2H, m), 1.13-1.37 (1H, m), 4.11 (2H, d, J=7.3 Hz), 6.93 (1H, d, J=4.1 Hz), 7.60 (1H, d, J=4.1 Hz).

B) cyclopropylmethyl 5-(cyclopropylmethoxy)thiophene-2-carboxylate

Using cyclopropylmethyl 5-chlorothiophene-2-carboxylate, and in the same manner as in Step A of Example 30, the title compound was obtained.

$^1$H NMR (300 MHz, CDCl$_3$) δ 0.30-0.43 (4H, m), 0.54-0.63 (2H, m), 0.64-0.72 (2H, m), 1.04-1.41 (2H, m), 3.92 (2H, d, J=7.2 Hz), 4.08 (2H, d, J=7.2 Hz), 6.22 (1H, d, J=4.2 Hz), 7.54 (1H, d, J=4.2 Hz).

C) 5-(cyclopropylmethoxy)thiophene-2-carboxylic Acid

Using cyclopropylmethyl 5-(cyclopropylmethoxy)thiophene-2-carboxylate, and in the same manner as in Step B of Example 33, the title compound was obtained.

$^1$H NMR (300 MHz, CDCl$_3$) δ 0.33-0.45 (2H, m), 0.63-0.74 (2H, m), 1.20-1.40 (1H, m), 3.94 (2H, d, J=7.1 Hz), 6.25 (1H, d, J=4.3 Hz), 7.63 (1H, d, J=4.2 Hz).

D) N-((2S)-1-((2-(5-(cyclopropylmethoxy)-2-thienyl)[1,3]oxazolo[4,5-c]pyridin-6-yl)oxy)propan-2-yl)acetamide Using 5-(cyclopropylmethoxy)thiophene-2-carboxylic acid, and in the same manner as in Step B, Step C and Step D of Example 31, the title compound was obtained.

Example 68

N-((2S)-1-((2-(4-(((1R)-2,2-difluorocyclopropyl)methoxy)phenyl)[1,3]oxazolo[4,5-c]pyridin-6-yl)oxy)propan-2-yl)acetamide A) (2,2-difluorocyclopropyl)methyl 4-nitrobenzenesulfonate To a solution of (2,2-difluorocyclopropyl)methanol (20.0 g) and triethylamine (32.2 mL) in THF (300 mL) was added 4-nitrobenzenesulfonyl chloride (41.0 g) at 0° C., and the mixture was stirred for 4 hr. To the reaction mixture was added saturated aqueous sodium hydrogen carbonate solution, and the mixture was extracted with ethyl acetate. The organic layer was dried over anhydrous magnesium sulfate, and the solvent was evaporated under reduced pressure. The residue was purified by silica gel column chromatography (hexane/ethyl acetate) to give the title compound (47.2 g) as a white solid.

$^1$H NMR (300 MHz, CDCl$_3$) δ 1.18-1.36 (1H, m), 1.58-1.70 (1H, m), 1.86-2.11 (1H, m), 4.07-4.22 (1H, m), 4.24-4.37 (1H, m), 8.07-8.17 (2H, m), 8.37-8.49 (2H, m).

B) ((1R)-2,2-difluorocyclopropyl)methyl 4-nitrobenzenesulfonate

A racemate (48.4 g) of (2,2-difluorocyclopropyl)methyl 4-nitrobenzenesulfonate was resolved by HPLC (column: CHIRALPAK AD (trade name), 50 mmID×500 mL, DAICEL CHEMICAL INDUSTRIES, LTD., mobile phase: hexane/ethanol=50:50) to give the title compound having a shorter retention time (18.4 g). The steric configuration was determined by X ray structure analysis.

$^1$H NMR (300 MHz, CDCl$_3$) δ 1.18-1.32 (1H, m), 1.56-1.69 (1H, m), 1.90-2.09 (1H, m), 4.10-4.21 (1H, m), 4.23-4.35 (1H, m), 8.09-8.17 (2H, m), 8.38-8.48 (2H, m).

analysis retention time 15.4 min.

optical purity >99.9% ee

C) tert-butyl ((2S)-1-((5-((4-(benzyloxy)benzoyl)amino)-4-chloropyridin-2-yl)oxy)propan-2-yl)carbamate To a solution of tert-butyl ((2S)-1-((4-chloro-5-nitropyridin-2-yl)oxy)propan-2-yl)carbamate (2.50 g) in ethanol (30 mL) were added reduced iron (4.21 g) and iron(III) chloride (1.22 g), and the mixture was stirred with heating under reflux for 1 hr. The reaction mixture was filtered, and the filtrate was diluted with ethyl acetate, washed with saturated brine, and dried over anhydrous magnesium sulfate. The solvent was evaporated under reduced pressure, and the obtained tert-butyl ((2S)-1-((5-amino-4-chloropyridin-2-yl)oxy)propan-2-yl)carbamate was used for the next reaction without further purification.

To a solution of 4-(benzyloxy)benzoic acid (1.72 g) in THF (20 mL) were added oxalyl dichloride (0.990 mL) and DMF (3 drops), and the mixture was stirred at room temperature for 30 min. The solvent was evaporated under reduced pressure, and to a solution of the obtained residue in pyridine (30 mL) was added a solution of tert-butyl ((2S)-1-((5-amino-4-chloropyridin-2-yl)oxy)propan-2-yl)carbamate (obtained in the above-mentioned reaction) in THF (10 mL), and the mixture was stirred at room temperature for 30 min. The reaction mixture was subjected to silica gel chromatography (NH, ethyl acetate), the solvent was evaporated, and the obtained solid was washed with diethyl ether to give the title compound (2.50 g).

MS (ESI+): [M+H]$^+$ 512.1.

D) tert-butyl ((2S)-1-((2-(4-(benzyloxy)phenyl)[1,3]oxazolo[4,5-c]pyridin-6-yl)oxy)propan-2-yl)carbamate A suspension of tert-butyl ((2S)-1-((5-((4-(benzyloxy)benzoyl)amino)-4-chloropyridin-2-yl)oxy)propan-2-yl)carbamate (2.50 g), potassium carbonate (1.35 g) and copper(I) iodide (93.9 mg) in DMF (20 mL) was stirred at 160° C. for 3.5 hr. The reaction mixture was subjected to silica gel chromatography (NH, ethyl acetate), washed with saturated brine, and dried over anhydrous magnesium sulfate. The solvent was evaporated, and the obtained solid was washed with ethyl acetate/hexane to give the title compound (830 mg).

$^1$H NMR (300 MHz, CDCl$_3$) δ 1.28 (3H, d, J=6.7 Hz), 1.45 (9H, s), 4.03-4.19 (1H, m), 4.33 (2H, d, J=4.6 Hz), 4.74-4.98 (1H, m), 5.16 (2H, s), 6.89 (1H, d, J=0.7 Hz), 7.11 (2H, d, J=9.0 Hz), 7.33-7.53 (5H, m), 8.16 (2H, d, J=9.0 Hz), 8.52 (1H, d, J=0.7 Hz).

E) N-((2S)-1-((2-(4-(benzyloxy)phenyl)[1,3]oxazolo[4,5-c]pyridin-6-yl)oxy)propan-2-yl)acetamide To tert-butyl ((2S)-1-((2-(4-(benzyloxy)phenyl)[1,3]oxazolo[4,5-c]pyridin-6-yl)oxy)propan-2-yl)carbamate (830 mg) was added 4 M hydrogen chloride/ethyl acetate (20 mL), and the reaction mixture was stirred at room temperature for 10 min, and concentrated. To the residue were added pyridine (10 mL) and acetic anhydride (10 mL), and the mixture was stirred at room temperature for 15 min. The reaction mixture was concentrated under reduced pressure, and the residue was dissolved in THF and methanol, and the solution was subjected to NH silica gel column chromatography (ethyl acetate). The solvent was evaporated, and the obtained solid was washed with ethyl acetate/hexane to give the title compound (660 mg).

$^1$H NMR (300 MHz, CDCl$_3$) δ 1.30 (3H, d, J=6.4 Hz), 1.97 (3H, s), 4.27-4.50 (3H, m), 5.16 (2H, s), 6.06 (1H, d, J=6.9 Hz), 6.90 (1H, d, J=0.8 Hz), 7.11 (2H, d, J=9.0 Hz), 7.32-7.51 (5H, m), 8.16 (2H, d, J=9.0 Hz), 8.52 (1H, d, J=0.8 Hz).

F) N-((2S)-1-((2-(4-(((1R)-2,2-difluorocyclopropyl)methoxy)phenyl)[1,3]oxazolo[4,5-c]pyridin-6-yl)oxy)propan-2-yl)acetamide A mixture of N-((2S)-1-((2-(4-(benzyloxy)phenyl) [1,3]oxazolo[4,5-c]pyridin-6-yl)oxy)propan-2-yl)acetamide (660 mg), 10% palladium-carbon (containing water (50%), 600 mg) and THF (10 mL) was stirred at room temperature for 20 min under a hydrogen atmosphere. The catalyst was removed by filtration, and the obtained filtrate was concentrated under reduced pressure. A suspension of 100 mg of the obtained residue, ((1R)-2,2-difluorocyclopropyl)methyl 4-nitrobenzenesulfonate (116 mg) and potassium carbonate (84.0 mg) in DMF (10 mL) was stirred at 70° C. for 1.5 hr. The reaction mixture was diluted with ethyl acetate, and washed with saturated brine, and the organic layer was subjected to silica gel chromatography (NH, ethyl acetate), and the solvent was evaporated. The residue was purified by silica gel column chromatography (hexane/ethyl acetate-ethyl acetate/methanol) to give the title compound (107 mg).

$^1$H NMR (300 MHz, CDCl$_3$) δ 1.24-1.42 (4H, m), 1.55-1.74 (1H, m), 1.97 (3H, s), 2.03-2.23 (1H, m), 4.03-4.22 (2H, m), 4.28-4.49 (3H, m), 6.05 (1H, d, J=6.8 Hz), 6.91 (1H, d, J=0.8 Hz), 7.04 (2H, d, J=9.0 Hz), 8.16 (2H, d, J=9.0 Hz), 8.53 (1H, d, J=0.8 Hz).

Anal. Calcd for C$_{21}$H$_{21}$N$_3$O$_4$F$_2$: C, 60.43; H, 5.07; N, 10.07. Found: C, 60.44; H, 5.13; N, 9.99.

mp 204.6-204.7° C.

Example 69

N-((2S)-1-((2-(4-(((1R)-2,2-difluorocyclopropyl)methoxy)-3-fluorophenyl) [1,3]oxazolo[4,5-c]pyridin-6-yl)oxy)propan-2-yl)acetamide A) tert-butyl ((2S)-1-((5-((4-(benzyloxy)-3-fluorobenzoyl)amino)-4-chloropyridin-2-yl)oxy)propan-2-yl)carbamate To a solution of tert-butyl ((2S)-1-((4-chloro-5-nitropyridin-2-yl)oxy)propan-2-yl)carbamate (5.00 g) in ethanol (50 mL) were added reduced iron (8.42 g) and iron(III) chloride (2.45 g), and the mixture was stirred with heating under reflux for 1 hr. The reaction mixture was filtered, and the filtrate was diluted with ethyl acetate, washed with saturated brine, and dried over anhydrous magnesium sulfate. The solvent was evaporated under reduced pressure, and the obtained tert-butyl ((2S)-1-((5-amino-4-chloropyridin-2-yl)oxy)propan-2-yl)carbamate was used for the next reaction without further purification.

To a solution of 4-(benzyloxy)-3-fluorobenzoic acid (3.71 g) in THF (50 mL) were added oxalyl dichloride (1.98 mL) and DMF (3 drops), and the mixture was stirred at room temperature for 30 min. The solvent was evaporated under reduced pressure, and to a solution of the obtained residue in pyridine (30 mL) was added a solution of tert-butyl ((2S)-1-((5-amino-4-chloropyridin-2-yl)oxy)propan-2-yl)carbamate (obtained in the above-mentioned reaction) in THF (10 mL), and the mixture was stirred at room temperature for 30 min. The reaction mixture was subjected to silica gel chromatography (NH, ethyl acetate), the solvent was evaporated, and the obtained solid was washed with diethyl ether to give the title compound (6.02 g).

$^1$H NMR (300 MHz, CDCl$_3$) δ 1.25 (3H, d, J=6.8 Hz), 1.44 (9H, s), 3.96-4.15 (1H, m), 4.27 (2H, d, J=4.8 Hz), 4.67-4.89 (1H, m), 5.23 (2H, s), 6.89 (1H, s), 7.09 (1H, t, J=8.3 Hz), 7.33-7.50 (5H, m), 7.61 (1H, dd, J=8.5, 3.2 Hz), 7.68 (1H, dd, J=11.4, 2.2 Hz), 7.87 (1H, s), 9.04 (1H, s).

B) tert-butyl ((2S)-1-((2-(4-(benzyloxy)-3-fluorophenyl)[1,3]oxazolo[4,5-c]pyridin-6-yl)oxy)propan-2-yl)carbamate A suspension of tert-butyl ((2S)-1-((5-((4-(benzyloxy)-3-fluorobenzoyl)amino)-4-chloropyridin-2-yl)oxy)propan-2- yl)carbamate (6.02 g), potassium carbonate (3.14 g) and copper(I) iodide (216 mg) in DMF (30 mL) was stirred at 160° C. for 2 hr. The reaction mixture was subjected to silica gel chromatography (NH, ethyl acetate), washed with saturated brine, and dried over anhydrous magnesium sulfate. The solvent was evaporated, and the obtained solid was washed with ethyl acetate/hexane to give the title compound (1.35 g).

$^1$H NMR (300 MHz, CDCl$_3$) δ 1.28 (3H, d, J=6.8 Hz), 1.44 (9H, s), 3.94-4.19 (1H, m), 4.33 (2H, d, J=4.8 Hz), 4.75-4.96 (1H, m), 5.24 (2H, s), 6.89 (1H, d, J=0.7 Hz), 7.13 (1H, t, J=8.5 Hz), 7.31-7.54 (5H, m), 7.85-7.99 (2H, m), 8.53 (1H, d, J=0.8 Hz).

C) N-((2S)-1-((2-(4-(benzyloxy)-3-fluorophenyl)[1,3]oxazolo[4,5-c]pyridin-6-yl)oxy)propan-2-yl)acetamide To tert-butyl ((2S)-1-((2-(4-(benzyloxy)-3-fluorophenyl)[1,3]oxazolo[4,5-c]pyridin-6-yl)oxy)propan-2-yl)carbamate (1.35 g) was added 4 M hydrogen chloride/ethyl acetate (20 mL), and the mixture was stirred at room temperature for 10 min, and then concentrated. To the residue were added pyridine (10 mL) and acetic anhydride (10 mL), and the mixture was stirred at room temperature for 15 min. The reaction mixture was concentrated under reduced pressure, and the residue was dissolved in THF and methanol, and the solution was subjected to NH silica gel column chromatography (ethyl acetate). The solvent was evaporated, and the obtained solid was washed with ethyl acetate/hexane to give the title compound (1.00 g).

$^1$H NMR (300 MHz, CDCl$_3$) δ 1.30 (3H, d, J=6.4 Hz), 1.98 (3H, s), 4.23-4.53 (3H, m), 5.24 (2H, s), 6.10 (1H, d, J=6.8 Hz), 6.90 (1H, d, J=0.8 Hz), 7.07-7.18 (1H, m), 7.31-7.51 (5H, m), 7.86-7.98 (2H, m), 8.53 (1H, d, J=0.8 Hz).

D) N-((2S)-1-((2-(4-(((1R)-2,2-difluorocyclopropyl)methoxy)-3-fluorophenyl)[1,3]oxazolo[4,5-c]pyridin-6-yl)oxy)propan-2-yl)acetamide A mixture of N-((2S)-1-((2-(4-(benzyloxy)-3-fluorophenyl)[1,3]oxazolo[4,5-c]pyridin-6-yl)oxy)propan-2-yl)acetamide (1.00 g), 10% palladium-carbon (containing water (50%), 1.00 g) and THF (10 mL) was stirred at room temperature for 20 min under a hydrogen atmosphere. The catalyst was removed by filtration, and the obtained filtrate was concentrated under reduced pressure. A suspension of the obtained residue, ((1R)-2,2-difluorocyclopropyl)methyl 4-nitrobenzenesulfonate (742 mg) and potassium carbonate (636 mg) in DMF (10 mL) was stirred at 70° C. for 1.5 hr. The reaction mixture was diluted with ethyl acetate, washed with saturated brine, and the organic layer was subjected to silica gel chromatography (NH, ethyl acetate), and the solvent was evaporated. The residue was purified by silica gel column chromatography (hexane/ethyl acetate-ethyl acetate/methanol) to give the title compound (461 mg).

$^1$H NMR (300 MHz, CDCl$_3$) δ 1.27-1.44 (4H, m), 1.59-1.75 (1H, m), 1.98 (3H, s), 2.07-2.26 (1H, m), 4.07-4.52 (5H, m), 6.02 (1H, d, J=6.8 Hz), 6.91 (1H, d, J=0.8 Hz), 7.08 (1H, t, J=8.5 Hz), 7.87-8.03 (2H, m), 8.54 (1H, d, J=0.8 Hz).

Anal. Calcd for C$_{21}$H$_{20}$N$_3$C$_4$F$_3$: C, 57.93; H, 4.63; N, 9.65. Found: C, 57.73; H, 4.73; N, 9.59.

mp 180.9-181.0° C.

Example 70

N-((2S)-1-((2-(4-(cyclopropylmethoxy)phenyl)[1,3]oxazolo[4,5-b]pyridin-6-yl)oxy)propan-2-yl)acetamide

A) 5-(benzyloxy)-3-bromopyridin-2-amine

To a solution of 5-(benzyloxy)pyridin-2-amine (10.2 g) in acetic acid (50 mL) was added bromine (2.61 mL) at 0° C., and the mixture was stirred for 2 hr. To the reaction mixture was added saturated aqueous sodium hydrogen carbonate solution, and the mixture was extracted with ethyl acetate. The obtained organic layer was dried over anhydrous magnesium sulfate, the solvent was evaporated, and the residue was purified by silica gel column chromatography (hexane/ethyl acetate) to give the title compound (8.50 g).

$^1$H NMR (300 MHz, CDCl$_3$) δ 4.99 (2H, s), 5.11-5.42 (2H, brs), 7.28-7.41 (5H, m), 7.46 (1H, d, J=2.6 Hz), 7.71 (1H, d, J=2.6 Hz).

B) N-(5-(benzyloxy)-3-bromopyridin-2-yl)-4-(cyclopropylmethoxy)benzamide

To a solution of 4-(cyclopropylmethoxy)benzoic acid (13.4 g) in THF (100 mL) were added oxalyl dichloride (9.18 mL) and DMF (2 drops), and the mixture was stirred at room temperature for 30 min. The solvent was evaporated under reduced pressure, and to a mixture of the obtained residue in pyridine (100 mL) was added 5-(benzyloxy)-3-bromopyridin-2-amine (9.76 g), and the mixture was stirred at room temperature for 20 min. The reaction mixture was subjected to silica gel chromatography (NH, ethyl acetate), and the solvent was evaporated under reduced pressure. The residue was purified by silica gel column chromatography (hexane/ethyl acetate) to give the title compound (700 mg).

$^1$H NMR (300 MHz, CDCl$_3$) δ 0.32-0.44 (2H, m), 0.62-0.75 (2H, m), 1.26-1.39 (1H, m), 3.87 (2H, d, J=6.8 Hz), 5.11 (2H, s), 6.97 (2H, d, J=9.1 Hz), 7.31-7.45 (5H, m), 7.57 (1H, d, J=2.6 Hz), 7.88 (2H, d, J=9.1 Hz), 8.10 (1H, s), 8.23 (1H, d, J=2.6 Hz).

C) 6-(benzyloxy)-2-(4-(cyclopropylmethoxy)phenyl)[1,3]oxazolo[4,5-b]pyridine To a solution of N-(5-(benzyloxy)-3-bromopyridin-2-yl)-4-(cyclopropylmethoxy)benzamide (780 mg) in THF (10 mL) were added copper iodide (49.2 mg), 1,10-phenanthroline (93.0 mg) and cesium carbonate (1.12 g), and the mixture was stirred with heating overnight at 70° C. The reaction mixture was allowed to cool to room temperature, water was added thereto, and the mixture was extracted with ethyl acetate. The obtained organic layer was dried over anhydrous magnesium sulfate, the solvent was evaporated, and the residue was purified by silica gel column chromatography (hexane/ethyl acetate) to give the title compound (157 mg).

MS (ESI+): [M+H]$^+$ 373.3

D) N-((2S)-1-((2-(4-(cyclopropylmethoxy)phenyl)[1,3]oxazolo[4,5-b]pyridin-6-yl)oxy)propan-2-yl)acetamide Using 6-(benzyloxy)-2-(4-(cyclopropylmethoxy)phenyl)[1,3]oxazolo[4,5-b]pyridine, and in the same manner as in Step A of Example 4, Step C and Step D of Example 1, the title compound was obtained.

Example 71

N-((2S)-1-((2-(4-(cyclopropylmethoxy)phenyl)[1,3]oxazolo[5,4-b]pyridin-5-yl)oxy)propan-2-yl)acetamide Using 6-(benzyloxy)pyridin-3-amine, and in the same manner as in Step A, Step B and Step C of Example 70, Step A of Example 4, Step C and Step D of Example 1, the title compound was obtained.

Example 72

N-((2S)-1-((2-(2-cyano-4-(cyclopropylmethoxy)phenyl)-1,3-benzoxazol-6-yl)oxy)propan-2-yl)acetamide Using 2-bromo-5-(cyclopropylmethoxy)benzonitrile and tert-butyl ((2S)-1-(1,3-benzoxazol-6-yloxy)propan-2-yl)carbamate, and in the same manner as in Step B of Example 22 and Step D of Example 1, the title compound was obtained.

Example 73

N-((2S)-1-((2-(2-(cyclopropylmethoxy)pyrimidin-5-yl)-1,3-benzoxazol-6-yl)oxy)propan-2-yl)acetamide Using 5-bromo-2-(cyclopropylmethoxy)pyrimidine and N-((2S)-1-(1,3-benzoxazol-6-yloxy)propan-2-yl)acetamide, and in the same manner as in Step B of Example 22, the title compound was obtained.

Example 74

N-((2S)-1-((2-(3-cyano-4-(cyclopropylmethoxy)phenyl)-1,3-benzoxazol-6-yl)oxy)propan-2-yl)acetamide A) tert-butyl ((2S)-1-((2-(3-bromo-4-(cyclopropylmethoxy)phenyl)-1,3-benzoxazol-6-yl)oxy)propan-2-yl)carbamate Using 3-bromo-4-(cyclopropylmethoxy)benzoic acid, and in the same manner as in Step B and Step C of Example 1, the title compound was obtained.
MS (ESI+): [M+H]$^+$ 519.2

B) tert-butyl ((2S)-1-((2-(3-cyano-4-(cyclopropylmethoxy)phenyl)-1,3-benzoxazol-6-yl)oxy)propan-2-yl)carbamate To a solution of tert-butyl ((2S)-1-((2-(3-bromo-4-(cyclopropylmethoxy)phenyl)-1,3-benzoxazol-6-yl)oxy)propan-2-yl)carbamate (200 mg) in DMF (5 mL) were added zinc cyanide (227 mg) and tetrakis(triphenylphosphine)palladium (0) (44.7 mg), and the mixture was stirred at 100° C. for 18 hr under an argon atmosphere. To the reaction mixture was added saturated brine, and the mixture was extracted with ethyl acetate. The obtained organic layer was dried over anhydrous magnesium sulfate, and the solvent was evaporated under reduced pressure. The obtained residue was purified by silica gel column chromatography (hexane/ethyl acetate) to give the title compound (27.8 mg).
MS (ESI+): [M+H]$^+$ 464.3

C) N-((2S)-1-((2-(3-cyano-4-(cyclopropylmethoxy)phenyl)-1,3-benzoxazol-6-yl)oxy)propan-2-yl)acetamide Using tert-butyl ((2S)-1-((2-(3-cyano-4-(cyclopropylmethoxy)phenyl)-1,3-benzoxazol-6-yl)oxy)propan-2-yl)carbamate, and in the same manner as in Step D of Example 1, the title compound was obtained.

Example 75

N-((2S)-1-((2-(6-(cyclopropylmethoxy)pyridin-3-yl)[1,3]oxazolo[4,5-c]pyridin-6-yl)oxy)propan-2-yl)acetamide Using 6-(cyclopropylmethoxy)nicotinic acid, and in the same manner as in Step B, Step C and Step D of Example 31, the title compound was obtained.

Example 76

N-((2S)-1-((2-(5-(cyclopropylmethoxy)-6-fluoropyridin-2-yl)-1,3-benzoxazol-6-yl)oxy)propan-2-yl)acetamide Using 6-bromo-2-fluoropyridin-3-ol and N-((2S)-1-(1,3-benzoxazol-6-yloxy)propan-2-yl)acetamide, and in the same manner as in Step C of Example 28 and Step B of Example 22, the title compound was obtained.

Example 77

N-((2S)-1-((2-(5-(cyclopropylmethoxy)pyridin-2-yl)[1,3]oxazolo[4,5-c]pyridin-6-yl)oxy)propan-2-yl)acetamide Using 5-(cyclopropylmethoxy)pyridine-2-carboxylic acid, and in the same manner as in Step E and Step F of Example 35, the title compound was obtained.

Example 78

N-((2S)-1-((2-(4-(cyclopropylmethoxy)-3-fluorophenyl)-5-fluoro-1,3-benzoxazol-6-yl)oxy)propan-2-yl)acetamide Using 1,5-bis(benzyloxy)-2-fluoro-4-nitrobenzene and 4-(cyclopropylmethoxy)-3-fluorobenzoic acid, and in the same manner as in Step B, Step C and Step D of Example 37, the title compound was obtained.

Example 79

N-((2S)-1-((2-(3,5-difluoro-4-((1-fluorocyclopropyl)methoxy)phenyl)-1,3-benzoxazol-6-yl)oxy)propan-2-yl)acetamide A) N-((2S)-1-((2-(4-(benzyloxy)-3,5-difluorophenyl)-1,3-benzoxazol-6-yl)oxy)propan-2-yl)acetamide Using 4-(benzyloxy)-3,5-difluorobenzoic acid, and in the same manner as in Step A, Step B, Step C and Step D of Example 44, the title compound was obtained.
MS (ESI+): [M+H]$^+$ 453.1

B) N-((2S)-1-((2-(3,5-difluoro-4-((1-fluorocyclopropyl)methoxy)phenyl)-1,3-benzoxazol-6-yl)oxy)propan-2-yl)acetamide Using N-((2S)-1-((2-(4-(benzyloxy)-3,5-difluorophenyl)-1,3-benzoxazol-6-yl)oxy)propan-2-yl)acetamide and (1-fluorocyclopropyl)methanol, and in the same manner as in Step A and Step B of Example 4, the title compound was obtained.

Example 80

Optically Active Form of N-((2S)-1-((2-(4-((2,2-difluorocyclopropyl)methoxy)-3-fluorophenyl)-7-fluoro-1,3-benzoxazol-6-yl)oxy)propan-2-yl)acetamide A diastereomer mixture (658 mg) of N-((2S)-1-((2-(4-((2,2-difluorocyclopropyl)methoxy)-3-fluorophenyl)-7-fluoro-1,3-benzoxazol-6-yl)oxy)propan-2-yl)acetamide was resolved by HPLC (column: CHIRALPAK AD (trade name), 50 mmID×500 mL, DAICEL CHEMICAL INDUSTRIES, LTD., mobile phase:hexane/ethanol=80:20) to give the title compound having a shorter retention time (267 mg).
analysis retention time 63.5 min
optical purity >99.9% ee

Example 81

Optically Active Form of N-((2S)-1-((2-(4-((2,2-difluorocyclopropyl)methoxy)-3-fluorophenyl)-7-fluoro-1,3-benzoxazol-6-yl)oxy)propan-2-yl)acetamide A diastereomer mixture (658 mg) of N-((2S)-1-((2-(4-((2,2-difluorocyclopropyl)methoxy)-3-fluorophenyl)-7-fluoro-1,3-benzoxazol-6-yl)oxy)propan-2-yl)acetamide was resolved by HPLC (column: CHIRALPAK AD (trade name), 50 mmID×500 mL, DAICEL CHEMICAL INDUSTRIES, LTD., mobile phase:
hexane/ethanol=80:20) to give the title compound having a longer retention time (262 mg).
analysis retention time 75.2 min
optical purity 98.1% ee

Example 82

N-((2S)-1-((2-(4-(cyclopropylmethoxy)-2,3-difluorophenyl)[1,3]oxazolo[4,5-c]pyridin-6-yl)oxy)propan-2-yl)acetamide

A) 4-(cyclopropylmethoxy)-2,3-difluorobenzoic Acid

To a solution of 1-(cyclopropylmethoxy)-2,3-difluorobenzene (19.0 g) in THF (200 mL) was added 1.6 M n-butyllithium hexane solution (64.5 mL) at −78° C., and the mixture was stirred at the same temperature for 1 hr. To the reaction mixture was added dry ice, and the mixture was allowed to warm to room temperature, and stirred for 15 min. To the reaction mixture was added saturated aqueous sodium hydrogen carbonate solution, and the aqueous layer was washed with diethyl ether, and acidified with 6N hydrochloric acid. This mixture was extracted with ethyl acetate, and the extract was dried over anhydrous magnesium sulfate. The solvent was evaporated under reduced pressure, and the obtained solid was washed with diethyl ether to give the title compound was obtained.
$^1$H NMR (300 MHz, CDCl$_3$) δ 0.35-0.44 (2H, m), 0.64-0.75 (2H, m), 1.19-1.38 (1H, m), 3.97 (2H, d, J=7.2 Hz), 6.71-6.82 (1H, m), 7.69-7.84 (1H, m).

B) N-((2S)-1-((2-(4-(cyclopropylmethoxy)-2,3-difluorophenyl)[1,3]oxazolo[4,5-c]pyridin-6-yl)oxy)propan-2-yl)acetamide Using 4-(cyclopropylmethoxy)-2,3-difluorobenzoic acid, and in the same manner as in Step B, Step C and Step D of Example 31, the title compound was obtained.

Example 83

N-((2S)-1-((2-(4-(cyclopropylmethoxy)phenyl)[1,3]thiazolo[4,5-c]pyridin-6-yl)oxy)propan-2-yl)acetamide

A) 2-ethylhexyl 3-((2-(((2S)-2-((tert-butoxycarbonyl)amino)propyl)oxy)-5-nitropyridin-4-yl)sulfanyl)propanoate A mixture of 2-ethylhexyl 3-sulfanylpropanoate (2.17 g), tert-butyl ((2S)-1-((4-chloro-5-nitropyridin-2-yl)oxy)propan-2-yl)carbamate (3.00 g), triethylamine (1.39 mL) and DMF (30 mL) was stirred at room temperature overnight. To the reaction mixture was added water, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (4.50 g). MS (ESI+): [M+H]$^+$ 514.3.

B) 2-ethylhexyl 3-((2-(((2S)-2-acetamidopropyl)oxy)-5-nitropyridin-4-yl)sulfanyl)propanoate Using 2-ethylhexyl 3-((2-(((2S)-2-((tert-butoxycarbonyl)amino)propyl)oxy)-5-nitropyridin-4-yl)sulfanyl)propanoate, and in the same manner as in Step D of Example 1, the title compound was obtained.
MS (ESI+): [M+H]$^+$ 456.2.

C) 2-ethylhexyl 3-((2-(((2S)-2-acetamidopropyl)oxy)-5-aminopyridin-4-yl)sulfanyl)propanoate A mixture of 2-ethylhexyl 3-((2-(((2S)-2-acetamidopropyl)oxy)-5-nitropyridin-4-yl)sulfanyl)propanoate (3.38 g), reduced iron (2.07 g), ammonium chloride (0.397 g), ethanol (40 mL) and water (10 mL) was stirred overnight at 80° C. The precipitate was removed by filtration, and the filtrate was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (2.83 g).
MS (ESI+): [M+H]$^+$ 426.2.

D) 2-ethylhexyl 3-((2-(((2S)-2-acetamidopropyl)oxy)-5-((4-(cyclopropylmethoxy)benzoyl)amino)pyridin-4-yl)sulfanyl)propanoate A mixture of 4-(cyclopropylmethoxy)benzoic acid (452 mg), 2-ethylhexyl 3-((2-(((2S)-2-acetamidopropyl)oxy)-5- aminopyridin-4-yl)sulfanyl)propanoate (1.00 g), HATU (0.893 g), N,N-diisopropylethylamine (0.821 mL) and DMF (10 mL) was stirred at 70° C. for 5 days. To the reaction mixture was added water, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (0.740 g).

MS (ESI+): [M+H]+ 600.2.

E) N-((2S)-1-((2-(4-hydroxyphenyl)[1,3]thiazolo[4,5-c]pyridin-6-yl)oxy)propan-2-yl)acetamide A mixture of 2-ethylhexyl 3-((2-(((2S)-2-acetamidopropyl)oxy)-5-((4-(cyclopropylmethoxy)benzoyl)amino)pyridin-4-yl)sulfanyl)propanoate (740 mg), sodium ethoxide (20% ethanol solution, 840 mg) and THF (10 mL) was stirred at room temperature for 30 min. The reaction mixture was cooled to 0° C., trifluoroacetic acid (0.475 mL) was added thereto, the obtained mixture was stirred at 70° C. for 1 hr. The reaction mixture was cooled to 0° C., and the precipitate was collected by filtration, and washed with diisopropyl ether. The obtained residue was dissolved in trifluoroacetic acid (5 mL), and the obtained solution was stirred at 70° C. for 1 hr. The reaction mixture was added to saturated aqueous sodium hydrogen carbonate solution, and the mixture was extracted with ethyl acetate. The combined organic layer were washed with saturated brine, and dried over anhydrous magnesium sulfate, and the solvent was evaporated under reduced pressure to give the title compound (379 mg).

MS (ESI+): [M+H]+ 344.2.

F) N-((2S)-1-((2-(4-(cyclopropylmethoxy)phenyl)[1,3]thiazolo[4,5-c]pyridin-6-yl)oxy)propan-2-yl)acetamide Using N-((2S)-1-((2-(4-hydroxyphenyl)[1,3]thiazolo[4,5-c]pyridin-6-yl)oxy)propan-2-yl)acetamide and (bromomethyl)cyclopropane, and in the same manner as in Example 5, the title compound was obtained.

Example 84

N-((2S)-1-((2-(3-fluoro-4-((1-fluorocyclopropyl)methoxy)phenyl) [1,3]oxazolo[4,5-c]pyridin-6-yl)oxy)propan-2-yl)acetamide Using N-((2S)-1-((2-(4-(benzyloxy)-3-fluorophenyl)[1,3]oxazolo[4,5-c]pyridin-6-yl)oxy)propan-2-yl)acetamide and (1-fluorocyclopropyl)methanol, and in the same manner as in Step A and Step B of Example 4, the title compound was obtained.

Example 85

N-((2S)-1-((2-(4-((1-fluorocyclopropyl)methoxy)phenyl) [1,3]oxazolo[4,5-c]pyridin-6-yl)oxy)propan-2-yl)acetamide Using N-((2S)-1-((2-(4-(benzyloxy)phenyl)[1,3]oxazolo[4,5-c]pyridin-6-yl)oxy)propan-2-yl)acetamide and (1-fluorocyclopropyl)methanol, and in the same manner as in Step A and Step B of Example 4, the title compound was obtained.

Example 86

N-((2S)-1-((2-(4-((2,2-difluorocyclopropyl)methoxy)-3,5-difluorophenyl)[1,3]oxazolo[4,5-c]pyridin-6-yl)oxy)propan-2-yl)acetamide A) 4-(benzyloxy)-3,5-difluorobenzoic Acid Using 3,4,5-trifluorobenzoic acid, and in the same manner as in Step A of Example 40, the title compound was obtained.
1H NMR (300 MHz, CDCl3) δ 5.31 (2H, s), 7.29-7.48 (5H, m), 7.55-7.70 (2H, m).

B) N-((2S)-1-((2-(4-(benzyloxy)-3,5-difluorophenyl)[1,3]oxazolo[4,5-c]pyridin-6-yl)oxy)propan-2-yl)acetamide Using 4-(benzyloxy)-3,5-difluorobenzoic acid and (2,2-difluorocyclopropyl)methanol, and in the same manner as in Step A, Step B and Step C of Example 49, the title compound was obtained.

MS (ESI+): [M+H]+ 454.1

C) N-((2S)-1-((2-(4-((2,2-difluorocyclopropyl)methoxy)-3,5-difluorophenyl)[1,3]oxazolo[4,5-c]pyridin-6-yl)oxy)propan-2-yl)acetamide Using N-((2S)-1-((2-(4-(benzyloxy)-3,5-difluorophenyl)[1,3]oxazolo[4,5-c]pyridin-6-yl)oxy)propan-2-yl)acetamide and (2,2-difluorocyclopropyl)methanol, and in the same manner as in Step A and Step B of Example 4, the title compound was obtained.

Example 87

N-((2S)-1-((2-(3,5-difluoro-4-((1-fluorocyclopropyl)methoxy)phenyl)[1,3]oxazolo[4,5-c]pyridin-6-yl)oxy)propan-2-yl)acetamide Using N-((2S)-1-((2-(4-(benzyloxy)-3,5-difluorophenyl)[1,3]oxazolo[4,5-c]pyridin-6-yl)oxy)propan-2-yl)acetamide and (1-fluorocyclopropyl)methanol, and in the same manner as in Step A and Step B of Example 4, the title compound was obtained.

Example 88

N-((2S)-1-((2-(4-((2,2-difluorocyclopropyl)methoxy)-2,3-difluorophenyl)[1,3]oxazolo[4,5-c]pyridin-6-yl)oxy)propan-2-yl)acetamide Using 4-(benzyloxy)-2,3-difluorobenzoic acid, and in the same manner as in Step A, Step B and Step C of Example 49 and Step A and Step B of Example 4, the title compound was obtained.

Example 89

N-((2S)-3-((2-(4-(cyclopropylmethoxy)-3-fluorophenyl)-1,3-benzoxazol-6-yl)oxy)butan-2-yl)acetamide A) 2-(4-(benzyloxy)-3-fluorophenyl)-1,3-benzoxazol-6-ol Using 4-(benzyloxy)-3-fluorobenzoic acid, and in the same manner as in Step B of Example 1, the title compound was obtained.
MS (ESI+): [M+H]+ 336.1

B) tert-butyl ((2S)-3-((2-(4-(benzyloxy)-3-fluorophenyl)-1,3-benzoxazol-6-yl)oxy)butan-2-yl)carbamate Using 2-(4-(benzyloxy)-3-fluorophenyl)-1,3-benzoxazol-6-ol and tert-butyl ((2S)-3-hydroxybutan-2-yl)carbamate, and in the same manner as in Step C of Example 1, the title compound was obtained.
MS (ESI+): [M+H]$^+$ 507.2

C) N-((2S)-3-((2-(4-(cyclopropylmethoxy)-3-fluorophenyl)-1,3-benzoxazol-6-yl)oxy)butan-2-yl)acetamide Using tert-butyl ((2S)-3-((2-(4-(benzyloxy)-3-fluorophenyl)-1,3-benzoxazol-6-yl)oxy)butan-2-yl)carbamate, and in the same manner as in Step D of Example 1, Step A of Example 4 and Example 5, the title compound was obtained.

Example 90

N-((2S)-1-((2-(4-ethoxy-2,3,5-trifluorophenyl)[1,3]oxazolo[4,5-c]pyridin-6-yl)oxy)propan-2-yl)acetamide A) 4-ethoxy-2,3,5-trifluorobenzoic Acid Using 2,3,5-trifluoro-4-hydroxybenzoic acid and iodoethane, and in the same manner as in Step A of Example 39, the title compound was obtained.
$^1$H NMR (300 MHz, CDCl$_3$) δ 1.45 (3H, t, J=7.0 Hz), 4.42 (2H, q, J=7.0 Hz), 7.48-7.61 (1H, m).

B) N-((2S)-1-((2-(4-ethoxy-2,3,5-trifluorophenyl)[1,3]oxazolo[4,5-c]pyridin-6-yl)oxy)propan-2-yl)acetamide Using 4-ethoxy-2,3,5-trifluorobenzoic acid, and in the same manner as in Step B, Step C and Step D of Example 31, the title compound was obtained.

Example 91

N-((2S)-1-((2-(4-ethoxy-3,5-difluorophenyl)-1,3-benzoxazol-6-yl)oxy)propan-2-yl)acetamide Using N-((2S)-1-((2-(4-(benzyloxy)-3,5-difluorophenyl)-1,3-benzoxazol-6-yl)oxy)propan-2-yl)acetamide and iodoethane, and in the same manner as in Example 5, the title compound was obtained.

Example 92

N-((2S)-1-((2-(4-ethoxy-2,3,5-trifluorophenyl)-1,3-benzoxazol-6-yl)oxy)propan-2-yl)acetamide Using 4-ethoxy-2,3,5-trifluorobenzoic acid, and in the same manner as in Step A, Step B, Step C and Step D of Example 44, the title compound was obtained.

Example 93

N-((2S)-1-((2-(4-ethoxy-3-fluoro-5-methoxyphenyl)-1,3-benzoxazol-6-yl)oxy)propan-2-yl)acetamide Using 3-fluoro-4-hydroxy-5-methoxybenzaldehyde and iodoethane, and in the same manner as in Step A and Step B of Example 62 and Step A, Step B, Step C and Step D of Example 44, the title compound was obtained.

Example 94

N-((2S)-1-((2-(3,5-difluoro-4-(2,2,2-trifluoroethoxy)phenyl)-1,3-benzoxazol-6-yl)oxy)propan-2-yl)acetamide Using N-((2S)-1-((2-(3,5-difluoro-4-hydroxyphenyl)-1,3-benzoxazol-6-yl)oxy)propan-2-yl)acetamide and 2,2,2-trifluoroethyl trifluoromethanesulfonate, and in the same manner as in Example 5, the title compound was obtained.

Example 95

N-((2S)-1-((2-(3-chloro-4-ethoxy-5-fluorophenyl)-1,3-benzoxazol-6-yl)oxy)propan-2-yl)acetamide Using 3-chloro-4-ethoxy-5-fluorobenzoic acid, and in the same manner as in Step A, Step B, Step C and Step D of Example 44, the title compound was obtained.

Example 96

N-((2S)-1-((2-(3-bromo-4-ethoxy-5-fluorophenyl)-1,3-benzoxazol-6-yl)oxy)propan-2-yl)acetamide Using methyl 3-bromo-5-fluoro-4-hydroxybenzoate, and in the same manner as in Step A of Example 21 and Step A, Step B, Step C and Step D of Example 44, the title compound was obtained.

Example 97

N-((2S)-1-((2-(3-acetyl-4-ethoxy-5-fluorophenyl)-1,3-benzoxazol-6-yl)oxy)propan-2-yl)acetamide To a mixture of N-((2S)-1-((2-(3-bromo-4-ethoxy-5-fluorophenyl)-1,3-benzoxazol-6-yl)oxy)propan-2-yl)acetamide (1.50 g) and toluene (10 mL) were added tributyl(1-ethoxyvinyl)stannane (2.25 mL) and tetrakis(triphenylphosphine)palladium(0) (192 mg), and the mixture was stirred at 110° C. for 5 hr under an argon atmosphere. To the reaction mixture was added 0.5N hydrochloric acid, and the mixture was stirred at room temperature for 1 hr, neutralized with saturated aqueous sodium hydrogen carbonate solution, and extracted with ethyl acetate. The organic layer was dried over anhydrous magnesium sulfate, and the solvent was evaporated. The obtained solid was washed with diethyl ether-hexane to give the title compound (1.22 g).

Example 98

N-((2S)-1-((2-(4-ethoxy-3-fluoro-5-(1-hydroxyethyl)phenyl)-1,3-benzoxazol-6-yl)oxy)propan-2-yl)acetamide To a mixture of N-((2S)-1-((2-(3-acetyl-4-ethoxy-5-fluorophenyl)-1,3-benzoxazol-6-yl)oxy)propan-2-yl)acetamide (660 mg), THF (10 mL) and methanol (5 mL) was added sodium borohydride (60.3 mg), and the mixture was stirred at room temperature for 10 min. To the reaction mixture was added saturated aqueous ammonium chloride solution, and the mixture was diluted with ethyl acetate, and dried over anhydrous magnesium sulfate. The solvent was evaporated, and the obtained residue was purified by silica gel column chromatography (hexane/ethyl acetate-ethyl acetate/methanol) to give the title compound (420 mg).

Example 99

N-((2S)-1-((2-(4-(cyanomethoxy)-3,5-difluorophenyl)-1,3-benzoxazol-6-yl)oxy)propan-2-yl)acetamide Using N-((2S)-1-((2-(4-(benzyloxy)-3,5-difluorophenyl)-1,3-benzoxazol-6-yl)oxy)propan-2-yl)acetamide and bromoacetonitrile, and in the same manner as in Example 5, the title compound was obtained.

Example 100

N-((2S)-1-((2-(4-(cyclopropylmethoxy)-3-fluoro-5-methoxyphenyl)-1,3-benzoxazol-6-yl)oxy)propan-2-yl)acetamide Using 4-(cyclopropylmethoxy)-3-fluoro-5-methoxybenzoic acid, and in the same manner as in Step A, Step B, Step C and Step D of Example 44, the title compound was obtained.

Example 101

1-((2S)-1-((2-(4-(cyclopropylmethoxy)-3-fluoro-5-methoxyphenyl) [1,3]oxazolo[4,5-c]pyridin-6-yl)oxy)propan-2-yl)urea Using tert-butyl ((2S)-1-((2-(4-(cyclopropylmethoxy)-3-fluoro-5-methoxyphenyl)[1,3]oxazolo[4,5-c]pyridin-6-yl)oxy)propan-2-yl)carbamate, and in the same manner as in Example 59, the title compound was obtained.

Example 102

N-((2S)-1-((2-(6-chloro-5-(cyclopropylmethoxy)pyridin-2-yl)[1,3]oxazolo[4,5-c]pyridin-6-yl)oxy)propan-2-yl)acetamide A) (6-chloro-5-(cyclopropylmethoxy)pyridin-2-yl)methanol Using 2-chloro-6-(hydroxymethyl)pyridin-3-ol and (bromomethyl)cyclopropane, and in the same manner as in Example 5, the title compound was obtained.
$^1$H NMR (300 MHz, CDCl$_3$) δ 0.36-0.44 (2H, m), 0.63-0.74 (2H, m), 1.27-1.42 (1H, m), 2.86 (1H, t, J=5.4 Hz), 3.91 (2H, d, J=6.8 Hz), 4.68 (2H, d, J=5.8 Hz), 7.15-7.24 (2H, m).

B) methyl 6-chloro-5-(cyclopropylmethoxy)pyridine-2-carboxylate

To a solution of (6-chloro-5-(cyclopropylmethoxy)pyridin-2-yl)methanol (14.0 g) in acetone (100 mL) was added dropwise a solution of potassium permanganate (14.5 g) in water (100 mL) over 40 min at 0° C., and the mixture was stirred at the same temperature for 20 min. The reaction mixture was acidified with 6N hydrochloric acid, and the mixture was extracted with ethyl acetate. The organic layer was dried over anhydrous magnesium sulfate, and the solvent was evaporated under reduced pressure. The residue was dissolved in DMF (100 mL), potassium carbonate (9.06 g) and methyl iodide (4.10 mL) were added thereto, and the mixture was stirred with heating at 70° C. for 20 min. The reaction mixture was diluted with ethyl acetate, washed with saturated brine, and dried over anhydrous magnesium sulfate. The solvent was evaporated under reduced pressure. The residue was purified by silica gel column chromatography (hexane/ethyl acetate) to give the title compound (7.27 g).
$^1$H NMR (300 MHz, CDCl$_3$) δ 0.37-0.50 (2H, m), 0.64-0.77 (2H, m), 1.29-1.44 (1H, m), 3.89-4.04 (5H, m), 7.22 (1H, d, J=8.5 Hz), 8.06 (1H, d, J=8.4 Hz).

C) N-((2S)-1-((2-(6-chloro-5-(cyclopropylmethoxy)pyridin-2-yl)[1,3]oxazolo[4,5-c]pyridin-6-yl)oxy)propan-2-yl)acetamide Using methyl 6-chloro-5-(cyclopropylmethoxy)pyridine-2-carboxylate, and in the same manner as in Step C, Step E and Step F of Example 35, the title compound was obtained.

Example 103

1-((2S)-1-((2-(4-(cyclopropylmethoxy)-3-fluoro-5-methoxyphenyl)[1,3]oxazolo[4,5-c]pyridin-6-yl)oxy)propan-2-yl)urea Using tert-butyl ((2S)-1-((2-(4-(cyclopropylmethoxy)-3-fluoro-5-methoxyphenyl)[1,3]oxazolo[4,5-c]pyridin-6-yl)oxy)propan-2-yl)carbamate, and in the same manner as in Example 59, the title compound was obtained.

Example 104

N-((2S)-1-((2-(3-chloro-4-ethoxy-5-fluorophenyl)[1,3]oxazolo[4,5-c]pyridin-6-yl)oxy)propan-2-yl)acetamide Using methyl 3-chloro-5-fluoro-4-hydroxybenzoate and iodoethane, and in the same manner as in Step A of Example 21 and Step B, Step C and Step D of Example 31, the title compound was obtained.

Example 105

N-((2S)-1-((2-(4-(((1R)-2,2-difluorocyclopropyl)methoxy)-3-methoxyphenyl)[1,3]oxazolo[4,5-c]pyridin-6-yl)oxy)propan-2-yl)acetamide Using 4-(benzyloxy)-3-methoxybenzoic acid, and in the same manner as in Step A, Step B, Step C and Step D of Example 68, the title compound was obtained.

Example 106

N-((2S)-1-((2-(4-(((1S)-2,2-difluorocyclopropyl)methoxy)-3-methoxyphenyl)[1,3]oxazolo[4,5-c]pyridin-6-yl)oxy)propan-2-yl)acetamide Using N-((2S)-1-((2-(4-(benzyloxy)-3-methoxyphenyl)[1,3]oxazolo[4,5-c]pyridin-6-yl)oxy)propan-2-yl)acetamide and ((1S)-2,2-difluorocyclopropyl)methyl 4-nitrobenzenesulfonate, and in the same manner as in Step D of Example 68, the title compound was obtained.

Example 107

N-((2S)-1-((2-(5-(cyclopropylmethoxy)-6-fluoropyridin-2-yl)[1,3]oxazolo[4,5-c]pyridin-6-yl)oxy)propan-2-yl)acetamide Using 6-bromo-2-fluoropyridin-3-ol and (bromomethyl)cyclopropane, and in the same manner as in Example 5 and Step A, Step B, Step D and Step E of Example 33, the title compound was obtained.

Example 108

N-((2S)-1-((2-(4-(((1R)-2,2-difluorocyclopropyl)methoxy)-3-fluoro-5-methoxyphenyl)[1,3]oxazolo[4,5-c]pyridin-6-yl)oxy)propan-2-yl)acetamide Using 3-fluoro-4-hydroxy-5-methoxybenzaldehyde and (bromomethyl)benzene, and in the same manner as in Step A and Step B of Example 62 and Step A, Step B, Step C and Step D of Example 68, the title compound was obtained.

Example 109

N-((2S)-1-((2-(4-chloro-5-(cyclopropylmethoxy)pyridin-2-yl)[1,3]oxazolo[4,5-c]pyridin-6-yl)oxy)propan-2-yl)acetamide Using 2-(((tert-butyl(dimethyl)silyl)oxy)methyl)-5-(methoxymethoxy)pyridine and hexachloroethane, and in the same manner as in Step B, Step C, Step D, Step E, Step F, Step G, Step H and Step I of Example 65, the title compound was obtained.

Example 110

1-((2S)-1-((2-(4-(((1R)-2,2-difluorocyclopropyl)methoxy)-3-fluoro-5-methoxyphenyl)[1,3]oxazolo[4,5-c]pyridin-6-yl)oxy)propan-2-yl)urea A) tert-butyl ((2S)-1-((2-(4-(((1R)-2,2-difluorocyclopropyl)methoxy)-3-fluoro-5-methoxyphenyl)[1,3]oxazolo[4,5-c]pyridin-6-yl)oxy)propan-2-yl)carbamate Using tert-butyl ((2S)-1-((2-(4-(benzyloxy)-3-fluoro-5-methoxyphenyl)[1,3]oxazolo[4,5-c]pyridin-6-yl)oxy)propan-2-yl)carbamate, and in the same manner as in Step D of Example 68, the title compound was obtained.

MS (ESI+): [M+H]$^+$ 524.1.

B) 1-((2S)-1-((2-(4-(((1R)-2,2-difluorocyclopropyl)methoxy)-3-fluoro-5-methoxyphenyl)[1,3]oxazolo[4,5-c]pyridin-6-yl)oxy)propan-2-yl)urea Using tert-butyl ((2S)-1-((2-(4-(((1R)-2,2-difluorocyclopropyl)methoxy)-3-fluoro-5-methoxyphenyl)[1,3]oxazolo[4,5-c]pyridin-6-yl)oxy)propan-2-yl)carbamate and 4-nitrophenyl carbonochloridate, and in the same manner as in Example 59, the title compound was obtained.

Example 111

N-((2S)-1-((2-(4-(cyclopropylmethoxy)-3-(trifluoromethyl)phenyl)[1,3]oxazolo[4,5-c]pyridin-6-yl)oxy)propan-2-yl)acetamide Using methyl 4-hydroxy-3-(trifluoromethyl)benzoate and (bromomethyl)cyclopropane, and in the same manner as in Step A of Example 21 and Step E and Step F of Example 35, the title compound was obtained.

Example 112

N-((2S)-1-((2-(5-(((1R)-2,2-difluorocyclopropyl)methoxy)pyridin-2-yl)[1,3]oxazolo[4,5-c]pyridin-6-yl)oxy)propan-2-yl)acetamide A) N-((2S)-1-((2-(5-hydroxypyridin-2-yl)[1,3]oxazolo[4,5-c]pyridin-6-yl)oxy)propan-2-yl)acetamide To a solution of N-((2S)-1-((4-chloro-5-nitropyridin-2-yl)oxy)propan-2-yl)acetamide (1.80 g) in ethanol (20 mL) were added iron powder (1.84 g) and iron(III) chloride (1.07 g), and the mixture was stirred with heating under reflux for 1 hr. The reaction mixture was filtered, and the filtrate was diluted with ethyl acetate, washed with saturated brine, and dried over anhydrous magnesium sulfate. The solvent was evaporated under reduced pressure to give N-((2S)-1-((5-amino-4-chloropyridin-2-yl)oxy)propan-2-yl)acetamide (1.46 g). To a solution of N-((2S)-1-((5-amino-4-chloropyridin-2-yl)oxy)propan-2-yl)acetamide (830 mg) and 5-(benzyloxy)pyridine-2-carboxylic acid (781 mg), diisopropylethylamine (1.19 mL) in DMF (10 mL) was added HATU (1.49 g), and the mixture was stirred at room temperature for 30 min. The precipitated solid was washed with ethyl acetate-hexane. A suspension of the obtained solid, potassium carbonate (1.22 g) and copper(I) iodide (84.0 mg) in DMF (10 mL) was stirred at 160° C. for 1.5 hr. The reaction mixture was subjected to silica gel chromatography (NH, ethyl acetate), and washed with saturated brine, and the solvent was evaporated. The obtained solid was washed with ethyl acetate/hexane. A mixture of the obtained solid, 10% palladium/carbon (containing water (50%), 200 mg) and THF (10 mL) was stirred at room temperature for 30 min under a hydrogen atmosphere. The catalyst was removed by filtration, and the obtained filtrate was concentrated under reduced pressure. The residue was purified by silica gel column chromatography (ethyl acetate/methanol) to give the title compound (37.4 mg).

MS (ESI+): [M+H]$^+$ 329.2.

B) N-((2S)-1-((2-(5-(((1R)-2,2-difluorocyclopropyl)methoxy)pyridin-2-yl) [1,3]oxazolo[4,5-c]pyridin-6-yl)oxy)propan-2-yl)acetamide A suspension of N-((2S)-1-((2-(5-hydroxypyridin-2-yl)[1,3]oxazolo[4,5-c]pyridin-6-yl)oxy)propan-2-yl)acetamide (37.4 mg), ((1R)-2,2-difluorocyclopropyl)methyl 4-nitrobenzenesulfonate (50.1 mg) and potassium carbonate (31.5 mg) in DMF (5 mL) was stirred at 70° C. for 30 min. The reaction mixture was diluted with ethyl acetate, and washed with saturated brine, and the organic layer was dried over anhydrous magnesium sulfate. The solvent was evaporated, and the obtained solid was washed with diethyl ether to give the title m compound (12.4 mg).

$^1$H NMR (300 MHz, CDCl$_3$) δ 1.20-1.46 (4H, m), 1.62-1.80 (1H, m), 1.98 (3H, s), 2.04-2.25 (1H, m), 4.20 (2H, dd, J=7.4, 1.4 Hz), 4.29-4.50 (3H, m), 6.01 (1H, d, J=7.0 Hz), 6.97 (1H, d, J=0.8 Hz), 7.37 (1H, dd, J=8.8, 2.8 Hz), 8.29 (1H, d, J=8.8 Hz), 8.50 (1H, d, J=2.6 Hz), 8.60 (1H, d, J=0.8 Hz).

Example 113

N-((2S)-1-((2-(4-(cyclopropylmethoxy)-2-methoxyphenyl) [1,3]oxazolo[4,5-c]pyridin-6-yl)oxy)propan-2-yl)acetamide A) 4-(cyclopropylmethoxy)-2-methoxybenzaldehyde Using 4-hydroxy-2-methoxybenzaldehyde, and in the same manner as in Example 5, the title compound was obtained.
$^1$H NMR (300 MHz, CDCl$_3$) δ 0.30-0.48 (2H, m), 0.59-0.76 (2H, m), 1.18-1.39 (1H, m), 3.85-3.93 (5H, m), 6.47 (1H, d, J=2.2 Hz), 6.52 (1H, dd, J=8.4, 1.9 Hz), 7.80 (1H, d, J=8.7 Hz), 10.28 (1H, d, J=0.6 Hz).

B) 4-(cyclopropylmethoxy)-2-methoxybenzoic Acid

Using 4-(cyclopropylmethoxy)-2-methoxybenzaldehyde, and in the same manner as in Step B of Example 62, the title compound was obtained.
$^1$H NMR (300 MHz, CDCl$_3$) δ 0.32-0.47 (2H, m), 0.62-0.75 (2H, m), 1.19-1.38 (1H, m), 3.88 (2H, d, J=7.0 Hz), 4.04 (3H, s), 6.56 (1H, d, J=2.3 Hz), 6.59-6.65 (1H, m), 8.12 (1H, d, J=8.8 Hz), 10.37-10.56 (1H, m).

C) N-((2S)-1-((2-(4-(cyclopropylmethoxy)-2-methoxyphenyl)[1,3]oxazolo[4,5-c]pyridin-6-yl)oxy)propan-2-yl)acetamide Using 4-(cyclopropylmethoxy)-2-methoxybenzoic acid, and in the same manner as in Step B, Step C and Step D of Example 31, the title compound was obtained.

Example 114

N-((2S)-1-((2-(4-(cyclopropylmethoxy)-3-(difluoromethoxy)phenyl)[1,3]oxazolo[4,5-c]pyridin-6-yl)oxy)propan-2-yl)acetamide A) N-((2S)-1-((2-(3-(difluoromethoxy)-4-hydroxyphenyl)[1,3]oxazolo[4,5-c]pyridin-6-yl)oxy)propan-2-yl)acetamide Using 4-(benzyloxy)-3-hydroxybenzaldehyde and ethyl chloro(difluoro)acetate and sodium chlorodifluoroacetate, and in the same manner as in Step A and Step B of Example 62 and Step A, Step B and Step C and Step D of Example 49, the title compound was obtained.
MS (ESI+): [M+H]$^+$ 394.1

B) N-((2S)-1-((2-(4-(cyclopropylmethoxy)-3-(difluoromethoxy)phenyl)[1,3]oxazolo[4,5-c]pyridin-6-yl)oxy)propan-2-yl)acetamide Using N-((2S)-1-((2-(3-(difluoromethoxy)-4-hydroxyphenyl)[1,3]oxazolo[4,5-c]pyridin-6-yl)oxy)propan-2-yl)acetamide and (bromomethyl)cyclopropane, and in the same manner as in Example 5, the title compound was obtained.

Example 115

N-((2S)-1-((2-(4-((2,2-difluorocyclopropyl)methoxy)-3-(difluoromethoxy)phenyl)[1,3]oxazolo[4,5-c]pyridin-6-yl)oxy)propan-2-yl)acetamide Using N-((2S)-1-((2-(3-(difluoromethoxy)-4-hydroxyphenyl)[1,3]oxazolo[4,5-c]pyridin-6-yl)oxy)propan-2-yl) acetamide and 2-(bromomethyl)-1,1-difluorocyclopropane, and in the same manner as in Example 5, the title compound was obtained.

Example 116

N-((2S)-1-((2-(4-(cyclopropylmethoxy)-3-(2,2,2-trifluoroethoxy)phenyl)[1,3]oxazolo[4,5-c]pyridin-6-yl)oxy)propan-2-yl)acetamide Using 4-(benzyloxy)-3-hydroxybenzaldehyde, 2,2,2-trifluoroethyl trifluoromethanesulfonate and (bromomethyl)cyclopropane, and in the same manner as in Step A and Step B of Example 62 and Step A, Step B and Step C and Step D of Example 49, the title compound was obtained.

Example 117

N-((2S)-1-((2-(4-(cyclopropylmethoxy)-2-methylphenyl)[1,3]oxazolo[4,5-c]pyridin-6-yl)oxy)propan-2-yl)acetamide A) 4-(cyclopropylmethoxy)-2-methylbenzoic Acid Using methyl 4-hydroxy-2-methylbenzoate, and in the same manner as in Step A of Example 21, the title compound was obtained.
$^1$H NMR (300 MHz, CDCl$_3$) δ 0.30-0.43 (2H, m), 0.59-0.73 (2H, m), 1.17-1.36 (1H, m), 2.50-2.64 (3H, m), 3.79-3.87 (5H, m), 6.68-6.78 (2H, m), 7.87-7.96 (1H, m).

B) N-((2S)-1-((2-(4-(cyclopropylmethoxy)-2-methylphenyl)[1,3]oxazolo[4,5-c]pyridin-6-yl)oxy)propan-2-yl)acetamide Using 4-(cyclopropylmethoxy)-2-methylbenzoic acid and N-((2S)-1-((4-chloro-5-nitropyridin-2-yl)oxy)propan-2-yl) acetamide, and in the same manner as in Step B and Step C of Example 31, the title compound was obtained.

Example 118

N-((2S)-1-((2-(5-(cyclopropylmethoxy)pyrazin-2-yl) [1,3]oxazolo[4,5-c]pyridin-6-yl)oxy)propan-2-yl) acetamide A) 5-(cyclopropylmethoxy)pyrazine-2-carboxylic Acid Using methyl 5-hydroxypyrazine-2-carboxylate, and in the same manner as in Step A of Example 21, the title compound was obtained.
$^1$H NMR (300 MHz, CDCl$_3$) δ 0.30-0.44 (2H, m), 0.59-0.72 (2H, m), 1.20-1.41 (1H, m), 3.95-4.03 (3H, m), 4.25 (2H, d, J=7.3 Hz), 8.30 (1H, d, J=1.3 Hz), 8.85 (1H, d, J=1.2 Hz).

B) N-((2S)-1-((2-(5-(cyclopropylmethoxy)pyrazin-2-yl)[1,3]oxazolo[4,5-c]pyridin-6-yl)oxy)propan-2-yl) acetamide Using 5-(cyclopropylmethoxy)pyrazine-2-carboxylic acid, and in the same manner as in Step E and Step F of Example 35, the title compound was obtained.

Example 119

N-((2S)-1-((2-(4-(cyclopropylmethoxy)-3-(trifluoromethoxy)phenyl)-1,3-benzoxazol-6-yl)oxy)propan-2-yl)acetamide Using 4-hydroxy-3-(trifluoromethoxy)benzaldehyde, and in the same manner as in Step A and Step B of Example 62 and Step B, Step C and Step D of Example 1, the title compound was obtained.

Example 120

N-((2S)-1-((2-(5-(cyclopropylmethoxy)-3-methylpyridin-2-yl)[1,3]oxazolo[4,5-c]pyridin-6-yl)oxy)propan-2-yl)acetamide A) 5-(cyclopropylmethoxy)-3-methylpyridine-2-carboxylic Acid Using 5-bromo-3-methylpyridine-2-carboxylic acid, and in the same manner as in Step A of Example 40, the title compound was obtained.
$^1$H NMR (300 MHz, CDCl$_3$) δ 0.32-0.46 (2H, m), 0.63-0.75 (2H, m), 1.23-1.35 (1H, m), 2.74 (3H, s), 3.92 (2H, m), 7.10 (1H, d, J=2.3 Hz), 8.09 (1H, d, J=2.6 Hz).

B) N-((2S)-1-((2-(5-(cyclopropylmethoxy)-3-methylpyridin-2-yl)[1,3]oxazolo[4,5-c]pyridin-6-yl)oxy)propan-2-yl)acetamide Using 5-(cyclopropylmethoxy)-3-methylpyridine-2-carboxylic acid, and in the same manner as in Step E and Step F of Example 35, the title compound was obtained.

Example 121

N-((2S)-1-((2-(6-(cyclopropylmethoxy)pyridazin-3-yl)[1,3]oxazolo[4,5-c]pyridin-6-yl)oxy)propan-2-yl)acetamide A) cyclopropylmethyl 6-(cyclopropylmethoxy)pyridazine-3-carboxylate To a solution of methyl 6-chloropyridazine-3-carboxylate (1.24 g) and cyclopropylmethanol (1.16 mL) in THF (20 mL) was added potassium tert-butoxide (1.05 g) at −78° C., and the mixture was stirred at the same temperature, allowed to warm to 0° C., and stirred for 3 hr. To the reaction mixture was added water, and the mixture was extracted with ethyl acetate. The organic layer was washed with saturated brine, dried over anhydrous magnesium sulfate, and concentrated under reduced pressure. The obtained residue was purified by silica gel chromatography (hexane/ethyl acetate) to give the title compound (0.48 g).
MS (ESI+): [M+H]$^+$ 249.2.

B) 6-(cyclopropylmethoxy)pyridazine-3-carboxylic Acid

To a solution of cyclopropylmethyl 6-(cyclopropylmethoxy)pyridazine-3-carboxylate (0.48 g) in a mixed solvent of THF (5 mL) and methanol (5 mL) was added 1 M aqueous lithium hydroxide solution (5 mL), and the mixture was stirred at room temperature for 1 hr. The reaction mixture was neutralized with 1 M hydrochloric acid, and the mixture was extracted with ethyl acetate. The obtained organic layer was washed with saturated brine, and dried over anhydrous magnesium sulfate, and the solvent was evaporated under reduced pressure to give the title compound (0.40 g).
$^1$H NMR (300 MHz, CDCl$_3$) δ 0.36-0.48 (2H, m), 0.61-0.75 (2H, m), 1.38 (1H, tt, J=7.8, 4.8 Hz), 4.45 (2H, d, J=7.4 Hz), 7.19 (1H, d, J=9.2 Hz), 8.19 (1H, d, J=9.2 Hz).

C) N-((2S)-1-((2-(6-(cyclopropylmethoxy)pyridazin-3-yl)[1,3]oxazolo[4,5-c]pyridin-6-yl)oxy)propan-2-yl)acetamide Using 6-(cyclopropylmethoxy)pyridazine-3-carboxylic acid, and in the same manner as in Step E and Step F of Example 35, the title compound was obtained.

Example 122

N-((2S)-1-((2-(6-(cyclopropylmethoxy)-4-methylpyridin-3-yl)[1,3]oxazolo[4,5-c]pyridin-6-yl)oxy)propan-2-yl)acetamide A) 6-(cyclopropylmethoxy)-4-methylnicotinic Acid Cyclopropylmethanol (3.92 mL) was added to a suspension of sodium hydride (60% oil, 1.93 g) in THF (30 mL) by small portions at 0° C., and the obtained mixture was stirred at room temperature for 1 hr. To the reaction mixture was added 6-fluoro-4-methylnicotinic acid, and the mixture was stirred at room temperature for 20 hr. The reaction mixture was neutralized with 1 M hydrochloric acid, and the mixture was extracted with ethyl acetate. The obtained organic layer was washed with saturated brine, and dried over anhydrous magnesium sulfate, and the solvent was evaporated under reduced pressure. The obtained solid was recrystallized (hexane/ethyl acetate) to give the title compound (1.14 g).
MS (ESI+): [M+H]$^+$ 208.1.

B) N-((2S)-1-((2-(6-(cyclopropylmethoxy)-4-methylpyridin-3-yl)[1,3]oxazolo[4,5-c]pyridin-6-yl)oxy)propan-2-yl)acetamide Using 6-(cyclopropylmethoxy)-4-methylnicotinic acid, and in the same manner as in Step E and Step F of Example 35, the title compound was obtained.

Example 123

N-((2S)-1-((2-(4-(((1R)-2,2-difluorocyclopropyl)methoxy)phenyl)[1,3]oxazolo[4,5-c]pyridin-6-yl)oxy)propan-2-yl)-1H-pyrazole-4-carboxamide A) methyl 4-(((1R)-2,2-difluorocyclopropyl)methoxy)benzoate Using methyl 4-hydroxybenzoate and ((1R)-2,2-difluorocyclopropyl)methyl 4-nitrobenzenesulfonate, and in the same manner as in Example 5, the title compound was obtained. $^1$H NMR (300 MHz, DMSO-d$_6$) δ 1.41-1.61 (1H, m), 1.66-1.84 (1H, m), 2.13-2.38 (1H, m), 3.81 (3H, s), 3.99-4.14 (1H, m), 4.18-4.31 (1H, m), 7.00-7.15 (2H, m), 7.85-7.97 (2H, m).

B) 4-(((1R)-2,2-difluorocyclopropyl)methoxy)benzoic Acid

A mixture of methyl 4-(((1R)-2,2-difluorocyclopropyl)methoxy)benzoate (637 mg), THF (10 mL), methanol (10 mL) and 1M aqueous sodium hydroxide solution (10 mL) was stirred at room temperature overnight. The reaction mixture was neutralized with 1M hydrochloric acid at 0° C., and the mixture was extracted with ethyl acetate. The combined organic layer were washed with saturated brine, and dried over anhydrous magnesium sulfate, and the solvent was evaporated under reduced pressure to give the title compound (559 mg).

MS (ESI−): [M−H]⁻ 227.2.

C) tert-butyl ((2S)-1-((4-hydroxy-5-nitropyridin-2-yl)oxy)propan-2-yl)carbamate

A mixture of tert-butyl ((2S)-1-((4-chloro-5-nitropyridin-2-yl)oxy)propan-2-yl)carbamate (5.00 g), cesium acetate (7.23 g) and DMF (40 mL) was stirred at 0° C. for 10 hr. To the reaction mixture was added water, and the mixture was extracted with ethyl acetate. The combined organic layer were washed with saturated brine, and dried over anhydrous magnesium sulfate, and the solvent was evaporated under reduced pressure.

The residue was purified by silica gel column chromatography (hexane/ethyl acetate) to give the title compound (4.02 g). MS (ESI+): [M+H]⁺ 314.2.

D) tert-butyl ((2S)-1-((5-amino-4-hydroxypyridin-2-yl)oxy)propan-2-yl)carbamate

Using tert-butyl ((2S)-1-((4-hydroxy-5-nitropyridin-2-yl)oxy)propan-2-yl)carbamate, and in the same manner as in Step A of Example 4, the title compound was obtained.

MS (ESI+): [M+H]⁺ 284.2.

E) 2-(((2S)-2-((tert-butoxycarbonyl)amino)propyl)oxy)-5-((4-(((1R)-2,2-difluorocyclopropyl)methoxy)benzoyl)amino)pyridin-4-yl 4-(((1R)-2,2-difluorocyclopropyl)methoxy)benzoate Using tert-butyl ((2S)-1-((5-amino-4-hydroxypyridin-2-yl)oxy)propan-2-yl)carbamate and 4-(((1R)-2,2-difluorocyclopropyl)methoxy)benzoic acid, and in the same manner as in Step D of Example 83, the title compound was obtained.

MS (ESI+): [M+H]⁺ 704.2.

F) tert-butyl ((2S)-1-((5-((4-(((1R)-2,2-difluorocyclopropyl)methoxy)benzoyl)amino)-4-hydroxypyridin-2-yl)oxy)propan-2-yl)carbamate Using 2-(((2S)-2-((tert-butoxycarbonyl)amino)propyl)oxy)-5-((4-(((1R)-2,2-difluorocyclopropyl)methoxy)benzoyl)amino)pyridin-4-yl 4-(((1R)-2,2-difluorocyclopropyl)methoxy)benzoate, and in the same manner as in Step B of Example 123, the title compound was obtained.

MS (ESI+): [M+H]⁺ 494.2.

G) tert-butyl ((2S)-1-((2-(4-(((1R)-2,2-difluorocyclopropyl)methoxy)phenyl) [1,3]oxazolo[4,5-c]pyridin-6-yl)oxy)propan-2-yl)carbamate Using tert-butyl ((2S)-1-((5-((4-(((1R)-2,2-difluorocyclopropyl)methoxy)benzoyl)amino)-4-hydroxypyridin-2-yl)oxy)propan-2-yl)carbamate, and in the same manner as in Step B of Example 41, the title compound was obtained.

MS (ESI+): [M+H]⁺ 476.2.

H) N-((2S)-1-((2-(4-(((1R)-2,2-difluorocyclopropyl)methoxy)phenyl)[1,3]oxazolo[4,5-c]pyridin-6-yl)oxy)propan-2-yl)-1H-pyrazole-4-carboxamide A mixture of tert-butyl ((2S)-1-((2-(4-(((1R)-2,2-difluorocyclopropyl)methoxy)phenyl) [1,3]oxazolo[4,5-c]pyridin-6-yl)oxy)propan-2-yl)carbamate (18.0 mg), 4M hydrogen chloride/ethyl acetate (1 mL) and ethyl acetate (1 mL) was stirred at room temperature for 6 hr. The reaction mixture was concentrated under reduced pressure, and the obtained residue was mixed with 1H-pyrazole-4-carboxylic acid (5.09 mg), 1-ethyl-3-(3-dimethylaminopropyl)carbodiimide hydrochloride (8.71 mg), 1-hydroxybenzotriazole (6.14 mg), triethylamine (0.026 mL) and DMF (1 mL). The obtained mixture was stirred at room temperature for 3 days. To the reaction mixture was added water, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (2.44 mg).

Example 124

N-((2S)-1-((2-(4-((2,2-difluorocyclopropyl)methoxy)phenyl) [1,3]oxazolo[5,4-d]pyrimidin-5-yl)oxy)propan-2-yl)acetamide A) 4-(benzyloxy)-2-chloro-5-nitropyrimidine Benzyl alcohol (5.57 g) was added to a suspension of sodium hydride (oil, 60%, 2.06 g) in DMF (100 mL) by small portions at 0° C., and the obtained mixture was stirred at 0° C. for 30 min. The reaction mixture was cooled to 0° C., 2,4-dichloro-5-nitropyrimidine (10.0 g) was added thereto, and the obtained mixture was stirred at 0° C. for 1 hr. To the reaction mixture was added water, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (670 mg). ¹H NMR (300 MHz, DMSO-d₆) δ 5.62 (2H, s), 7.24-7.73 (5H, m), 9.28 (1H, s).

B) tert-butyl ((2S)-1-((4-(benzyloxy)-5-nitropyrimidin-2-yl)oxy)propan-2-yl)carbamate A mixture of 4-(benzyloxy)-2-chloro-5-nitropyrimidine (670 mg), tert-butyl ((2S)-1-hydroxypropan-2-yl)carbamate (530 mg), potassium phosphate (642 mg) and propionitrile (10 mL) was stirred at 50° C. for 1 hr, and then at 100° C. for 5 hr. To the reaction mixture was added water, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (170 mg).

MS (ESI+): [M+H]⁺ 405.2.

C) tert-butyl ((2S)-1-((5-((4-((2,2-difluorocyclopropyl)methoxy)benzoyl)amino)-4-hydroxypyrimidin-2-yl)oxy)propan-2-yl)carbamate Using tert-butyl ((2S)-1-((4-(benzyloxy)-5-nitropyrimidin-2-yl)oxy)propan-2-yl)carbamate and 4-((2,2-difluorocyclopropyl)methoxy)benzoic acid, and in the same manner as in Step A of Example 4 and Step D of Example 83, the title compound was obtained.
MS (ESI+): [M+H]+ 495.2.

D) tert-butyl ((2S)-1-((2-(4-((2,2-difluorocyclopropyl)methoxy)phenyl)[1,3]oxazolo[5,4-d]pyrimidin-5-yl)oxy)propan-2-yl)carbamate Using tert-butyl ((2S)-1-((5-((4-((2,2-difluorocyclopropyl)methoxy)benzoyl)amino)-4-hydroxypyrimidin-2-yl)oxy)propan-2-yl)carbamate, and in the same manner as in Step B of Example 41, the title compound was obtained.
MS (ESI+): [M+H]+ 477.2.

E) N-((2S)-1-((2-(4-((2,2-difluorocyclopropyl)methoxy)phenyl)[1,3]oxazolo[5,4-d]pyrimidin-5-yl)oxy)propan-2-yl)acetamide Using tert-butyl ((2S)-1-((2-(4-((2,2-difluorocyclopropyl)methoxy)phenyl)[1,3]oxazolo[5,4-d]pyrimidin-5-yl)oxy)propan-2-yl)carbamate, and in the same manner as in Step D of Example 1, the title compound was obtained.

Example 125

N-((2S)-1-((2-(4-(cyclopropylmethoxy)-2-fluorophenyl)[1,3]oxazolo[4,5-c]pyridin-6-yl)oxy)propan-2-yl)acetamide Using 4-(cyclopropylmethoxy)-2-fluorobenzoic acid, and in the same manner as in Step A, Step B and Step C of Example 49, the title compound was obtained.

Example 126

N-((2S)-1-((2-(2-chloro-4-(cyclopropylmethoxy)phenyl)[1,3]oxazolo[4,5-c]pyridin-6-yl)oxy)propan-2-yl)acetamide A) tert-butyl ((2S)-1-((4-hydroxy-5-nitropyridin-2-yl)oxy)propan-2-yl)carbamate A mixture of tert-butyl ((2S)-1-((4-chloro-5-nitropyridin-2-yl)oxy)propan-2-yl)carbamate (4.83 g), cesium acetate (6.99 g) and DMF (40 mL) was stirred at 80° C. for 1 hr. The mixture was allowed to cool to room temperature, and concentrated under reduced pressure. The residue was diluted with ethyl acetate and water, and the organic layer was separated. The organic layer was washed with saturated brine, dried over anhydrous magnesium sulfate, and concentrated under reduced pressure to give the title compound (3.84 g).
$^1$H NMR (300 MHz, DMSO-$d_6$) δ 1.08 (3H, d, J=6.8 Hz), 1.37 (9H, s), 3.69-3.93 (1H, m), 4.06-4.30 (2H, m), 6.28 (1H, s), 6.86 (1H, d, J=7.8 Hz), 8.73 (1H, s), 12.22 (1H, brs).

B) tert-butyl ((2S)-1-((5-amino-4-hydroxypyridin-2-yl)oxy)propan-2-yl)carbamate

A mixture of tert-butyl ((2S)-1-((4-hydroxy-5-nitropyridin-2-yl)oxy)propan-2-yl)carbamate (3.84 g) and 10% palladium/carbon (containing water (50%), 0.40 g) and methanol (50 mL) was stirred at room temperature for 15 hr under a hydrogen atmosphere. The catalyst was removed by filtration, and the obtained filtrate was concentrated under reduced pressure to give the title compound (3.35 g).
$^1$H NMR (300 MHz, DMSO-$d_6$) δ 1.05 (3H, d, J=6.6 Hz), 1.37 (9H, s), 3.67-3.80 (1H, m), 3.80-3.96 (2H, m), 6.05 (1H, s), 6.77 (1H, d, J=7.5 Hz), 7.34 (1H, s).

C) tert-butyl ((2S)-1-(4-((2-chloro-4-(cyclopropylmethoxy)benzoyl)amino)-3-hydroxyphenoxy)propan-2-yl)carbamate Using 4-(cyclopropylmethoxy)-2-chlorobenzoic acid and tert-butyl ((2S)-1-((5-amino-4-hydroxypyridin-2-yl)oxy)propan-2-yl)carbamate, and in the same manner as in Step B of Example 14, the title compound was obtained.
MS (ESI+): [M+H]+ 492.2.

D) tert-butyl ((2S)-1-((2-(2-chloro-4-(cyclopropylmethoxy)phenyl) [1,3]oxazolo[4,5-c]pyridin-6-yl)oxy)propan-2-yl)carbamate To a solution of tert-butyl ((2S)-1-(4-((2-chloro-4-(cyclopropylmethoxy)benzoyl)amino)-3-hydroxyphenoxy)propan-2-yl)carbamate (200 mg), hexachloroethane (241 mg) and triphenylphosphine (321 mg) in acetonitrile (3 mL) was added triethylamine (0.454 mL), and the mixture was stirred at room temperature for 15 hr. The reaction mixture was diluted with water, and the mixture was extracted with ethyl acetate. The organic layer was washed with saturated brine, dried over anhydrous magnesium sulfate, and concentrated under reduced pressure. The residue was purified by silica gel column chromatography (hexane/ethyl acetate) to give the title compound (65 mg).
$^1$H NMR (300 MHz, DMSO-$d_6$) δ 0.28-0.43 (2H, m), 0.52-0.70 (2H, m), 1.12 (3H, d, J=6.7 Hz), 1.20-1.36 (1H, m), 1.38 (9H, s), 3.77-3.95 (1H, m), 3.97 (2H, d, J=7.1 Hz), 4.20 (2H, d, J=6.2 Hz), 6.90 (1H, d, J=7.9 Hz), 7.15 (1H, dd, J=8.9, 2.5 Hz), 7.20 (1H, s), 7.27 (1H, d, J=2.5 Hz), 8.07 (1H, d, J=8.8 Hz), 8.68 (1H, d, J=0.8 Hz).

E) N-((2S)-1-((2-(2-chloro-4-(cyclopropylmethoxy)phenyl)[1,3]oxazolo[4,5-c]pyridin-6-yl)oxy)propan-2-yl)acetamide Using tert-butyl ((2S)-1-((2-(2-chloro-4-(cyclopropylmethoxy)phenyl)[1,3]oxazolo[4,5-c]pyridin-6-yl)oxy)propan-2-yl)carbamate, and in the same manner as in Step C of Example 49, the title compound was obtained.

Example 127

N-((2S)-1-((2-(6-(cyclopropylmethoxy)-2-methylpyridin-3-yl)[1,3]oxazolo[4,5-c]pyridin-6-yl)oxy)propan-2-yl)acetamide A) 6-(cyclopropylmethoxy)-2-methylnicotinic Acid Using 6-fluoro-2-methylnicotinic acid, and in the same manner as in Step A of Example 122, the title compound was obtained.
MS (ESI+): [M+H]+ 208.1.

B) N-((2S)-1-((2-(6-(cyclopropylmethoxy)-2-methylpyridin-3-yl)[1,3]oxazolo[4,5-c]pyridin-6-yl)oxy)propan-2-yl)acetamide Using 6-(cyclopropylmethoxy)-2-methylnicotinic acid, and in the same manner as in Step E and Step F of Example 35, the title compound was obtained.

Example 128

Optically Active Form of N-((2S)-1-((2-(4-((2,2-difluorocyclopropyl)methoxy)-2,5-difluorophenyl)[1,3]oxazolo[4,5-c]pyridin-6-yl)oxy)propan-2-yl)acetamide A diastereomer mixture (51.8 mg) of N-((2S)-1-((2-(4-((2,2-difluorocyclopropyl)methoxy)-2,5-difluorophenyl)[1,3]oxazolo[4,5-c]pyridin-6-yl)oxy)propan-2-yl)acetamide was resolved by HPLC (column: CHIRALCEL CJ (registered trade mark) (trade name), 50 mmID×500 mL, DAICEL CHEMICAL INDUSTRIES, LTD., mobile phase:hexane/ethanol=300:700) to give the title compound having a shorter retention time (22.4 mg).
analysis retention time 10.4 min.
optical purity >99.9% ee

Example 129

Optically Active Form of N-((2S)-1-((2-(4-((2,2-difluorocyclopropyl)methoxy)-2,5-difluorophenyl)[1,3]oxazolo[4,5-c]pyridin-6-yl)oxy)propan-2-yl)acetamide A diastereomer mixture (51.8 mg) of N-((2S)-1-((2-(4-((2,2-difluorocyclopropyl)methoxy)-2,5-difluorophenyl)[1,3]oxazolo[4,5-c]pyridin-6-yl)oxy)propan-2-yl)acetamide was resolved by HPLC (column: CHIRALCEL CJ (registered trade mark) (trade name), 50 mmID×500 mL, DAICEL CHEMICAL INDUSTRIES, LTD., mobile phase: hexane/ethanol=300:700) to give the title compound having a longer retention time (18.2 mg).
analysis retention time 13.6 min.
optical purity 99.6% ee

Example 130

Optically Active Form of N-((2S)-1-((2-(4-((2,2-difluorocyclopropyl)methoxy)-3,5-difluorophenyl)[1,3]oxazolo[4,5-c]pyridin-6-yl)oxy)propan-2-yl)acetamide A diastereomer mixture (240 mg) of N-((2S)-1-((2-(4-((2,2-difluorocyclopropyl)methoxy)-3,5-difluorophenyl)[1,3]oxazolo[4,5-c]pyridin-6-yl)oxy)propan-2-yl)acetamide was resolved by HPLC (column: CHIRALCEL CJ (registered trade mark) (trade name), 50 mmID×500 mL, DAICEL CHEMICAL INDUSTRIES, LTD., mobile phase:hexane/isopropyl alcohol=400:600), and recrystallized (ethyl acetate) to give the title compound having a shorter retention time (103 mg). analysis retention time 12.7 min.
optical purity >99.9% ee

Example 131

Optically Active Form of N-((2S)-1-((2-(4-((2,2-difluorocyclopropyl)methoxy)-3,5-difluorophenyl)[1,3]oxazolo[4,5-c]pyridin-6-yl)oxy)propan-2-yl)acetamide A diastereomer mixture (240 mg) of N-((2S)-1-((2-(4-((2,2-difluorocyclopropyl)methoxy)-3,5-difluorophenyl)[1,3]oxazolo[4,5-c]pyridin-6-yl)oxy)propan-2-yl)acetamide was resolved by HPLC (column: CHIRALCEL CJ (registered trade mark) (trade name), 50 mmID×500 mL, DAICEL CHEMICAL INDUSTRIES, LTD., mobile phase:hexane/isopropyl alcohol=400:600), and recrystallized (ethyl acetate) to give the title compound having a longer retention time (83.8 mg).
analysis retention time 17.5 min.
optical purity 99.7% ee

Example 132

N-((2S)-1-((2-(4-(cyclopropylmethoxy)-2-(trifluoromethyl)phenyl)[1,3]oxazolo[4,5-c]pyridin-6-yl)oxy)propan-2-yl)acetamide Using methyl 4-hydroxy-2-(trifluoromethyl)benzoate and (bromomethyl)cyclopropane, and in the same manner as in Step A of Example 21 and Step B and Step C of Example 31, the title compound was obtained.

Example 133

N-((2S)-1-((2-(6-(cyclopropylmethoxy)-5-methylpyridin-3-yl)[1,3]oxazolo[4,5-c]pyridin-6-yl)oxy)propan-2-yl)acetamide Using cyclopropylmethanol and 2,5-dibromo-3-methylpyridine, and in the same manner as in Step A of Example 40 and Step B of Example 22, the title compound was obtained.

Example 134

N-((2S)-1-((2-(6-((2,2-difluorocyclopropyl)methoxy)-5-methylpyridin-3-yl)[1,3]oxazolo[4,5-c]pyridin-6-yl)oxy)propan-2-yl)acetamide Using (2,2-difluorocyclopropyl)methanol and 2,5-dibromo-3-methylpyridine, and in the same manner as in Example 133, the title compound was obtained.

Example 135

N-((2S)-1-((2-(4-(cyclopropylmethoxy)-2,6-dimethylphenyl)[1,3]oxazolo[4,5-c]pyridin-6-yl)oxy)propan-2-yl)acetamide A) cyclopropylmethyl 4-(cyclopropylmethoxy)-2,6-dimethylbenzoate Using 4-hydroxy-2,6-dimethylbenzoic acid and (bromomethyl)cyclopropane, and in the same manner as in Example 5, the title compound was obtained.
$^1$H NMR (300 MHz, DMSO-$d_6$) δ 0.23-0.40 (4H, m), 0.47-0.64 (4H, m), 1.03-1.41 (2H, m), 2.24 (6H, s), 3.81 (2H, d, J=7.0 Hz), 4.08 (2H, d, J=7.5 Hz), 6.65 (2H, s).

B) 4-(cyclopropylmethoxy)-2,6-dimethylbenzoic Acid

A mixture of cyclopropylmethyl 4-(cyclopropylmethoxy)-2,6-dimethylbenzoate (1.35 g), THF (15 mL), methanol (15 mL) and 1M sodium hydroxide (15 mL) was stirred at room temperature for 2 hr, and then at 70° C. for 2 hr. To the reaction mixture was added 4M lithium hydroxide (10 mL), and the obtained mixture was stirred overnight at 70° C., and then at 100° C. for 2 hr. To the reaction mixture was added 2-ethoxyethanol (10 mL), and the obtained mixture was stirred at 120° C. for 2 days. The reaction mixture was cooled to 0° C., and acidified with 6M hydrochloric acid, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (960 mg).

MS (ESI−): [M−H]⁻ 219.2.

C) tert-butyl ((2S)-1-((5-((4-(cyclopropylmethoxy)-2,6-dimethylbenzoyl)amino)-4-hydroxypyridin-2-yl)oxy)propan-2-yl)carbamate To a mixture of 4-(cyclopropylmethoxy)-2,6-dimethylbenzoic acid (300 mg), oxalyl dichloride (0.178 mL) and THF (3 mL) was added DMF (1 drop) at room temperature, the obtained mixture was stirred at room temperature for 30 min. The reaction mixture was concentrated under reduced pressure, and the obtained residue was mixed with N,N-dimethylacetamide (3 mL) and tert-butyl ((2S)-1-((5-amino-4-hydroxypyridin-2-yl)oxy)propan-2-yl)carbamate (386 mg). The obtained mixture was stirred at room temperature for 1 hr, and then at 70° C. for 2 hr. To the reaction mixture was added water, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (123 mg).

MS (ESI+): [M+H]⁺ 486.2.

D) tert-butyl ((2S)-1-((2-(4-(cyclopropylmethoxy)-2,6-dimethylphenyl)[1,3]oxazolo[4,5-c]pyridin-6-yl)oxy)propan-2-yl)carbamate Using tert-butyl ((2S)-1-((5-((4-(cyclopropylmethoxy)-2,6-dimethylbenzoyl)amino)-4-hydroxypyridin-2-yl)oxy)propan-2-yl)carbamate, and in the same manner as in Step B of Example 41, the title compound was obtained.

MS (ESI+): [M+H]⁺ 468.2.

E) N-((2S)-1-((2-(4-(cyclopropylmethoxy)-2,6-dimethylphenyl) [1,3]oxazolo[4,5-c]pyridin-6-yl)oxy)propan-2-yl)acetamide Using tert-butyl ((2S)-1-((2-(4-(cyclopropylmethoxy)-2,6-dimethylphenyl)[1,3]oxazolo[4,5-c]pyridin-6-yl)oxy)propan-2-yl)carbamate, and in the same manner as in Step D of Example 1, the title compound was obtained.

Example 136

Optically Active Form of N-((2S)-1-((2-(4-((2,2-difluorocyclopropyl)methoxy)phenyl) [1,3]oxazolo [5,4-d]pyrimidin-5-yl)oxy)propan-2-yl)acetamide A diastereomer mixture (10.9 mg) of N-((2S)-1-((2-(4-((2,2-difluorocyclopropyl)methoxy)phenyl) [1,3]oxazolo[5,4-d]pyrimidin-5-yl)oxy)propan-2-yl)acetamide was resolved by supercritical fluid chromatography (column: CHIRALPAK AY-H (registered trade mark) (trade name), 50 mmID×500 mL, DAICEL CHEMICAL INDUSTRIES, LTD., mobile phase:carbon dioxide/methanol/acetonitrile=600/200/200) to give the title compound having a shorter retention time (4.7 mg).

analysis retention time 1.15 min.
optical purity >99.9% ee

Example 137

Optically Active Form of N-((2S)-1-((2-(4-((2,2-difluorocyclopropyl)methoxy)phenyl)[1,3]oxazolo [5,4-d]pyrimidin-5-yl)oxy)propan-2-yl)acetamide A diastereomer mixture (10.9 mg) of N-((2S)-1-((2-(4-((2,2-difluorocyclopropyl)methoxy)phenyl) [1,3]oxazolo[5,4-d]pyrimidin-5-yl)oxy)propan-2-yl)acetamide was resolved by supercritical fluid chromatography (column: CHIRALPAK AY-H (registered trade mark) (trade name), 50 mmID×500 mL, DAICEL CHEMICAL INDUSTRIES, LTD., mobile phase:carbon dioxide/methanol/acetonitrile=600/200/200) to give the title compound having a longer retention time (4.0 mg).

analysis retention time 2.09 min.
optical purity >99.9% ee

Example 138

N-((2S)-1-((2-(6-(((1R)-2,2-difluorocyclopropyl)methoxy)-5-methoxypyridin-3-yl)[1,3]oxazolo[4,5-c]pyridin-6-yl)oxy)propan-2-yl)acetamide A) methyl 6-(((1R)-2,2-difluorocyclopropyl)methoxy)-5-methoxynicotinate To a solution of 6-hydroxy-5-methoxynicotinic acid (2.00 g) in methanol (40 mL) was added dropwise thionyl chloride (0.86 mL) at 0° C., and the mixture was stirred at 70° C. for 16 hr, and concentrated under reduced pressure. A mixture of the obtained residue, ((1R)-2,2-difluorocyclopropyl)methyl 4-nitrobenzenesulfonate (742 mg), silver carbonate (3.23 g), toluene (50 mL) and DMF (50 mL) was stirred with heating under reflux for 1 hr. The reaction mixture was filtered, and the filtrate was concentrated under reduced pressure, and the obtained residue was purified by silica gel chromatography (hexane/ethyl acetate) to give the title compound (0.33 g). ¹H NMR (300 MHz, CDCl₃) δ 1.34 (1H, m), 1.48-1.55 (1H, m), 2.12-2.33 (1H, m), 3.88-3.98 (6H, m), 4.43-4.62 (2H, m), 7.62 (1H, m), 8.35-8.44 (1H, m).

B) N-((2S)-1-((2-(6-(((1R)-2,2-difluorocyclopropyl)methoxy)-5-methoxypyridin-3-yl)[1,3]oxazolo[4,5-c]pyridin-6-yl)oxy)propan-2-yl)acetamide Using methyl 6-(((1R)-2,2-difluorocyclopropyl)methoxy)-5-methoxynicotinate, and in the same manner as in Step B of Example 33 and Step E and Step F of Example 35, the title compound was obtained.

Example 139

N-((2S)-1-((2-(5-(((1R)-2,2-difluorocyclopropyl)methoxy)-3-fluoropyridin-2-yl)[1,3]oxazolo[4,5-c]pyridin-6-yl)oxy)propan-2-yl)acetamide A) 5-((tert-butyl(diphenyl)silyl)oxy)-2-chloro-3-fluoropyridine A mixture of 6-chloro-5-fluoropyridin-3-ol (13.1 g), tert-butyl (chloro)diphenylsilane (27.7 mL), 1H-imidazole (7.25 g) and DMF (100 mL) was stirred at room temperature overnight. To the reaction mixture was added water, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (29.5 g).

$^1$H NMR (300 MHz, DMSO-d$_6$) δ 1.08 (9H, s), 7.33-7.60 (7H, m), 7.62-7.72 (5H, m).

B) ethyl 3-fluoro-5-hydroxypyridine-2-carboxylate

A mixture of 5-((tert-butyl(diphenyl)silyl)oxy)-2-chloro-3-fluoropyridine (29.5 g), 1,1'-bis(diphenylphosphino)ferrocene-palladium(II) dichloride (5.59 g), triethylamine (10.7 mL), ethanol (300 mL) and DMF (300 mL) was stirred overnight at 80° C. under a carbon monoxide atmosphere. To the reaction mixture was added water, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (30.8 g) as a mixture with DMF.

MS (ESI+): [M+H]$^+$ 186.1.

C) ethyl 5-(((1R)-2,2-difluorocyclopropyl)methoxy)-3-fluoropyridine-2-carboxylate Using ethyl 3-fluoro-5-hydroxypyridine-2-carboxylate and ((1R)-2,2-difluorocyclopropyl)methyl 4-nitrobenzenesulfonate, and in the same manner as in Example 5, the title compound was obtained.

MS (ESI+): [M+H]$^+$ 276.1.

D) 5-(((1R)-2,2-difluorocyclopropyl)methoxy)-3-fluoropyridine-2-carboxylic Acid

A mixture of ethyl 5-(((1R)-2,2-difluorocyclopropyl)methoxy)-3-fluoropyridine-2-carboxylate (808 mg), THF (10 mL), ethanol (10 mL) and 1M lithium hydroxide (10 mL) was stirred at 0° C. for 2 hr. The reaction mixture was neutralized with 1M hydrochloric acid at 0° C., and the mixture was extracted with ethyl acetate. The combined organic layer were washed with saturated brine, and dried over anhydrous magnesium sulfate, and the solvent was evaporated under reduced pressure to give the title compound (594 mg).

MS (ESI−): [M−H]$^−$ 246.1.

E) tert-butyl ((2S)-1-((5-(((5-(((1R)-2,2-difluorocyclopropyl)methoxy)-3-fluoropyridin-2-yl)carbonyl)amino)-4-hydroxypyridin-2-yl)oxy)propan-2-yl)carbamate To a mixture of 5-(((1R)-2,2-difluorocyclopropyl)methoxy)-3-fluoropyridine-2-carboxylic acid (594 mg), oxalyl dichloride (0.314 mL) and THF (5 mL) was added DMF (1 drop) at room temperature, the obtained mixture was stirred at room temperature for 30 min. The reaction mixture was concentrated under reduced pressure, and the obtained residue was mixed with pyridine (5 mL) and tert-butyl ((2S)-1-((5-amino-4-hydroxypyridin-2-yl)oxy)propan-2-yl)carbamate (681 mg). The obtained mixture was stirred at room temperature for 2 hr. To the reaction mixture was added 1M hydrochloric acid, and the mixture was extracted with ethyl acetate. The combined organic layer were washed with saturated brine, and dried over anhydrous magnesium sulfate, and the solvent was evaporated under reduced pressure. The residue was mixed with THF (10 mL), methanol (10 mL) and 1M sodium hydroxide (10 mL), the obtained mixture was stirred at room temperature for 1 hr. The reaction mixture was neutralized with 1M hydrochloric acid at 0° C., and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (623 mg) as a mixture with impurity.

MS (ESI+): [M+H]$^+$ 513.2.

F) tert-butyl ((2S)-1-((2-(5-(((1R)-2,2-difluorocyclopropyl)methoxy)-3-fluoropyridin-2-yl)[1,3]oxazolo[4,5-c]pyridin-6-yl)oxy)propan-2-yl)carbamate Using tert-butyl ((2S)-1-((5-(((5-(((1R)-2,2-difluorocyclopropyl)methoxy)-3-fluoropyridin-2-yl)carbonyl)amino)-4-hydroxypyridin-2-yl)oxy)propan-2-yl)carbamate, and in the same manner as in Step B of Example 41, the title compound was obtained.

MS (ESI+): [M+H]$^+$ 495.2

G) N-((2S)-1-((2-(5-(((1R)-2,2-difluorocyclopropyl)methoxy)-3-fluoropyridin-2-yl)[1,3]oxazolo[4,5-c]pyridin-6-yl)oxy)propan-2-yl)acetamide Using tert-butyl ((2S)-1-((2-(5-(((1R)-2,2-difluorocyclopropyl)methoxy)-3-fluoropyridin-2-yl) [1,3]oxazolo[4,5-c]pyridin-6-yl)oxy)propan-2-yl)carbamate, and in the same manner as in Step D of Example 1, the title compound was obtained.

Example 140

N-((2S)-1-((2-(4-(((1R)-2,2-difluorocyclopropyl)methoxy)phenyl)-7-fluoro[1,3]oxazolo[4,5-c]pyridin-6-yl)oxy)propan-2-yl)acetamide A) 2-((2S)-1-((5-bromo-3-fluoropyridin-2-yl)oxy)propan-2-yl)-1H-isoindole-1,3(2H)-dione Using 5-bromo-3-fluoropyridin-2-ol and 2-((2S)-1-hydroxypropan-2-yl)-1H-isoindole-1,3(2H)-dione, and in the same manner as in Step C of Example 1, the title compound was obtained.

$^1$H NMR (300 MHz, DMSO-d$_6$) δ 1.48 (3H, d, J=6.7 Hz), 4.50-4.86 (3H, m), 7.76-7.95 (4H, m), 7.98-8.14 (2H, m).

B) tert-butyl (6-(((2S)-2-(1,3-dioxo-1,3-dihydro-2H-isoindol-2-yl)propyl)oxy)-5-fluoropyridin-3-yl)carbamate A mixture of 2-((2S)-1-((5-bromo-3-fluoropyridin-2-yl)oxy)propan-2-yl)-1H-isoindole-1,3(2H)-dione (3.10 g), tert-butyl carbamate (0.958 g), tris(dibenzylideneacetone)dipalladium(0) (0.374 g), 4,5-bis(diphenylphosphino)-9,9-dimethylxanthene (0.710 g), cesium carbonate (5.33 g) and toluene (30 mL) was stirred at 110° C. overnight under an argon atmosphere. To the reaction mixture was added water, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (1.62 g).

MS (ESI+): [M+H]$^+$ 416.2.

C) tert-butyl (6-(((2S)-2-acetamidopropyl)oxy)-5-fluoropyridin-3-yl)carbamate

A mixture of tert-butyl (6-(((2S)-2-(1,3-dioxo-1,3-dihydro-2H-isoindol-2-yl)propyl)oxy)-5-fluoropyridin-3-yl)carbamate (1.62 g), hydrazine monohydrate (0.976 g) and THF (15 mL) was stirred overnight at 60° C. The precipitate was removed by filtration, and the obtained filtrate was concentrated under reduced pressure. The obtained residue was mixed with acetic anhydride (0.736 mL), triethylamine (1.09 mL) and ethyl acetate (15 mL), and the obtained mixture was stirred at 60° C. for 1 hr. The reaction mixture was concentrated under reduced pressure, and the residue was purified by silica gel column chromatography (hexane/ethyl acetate) to give the title compound (1.05 g).

MS (ESI+): [M+H]$^+$ 328.1.

D) tert-butyl (6-(((2S)-2-acetamidopropyl)oxy)-5-fluoro-4-hydroxypyridin-3-yl)carbamate n-Butyllithium (1.6M hexane solution, 11.4 mL) was added dropwise to a mixture of tert-butyl (6-(((2S)-2-acetamidopropyl)oxy)-5-fluoropyridin-3-yl)carbamate (1.70 g) and THF (20 mL) at –78° C. under an argon atmosphere, and the obtained mixture was stirred at –78° C. for 1 hr. To the reaction mixture was added trimethyl borate (2.36 mL), the obtained mixture was allowed to warm to room temperature, and stirred at room temperature overnight. The reaction mixture was cooled to 0° C., and a mixture of 8M aqueous sodium hydroxide solution (2.60 mL) and aqueous hydrogen peroxide (30%, 5 mL) were added thereto. The obtained mixture was stirred at room temperature for 2 hr. To the reaction mixture was added saturated aqueous sodium thiosulfate solution at 0° C., and the mixture was acidified with 6M hydrochloric acid, and extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (0.541 g).

MS (ESI+): [M+H]$^+$ 344.2.

E) N-(6-(((2S)-2-acetamidopropyl)oxy)-5-fluoro-4-hydroxypyridin-3-yl)-4-(((1R)-2,2-difluorocyclopropyl)methoxy)benzamide A mixture of tert-butyl (6-(((2S)-2-acetamidopropyl)oxy)-5-fluoro-4-hydroxypyridin-3-yl)carbamate (541 mg), 4M hydrogen chloride/ethyl acetate (5 mL) and ethyl acetate (5 mL) was stirred at room temperature for 2 hr, and then at 50° C. for 4 hr. The reaction mixture was concentrated under reduced pressure. Using the obtained residue and 4-(((1R)-2,2-difluorocyclopropyl)methoxy)benzoic acid, and in the same manner as in Step E of Example 139, the title compound was obtained.

MS (ESI+): [M+H]$^+$ 454.1.

F) N-((2S)-1-((2-(4-(((1R)-2,2-difluorocyclopropyl)methoxy)phenyl)-7-fluoro[1,3]oxazolo[4,5-c]pyridin-6-yl)oxy)propan-2-yl)acetamide Using N-(6-(((2S)-2-acetamidopropyl)oxy)-5-fluoro-4-hydroxypyridin-3-yl)-4-(((1R)-2,2-difluorocyclopropyl)methoxy)benzamide, and in the same manner as in Step B of Example 41, the title compound was obtained.

Example 141

N-((2S)-1-((2-(5-(((1R)-2,2-difluorocyclopropyl)methoxy)-4-methylpyridin-2-yl)[1,3]oxazolo[4,5-c]pyridin-6-yl)oxy)propan-2-yl)acetamide A) 2-bromo-5-(((1R)-2,2-difluorocyclopropyl)methoxy)-4-methylpyridine To a solution of 6-bromo-4-methylpyridin-3-ol (0.50 g) and ((1R)-2,2-difluorocyclopropyl)methyl 4-nitrobenzenesulfonate (1.077 g) in DMF (50 mL) was added sodium hydride (60% in oil, 0.106 g) under ice-cooling, and the mixture was stirred for 15 hr. The reaction mixture was concentrated under reduced pressure. The residue was diluted with ethyl acetate, and the mixture was washed with saturated brine. The obtained organic layer was dried over anhydrous magnesium sulfate, and the solvent was evaporated under reduced pressure. The residue was purified by silica gel column chromatography (hexane/ethyl acetate) to give the title compound (0.35 g).

$^1$H NMR (300 MHz, DMSO-d$_6$) δ 1.40-1.58 (1H, m), 1.65-1.83 (1H, m), 2.18 (3H, d, J=0.7 Hz), 2.19-2.33 (1H, m), 3.99-4.22 (1H, m), 4.22-4.40 (1H, m), 7.47 (1H, d, J=0.4 Hz), 8.07 (1H, s).

B) N-((2S)-1-((2-(5-(((1R)-2,2-difluorocyclopropyl)methoxy)-4-methylpyridin-2-yl)[1,3]oxazolo[4,5-c]pyridin-6-yl)oxy)propan-2-yl)acetamide Using 2-bromo-5-(((1R)-2,2-difluorocyclopropyl)methoxy)-4-methylpyridine, and in the same manner as in Step B of Example 22, the title compound was obtained.

Example 142

N-((2S)-1-((2-(4-(cyclopropylmethoxy)-2-ethylphenyl)[1,3]oxazolo[4,5-c]pyridin-6-yl)oxy)propan-2-yl)acetamide A) 4-(benzyloxy)-2-ethylbenzoic Acid Using 4-(benzyloxy)-2-ethylbenzaldehyde, and in the same manner as in Step B of Example 62, the title compound was obtained.

$^1$H NMR (300 MHz, CDCl$_3$) δ 1.25 (3H, t, J=7.5 Hz), 1.50-1.60 (1H, m), 3.05 (2H, q, J=7.4 Hz), 5.12 (2H, s), 6.80-6.92 (2H, m), 7.31-7.48 (5H, m), 8.04 (1H, d, J=8.7 Hz).

B) N-((2S)-1-((2-(4-(benzyloxy)-2-ethylphenyl)[1,3]oxazolo[4,5-c]pyridin-6-yl)oxy)propan-2-yl)acetamide Using 4-(benzyloxy)-2-ethylbenzoic acid, and in the same manner as in Step E and Step F of Example 35, the title compound was obtained.

MS (ESI+): [M+H]$^+$ 446.2.

C) N-((2S)-1-((2-(4-(cyclopropylmethoxy)-2-ethylphenyl)[1,3]oxazolo[4,5-c]pyridin-6-yl)oxy)propan-2-yl)acetamide Using N-((2S)-1-((2-(4-(benzyloxy)-2-ethylphenyl)[1,3]oxazolo[4,5-c]pyridin-6-yl)oxy)propan-2-yl)acetamide and (bromomethyl)cyclopropane, and in the same manner as in Step D of Example 68, the title compound was obtained.

Example 143

N-((2S)-1-((2-(5-(((1R)-2,2-difluorocyclopropyl)methoxy)-3-fluoropyridin-2-yl)[1,3]oxazolo[5,4-d]pyrimidin-5-yl)oxy)propan-2-yl)acetamide A) tert-butyl ((2S)-1-((5-(((5-(((1R)-2,2-difluorocyclopropyl)methoxy)-3-fluoropyridin-2-yl)carbonyl)amino)-4-hydroxypyrimidin-2-yl)oxy)propan-2-yl)carbamate Using tert-butyl ((2S)-1-((4-(benzyloxy)-5-nitropyrimidin-2-yl)oxy)propan-2-yl)carbamate and 5-(((1R)-2,2-difluorocyclopropyl)methoxy)-3-fluoropyridine-2-carboxylic acid, and in the same manner as in Step A of Example 4 and Step D of Example 83, the title compound was obtained.
MS (ESI+): [M+H]$^+$ 514.1.

B) tert-butyl ((2S)-1-((2-(5-(((1R)-2,2-difluorocyclopropyl)methoxy)-3-fluoropyridin-2-yl)[1,3]oxazolo[5,4-d]pyrimidin-5-yl)oxy)propan-2-yl)carbamate Using tert-butyl ((2S)-1-((5-(((5-(((1R)-2,2-difluorocyclopropyl)methoxy)-3-fluoropyridin-2-yl)carbonyl)amino)-4-hydroxypyrimidin-2-yl)oxy)propan-2-yl)carbamate, and in the same manner as in Step B of Example 41, the title compound was obtained.
MS (ESI+): [M+H]$^+$ 496.1.

C) N-((2S)-1-((2-(5-(((1R)-2,2-difluorocyclopropyl)methoxy)-3-fluoropyridin-2-yl)[1,3]oxazolo[5,4-d]pyrimidin-5-yl)oxy)propan-2-yl)acetamide Using tert-butyl ((2S)-1-((2-(5-(((1R)-2,2-difluorocyclopropyl)methoxy)-3-fluoropyridin-2-yl)[1,3]oxazolo[5,4-d]pyrimidin-5-yl)oxy)propan-2-yl)carbamate, and in the same manner as in Step B of Example 41, the title compound was obtained.

Example 144

N-((2S)-1-((2-(5-(cyclopropylmethoxy)-3-fluoropyridin-2-yl)[1,3]oxazolo[4,5-c]pyridin-6-yl)oxy)propan-2-yl)acetamide A) ethyl 5-(cyclopropylmethoxy)-3-fluoropyridine-2-carboxylate Using ethyl 3-fluoro-5-hydroxypyridine-2-carboxylate and (bromomethyl)cyclopropane, and in the same manner as in Example 5, the title compound was obtained.
MS (ESI+): [M+H]$^+$ 240.2.

B) 5-(cyclopropylmethoxy)-3-fluoropyridine-2-carboxylic Acid

Using ethyl 5-(cyclopropylmethoxy)-3-fluoropyridine-2-carboxylate, and in the same manner as in Step D of Example 139, the title compound was obtained.
MS (ESI+): [M+H]$^+$ 212.2.

C) tert-butyl ((2S)-1-((5-(((5-(cyclopropylmethoxy)-3-fluoropyridin-2-yl)carbonyl)amino)-4-hydroxypyridin-2-yl)oxy)propan-2-yl)carbamate Using tert-butyl ((2S)-1-((4-(benzyloxy)-5-nitropyrimidin-2-yl)oxy)propan-2-yl)carbamate and 5-(cyclopropylmethoxy)-3-fluoropyridine-2-carboxylic acid, and in the same manner as in Step A of Example 4 and Step D of Example 83, the title compound was obtained.
MS (ESI+): [M+H]$^+$ 477.2.

D) tert-butyl ((2S)-1-((2-(5-(cyclopropylmethoxy)-3-fluoropyridin-2-yl)[1,3]oxazolo[4,5-c]pyridin-6-yl)oxy)propan-2-yl)carbamate Using tert-butyl ((2S)-1-((5-(((5-(cyclopropylmethoxy)-3-fluoropyridin-2-yl)carbonyl)amino)-4-hydroxypyridin-2-yl)oxy)propan-2-yl)carbamate, and in the same manner as in Step B of Example 41, the title compound was obtained.
MS (ESI+): [M+H]$^+$ 459.2.

E) N-((2S)-1-((2-(5-(cyclopropylmethoxy)-3-fluoropyridin-2-yl)[1,3]oxazolo[4,5-c]pyridin-6-yl)oxy)propan-2-yl)acetamide Using tert-butyl ((2S)-1-((2-(5-(cyclopropylmethoxy)-3-fluoropyridin-2-yl) [1,3]oxazolo[4,5-c]pyridin-6-yl)oxy)propan-2-yl)carbamate, and in the same manner as in Step D of Example 1, the title compound was obtained.

Example 145

N-((2S)-1-((2-(3-chloro-5-(((1R)-2,2-difluorocyclopropyl)methoxy)pyridin-2-yl) [1,3]oxazolo[5,4-d]pyrimidin-5-yl)oxy)propan-2-yl)acetamide A) 5-((tert-butyl(diphenyl)silyl)oxy)-2,3-dichloropyridine Using 5,6-dichloropyridin-3-ol, and in the same manner as in Step A of Example 139, the title compound was obtained.
$^1$H NMR (300 MHz, DMSO-d$_6$) δ 1.08 (9H, s), 7.42-7.60 (7H, m), 7.63-7.71 (4H, m), 7.77 (1H, d, J=2.6 Hz).

B) ethyl 3-chloro-5-hydroxypyridine-2-carboxylate

Using 5-((tert-butyl(diphenyl)silyl)oxy)-2,3-dichloropyridine, and in the same manner as in Step B of Example 139, the title compound was obtained.
MS (ESI+): [M+H]$^+$ 202.1.

C) ethyl 3-chloro-5-(((1R)-2,2-difluorocyclopropyl)methoxy)pyridine-2-carboxylate Using ethyl 3-chloro-5-hydroxypyridine-2-carboxylate and ((1R)-2,2-difluorocyclopropyl)methyl 4-nitrobenzenesulfonate, and in the same manner as in Example 5, the title compound was obtained.
MS (ESI+): [M+H]$^+$ 292.1.

D) 3-chloro-5-(((1R)-2,2-difluorocyclopropyl)methoxy)pyridine-2-carboxylic Acid

Using ethyl 3-chloro-5-(((1R)-2,2-difluorocyclopropyl)methoxy)pyridine-2-carboxylate, and in the same manner as in Step D of Example 139, the title compound was obtained.
MS (ESI+): [M+H]$^+$ 264.1.

E) tert-butyl ((2S)-1-((5-(((3-chloro-5-(((1R)-2,2-difluorocyclopropyl)methoxy)pyridin-2-yl)carbonyl)amino)-4-hydroxypyrimidin-2-yl)oxy)propan-2-yl)carbamate Using tert-butyl ((2S)-1-((4-(benzyloxy)-5-nitropyrimidin-2-yl)oxy)propan-2-yl)carbamate and 3-chloro-5-(((1R)-2,2-difluorocyclopropyl)methoxy)pyridine-2-carboxylic acid, and in the same manner as in Step A of Example 4 and Step D of Example 83, the title compound was obtained.
MS (ESI+): [M+H]$^+$ 514.1.

F) tert-butyl ((2S)-1-((2-(3-chloro-5-(((1R)-2,2-difluorocyclopropyl)methoxy)pyridin-2-yl)[1,3]oxazolo[5,4-d]pyrimidin-5-yl)oxy)propan-2-yl)carbamate Using tert-butyl ((2S)-1-((5-(((3-chloro-5-(((1R)-2,2-difluorocyclopropyl)methoxy)pyridin-2-yl)carbonyl)amino)-4- hydroxypyrimidin-2-yl)oxy)propan-2-yl)carbamate, and in the same manner as in Step B of Example 41, the title compound was obtained.
MS (ESI+): [M+H]⁺ 496.1.

G) N-((2S)-1-((2-(3-chloro-5-(((1R)-2,2-difluorocyclopropyl)methoxy)pyridin-2-yl)[1,3]oxazolo[5,4-d]pyrimidin-5-yl)oxy)propan-2-yl)acetamide Using tert-butyl ((2S)-1-((2-(3-chloro-5-(((1R)-2,2-difluorocyclopropyl)methoxy)pyridin-2-yl)[1,3]oxazolo[5,4-d]pyrimidin-5-yl)oxy)propan-2-yl)carbamate, and in the same manner as in Step D of Example 1, the title compound was obtained.

Example 146

N-((2S)-1-((2-(4-(((1R)-2,2-difluorocyclopropyl)methoxy)phenyl)[1,3]thiazolo[4,5-c]pyridin-6-yl)oxy)propan-2-yl)acetamide Using N-((2S)-1-((2-(4-hydroxyphenyl)[1,3]thiazolo[4,5-c]pyridin-6-yl)oxy)propan-2-yl)acetamide and ((1R)-2,2-difluorocyclopropyl)methyl 4-nitrobenzenesulfonate, and in the same manner as in Example 5, the title compound was obtained.

Example 147

N-((2S)-1-((2-(4-(cyclopropylmethoxy)-2-(2,2,2-trifluoroethoxy)phenyl)[1,3]oxazolo[4,5-c]pyridin-6-yl)oxy)propan-2-yl)acetamide A) N-((2S)-1-((2-(4-(benzyloxy)-2-(2,2,2-trifluoroethoxy)phenyl)[1,3]oxazolo[4,5-c]pyridin-6-yl)oxy)propan-2-yl)acetamide Using 4-(benzyloxy)-2-hydroxybenzaldehyde, 2,2,2-trifluoroethyl trifluoromethanesulfonate and N-((2S)-1-((4-chloro-5-nitropyridin-2-yl)oxy)propan-2-yl)acetamide, and in the same manner as in Step A and Step B of Example 62 and Step B and Step C of Example 31, the title compound was obtained. MS (ESI+): [M+H]⁺ 516.1.

B) N-((2S)-1-((2-(4-(cyclopropylmethoxy)-2-(2,2,2-trifluoroethoxy)phenyl)[1,3]oxazolo[4,5-c]pyridin-6-yl)oxy)propan-2-yl)acetamide Using N-((2S)-1-((2-(4-(benzyloxy)-2-(2,2,2-trifluoroethoxy)phenyl)[1,3]oxazolo[4,5-c]pyridin-6-yl)oxy)propan-2-yl)acetamide and (bromomethyl)cyclopropane, and in the same manner as in Step D of Example 68, the title compound was obtained.

Example 148

N-((2S)-1-((2-(4-(((1R)-2,2-difluorocyclopropyl)methoxy)-2-(2,2,2-trifluoroethoxy)phenyl)[1,3]oxazolo[4,5-c]pyridin-6-yl)oxy)propan-2-yl)acetamide Using N-((2S)-1-((2-(4-(benzyloxy)-2-(2,2,2-trifluoroethoxy)phenyl)[1,3]oxazolo[4,5-c]pyridin-6-yl)oxy)propan-2-yl)acetamide, and in the same manner as in Step D of Example 68, the title compound was obtained.

Example 149

N-((2S)-1-((2-(5-(((1R)-2,2-difluorocyclopropyl)methoxy)pyridin-2-yl)-7-fluoro[1,3]oxazolo[4,5-c]pyridin-6-yl)oxy)propan-2-yl)acetamide A) N-(6-((((2S)-2-acetamidopropyl)oxy)-5-fluoro-4-hydroxypyridin-3-yl)-5-(benzyloxy)pyridine-2-carboxamide A mixture of tert-butyl (6-((((2S)-2-acetamidopropyl)oxy)-5-fluoro-4-hydroxypyridin-3-yl)carbamate (453 mg), 4M hydrogen chloride/ethyl acetate (15 mL) and ethyl acetate (5 mL) was stirred at room temperature overnight. The reaction mixture was concentrated under reduced pressure. Using the obtained residue and 5-(benzyloxy)pyridine-2-carboxylic acid, and in the same manner as in Step D of Example 83 and Step B of Example 123, the title compound was obtained.
MS (ESI+): [M+H]⁺ 455.2.

B) N-((2S)-1-((2-(5-(benzyloxy)pyridin-2-yl)-7-fluoro[1,3]oxazolo[4,5-c]pyridin-6-yl)oxy)propan-2-yl)acetamide Using N-(6-((((2S)-2-acetamidopropyl)oxy)-5-fluoro-4-hydroxypyridin-3-yl)-5-(benzyloxy)pyridine-2-carboxamide, and in the same manner as in Step B of Example 41, the title compound was obtained.
MS (ESI+): [M+H]⁺ 437.2.

C) N-((2S)-1-((2-(5-(((1R)-2,2-difluorocyclopropyl)methoxy)pyridin-2-yl)-7-fluoro[1,3]oxazolo[4,5-c]pyridin-6-yl)oxy)propan-2-yl)acetamide Using N-((2S)-1-((2-(5-(benzyloxy)pyridin-2-yl)-7-fluoro[1,3]oxazolo[4,5-c]pyridin-6-yl)oxy)propan-2-yl)acetamide and ((1R)-2,2-difluorocyclopropyl)methyl 4-nitrobenzenesulfonate, and in the same manner as in Step A of Example 4 and Example 5, the title compound was obtained.

Example 150

N-((2S)-1-((2-(4-(((1R)-2,2-difluorocyclopropyl)methoxy)-3-fluorophenyl)[1,3]oxazolo[5,4-d]pyrimidin-5-yl)oxy)propan-2-yl)acetamide A) tert-butyl ((2S)-1-((5-((4-(benzyloxy)-3-fluorobenzoyl)amino)-4-hydroxypyrimidin-2-yl)oxy)propan-2-yl)carbamate Using tert-butyl ((2S)-1-((4-(benzyloxy)-5-nitropyrimidin-2-yl)oxy)propan-2-yl)carbamate and 4-(benzyloxy)-3-fluorobenzoic acid, and in the same manner as in Step A of Example 4, Step D of Example 83 and Step B of Example 123, the title compound was obtained.
MS (ESI+): [M+H]⁺ 513.1.

B) tert-butyl ((2S)-1-((2-(4-(benzyloxy)-3-fluorophenyl)[1,3]oxazolo[5,4-d]pyrimidin-5-yl)oxy)propan-2-yl)carbamate Using tert-butyl ((2S)-1-((5-((4-(benzyloxy)-3-fluorobenzoyl)amino)-4-hydroxypyrimidin-2-yl)oxy)propan-2-yl)carbamate, and in the same manner as in Step B of Example 41, the title compound was obtained.
MS (ESI+): [M+H]+ 495.2.

C) tert-butyl ((2S)-1-((2-(4-(((1R)-2,2-difluorocyclopropyl)methoxy)-3-fluorophenyl)[1,3]oxazolo[5,4-d]pyrimidin-5-yl)oxy)propan-2-yl)carbamate Using tert-butyl ((2S)-1-((2-(4-(benzyloxy)-3-fluorophenyl)[1,3]oxazolo[5,4-d]pyrimidin-5-yl)oxy)propan-2-yl)carbamate and ((1R)-2,2-difluorocyclopropyl)methyl 4-nitrobenzenesulfonate, and in the same manner as in Step A of Example 4 and Example 5, the title compound was obtained.
MS (ESI+): [M+H]+ 495.2.

D) N-((2S)-1-((2-(4-(((1R)-2,2-difluorocyclopropyl)methoxy)-3-fluorophenyl)[1,3]oxazolo[5,4-d]pyrimidin-5-yl)oxy)propan-2-yl)acetamide Using tert-butyl ((2S)-1-((2-(4-(((1R)-2,2-difluorocyclopropyl)methoxy)-3-fluorophenyl)[1,3]oxazolo[5,4-d]pyrimidin-5-yl)oxy)propan-2-yl)carbamate, and in the same manner as in Step D of Example 1, the title compound was obtained.

Example 151

N-((2S)-1-((2-(4-((3,3-difluorocyclobutyl)methoxy)-3-fluorophenyl)[1,3]oxazolo[4,5-c]pyridin-6-yl)oxy)propan-2-yl)acetamide Using N-((2S)-1-((2-(3-fluoro-4-hydroxyphenyl)[1,3]oxazolo[4,5-c]pyridin-6-yl)oxy)propan-2-yl)acetamide and (3,3-difluorocyclobutyl)methyl methanesulfonate, and in the same manner as in Example 5, the title compound was obtained.

Example 152

N-((2S)-1-((2-(4-(2-(2,2-difluorocyclopropyl)ethoxy)-3-fluorophenyl)[1,3]oxazolo[4,5-c]pyridin-6-yl)oxy)propan-2-yl)acetamide A mixture of N-((2S)-1-((2-(3-fluoro-4-hydroxyphenyl)[1,3]oxazolo[4,5-c]pyridin-6-yl)oxy)propan-2-yl)acetamide (100 mg), 2-(2,2-difluorocyclopropyl)ethyl methanesulfonate (232 mg), potassium carbonate (160 mg) and DMF (1 mL) was stirred overnight at 70° C. To the reaction mixture was added water, and the mixture was extracted with ethyl acetate. The combined organic layer were washed with saturated brine, and dried over anhydrous magnesium sulfate, and the solvent was evaporated under reduced pressure. The residue was recrystallized (ethyl acetate) to give the title compound (107 mg).

Example 153

N-((2S)-1-((2-(5-(((1R)-2,2-difluorocyclopropyl)methoxy)-3-fluoropyridin-2-yl)-7-fluoro[1,3]oxazolo[4,5-c]pyridin-6-yl)oxy)propan-2-yl)acetamide A) tert-butyl (6-(benzyloxy)-5-fluoropyridin-3-yl)carbamate Using 2-(benzyloxy)-5-bromo-3-fluoropyridine, and in the same manner as in Step B of Example 140, the title compound was obtained.

$^1$H NMR (300 MHz, DMSO-$d_6$) δ1.39-1.52 (9H, m), 5.37 (2H, s), 7.20-7.54 (5H, m), 7.80 (1H, d, J=12.1 Hz), 8.00 (1H, s), 9.53 (1H, brs).

B) tert-butyl (6-(benzyloxy)-5-fluoro-4-hydroxypyridin-3-yl)carbamate

Using tert-butyl (6-(benzyloxy)-5-fluoropyridin-3-yl)carbamate, and in the same manner as in Step D of Example 140, the title compound was obtained.
MS (ESI+): [M+H]+ 335.2.

C) N-(6-(benzyloxy)-5-fluoro-4-hydroxypyridin-3-yl)-5-(((1R)-2,2-difluorocyclopropyl)methoxy)-3-fluoropyridine-2-carboxamide A mixture of tert-butyl (6-(benzyloxy)-5-fluoro-4-hydroxypyridin-3-yl)carbamate (345 mg), 4M hydrogen chloride/ethyl acetate (10 mL) and ethyl acetate (3 mL) was stirred at room temperature overnight. The reaction mixture was concentrated under reduced pressure. Using the obtained residue and 5-(((1R)-2,2-difluorocyclopropyl)methoxy)-3-fluoropyridine-2-carboxylic acid, and in the same manner as in Step D of Example 83, the title compound was obtained.
MS (ESI+): [M+H]+ 464.2.

D) 6-(benzyloxy)-2-(5-(((1R)-2,2-difluorocyclopropyl)methoxy)-3-fluoropyridin-2-yl)-7-fluoro[1,3]oxazolo[4,5-c]pyridine Using N-(6-(benzyloxy)-5-fluoro-4-hydroxypyridin-3-yl)-5-(((1R)-2,2-difluorocyclopropyl)methoxy)-3-fluoropyridine-2-carboxamide, and in the same manner as in Step B of Example 41, the title compound was obtained.
MS (ESI+): [M+H]+ 446.0.

E) tert-butyl ((2S)-1-((2-(5-(((1R)-2,2-difluorocyclopropyl)methoxy)-3-fluoropyridin-2-yl)-7-fluoro[1,3]oxazolo[4,5-c]pyridin-6-yl)oxy)propan-2-yl)carbamate A mixture of 6-(benzyloxy)-2-(5-(((1R)-2,2-difluorocyclopropyl)methoxy)-3-fluoropyridin-2-yl)-7-fluoro[1,3]oxazolo[4,5-c]pyridine (97.1 mg), 10% palladium/carbon (containing water (50%), 10 mg), methanol (3 mL) and THF (3 mL) was stirred at room temperature overnight under a hydrogen atmosphere. The catalyst was removed by filtration, and the obtained filtrate was concentrated under reduced pressure. The obtained residue was mixed with tert-butyl ((2S)-1-hydroxypropan-2-yl)carbamate (76 mg), triphenylphosphine (114 mg) and THF (10 mL). To the obtained mixture was added dropwise diisopropyl azodicarboxylate (1.9M toluene solution, 0.229 mL) at 0° C., and the obtained mixture was stirred at 0° C. for 2 hr, and then at room temperature for 1 hr. To the reaction mixture were added 2-((2S)-1-hydroxypropan-2-yl)-1H-isoindole-1,3(2H)-dione (89 mg) and triphenylphosphine (114 mg), and diisopropyl azodicarboxylate (1.9M toluene solution, 0.229 mL) was added thereto at room temperature. The obtained mixture was stirred at room temperature for 1 hr, and then at 70° C. for 1 hr. To the reaction mixture were added 2-((2S)-1-hydroxypropan-2-yl)-1H-isoindole-1,3(2H)-dione (89 mg) and triphenylphosphine (114 mg), and diisopropyl azodicarboxylate (1.9M toluene solution, 0.229 mL) was added thereto at 70° C. The obtained mixture was stirred at room temperature for 1 hr. The reaction mixture was concentrated under reduced pressure, and the residue was purified by silica gel column chromatography (hexane/ethyl acetate) to give the title compound (501 mg) as a mixture with impurity.
MS (ESI+): [M+H]+ 513.1.

F) N-((2S)-1-((2-(5-(((1R)-2,2-difluorocyclopropyl)methoxy)-3-fluoropyridin-2-yl)-7-fluoro[1,3]oxazolo[4,5-c]pyridin-6-yl)oxy)propan-2-yl)acetamide Using tert-butyl ((2S)-1-((2-(5-(((1R)-2,2-difluorocyclopropyl)methoxy)-3-fluoropyridin-2-yl)-7-fluoro[1,3]oxazolo[4,5-c]pyridin-6-yl)oxy)propan-2-yl)carbamate, and in the same manner as in Step D of Example 1, the title compound was obtained.

Example 154

N-((2S)-1-((2-(4-(cyclopropylmethoxy)phenyl)[1,3]oxazolo[5,4-c]pyridin-6-yl)oxy)propan-2-yl)acetamide A) 2-(benzyloxy)-5-(methoxymethoxy)isonicotinic Acid To a solution of 2-(benzyloxy)-5-(methoxymethoxy)pyridine (8.00 g) in THF (50 mL) was added 1.6 M n-butyllithium-hexane solution (30.6 mL) at −78° C., and the mixture was stirred at the same temperature for 1 hr. To the reaction mixture was added an excess amount of dry ice, and the mixture was allowed to warm to room temperature. 1 M Hydrochloric acid was added thereto, and the mixture was extracted with ethyl acetate. The combined organic layer were washed with saturated brine, and dried over anhydrous magnesium sulfate. The solvent was evaporated under reduced pressure to give the title compound (9.30 g).
$^1$H NMR (300 MHz, DMSO-$d_6$) δ 3.41 (3H, s), 5.15 (2H, s), 5.32 (2H, s), 7.01 (1H, s), 7.19-7.53 (5H, m), 8.07 (1H, s), 13.54 (1H, brs).

B) tert-butyl (2-(benzyloxy)-5-(methoxymethoxy)pyridin-4-yl)carbamate

To a solution of 2-(benzyloxy)-5-(methoxymethoxy)isonicotinic acid (9.20 g) in tert-butyl alcohol (30 mL) were added diphenylphosphoryl azide (26.3 mL) and N,N-diisopropylethylamine (13.3 mL), and the mixture was stirred at room temperature for 1 hr, and then with refluxing at 80° C. for 3 hr. The reaction mixture was allowed to cool to room temperature, and the solvent was evaporated under reduced pressure. To the residue was added water, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (11.4 g).
$^1$H NMR (300 MHz, DMSO-$d_6$) δ 1.47 (9H, s), 3.43 (3H, s), 5.11 (2H, s), 5.27 (2H, s), 7.19-7.53 (6H, m), 7.83 (1H, s), 8.50 (1H, s).

C) 4-amino-6-(benzyloxy)pyridin-3-ol monohydrochloride

A mixture of tert-butyl (2-(benzyloxy)-5-(methoxymethoxy)pyridin-4-yl)carbamate (11.0 g) in THF (10 mL) and 6 M hydrochloric acid (30 mL) was stirred at 60° C. for 8 hr. The reaction mixture was cooled to 0° C., and the precipitate was collected by filtration, and washed with hexane. The obtained solid was dried under reduced pressure to give the title compound (5.87 g).
$^1$H NMR (300 MHz, DMSO-$d_6$) δ 4.94 (1H, brs), 5.43 (2H, s), 7.05 (1H, s), 7.34-7.50 (4H, m), 7.52-7.61 (2H, m), 8.61 (1H, brs), 11.08 (1H, brs), 13.61 (1H, brs).

D) N-(2-(benzyloxy)-5-hydroxypyridin-4-yl)-4-(cyclopropylmethoxy)benzamide

To a solution of 4-(cyclopropylmethoxy)benzoic acid (6.36 g) in THF (10 mL) were added oxalyl dichloride (4.20 g) and DMF (3 drops), and the mixture was stirred at room temperature for 1 hr. The solvent was evaporated under reduced pressure, and the obtained residue was dissolved in THF (20 mL). The mixture was added dropwise to a solution of 4-amino-6-(benzyloxy)pyridin-3-ol monohydrochloride (3.80 g) in a mixed solvent of pyridine (20 mL) and DMF (20 mL) under ice-cooling. The reaction mixture was stirred at room temperature for 2 hr, and 2 M aqueous sodium hydroxide solution (20 mL) and methanol (20 mL) were added thereto, and the mixture was stirred at room temperature for 15 hr. To the reaction mixture was added 1 M hydrochloric acid, and the mixture was extracted with ethyl acetate. The combined organic layer were washed with saturated brine, and dried over anhydrous magnesium sulfate. The solvent was evaporated under reduced pressure. The residue was purified by silica gel column chromatography (hexane/ethyl acetate) to give the title compound (2.25 g).
MS (ESI−): [M−H]− 389.2

E) 6-(benzyloxy)-2-(4-(cyclopropylmethoxy)phenyl)[1,3]oxazolo[5,4-c]pyridine

To a solution of hexachloroethane (4.09 g), triphenylphosphine (4.53 g) and triethylamine (2.41 mL) in acetonitrile (50 mL) was added N-(2-(benzyloxy)-5-hydroxypyridin-4-yl)-4-(cyclopropylmethoxy)benzamide (2.25 g), and the mixture was stirred at room temperature for 15 hr. To the reaction mixture was added 1 M hydrochloric acid, and the mixture was extracted with ethyl acetate. The combined organic layer were washed with saturated brine, and dried over anhydrous magnesium sulfate. The solvent was evaporated under reduced pressure. The residue was purified by silica gel column chromatography (hexane/ethyl acetate) to give the title compound (0.25 g).
$^1$H NMR (300 MHz, DMSO-$d_6$) δ 0.29-0.44 (2H, m), 0.51-0.69 (2H, m), 1.26 (1H, d, J=7.6 Hz), 3.96 (2H, d, J=7.1 Hz), 5.40 (2H, s), 7.09-7.21 (3H, m), 7.26-7.44 (3H, m), 7.43-7.56 (2H, m), 8.17 (2H, d, J=8.9 Hz), 8.64 (1H, s).

F) tert-butyl ((2S)-1-((2-(4-(cyclopropylmethoxy)phenyl)[1,3]oxazolo[5,4-c]pyridin-6-yl)oxy)propan-2-yl)carbamate A mixture of 6-(benzyloxy)-2-(4-(cyclopropylmethoxy)phenyl)[1,3]oxazolo[5,4-c]pyridine (0.21 g), 10% palladium-carbon (containing water (50%), 40 mg) and THF (40 mL) was stirred at room temperature for 15 hr under a hydrogen atmosphere. The catalyst was removed by filtration, and the obtained filtrate was concentrated under reduced pressure. To a solution of the obtained residue, tert-butyl ((2S)-1-hydroxypropan-2-yl)carbamate (149 mg) and triphenylphosphine (223 mg) in THF (10 mL) was added dropwise diisopropyl azodicarboxylate toluene solution (1.9 M, 0.447 mL), and the mixture was stirred at room temperature overnight. The reaction mixture was concentrated under reduced pressure, and the residue was purified by silica gel column chromatography (NH, hexane/ethyl acetate) to give the title compound (46 mg). $^1$H NMR (300 MHz, DMSO-d$_6$) δ 0.26-0.45 (2H, m), 0.53-0.63 (2H, m), 1.18 (3H, d, J=6.2 Hz), 1.21-1.33 (1H, m), 1.38 (9H, s), 3.79-3.93 (1H, m), 3.96 (2H, d, J=7.0 Hz), 4.15 (2H, d, J=5.0 Hz), 6.87 (1H, d, J=8.1 Hz), 7.08 (1H, s), 7.17 (2H, d, J=8.7 Hz), 8.16 (2H, d, J=8.7 Hz), 8.60 (1H, s).

G) N-((2S)-1-((2-(4-(cyclopropylmethoxy)phenyl)[1,3]oxazolo[5,4-c]pyridin-6-yl)oxy)propan-2-yl)acetamide Using tert-butyl ((2S)-1-((2-(4-(cyclopropylmethoxy)phenyl)[1,3]oxazolo[5,4-c]pyridin-6-yl)oxy)propan-2-yl)carbamate, and in the same manner as in Step D of Example 1, the title compound was obtained.

Example 155

N-((2S)-1-((2-(5-(cyclopropylmethoxy)pyrimidin-2-yl)[1,3]oxazolo[4,5-c]pyridin-6-yl)oxy)propan-2-yl)acetamide A) 2-chloro-5-(cyclopropylmethoxy)pyrimidine To a solution of cyclopropylmethanol (276 mg), 2-chloropyrimidin-5-ol (500 mg) and triphenylphosphine (1.51 g) in toluene (20 mL) was added dropwise diisopropyl azodicarboxylate toluene solution (1.9 M, 3 mL), and the mixture was stirred at room temperature overnight. The reaction mixture was concentrated under reduced pressure, and the residue was purified by silica gel column chromatography (hexane/ethyl acetate) to give the title compound (659 mg). $^1$H NMR (300 MHz, DMSO-d$_6$) δ 0.21-0.49 (2H, m), 0.49-0.69 (2H, m), 1.07-1.46 (1H, m), 4.00 (2H, d, J=7.2 Hz), 8.53 (2H, s).

B) tert-butyl ((2S)-1-((2-(5-(cyclopropylmethoxy)pyrimidin-2-yl)[1,3]oxazolo[4,5-c]pyridin-6-yl)oxy)propan-2-yl)carbamate Using 2-chloro-5-(cyclopropylmethoxy)pyrimidine and tert-butyl ((2S)-1-([1,3]oxazolo[4,5-c]pyridin-6-yloxy)propan-2-yl)carbamate, and in the same manner as in Step B of Example 22, the title compound was obtained.
MS (ESI+): [M+H]$^+$ 442.1.

C) N-((2S)-1-((2-(5-(cyclopropylmethoxy)pyrimidin-2-yl)[1,3]oxazolo[4,5-c]pyridin-6-yl)oxy)propan-2-yl)acetamide Using tert-butyl ((2S)-1-((2-(5-(cyclopropylmethoxy)pyrimidin-2-yl)[1,3]oxazolo[4,5-c]pyridin-6-yl)oxy)propan-2-yl)carbamate, and in the same manner as in Step D of Example 1, the title compound was obtained.

Example 156

N-((2S)-1-((2-(4-(cyclopropylmethoxy)-2-(difluoromethoxy)phenyl)[1,3]oxazolo[4,5-c]pyridin-6-yl)oxy)propan-2-yl)acetamide A) N-((2S)-1-((2-(4-(benzyloxy)-2-(difluoromethoxy)phenyl)[1,3]oxazolo[4,5-c]pyridin-6-yl)oxy)propan-2-yl)acetamide Using 4-(benzyloxy)-2-hydroxybenzaldehyde and sodium chlorodifluoroacetate, and in the same manner as in Step A and Step B of Example 62 and Step A, Step B and Step C of Example 49, the title compound was obtained.
MS (ESI+): [M+H]$^+$ 484.1.

B) N-((2S)-1-((2-(4-(cyclopropylmethoxy)-2-(difluoromethoxy)phenyl) [1,3]oxazolo[4,5-c]pyridin-6-yl)oxy)propan-2-yl)acetamide Using N-((2S)-1-((2-(4-(benzyloxy)-2-(difluoromethoxy)phenyl) [1,3]oxazolo[4,5-c]pyridin-6-yl)oxy)propan-2-yl)acetamide and (bromomethyl)cyclopropane, and in the same manner as in Step D of Example 68, the title compound was obtained.

Example 157

N-((2S)-1-((2-(4-(((1R)-2,2-difluorocyclopropyl)methoxy)-2-(difluoromethoxy)phenyl) [1,3]oxazolo[4,5-c]pyridin-6-yl)oxy)propan-2-yl)acetamide Using N-((2S)-1-((2-(4-(benzyloxy)-2-(difluoromethoxy)phenyl) [1,3]oxazolo[4,5-c]pyridin-6-yl)oxy)propan-2-yl)acetamide, and in the same manner as in Step D of Example 68, the title compound was obtained.

Example 158

N-((2S)-1-((2-(4-(3,3-difluorobutoxy)-3-fluorophenyl)[1,3]oxazolo[4,5-c]pyridin-6-yl)oxy)propan-2-yl)acetamide A) N-((2S)-1-((2-(3-fluoro-4-(3-hydroxybutoxy)phenyl)[1,3]oxazolo[4,5-c]pyridin-6-yl)oxy)propan-2-yl)acetamide Using N-((2S)-1-((2-(3-fluoro-4-hydroxyphenyl)[1,3]oxazolo[4,5-c]pyridin-6-yl)oxy)propan-2-yl)acetamide and 3-hydroxybutyl 4-methylbenzenesulfonate, and in the same manner as in Example 5, the title compound was obtained.
MS (ESI+): [M+H]$^+$ 418.1.

B) N-((2S)-1-((2-(3-fluoro-4-(3-oxobutoxy)phenyl) [1,3]oxazolo[4,5-c]pyridin-6-yl)oxy)propan-2-yl)acetamide A solution of N-((2S)-1-((2-(3-fluoro-4-(3-hydroxybutoxy)phenyl)[1,3]oxazolo[4,5-c]pyridin-6-yl)oxy)propan-2-yl)acetamide (300 mg) and Dess-Martin reagent (914 mg) in DMF (30 mL) was stirred at room temperature for 15 hr. To the mixture was added saturated aqueous sodium thiosulfate solution, and the mixture was stirred at room temperature for 10 min. Water was added thereto, and the mixture was extracted with ethyl acetate. The combined organic layer were washed with saturated brine, and dried over anhydrous magnesium sulfate, and the solvent was evaporated under reduced pressure. The residue was purified by silica gel column chromatography (ethyl acetate/methanol) to give the title compound (165 mg).
MS (ESI+): [M+H]$^+$ 416.2.

C) N-((2S)-1-((2-(4-(3,3-difluorobutoxy)-3-fluorophenyl)[1,3]oxazolo[4,5-c]pyridin-6-yl)oxy)propan-2-yl)acetamide A mixture of N-((2S)-1-((2-(3-fluoro-4-(3-oxobutoxy)phenyl)[1,3]oxazolo[4,5-c]pyridin-6-yl)oxy)propan-2-yl)acetamide (165 mg) and bis(2-methoxyethyl)aminosulfur trifluoride (3.0 mL) was stirred at 80° C. for 20 min. To the mixture was added saturated aqueous sodium hydrogen carbonate solution under ice-cooling, and the mixture was extracted with ethyl acetate. The combined organic layer were washed with saturated brine, and dried over anhydrous magnesium sulfate, and the solvent was evaporated under reduced pressure. The residue was purified by silica gel column chromatography (ethyl acetate/methanol) to give the title compound (7.8 mg).

Example 159

N-((2S)-1-((2-(4-((2,2-difluoro-1-methylcyclopropyl)methoxy)-3-fluorophenyl)[1,3]oxazolo[4,5-c]pyridin-6-yl)oxy)propan-2-yl)acetamide Using (2,2-difluoro-1-methylcyclopropyl)methanol and N-((2S)-1-((2-(3-fluoro-4-hydroxyphenyl)[1,3]oxazolo[4,5-c]pyridin-6-yl)oxy)propan-2-yl)acetamide, and in the same manner as in Step B of Example 4, the title compound was obtained.

Example 160

N-((2S)-1-((2-(4-(2,2-difluorobutoxy)-3-fluorophenyl)[1,3]oxazolo[4,5-c]pyridin-6-yl)oxy)propan-2-yl)acetamide A) N-((2S)-1-((2-(3-fluoro-4-(2-oxobutoxy)phenyl)[1,3]oxazolo[4,5-c]pyridin-6-yl)oxy)propan-2-yl)acetamide Using N-((2S)-1-((2-(3-fluoro-4-hydroxyphenyl)[1,3]oxazolo[4,5-c]pyridin-6-yl)oxy)propan-2-yl)acetamide and 1-bromobutan-2-one, and in the same manner as in Example 5, the title compound was obtained.
MS (ESI+): [M+H]+ 416.2.

B) N-((2S)-1-((2-(4-(2,2-difluorobutoxy)-3-fluorophenyl)[1,3]oxazolo[4,5-c]pyridin-6-yl)oxy)propan-2-yl)acetamide To a solution of N-((2S)-1-((2-(3-fluoro-4-(2-oxobutoxy)phenyl)[1,3]oxazolo[4,5-c]pyridin-6-yl)oxy)propan-2-yl)acetamide (163 mg) in methylene chloride (6.00 mL) was added bis(2-methoxyethyl)aminosulfur trifluoride (0.15 mL), and the mixture was stirred at room temperature for 2 days. To the mixture was added saturated aqueous sodium hydrogen carbonate solution under ice-cooling, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (36 mg).

Example 161

Optically Active Form of N-((2S)-1-((2-(4-((2,2-difluoro-1-methylcyclopropyl)methoxy)-3-fluorophenyl)[1,3]oxazolo[4,5-c]pyridin-6-yl)oxy)propan-2-yl)acetamide A diastereomer mixture (90 mg) of N-((2S)-1-((2-(4-((2,2-difluoro-1-methylcyclopropyl)methoxy)-3-fluorophenyl)[1,3]oxazolo[4,5-c]pyridin-6-yl)oxy)propan-2-yl)acetamide was resolved by HPLC (column: CHIRALCEL CJ (registered trade mark) (trade name), 50 mmID×500 mL, DAICEL CHEMICAL INDUSTRIES, LTD., mobile phase:hexane/ethanol=700:300), and recrystallized (ethyl acetate) to give the title compound having a shorter retention time (16 mg). analysis retention time 12.8 min.
optical purity >99.9% ee Example 162

Optically Active Form of N-((2S)-1-((2-(4-((2,2-difluoro-1-methylcyclopropyl)methoxy)-3-fluorophenyl)[1,3]oxazolo[4,5-c]pyridin-6-yl)oxy)propan-2-yl)acetamide A diastereomer mixture (90 mg) of N-((2S)-1-((2-(4-((2,2-difluoro-1-methylcyclopropyl)methoxy)-3-fluorophenyl)[1,3]oxazolo[4,5-c]pyridin-6-yl)oxy)propan-2-yl)acetamide was resolved by HPLC (column: CHIRALCEL CJ (registered trade mark) (trade name), 50 mmID×500 mL, DAICEL CHEMICAL INDUSTRIES, LTD., mobile phase:
hexane/ethanol=700:300), and recrystallized (ethyl acetate) to give the title compound having a longer retention time (15 mg). analysis retention time 15.8 min.
optical purity 99.2% ee Example 163

N-((2S)-1-((2-(3-chloro-5-(((1R)-2,2-difluorocyclopropyl)methoxy)pyridin-2-yl)[1,3]oxazolo[4,5-c]pyridin-6-yl)oxy)propan-2-yl)acetamide A) tert-butyl ((2S)-1-((5-(((3-chloro-5-(((1R)-2,2-difluorocyclopropyl)methoxy)pyridin-2-yl)carbonyl)amino)-4-hydroxypyridin-2-yl)oxy)propan-2-yl)carbamate Using 3-chloro-5-(((1R)-2,2-difluorocyclopropyl)methoxy)pyridine-2-carboxylic acid and tert-butyl ((2S)-1-((5-amino-4-hydroxypyridin-2-yl)oxy)propan-2-yl)carbamate, and in the same manner as in Step E of Example 139, the title compound was obtained.
MS (ESI+): [M+H]+ 529.1.

B) tert-butyl ((2S)-1-((2-(3-chloro-5-(((1R)-2,2-difluorocyclopropyl)methoxy)pyridin-2-yl)[1,3]oxazolo[4,5-c]pyridin-6-yl)oxy)propan-2-yl)carbamate Using tert-butyl ((2S)-1-((5-(((3-chloro-5-(((1R)-2,2-difluorocyclopropyl)methoxy)pyridin-2-yl)carbonyl)amino)-4-hydroxypyridin-2-yl)oxy)propan-2-yl)carbamate, and in the same manner as in Step B of Example 41, the title compound was obtained.
MS (ESI+): [M+H]+ 511.1.

C) N-((2S)-1-((2-(3-chloro-5-(((1R)-2,2-difluorocyclopropyl)methoxy)pyridin-2-yl)[1,3]oxazolo[4,5-c]pyridin-6-yl)oxy)propan-2-yl)acetamide Using tert-butyl ((2S)-1-((2-(3-chloro-5-(((1R)-2,2-difluorocyclopropyl)methoxy)pyridin-2-yl)[1,3]oxazolo[4,5-c]pyridin-6-yl)oxy)propan-2-yl)carbamate, and in the same manner as in Step D of Example 1, the title compound was obtained.

Example 164

N-((2S)-4-(2-(4-(((1R)-2,2-difluorocyclopropyl)methoxy)phenyl)[1,3]oxazolo[5,4-d]pyrimidin-5-yl)butan-2-yl)acetamide A) tert-butyl ((2S)-4-(2-(4-(benzyloxy)phenyl)[1,3]oxazolo[5,4-d]pyrimidin-5-yl)but-3-yn-2-yl)carbamate A mixture of 4-(benzyloxy)benzoic acid (1.04 g) and phosphorus oxychloride (12.2 mL) was stirred at room temperature for 5 min, and 2,4-dichloropyrimidin-5-amine (500 mg) was added thereto, and the obtained mixture was stirred at 100° C. for 2 hr. The reaction mixture was added to 1M aqueous sodium hydroxide solution at 0° C., and the precipitate was collected by filtration, and dissolved in THF and ethyl acetate. The obtained solution was dried over anhydrous sodium sulfate, and the solvent was evaporated under reduced pressure. The residue was purified by silica gel column chromatography (hexane/ethyl acetate) to give 2-(4-(benzyloxy)phenyl)-5-chloro[1,3]oxazolo[5,4-d]pyrimidine (3.07 g) as a mixture with impurity. A mixture of 2-(4-(benzyloxy)phenyl)-5-chloro[1,3]oxazolo[5,4-d]pyrimidine (100 mg, a mixture with impurity), tert-butyl (2S)-but-3-yn-2-ylcarbamate (50.1 mg), dichlorobis(triphenylphosphine)palladium(II) (10.4 mg), copper(I) iodide (5.64 mg), triethylamine (0.041 mL) and DMF (2 mL) was stirred at 100° C. for 6 hr under an argon atmosphere. In another reaction container, A mixture of 2-(4-(benzyloxy)phenyl)-5-chloro[1,3]oxazolo[5,4-d]pyrimidine (100 mg, a mixture with impurity), tert-butyl (2S)-but-3-yn-2-ylcarbamate (50.1 mg), dichlorobis(triphenylphosphine)palladium(II) (10.4 mg), copper(I) iodide (5.64 mg), triethylamine (0.041 mL) and toluene (2 mL) was stirred at 100° C. for 6 hr under an argon atmosphere. The two reaction mixtures were combined, water was added thereto, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (44.4 mg).

MS (ESI+): [M+H]$^+$ 471.2.

B) tert-butyl ((2S)-4-(2-(4-(((1R)-2,2-difluorocyclopropyl)methoxy)phenyl)[1,3]oxazolo[5,4-d]pyrimidin-5-yl)butan-2-yl)carbamate Using tert-butyl ((2S)-4-(2-(4-(benzyloxy)phenyl) [1,3]oxazolo[5,4-d]pyrimidin-5-yl)but-3-yn-2-yl)carbamate and ((1R)-2,2-difluorocyclopropyl)methyl 4-nitrobenzenesulfonate, and in the same manner as in Step A of Example 4 and Example 5, the title compound was obtained.

MS (ESI+): [M+H]$^+$ 475.1.

C) N-((2S)-1-((2-(4-((2,2-difluorocyclopropyl)methoxy)phenyl)[1,3]oxazolo[5,4-d]pyrimidin-5-yl)oxy)propan-2-yl)acetamide Using tert-butyl ((2S)-4-(2-(4-(((1R)-2,2-difluorocyclopropyl)methoxy)phenyl)[1,3]oxazolo[5,4-d]pyrimidin-5-yl)butan-2-yl)carbamate, and in the same manner as in Step D of Example 1, the title compound was obtained.

Example 165

Optically Active Form of N-((2S)-1-((2-(4-(2-(2,2-difluorocyclopropyl)ethoxy)-3-fluorophenyl)[1,3]oxazolo[4,5-c]pyridin-6-yl)oxy)propan-2-yl)acetamide A diastereomer mixture (103 mg) of N-((2S)-1-((2-(4-(2-(2,2-difluorocyclopropyl)ethoxy)-3-fluorophenyl)[1,3]oxazolo[4,5-c]pyridin-6-yl)oxy)propan-2-yl)acetamide was resolved by supercritical fluid chromatography (column: CHIRALCEL OJ-H (registered trade mark) (trade name), 20 mmID×250 mL, DAICEL CHEMICAL INDUSTRIES, LTD., mobile phase:carbon dioxide/methanol/acetonitrile=860/70/70), and recrystallized (ethyl acetate) to give the title compound having a shorter retention time (28.3 mg).

analysis retention time 10.9 min.
optical purity >99% ee
$^1$H NMR (300 MHz, DMSO-d$_6$) δ 1.04-2.16 (11H, m), 3.95-4.37 (5H, m), 7.21 (1H, s), 7.32-7.56 (1H, m), 7.80-8.07 (3H, m), 8.63 (1H, s).

Example 166

Optically Active Form of N-((2S)-1-((2-(4-(2-(2,2-difluorocyclopropyl)ethoxy)-3-fluorophenyl)[1,3]oxazolo[4,5-c]pyridin-6-yl)oxy)propan-2-yl)acetamide A diastereomer mixture (103 mg) of N-((2S)-1-((2-(4-(2-(2,2-difluorocyclopropyl)ethoxy)-3-fluorophenyl)[1,3]oxazolo[4,5-c]pyridin-6-yl)oxy)propan-2-yl)acetamide was resolved by supercritical fluid chromatography (column: CHIRALCEL OJ-H (registered trade mark) (trade name), 20 mmID×250 mL, DAICEL CHEMICAL INDUSTRIES, LTD., mobile phase:carbon dioxide/methanol/acetonitrile=860/70/70), and recrystallized (ethyl acetate) to give the title compound having a longer retention time (28.3 mg).

analysis retention time 11.9 min.
optical purity >99% ee
$^1$H NMR (300 MHz, DMSO-d$_6$) δ 1.00-2.14 (11H, m), 3.95-4.41 (5H, m), 7.21 (1H, s), 7.34-7.55 (1H, m), 7.77-8.05 (3H, m), 8.63 (1H, s).

Example 167

N-((2S)-1-((2-(4-(((1R)-2,2-difluorocyclopropyl)methoxy)-3,5-difluorophenyl)[1,3]oxazolo[5,4-d]pyrimidin-5-yl)oxy)propan-2-yl)acetamide A) tert-butyl ((2S)-1-((5-((4-(benzyloxy)-3,5-difluorobenzoyl)amino)-4-hydroxypyrimidin-2-yl)oxy)propan-2-yl)carbamate Using tert-butyl ((2S)-1-((4-(benzyloxy)-5-nitropyrimidin-2-yl)oxy)propan-2-yl)carbamate and 4-(benzyloxy)-3,5-difluorobenzoic acid, and in the same manner as in Step A of Example 4, Step D of Example 83 and Step B of Example 123, the title compound was obtained.

MS (ESI+): [M+H]$^+$ 531.1.

B) tert-butyl ((2S)-1-((2-(4-(benzyloxy)-3,5-difluorophenyl)[1,3]oxazolo[5,4-d]pyrimidin-5-yl)oxy)propan-2-yl)carbamate Using tert-butyl ((2S)-1-((5-((4-(benzyloxy)-3,5-difluorobenzoyl)amino)-4-hydroxypyrimidin-2-yl)oxy)propan-2- yl)carbamate, and in the same manner as in Step B of Example 41, the title compound was obtained.
MS (ESI+): [M+H]+ 513.1.

C) tert-butyl ((2S)-1-((2-(4-(((1R)-2,2-difluorocyclopropyl)methoxy)-3,5-difluorophenyl) [1,3]oxazolo[5,4-d]pyrimidin-5-yl)oxy)propan-2-yl)carbamate Using tert-butyl ((2S)-1-((2-(4-(benzyloxy)-3,5-difluorophenyl)[1,3]oxazolo[5,4-d]pyrimidin-5-yl)oxy)propan-2-yl)carbamate, and in the same manner as in Step A of Example 4 and Example 5, the title compound was obtained.
MS (ESI+): [M+H]+ 513.1.

D) N-((2S)-1-((2-(4-(((1R)-2,2-difluorocyclopropyl)methoxy)-3,5-difluorophenyl)[1,3]oxazolo[5,4-d]pyrimidin-5-yl)oxy)propan-2-yl)acetamide Using tert-butyl ((2S)-1-((2-(4-(((1R)-2,2-difluorocyclopropyl)methoxy)-3,5-difluorophenyl)[1,3]oxazolo[5,4-d]pyrimidin-5-yl)oxy)propan-2-yl)carbamate, and in the same manner as in Step D of Example 1, the title compound was obtained.

Example 168

N-((2S)-1-((2-(4-(2-(2,2-difluorocyclopropyl)ethoxy)phenyl)[1,3]oxazolo[4,5-c]pyridin-6-yl)oxy)propan-2-yl)acetamide A) tert-butyl ((2S)-1-((2-(4-hydroxyphenyl) [1,3]oxazolo[4,5-c]pyridin-6-yl)oxy)propan-2-yl)carbamate A mixture of tert-butyl ((2S)-1-((2-(4-(benzyloxy)phenyl)[1,3]oxazolo[4,5-c]pyridin-6-yl)oxy)propan-2-yl)carbamate (2.5 g), 10% palladium/carbon (containing water (50%), 0.5 g), THF (200 mL) and DMF (50 mL) was stirred for 15 hr under a hydrogen atmosphere. The catalyst was removed by filtration, and the obtained filtrate was concentrated under reduced pressure. The obtained solid was collected by filtration, washed with hexane/ethyl acetate (4/1), dried to give the title compound (1.45 g).
1H NMR (300 MHz, DMSO-d6) δ 1.12 (3H, d, J=6.8 Hz), 1.38 (9H, s), 3.77-3.97 (1H, m), 4.12-4.31 (2H, m), 6.88 (1H, d, J=7.7 Hz), 6.97 (2H, d, J=8.8 Hz), 7.14 (1H, s), 8.01 (2H, d, J=8.8 Hz), 8.56 (1H, d, J=0.7 Hz), 10.46 (1H, brs).

B) tert-butyl ((2S)-1-((2-(4-(2-(2,2-difluorocyclopropyl)ethoxy)phenyl)[1,3]oxazolo[4,5-c]pyridin-6-yl)oxy)propan-2-yl)carbamate A mixture of tert-butyl ((2S)-1-((2-(4-hydroxyphenyl)[1,3]oxazolo[4,5-c]pyridin-6-yl)oxy)propan-2-yl)carbamate (300 mg), 2-(2,2-difluorocyclopropyl)ethyl methanesulfonate (312 mg), potassium carbonate (215 mg) and DMF (5 mL) was stirred overnight at 70° C. The reaction mixture was allowed to cool to room temperature, and 2-(2,2-difluorocyclopropyl)ethyl methanesulfonate (935 mg) and potassium carbonate (645 mg) were added thereto. The obtained mixture was stirred overnight at 70° C. To the reaction mixture was added water, and the mixture was extracted with ethyl acetate. The combined organic layer were washed with saturated brine, and dried over anhydrous magnesium sulfate, and the solvent was evaporated under reduced pressure. The residue was purified by silica gel column chromatography (hexane/ethyl acetate) to give the title compound (239 mg).
MS (ESI+): [M+H]+ 490.1.

C) N-((2S)-1-((2-(4-(2-(2,2-difluorocyclopropyl)ethoxy)phenyl)[1,3]oxazolo[4,5-c]pyridin-6-yl)oxy)propan-2-yl)acetamide A mixture of tert-butyl ((2S)-1-((2-(4-(2-(2,2-difluorocyclopropyl)ethoxy)phenyl)[1,3]oxazolo[4,5-c]pyridin-6-yl)oxy)propan-2-yl)carbamate (239 mg), 4M hydrogen chloride/ethyl acetate (3 mL) and ethyl acetate (3 mL) was stirred at room temperature overnight. The reaction mixture was concentrated under reduced pressure, and the obtained residue was mixed with acetic anhydride (0.138 mL) and pyridine (3 mL), and the obtained mixture was stirred at room temperature for 1 hr. To the reaction mixture was added 1M hydrochloric acid, and the mixture was extracted with ethyl acetate. The combined organic layer were washed with saturated brine, and dried over anhydrous magnesium sulfate, and the solvent was evaporated under reduced pressure. The residue was recrystallized (ethyl acetate) to give the title compound (155 mg).
1H NMR (300 MHz, DMSO-d6) δ 1.15 (3H, d, J=6.5 Hz), 1.19-1.37 (1H, m), 1.49-1.67 (1H, m), 1.71-2.10 (6H, m), 4.04-4.31 (5H, m), 7.04-7.26 (3H, m), 7.93 (1H, d, J=7.5 Hz), 8.11 (2H, d, J=9.0 Hz), 8.60 (1H, d, J=0.8 Hz).

Table 1 to Table 20 show compound names, structural formulas and measured MS values of the Example compounds.

The measured values of MS in a positive mode (ESI+) are shown as measured MS values.

TABLE 1

| Example | IUPAC name | Structure | MS |
|---|---|---|---|
| 1 | N-((2S)-1-((2-(4-(cyclopropylmethoxy)-3-fluorophenyl)-1,3-benzoxazol-6-yl)oxy)propan-2-yl)acetamide | 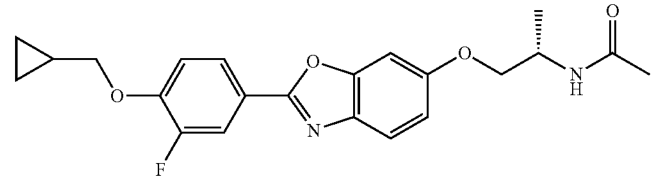 [SMILES: CC(=O)N[C@@H](C)COc1ccc2nc(-c3ccc(OCC4CC4)c(F)c3)oc2c1] | 399.1 |
| 2 | N-((2S)-1-((2-(4-(benzyloxy)-3-fluorophenyl)-1,3-benzoxazol-6-yl)oxy)propan-2-yl)acetamide | 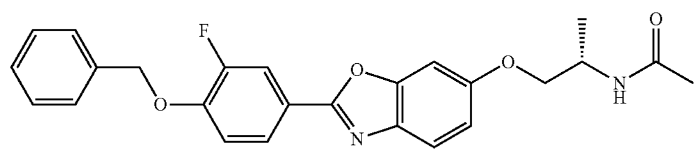 [SMILES: CC(=O)N[C@@H](C)COc1ccc2nc(-c3ccc(OCc4ccccc4)c(F)c3)oc2c1] | 435.3 |

TABLE 1-continued

| Example | IUPAC name | Structure | MS |
|---|---|---|---|
| 3 | N-((2S)-1-((2-(4-(2,2-difluoropropoxy)-3-fluorophenyl)-1,3-benzoxazol-6-yl)oxy)propan-2-yl)acetamide | 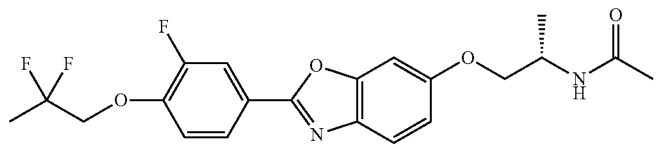 [SMILES: CC(=O)N[C@@H](C)COc1ccc2nc(-c3ccc(OCC(C)(F)F)c(F)c3)oc2c1] | 423.1 |
| 4 | N-((2S)-1-((2-(4-(2-cyclopropylethoxy)-3-fluorophenyl)-1,3-benzoxazol-6-yl)oxy)propan-2-yl)acetamide | 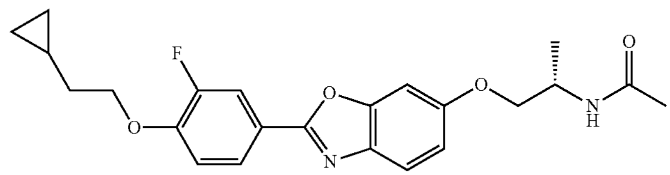 [SMILES: CC(=O)N[C@@H](C)COc1ccc2nc(-c3ccc(OCCC4CC4)c(F)c3)oc2c1] | 413.2 |
| 5 | N-((2S)-1-((2-(4-ethoxy-3-fluorophenyl)-1,3-benzoxazol-6-yl)oxy)propan-2-yl)acetamide | 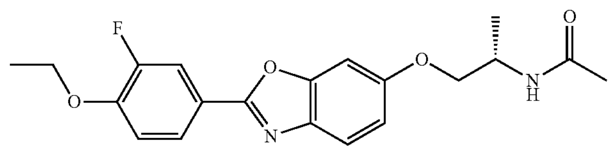 [SMILES: CCOc1ccc(-c2nc3ccc(OC[C@H](C)NC(C)=O)cc3o2)cc1F] | 373.0 |
| 6 | N-((2S)-1-((2-(3-fluoro-4-methoxyphenyl)-1,3-benzoxazol-6-yl)oxy)propan-2-yl)acetamide | 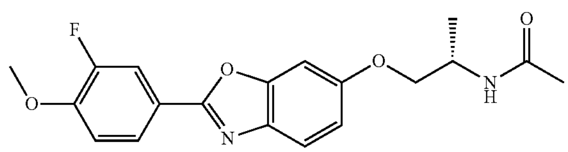 [SMILES: COc1ccc(-c2nc3ccc(OC[C@H](C)NC(C)=O)cc3o2)cc1F] | 359.0 |
| 7 | N-((2S)-1-((2-(3-fluoro-4-isopropoxyphenyl)-1,3-benzoxazol-6-yl)oxy)propan-2-yl)acetamide | 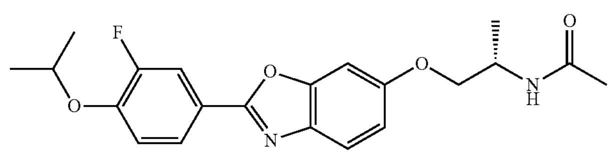 [SMILES: CC(=O)N[C@@H](C)COc1ccc2nc(-c3ccc(OC(C)C)c(F)c3)oc2c1] | 387.1 |
| 8 | N-((2S)-1-((2-(3-fluoro-4-(2-hydroxyethoxy)phenyl)-1,3-benzoxazol-6-yl)oxy)propan-2-yl)acetamide | 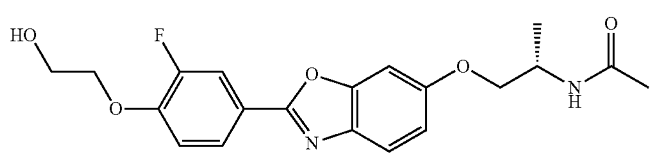 [SMILES: CC(=O)N[C@@H](C)COc1ccc2nc(-c3ccc(OCCO)c(F)c3)oc2c1] | 389.0 |
| 9 | N-((2S)-1-((2-(3-fluoro-4-(2-hydroxy-2-methylpropoxy)phenyl)-1,3-benzoxazol-6-yl)oxy)propan-2-yl)acetamide | 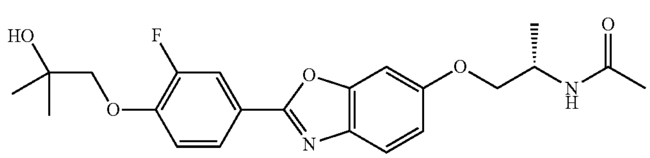 [SMILES: CC(=O)N[C@@H](C)COc1ccc2nc(-c3ccc(OCC(C)(C)O)c(F)c3)oc2c1] | 417.0 |

TABLE 2

| Example | IUPAC name | Structure | MS |
|---|---|---|---|
| 10 | 3-((2S)-1-((2-(4-(cyclopropylmethoxy)-3-fluorophenyl)-1,3-benzoxazol-6-yl)oxy)propan-2-yl)-1,1-dimethylurea | 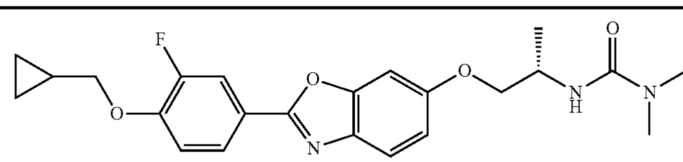 | 428.2 |
| 11 | 1-((2S)-1-((2-(4-(cyclopropylmethoxy)-3-fluorophenyl)-1,3-benzoxazol-6-yl)oxy)propan-2-yl)-3-methylurea | 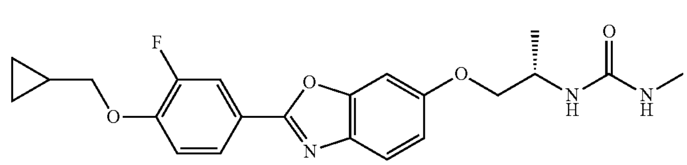 [SMILES: CNC(=O)N[C@@H](C)COc1ccc2nc(-c3ccc(OCC4CC4)c(F)c3)oc2c1] | 414.1 |

TABLE 2-continued

| Example | IUPAC name | Structure | MS |
|---|---|---|---|
| 12 | methyl ((2S)-1-((2-(4-(cyclopropylmethoxy)-3-fluorophenyl)-1,3-benzoxazol-6-yl)oxy)propan-2-yl)carbamate | 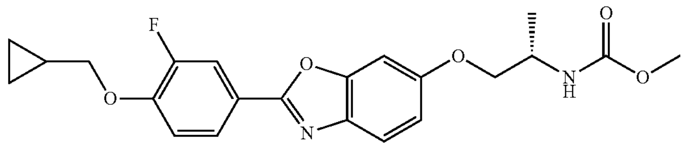 [SMILES: COC(=O)N[C@@H](C)COc1ccc2nc(-c3ccc(OCC4CC4)c(F)c3)oc2c1] | 415.2 |
| 13 | 1-((2S)-1-((2-(4-(cyclopropylmethoxy)-3-fluorophenyl)-1,3-benzoxazol-6-yl)oxy)propan-2-yl)urea | 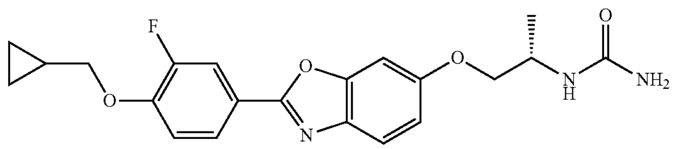 [SMILES: C[C@@H](COc1ccc2nc(-c3ccc(OCC4CC4)c(F)c3)oc2c1)NC(N)=O] | 400.2 |
| 14 | N-((2S)-1-((2-(4-(cyclopropylmethoxy)phenyl)-1H-benzimidazol-6-yl)oxy)propan-2-yl)acetamide | 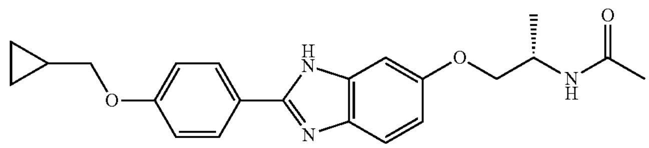 [SMILES: CC(=O)N[C@@H](C)COc1ccc2nc(-c3ccc(OCC4CC4)cc3)[nH]c2c1] | 380.1 |
| 15 | N-((2S)-1-((2-(4-propoxyphenyl)-1-benzofuran-6-yl)oxy)propan-2-yl)acetamide | 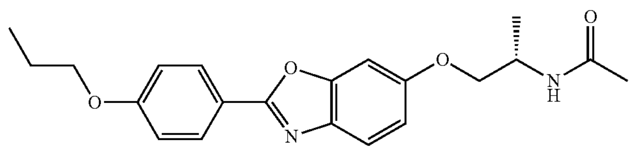 [SMILES: CCCOc1ccc(-c2nc3ccc(OC[C@H](C)NC(C)=O)cc3o2)cc1] | 368.3 |
| 16 | N-((2S)-1-((2-(4-(cyclopropylmethoxy)phenyl)-1,3-benzoxazol-6-yl)oxy)propan-2-yl)acetamide | 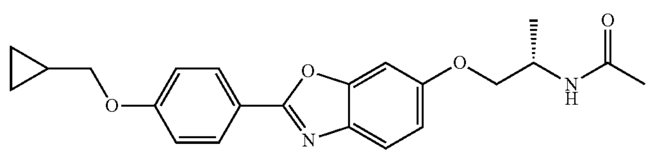 [SMILES: CC(=O)N[C@@H](C)COc1ccc2nc(-c3ccc(OCC4CC4)cc3)oc2c1] | 381.4 |
| 17 | N-((2S)-1-((2-(4-(cyclopropylmethoxy)phenyl)-1,3-benzoxazol-5-yl)oxy)propan-2-yl)acetamide | 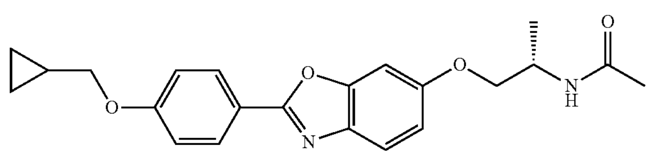 [SMILES: CC(=O)N[C@@H](C)COc1ccc2nc(-c3ccc(OCC4CC4)cc3)oc2c1] | 381.4 |
| 18 | N-((2S)-1-((2-(4-(cyclopropylmethoxy)-3-fluorophenyl)-2H-indazol-6-yl)oxy)propan-2-yl)acetamide | 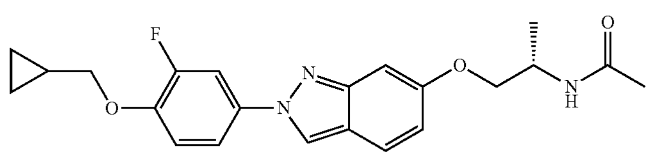 [SMILES: CC(=O)N[C@@H](C)COc1ccc2cn(-c3ccc(OCC4CC4)c(F)c3)nc2c1] | 398.2 |

TABLE 3

| Example | IUPAC name | Structure | MS |
|---|---|---|---|
| 19 | N-((2S)-1-((2-(4-(cyclopropylmethoxy)-3-fluorophenyl)-4,5,6,7-tetrahydro-2H-indazol-6-yl)oxy)propan-2-yl)acetamide | 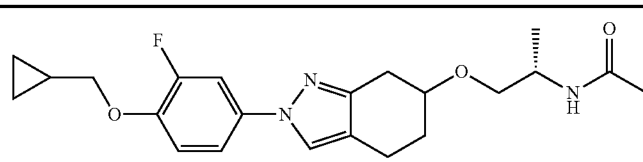 | 402.1 |
| 20 | N-((2S)-1-((2-(4-(cyclopropylmethoxy)-2-fluorophenyl)-1,3-benzoxazol-6-yl)oxy)propan-2-yl)acetamide | 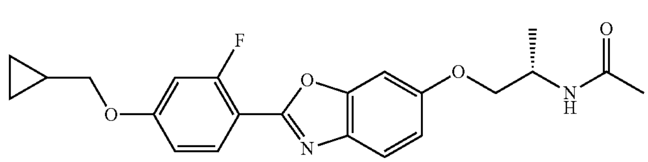 [SMILES: CC(=O)N[C@@H](C)COc1ccc2nc(-c3ccc(OCC4CC4)cc3F)oc2c1] | 399.1 |

TABLE 3-continued

| Example | IUPAC name | Structure | MS |
|---|---|---|---|
| 21 | N-((2S)-1-((2-(3-(cyclopropylmethoxy)phenyl)-1,3-benzoxazol-6-yl)oxy)propan-2-yl)acetamide | 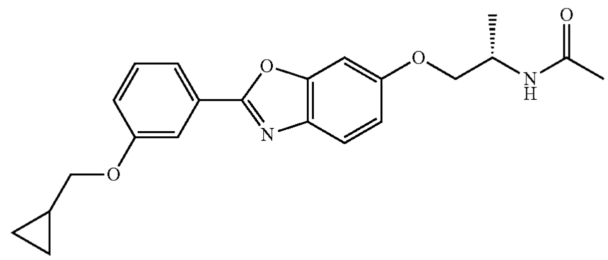 [SMILES: CC(=O)N[C@@H](C)COc1ccc2nc(-c3cccc(OCC4CC4)c3)oc2c1] | 381.1 |
| 22 | N-((2S)-1-((2-(5-(cyclopropylmethoxy)pyridin-2-yl)-1,3-benzoxazol-6-yl)oxy)propan-2-yl)acetamide | 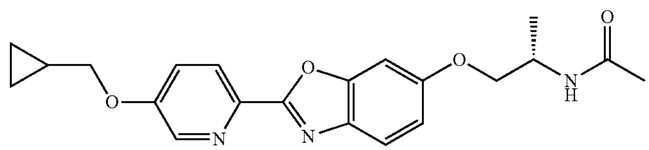 | 382.2 |
| 23 | N-((2S)-1-((2-(6-(cyclopropylmethoxy)pyridin-3-yl)-1,3-benzoxazol-6-yl)oxy)propan-2-yl)acetamide | 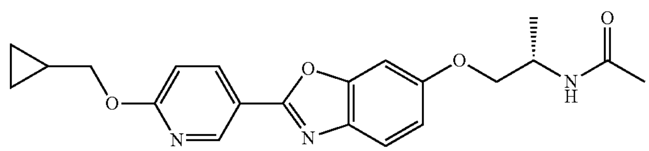 | 382.2 |
| 24 | N-((2S)-1-((2-(3-(cyclopropylmethoxy)-1,2-oxazol-5-yl)-1,3-benzoxazol-6-yl)oxy)propan-2-yl)acetamide | 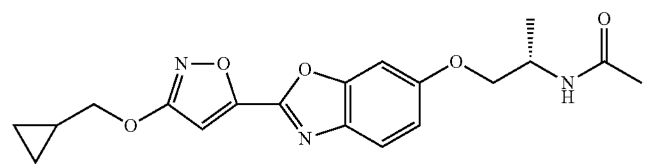 [SMILES: CC(=O)N[C@@H](C)COc1ccc2nc(-c3cc(OCC4CC4)no3)oc2c1] | 372.3 |
| 25 | N-((2S)-1-((2-(4-(cyclopropylmethoxy)-3-methoxyphenyl)-1,3-benzoxazol-6-yl)oxy)propan-2-yl)acetamide | 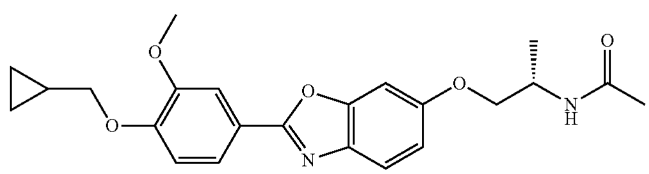 [SMILES: COc1cc(-c2nc3ccc(OC[C@H](C)NC(C)=O)cc3o2)ccc1OCC1CC1] | 411.2 |
| 26 | N-((2S)-1-((2-(3-bromo-4-(cyclopropylmethoxy)phenyl)-1,3-benzoxazol-6-yl)oxy)propan-2-yl)acetamide | 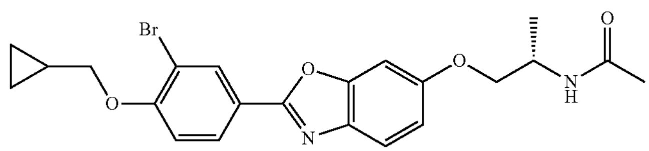 | 461.1 |
| 27 | N-((2S)-1-((2-(4-(cyclopropylmethoxy)-3-methylphenyl)-1,3-benzoxazol-6-yl)oxy)propan-2-yl)acetamide | 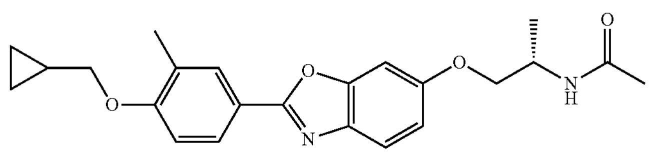 | 453.7 |

TABLE 4

| Example | IUPAC name | Structure | MS |
|---|---|---|---|
| 28 | N-((2S)-1-((2-(6-(cyclopropylmethoxy)-5-fluoropyridin-3-yl)-1,3-benzoxazol-6-yl)oxy)propan-2-yl)acetamide | 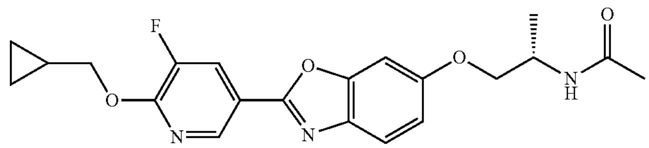 | 400.1 |
| 29 | N-((2S)-1-((2-(3-chloro-4-(cyclopropylmethoxy)phenyl)-1,3-benzoxazol-6-yl)oxy)propan-2-yl)acetamide | 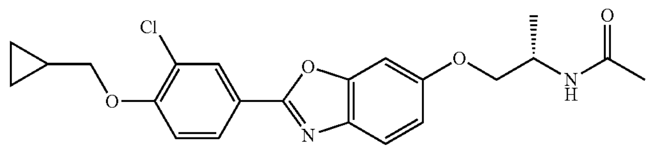 | 415.2 |
| 30 | N-((2S)-1-((2-(5-chloro-6-(cyclopropylmethoxy)pyridin-3-yl)-1,3-benzoxazol-6-yl)oxy)propan-2-yl)acetamide | 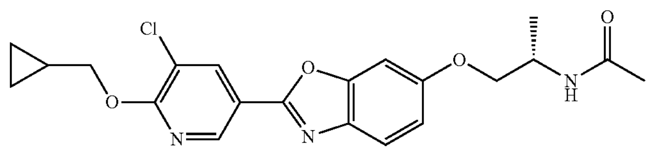 | 416.0 |
| 31 | N-((2S)-1-((2-(4-(cyclopropylmethoxy)phenyl)[1,3]oxazolo[4,5-c]pyridin-6-yl)oxy)propan-2-yl)acetamide | 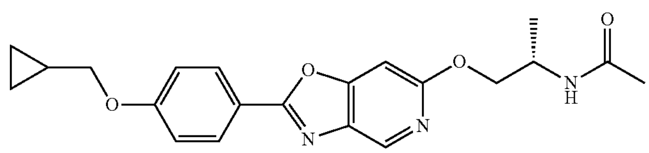 | 382.1 |
| 32 | N-((2S)-1-((2-(4-(cyclopropylmethoxy)-3-fluorophenyl)[1,3]oxazolo[4,5-c]pyridin-6-yl)oxy)propan-2-yl)acetamide | 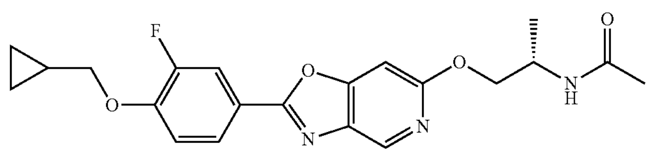 | 400.2 |
| 33 | N-((2S)-1-((2-(6-(cyclopropylmethoxy)-5-fluoropyridin-3-yl)[1,3]oxazolo[4,5-c]pyridin-6-yl)oxy)propan-2-yl)acetamide | 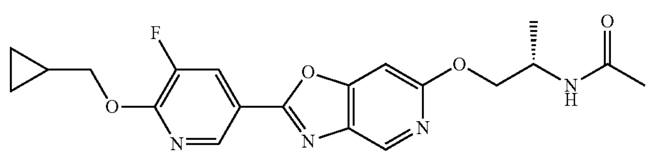 | 401.2 |
| 34 | N-((2S)-1-((2-(3-chloro-4-(cyclopropylmethoxy)phenyl)[1,3]oxazolo[4,5-c]pyridin-6-yl)oxy)propan-2-yl)acetamide | 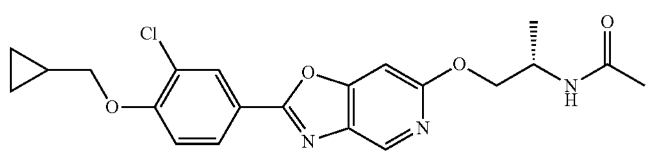 | 416.2 |
| 35 | N-((2S)-1-((2-(5-chloro-6-(cyclopropylmethoxy)pyridin-3-yl)[1,3]oxazolo[4,5-c]pyridin-6-yl)oxy)propan-2-yl)acetamide | 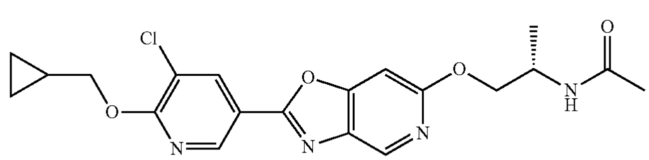 | 417.1 |
| 36 | N-((2S)-4-(2-(4-(cyclopropylmethoxy)phenyl)[1,3]oxazolo[4,5-c]pyridin-6-yl)butan-2-yl)acetamide | 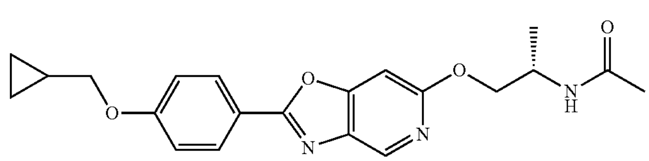 [SMILES: CC(=O)N[C@@H](C)COc1cc2oc(-c3ccc(OCC4CC4)cc3)nc2cn1] | 380.2 |

TABLE 5

| Example | IUPAC name | Structure | MS |
|---------|-----------|-----------|-----|
| 37 | N-((2S)-1-((2-(4-(cyclopropylmethoxy)-3-fluorophenyl)-7-fluoro-1,3-benzoxazol-6-yl)oxy)propan-2-yl)acetamide | 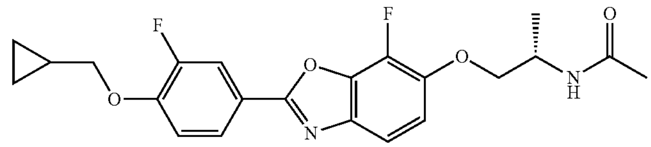 | 416.8 |
| 38 | N-((2S)-1-((2-(4-(cyclopropylmethoxy)-3-fluorophenyl)-7-fluoro-1,3-benzoxazol-6-yl)oxy)propan-2-yl)acetamide | 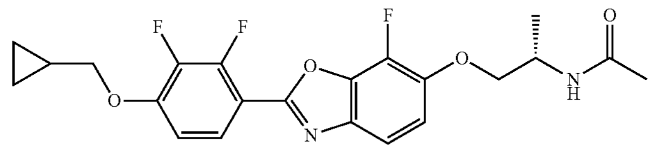 | 435.0 |
| 39 | N-((2S)-1-((2-(4-(cyclopropylmethoxy)-2,5-difluorophenyl)-7-fluoro-1,3-benzoxazol-6-yl)oxy)propan-2-yl)acetamide | 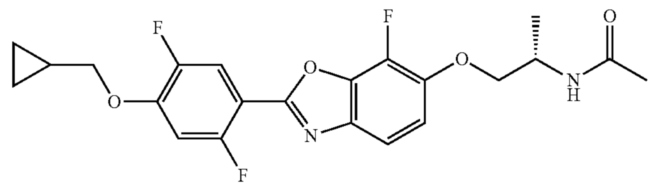 [SMILES: CC(=O)N[C@@H](C)COc1ccc2nc(-c3cc(F)c(OCC4CC4)cc3F)oc2c1F] | 434.9 |
| 40 | N-((2S)-1-((2-(4-(cyclopropylmethoxy)-3,5-difluorophenyl)-7-fluoro-1,3-benzoxazol-6-yl)oxy)propan-2-yl)acetamide | 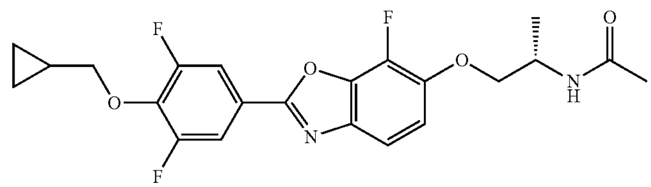 [SMILES: CC(=O)N[C@@H](C)COc1ccc2nc(-c3cc(F)c(OCC4CC4)c(F)c3)oc2c1F] | 435.0 |
| 41 | N-((2S)-1-((2-(4-(benzyloxy)-3-fluorophenyl)-7-fluoro-1,3-benzoxazol-6-yl)oxy)propan-2-yl)acetamide | 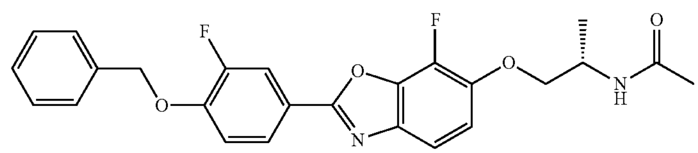 [SMILES: CC(=O)N[C@@H](C)COc1ccc2nc(-c3ccc(OCc4ccccc4)c(F)c3)oc2c1F] | 453.0 |
| 42 | N-((2S)-1-((2-(4-((2,2-difluorocyclopropyl)methoxy)-3-fluorophenyl)-7-fluoro-1,3-benzoxazol-6-yl)oxy)propan-2-yl)acetamide | 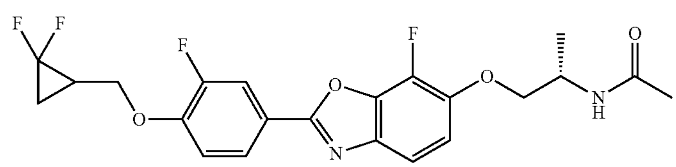 | 453.1 |
| 43 | N-((2S)-1-((2-(4-(cyclopropylmethoxy)-3-fluorophenyl)-4-fluoro-1,3-benzoxazol-6-yl)oxy)propan-2-yl)acetamide | 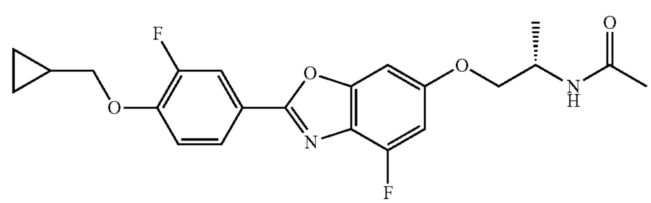 [SMILES: CC(=O)N[C@@H](C)COc1cc(F)c2nc(-c3ccc(OCC4CC4)c(F)c3)oc2c1] | 417.0 |
| 44 | N-((2S)-1-((2-(4-(cyclopropylmethoxy)-3,5-difluorophenyl)-1,3-benzoxazol-6-yl)oxy)propan-2-yl)acetamide | 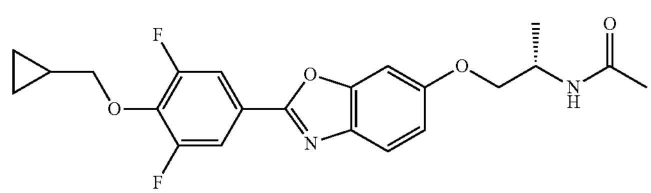 [SMILES: CC(=O)N[C@@H](C)COc1cc2oc(-c3cc(F)c(OCC4CC4)c(F)c3)nc2cn1] | 417.0 |
| 45 | N-((2S)-1-((2-(4-((2,2-difluorocyclopropyl)methoxy)-3-fluorophenyl)-1,3-benzoxazol-6-yl)oxy)propan-2-yl)acetamide | 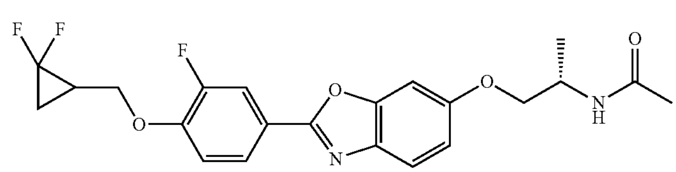 [SMILES: CC(=O)N[C@@H](C)COc1cc2oc(-c3ccc(OCC4CC4(F)F)c(F)c3)nc2cn1] | 435.0 |

TABLE 6

| Example | IUPAC name | MS |
|---------|------------|-----|
| 46 | N-((2S)-1-((2-(4-((2,2-difluorocyclopropyl)methoxy)-3,5-difluorophenyl)-7-fluoro-1,3-benzoxazol-6-yl)oxy)propan | 453.0 |
| 47 | N-((2S)-1-((2-(4-(cyclopropylmethoxy)-3,5-difluorophenyl)[1,3]oxazolo[4,5-c]pyridin-6-yl)oxy)propan-2-yl)acetamide | 440.2 |
| 48 | N-((2S)-1-((2-(4-(cyclopropylmethoxy)-2,5-difluorophenyl)[1,3]oxazolo[4,5-c]pyridin-6-yl)oxy)propan-2-yl)acetamide | 440.0 |
| 49 | N-((2S)-1-((2-(4-((2,2-difluorocyclopropyl)methoxy)-3-fluorophenyl)[1,3]oxazolo[4,5-c]pyridin-6-yl)oxy)propan-2-yl)acetamide | 458.0 |
| 50 | N-(1-((2-(4-(cyclopropylmethoxy)-3-fluorophenyl)-4,5,6,7-tetrahydro-1,3-benzoxazol-5-yl)oxy)propan-2-yl)acetamide | 402.9 |
| 51a | optically active form of N-(1-((2-(4-(cyclopropylmethoxy)-3-fluorophenyl)-4,5,6,7-tetrahydro-1,3-benzoxazol-5-yl)oxy)propan-2-yl)acetamide | 403.0 |
| 51b | optically active form of N-(1-((2-(4-(cyclopropylmethoxy)-3-fluorophenyl)-4,5,6,7-tetrahydro-1,3-benzoxazol-5-yl)oxy)propan-2-yl)acetamide | 403.0 |
| 51c | optically active form of N-(1-((2-(4-(cyclopropylmethoxy)-3-fluorophenyl)-4,5,6,7-tetrahydro-1,3-benzoxazol-5-yl)oxy)propan-2-yl)acetamide | 403.0 |
| 51d | optically active form of N-(1-((2-(4-(cyclopropylmethoxy)-3-fluorophenyl)-4,5,6,7-tetrahydro-1,3-benzoxazol-5-yl)oxy)propan-2-yl)acetamide | 403.0 |

TABLE 7

| Example | IUPAC name | Structure | MS |
|---|---|---|---|
| 52 | N-(1-((2-(4-(cyclopropylmethoxy)-3-fluorophenyl)-4,5,6,7-tetrahydro-1,3-benzoxazol-6-yl)oxy)propan-2-yl)acetamide | 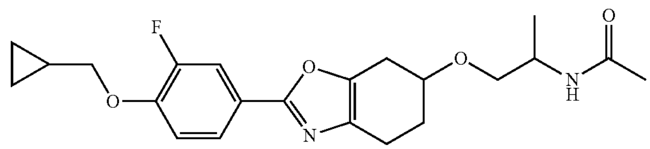 [SMILES: CC(=O)NC(C)COC1CCc2nc(-c3ccc(OCC4CC4)c(F)c3)oc2C1] | 403.1 |
| 53a | optically active form of N-(1-((2-(4-(cyclopropylmethoxy)-3-fluorophenyl)-4,5,6,7-tetrahydro-1,3-benzoxazol-6-yl)oxy)propan-2-yl)acetamide | 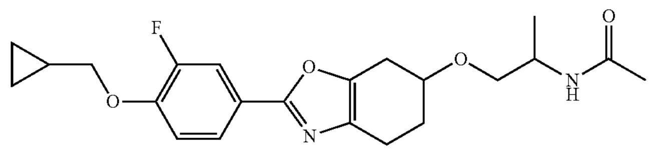 [SMILES: CC(=O)NC(C)COC1CCc2nc(-c3ccc(OCC4CC4)c(F)c3)oc2C1] | 403.2 |
| 53b | optically active form of N-(1-((2-(4-(cyclopropylmethoxy)-3-fluorophenyl)-4,5,6,7-tetrahydro-1,3-benzoxazol-6-yl)oxy)propan-2-yl)acetamide | 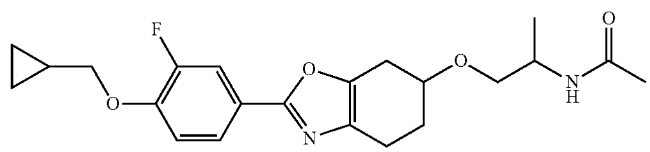 | 403.2 |
| 53c | optically active form of N-(1-((2-(4-(cyclopropylmethoxy)-3-fluorophenyl)-4,5,6,7-tetrahydro-1,3-benzoxazol-6-yl)oxy)propan-2-yl)acetamide | 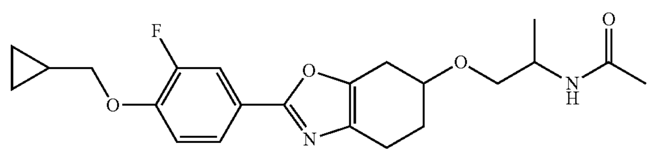 [SMILES: CC(=O)NC(C)COC1CCc2nc(-c3ccc(OCC4CC4)c(F)c3)oc2C1] | 403.2 |
| 53d | optically active form of N-(1-((2-(4-(cyclopropylmethoxy)-3-fluorophenyl)-4,5,6,7-tetrahydro-1,3-benzoxazol-6-yl)oxy)propan-2-yl)acetamide | 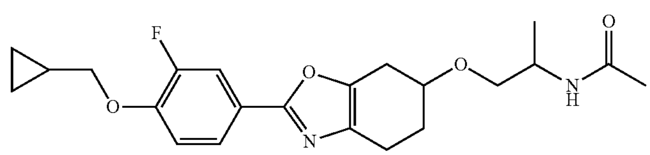 [SMILES: CC(=O)NC(C)COC1CCc2nc(-c3ccc(OCC4CC4)c(F)c3)oc2C1] | 403.2 |
| 54 | N-(1-((2-(3-chloro-4-(cyclopropylmethoxy)phenyl)-4,5,6,7-tetrahydro-1,3-benzoxazol-5-yl)oxy)propan-2-yl)acetamide | 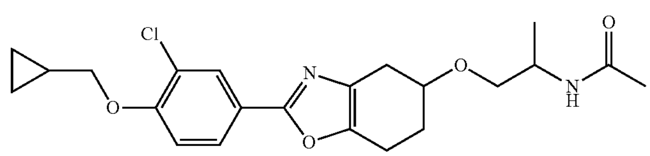 [SMILES: CC(=O)NC(C)COC1CCc2oc(-c3ccc(OCC4CC4)c(Cl)c3)nc2C1] | 419.0 |
| 55a | optically active form of N-(1-((2-(3-chloro-4-(cyclopropylmethoxy)phenyl)-4,5,6,7-tetrahydro-1,3-benzoxazol-5-yl)oxy)propan-2-yl)acetamide | 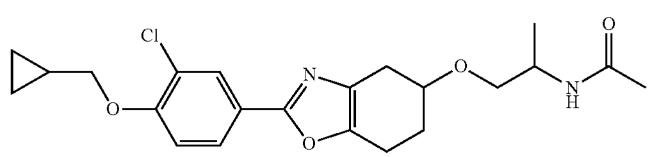 [SMILES: CC(=O)NC(C)COC1CCc2oc(-c3ccc(OCC4CC4)c(Cl)c3)nc2C1] | 418.9 |
| 55b | optically active form of N-(1-((2-(3-chloro-4-(cyclopropylmethoxy)phenyl)-4,5,6,7-tetrahydro-1,3-benzoxazol-5-yl)oxy)propan-2-yl)acetamide | 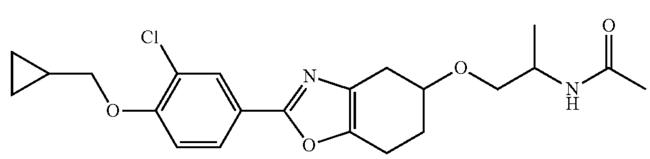 | 418.9 |
| 55c | optically active form of N-(1-((2-(3-chloro-4-(cyclopropylmethoxy)phenyl)-4,5,6,7-tetrahydro-1,3-benzoxazol-5-yl)oxy)propan-2-yl)acetamide | 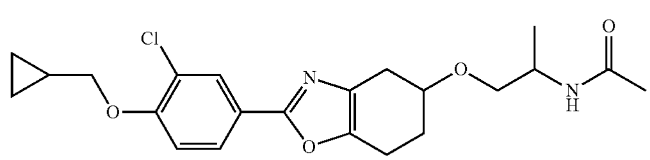 [SMILES: CC(=O)NC(C)COC1CCc2oc(-c3ccc(OCC4CC4)c(Cl)c3)nc2C1] | 418.9 |

TABLE 8

| Example | IUPAC name | Structure | MS |
|---|---|---|---|
| 55d | optically active form of N-(1-((2-(3-chloro-4-(cyclopropylmethoxy)phenyl)-4,5,6,7-tetrahydro-1,3-benzoxazol-5-yl)oxy)propan-2-yl)acetamide | 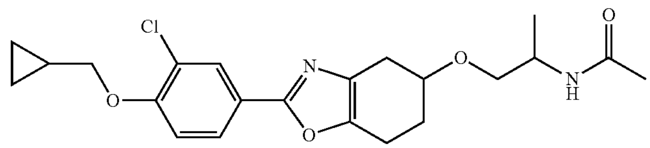 [SMILES: CC(=O)NC(C)COC1CCc2oc(-c3ccc(OCC4CC4)c(Cl)c3)nc2C1] | 419.0 |
| 56 | N-(1-((2-(3-chloro-4-(cyclopropylmethoxy)phenyl)-4,5,6,7-tetrahydro-1,3-benzoxazol-6-yl)oxy)propan-2-yl)acetamide | 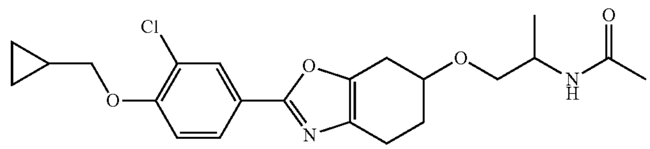 [SMILES: CC(=O)NC(C)COC1CCc2nc(-c3ccc(OCC4CC4)c(Cl)c3)oc2C1] | 419.0 |
| 57a | optically active form of N-(1-((2-(3-chloro-4-(cyclopropylmethoxy)phenyl)-4,5,6,7-tetrahydro-1,3-benzoxazol-6-yl)oxy)propan-2-yl)acetamide | 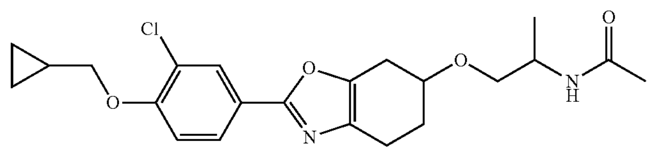 [SMILES: CC(=O)NC(C)COC1CCc2nc(-c3ccc(OCC4CC4)c(Cl)c3)oc2C1] | 419.0 |
| 57b | optically active form of N-(1-((2-(3-chloro-4-(cyclopropylmethoxy)phenyl)-4,5,6,7-tetrahydro-1,3-benzoxazol-6-yl)oxy)propan-2-yl)acetamide | 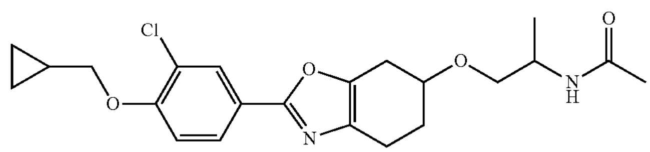 | 419.0 |
| 57c | optically active form of N-(1-((2-(3-chloro-4-(cyclopropylmethoxy)phenyl)-4,5,6,7-tetrahydro-1,3-benzoxazol-6-yl)oxy)propan-2-yl)acetamide | 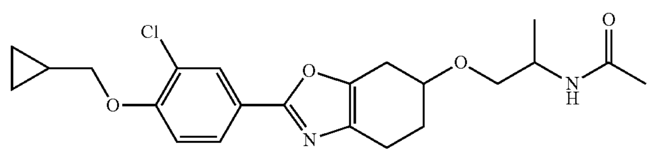 [SMILES: CC(=O)NC(C)COC1CCc2nc(-c3ccc(OCC4CC4)c(Cl)c3)oc2C1] | 419.0 |
| 57d | optically active form of N-(1-((2-(3-chloro-4-(cyclopropylmethoxy)phenyl)-4,5,6,7-tetrahydro-1,3-benzoxazol-6-yl)oxy)propan-2-yl)acetamide | 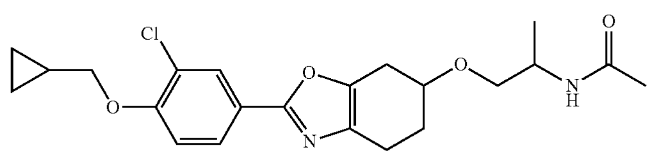 [SMILES: CC(=O)NC(C)COC1CCc2nc(-c3ccc(OCC4CC4)c(Cl)c3)oc2C1] | 419.0 |
| 58 | N-(4-(2-(4-(cyclopropylmethoxy)phenyl)-6,7-dihydro[1,3]oxazolo[5,4-c]pyridin-5(4H)-yl)-4-oxobutan-2-yl)acetamide | 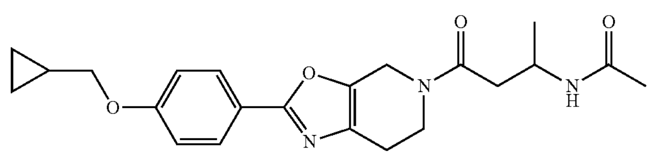 [SMILES: CC(=O)NC(C)CC(=O)N1CCc2nc(-c3ccc(OCC4CC4)cc3)oc2C1] | 398.1 |

TABLE 9

| Example | IUPAC name | Structure | MS |
|---|---|---|---|
| 59 | 1-((2S)-1-((2-(4-(cyclopropylmethoxy)-3,5-difluorophenyl)[1,3]oxazolo[4,5-c]pyridin-6-yl)oxy)propan-2-yl)urea | 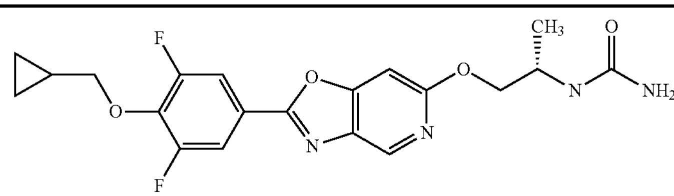 | 419.2 |
| 60 | N-((2S)-1-((2-(3-fluoro-4-(3,3,3-trifluoropropoxy)phenyl)-1,3-benzoxazol-6-yl)oxy)propan-2-yl)acetamide | 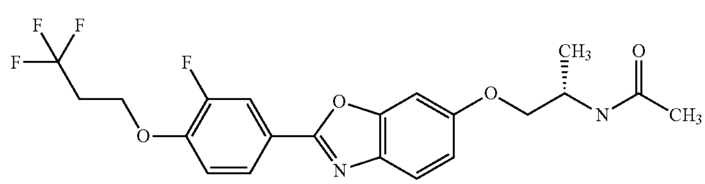 [SMILES: CC(=O)N[C@@H](C)COc1ccc2nc(-c3ccc(OCCC(F)(F)F)c(F)c3)oc2c1] | 441.2 |

TABLE 9-continued

| Example | IUPAC name | Structure | MS |
|---|---|---|---|
| 61 | N-((2S)-1-((2-(4-((2,2-difluorocyclopropyl)methoxy)-2,5-difluorophenyl)[1,3]oxazolo[4,5-c]pyridin-6-yl)oxy)propan-2-yl)acetamide | 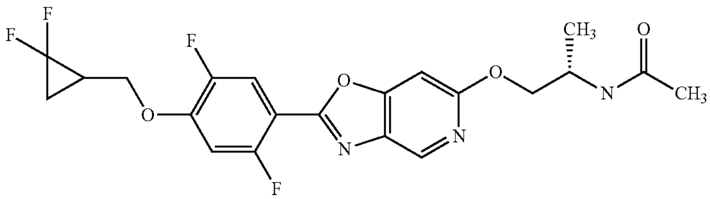 [SMILES: CC(=O)N[C@@H](C)COc1cc2oc(-c3cc(F)c(OCC4CC4(F)F)cc3F)nc2cn1] | 454.1 |
| 62 | N-((2S)-1-((2-(4-(cyclopropylmethoxy)-3-fluoro-5-methoxyphenyl)[1,3]oxazolo[4,5-c]pyridin-6-yl)oxy)propan-2-yl)acetamide | 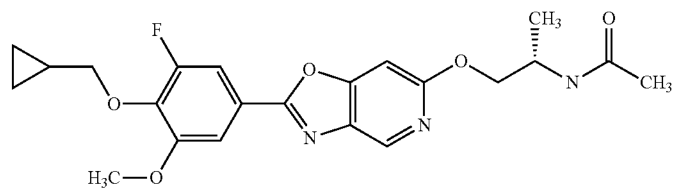 [SMILES: COc1cc(-c2nc3cnc(OC[C@H](C)NC(C)=O)cc3o2)cc(F)c1OCC1CC1] | 430.1 |
| 63 | N-((2S)-1-((2-(4-(cyclopropylmethoxy)-3,5-difluorophenyl)[1,3]oxazolo[4,5-c]pyridin-6-yl)oxy)propan-2-yl)azetidine-1-carboxamide | 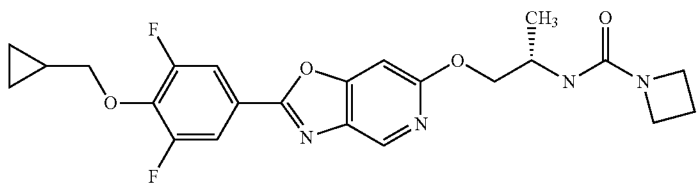 [SMILES: C[C@@H](COc1cc2oc(-c3cc(F)c(OCC4CC4)c(F)c3)nc2cn1)NC(=O)N1CCC1] | 459.2 |
| 64 | N-((2S)-1-((2-(4-(cyclopropylmethoxy)-2,5-difluorophenyl)-1,3-benzoxazol-6-yl)oxy)propan-2-yl)acetamide | 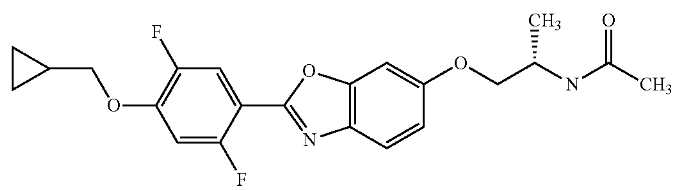 [SMILES: CC(=O)N[C@@H](C)COc1ccc2nc(-c3cc(F)c(OCC4CC4)cc3F)oc2c1] | 417.2 |
| 65 | N-((2S)-1-((2-(5-(cyclopropylmethoxy)-4-fluoropyridin-2-yl)[1,3]oxazolo[4,5-c]pyridin-6-yl)oxy)propan-2-yl)acetamide | 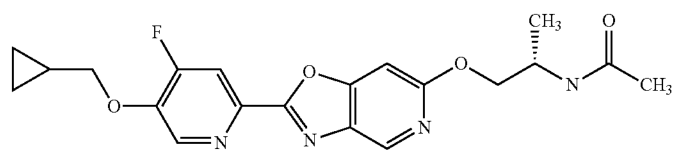 [SMILES: CC(=O)N[C@@H](C)COc1cc2oc(-c3cc(F)c(OCC4CC4)cn3)nc2cn1] | 401.2 |
| 66 | N-((2S)-1-((2-(6-(2,2-difluorocyclopropylmethoxy)pyridin-3-yl)[1,3]oxazolo[4,5-c]pyridin-6-yl)oxy)propan-2-yl)acetamide | 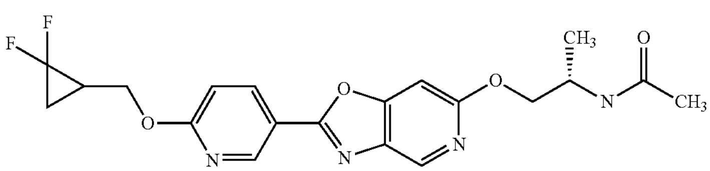 [SMILES: CC(=O)N[C@@H](C)COc1cc2oc(-c3ccc(OCC4CC4(F)F)nc3)nc2cn1] | 419.2 |
| 67 | N-((2S)-1-((2-(5-(cyclopropylmethoxy)-2-thienyl)[1,3]oxazolo[4,5-c]pyridin-6-yl)oxy)propan-2-yl)acetamide | 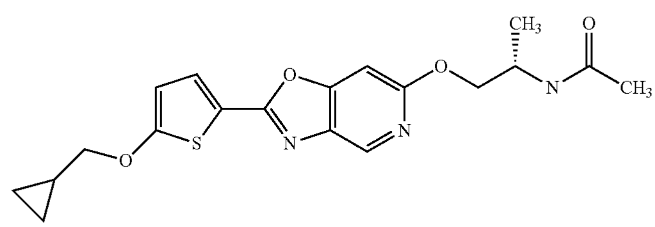 [SMILES: CC(=O)N[C@@H](C)COc1cc2oc(-c3ccc(OCC4CC4)s3)nc2cn1] | 388.1 |
| 68 | N-((2S)-1-((2-(4-(((1R)-2,2-difluorocyclopropyl)methoxy)phenyl)[1,3]oxazolo[4,5-c]pyridin-6-yl)oxy)propan-2-yl)acetamide | 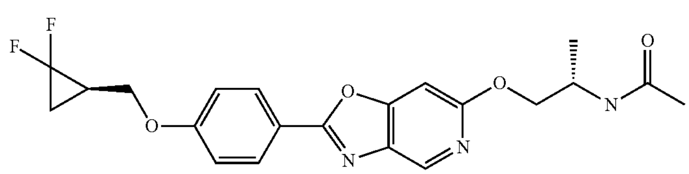 [SMILES: CC(=O)N[C@@H](C)COc1cc2oc(-c3ccc(OC[C@H]4CC4(F)F)cc3)nc2cn1] | 418.1 |

TABLE 9-continued

| Example | IUPAC name | Structure | MS |
|---|---|---|---|
| 69 | N-((2S)-1-((2-(4-(((1R)-2,2-difluorocyclopropyl)methoxy)-3-fluorophenyl)[1,3]oxazolo[4,5-c]pyridin-6-yl)oxy)propan-2-yl)acetamide | 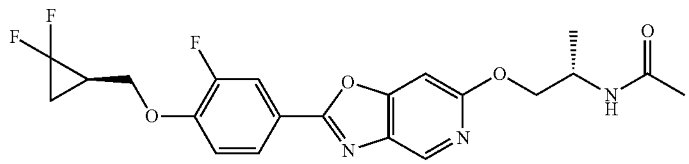 [SMILES: CC(=O)N[C@@H](C)COc1cc2oc(-c3ccc(OC[C@H]4CC4(F)F)c(F)c3)nc2cn1] | 436.1 |

TABLE 10

| Example | IUPAC name | Structure | MS |
|---|---|---|---|
| 70 | N-((2S)-1-((2-(4-(cyclopropylmethoxy)phenyl)[1,3]oxazolo[4,5-b]pyridin-6-yl)oxy)propan-2-yl)acetamide | 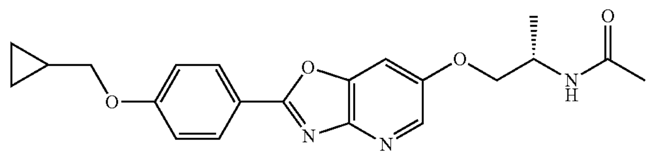 [SMILES: CC(=O)N[C@@H](C)COc1cnc2nc(-c3ccc(OCC4CC4)cc3)oc2c1] | 382.3 |
| 71 | N-((2S)-1-((2-(4-(cyclopropylmethoxy)phenyl)[1,3]oxazolo[5,4-b]pyridin-5-yl)oxy)propan-2-yl)acetamide | 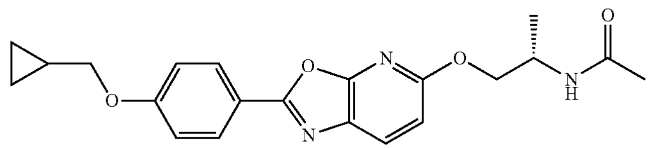 | 382.4 |
| 72 | N-((2S)-1-((2-(2-cyano-4-(cyclopropylmethoxy)phenyl)-1,3-benzoxazol-6-yl)oxy)propan-2-yl)acetamide | 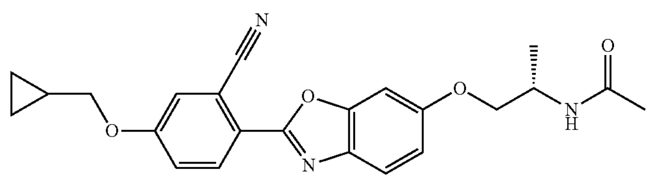 [SMILES: CC(=O)N[C@@H](C)COc1ccc2nc(-c3ccc(OCC4CC4)cc3C#N)oc2c1] | 406.2 |
| 73 | N-((2S)-1-((2-(2-(cyclopropylmethoxy)pyrimidin-5-yl)-1,3-benzoxazol-6-yl)oxy)propan-2-yl)acetamide | 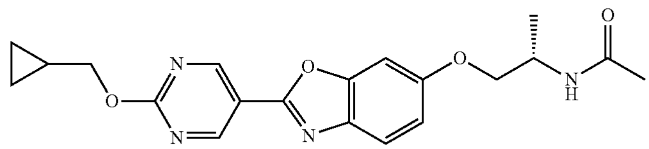 [SMILES: CC(=O)N[C@@H](C)COc1ccc2nc(-c3cnc(OCC4CC4)nc3)oc2c1] | 383.2 |
| 74 | N-((2S)-1-((2-(3-cyano-4-(cyclopropylmethoxy)phenyl)-1,3-benzoxazol-6-yl)oxy)propan-2-yl)acetamide | 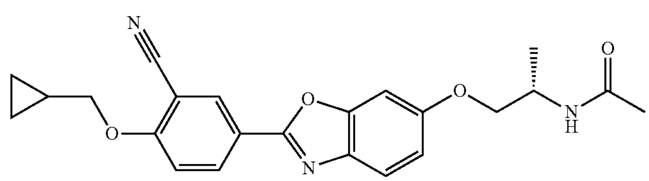 [SMILES: CC(=O)N[C@@H](C)COc1ccc2nc(-c3ccc(OCC4CC4)c(C#N)c3)oc2c1] | 406.1 |
| 75 | N-((2S)-1-((2-(6-(cyclopropylmethoxy)pyridin-3-yl)[1,3]oxazolo[4,5-c]pyridin-6-yl)oxy)propan-2-yl)acetamide | 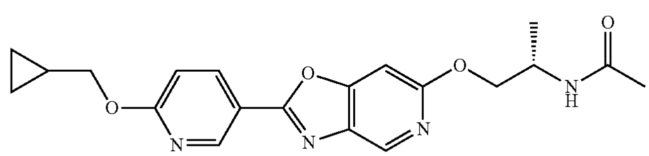 | 383.2 |
| 76 | N-((2S)-1-((2-(5-(cyclopropylmethoxy)-6-fluoropyridin-2-yl)-1,3-benzoxazol-6-yl)oxy)propan-2-yl)acetamide | 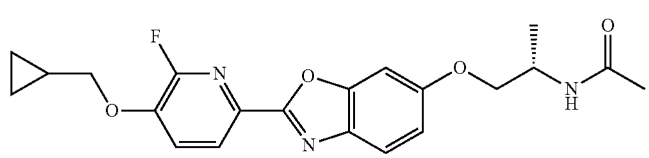 [SMILES: CC(=O)N[C@@H](C)COc1ccc2nc(-c3ccc(OCC4CC4)c(F)n3)oc2c1] | 400.2 |

TABLE 10-continued

| Example | IUPAC name | Structure | MS |
|---|---|---|---|
| 77 | N-((2S)-1-((2-(5-(cyclopropylmethoxy)pyridin-2-yl)[1,3]oxazolo[4,5-c]pyridin-6-yl)oxy)propan-2-yl)acetamide | 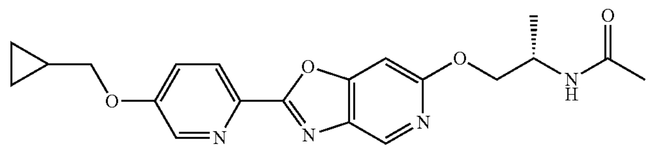 [SMILES: CC(=O)N[C@@H](C)COc1cc2oc(-c3ccc(OCC4CC4)cn3)nc2cn1] | 383.2 |
| 78 | N-((2S)-1-((2-(4-(cyclopropylmethoxy)-3-fluorophenyl)-5-fluoro-1,3-benzoxazol-6-yl)oxy)propan-2-yl)acetamide | 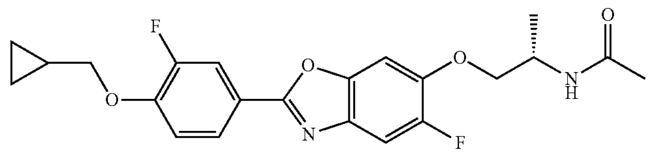 [SMILES: CC(=O)N[C@@H](C)COc1cc2oc(-c3ccc(OCC4CC4)c(F)c3)nc2cc1F] | 416.9 |

TABLE 11

| Example | IUPAC name | Structure | MS |
|---|---|---|---|
| 79 | N-((2S)-1-((2-(3,5-difluoro-4-((1-fluorocyclopropyl)methoxy)phenyl)-1,3-benzoxazol-6-yl)oxy)propan-2-yl)acetamide | 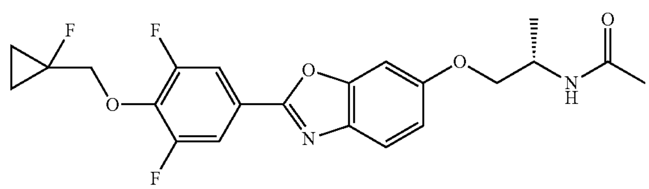 [SMILES: CC(=O)N[C@@H](C)COc1ccc2nc(-c3cc(F)c(OCC4(F)CC4)c(F)c3)oc2c1] | 435.1 |
| 80 | optically active form of N-((2S)-1-((2-(4-((2,2-difluorocyclopropyl)methoxy)-3-fluorophenyl)-7-fluoro-1,3-benzoxazol-6-yl)oxy)propan-2-yl)acetamide | 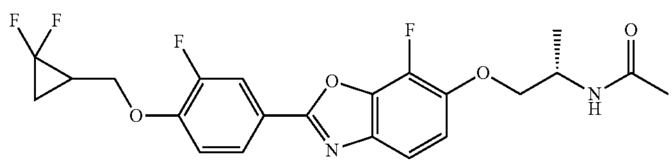 | 453.1 |
| 81 | optically active form of N-((2S)-1-((2-(4-((2,2-difluorocyclopropyl)methoxy)-3-fluorophenyl)-7-fluoro-1,3-benzoxazol-6-yl)oxy)propan-2-yl)acetamide | 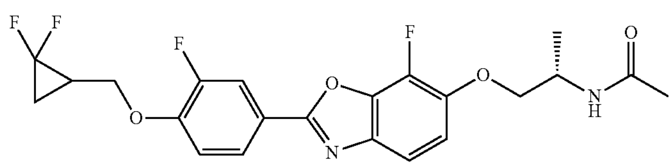 [SMILES: CC(=O)N[C@@H](C)COc1ccc2nc(-c3ccc(OCC4CC4(F)F)c(F)c3)oc2c1F] | 453.1 |
| 82 | N-((2S)-1-((2-(4-(cyclopropylmethoxy)-2,3-difluorophenyl)[1,3]oxazolo[4,5-c]pyridin-6-yl)oxy)propan-2-yl)acetamide | 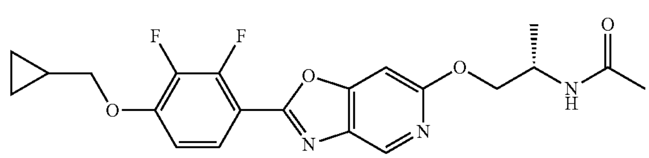 | 440.0 |
| 83 | N-((2S)-1-((2-(4-(cyclopropylmethoxy)phenyl)[1,3]thiazolo[4,5-c]pyridin-6-yl)oxy)propan-2-yl)acetamide | 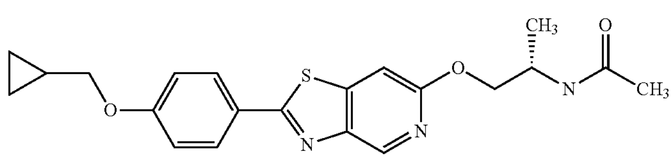 [SMILES: CC(=O)N[C@@H](C)COc1cc2sc(-c3ccc(OCC4CC4)cc3)nc2cn1] | 398.2 |
| 84 | N-((2S)-1-((2-(3-fluoro-4-((1-fluorocyclopropyl)methoxy)phenyl)[1,3]oxazolo[4,5-c]pyridin-6-yl)oxy)propan-2-yl)acetamide | 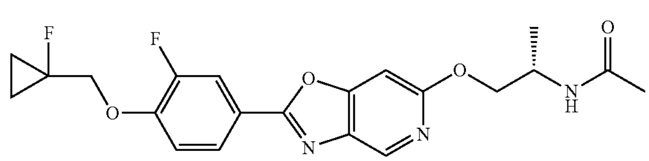 | 418.1 |

TABLE 11-continued

| Example | IUPAC name | Structure | MS |
|---|---|---|---|
| 85 | N-((2S)-1-((2-(4-((1-fluorocyclopropyl)methoxy)phenyl)[1,3]oxazolo[4,5-c]pyridin-6-yl)oxy)propan-2-yl)acetamide | 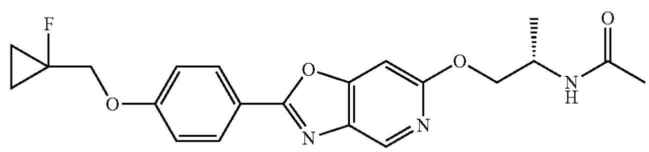 [SMILES: CC(=O)N[C@@H](C)COc1cc2oc(-c3ccc(OCC4(F)CC4)cc3)nc2cn1] | 400.1 |
| 86 | N-((2S)-1-((2-(4-((2,2-difluorocyclopropyl)methoxy)-3,5-difluorophenyl)[1,3]oxazolo[4,5-c]pyridin-6-yl)oxy)propan-2-yl)acetamide | 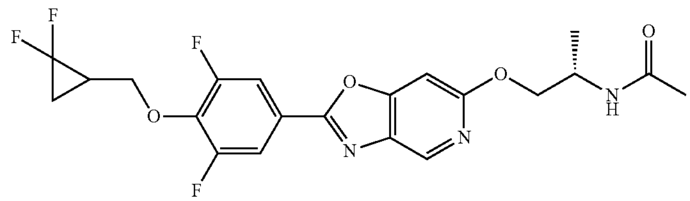 [SMILES: CC(=O)N[C@@H](C)COc1cc2oc(-c3cc(F)c(OCC4CC4(F)F)c(F)c3)nc2cn1] | 454.1 |
| 87 | N-((2S)-1-((2-(3,5-difluoro-4-((1-fluorocyclopropyl)methoxy)phenyl)[1,3]oxazolo[4,5-c]pyridin-6-yl)oxy)propan-2-yl)acetamide | 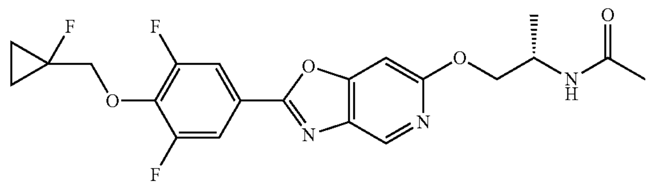 [SMILES: CC(=O)N[C@@H](C)COc1cc2oc(-c3cc(F)c(OCC4(F)CC4)c(F)c3)nc2cn1] | 436.1 |

TABLE 12

| Example | IUPAC name | Structure | MS |
|---|---|---|---|
| 88 | N-((2S)-1-((2-(4-((2,2-difluorocyclopropyl)methoxy)-2,3-difluorophenyl)[1,3]oxazolo[4,5-c]pyridin-6-yl)oxy)propan-2-yl)acetamide | 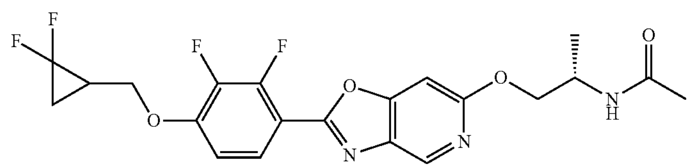 [SMILES: CC(=O)N[C@@H](C)COc1cc2oc(-c3ccc(OCC4CC4(F)F)c(F)c3F)nc2cn1] | 454.0 |
| 89 | N-((2S)-3-((2-(4-(cyclopropylmethoxy)-3-fluorophenyl)-1,3-benzoxazol-6-yl)oxy)butan-2-yl)acetamide | 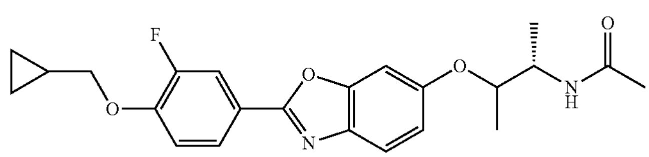 [SMILES: CC(=O)N[C@@H](C)C(C)Oc1ccc2nc(-c3ccc(OCC4CC4)c(F)c3)oc2c1] | 413.2 |
| 90 | N-((2S)-1-((2-(4-ethoxy-2,3,5-trifluorophenyl)[1,3]oxazolo[4,5-c]pyridin-6-yl)oxy)propan-2-yl)acetamide | 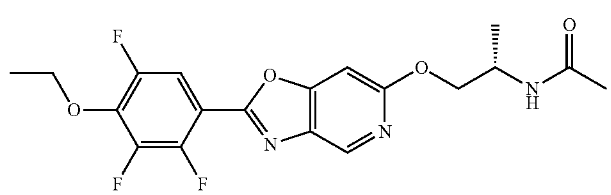 [SMILES: CCOc1c(F)cc(-c2nc3cnc(OC[C@H](C)NC(C)=O)cc3o2)c(F)c1F] | 410.2 |
| 91 | N-((2S)-1-((2-(4-ethoxy-3,5-difluorophenyl)-1,3-benzoxazol-6-yl)oxy)propan-2-yl)acetamide | 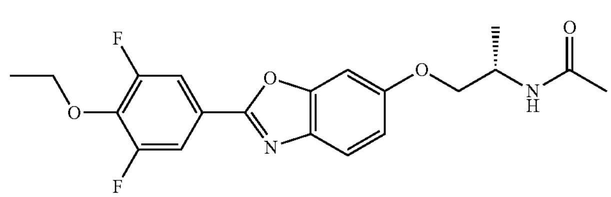 [SMILES: CCOc1c(F)cc(-c2nc3ccc(OC[C@H](C)NC(C)=O)cc3o2)cc1F] | 391.1 |

TABLE 12-continued

| Example | IUPAC name | Structure | MS |
|---|---|---|---|
| 92 | N-((2S)-1-((2-(4-ethoxy-2,3,5-trifluorophenyl)-1,3-benzoxazol-6-yl)oxy)propan-2-yl)acetamide | 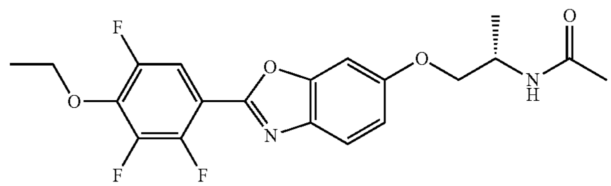 [SMILES: CCOc1c(F)cc(-c2nc3ccc(OC[C@H](C)NC(C)=O)cc3o2)c(F)c1F] | 409.1 |
| 93 | N-((2S)-1-((2-(4-ethoxy-3-fluoro-5-methoxyphenyl)-1,3-benzoxazol-6-yl)oxy)propan-2-yl)acetamide | 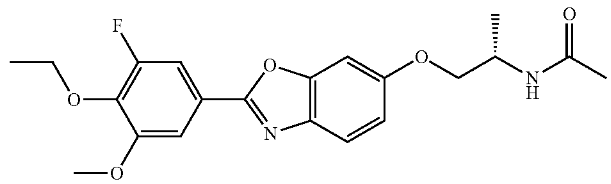 [SMILES: CCOc1c(F)cc(-c2nc3ccc(OC[C@H](C)NC(C)=O)cc3o2)cc1OC] | 403.1 |
| 94 | N-((2S)-1-((2-(3,5-difluoro-4-(2,2,2-trifluoroethoxy)phenyl)-1,3-benzoxazol-6-yl)oxy)propan-2-yl)acetamide | 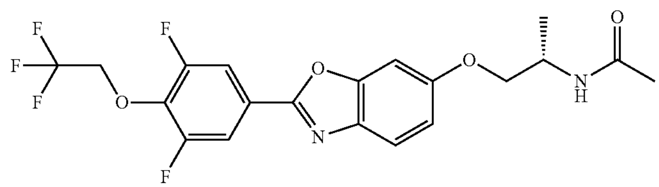 [SMILES: CC(=O)N[C@@H](C)COc1ccc2nc(-c3cc(F)c(OCC(F)(F)F)c(F)c3)oc2c1] | 445.1 |
| 95 | N-((2S)-1-((2-(3-chloro-4-ethoxy-5-fluorophenyl)-1,3-benzoxazol-6-yl)oxy)propan-2-yl)acetamide | 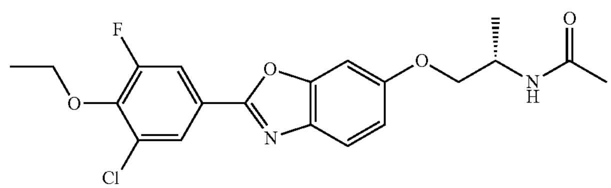 [SMILES: CCOc1c(F)cc(-c2nc3ccc(OC[C@H](C)NC(C)=O)cc3o2)cc1Cl] | 407.2 |
| 96 | N-((2S)-1-((2-(3-bromo-4-ethoxy-5-fluorophenyl)-1,3-benzoxazol-6-yl)oxy)propan-2-yl)acetamide | 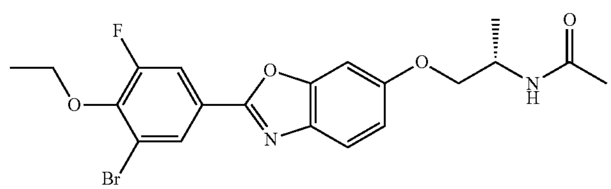 [SMILES: CCOc1c(F)cc(-c2nc3ccc(OC[C@H](C)NC(C)=O)cc3o2)cc1Br] | 451.1 |

TABLE 13

| Example | IUPAC name | Structure | MS |
|---|---|---|---|
| 97 | N-((2S)-1-((2-(3-acetyl-4-ethoxy-5-fluorophenyl)-1,3-benzoxazol-6-yl)oxy)propan-2-yl)acetamide | 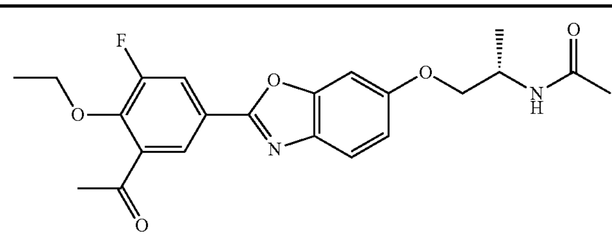 | 415.1 |
| 98 | N-((2S)-1-((2-(4-ethoxy-3-fluoro-5-(1-hydroxyethyl)phenyl)-1,3-benzoxazol-6-yl)oxy)propan-2-yl)acetamide | 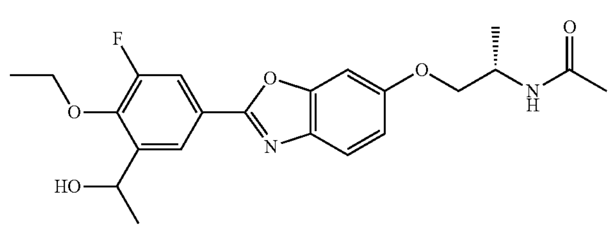 [SMILES: CCOc1c(F)cc(-c2nc3ccc(OC[C@H](C)NC(C)=O)cc3o2)cc1C(C)O] | 417.2 |

TABLE 13-continued

| Example | IUPAC name | Structure | MS |
|---|---|---|---|
| 99 | N-((2S)-1-((2-(4-(cyanomethoxy)-3,5-difluorophenyl)-1,3-benzoxazol-6-yl)oxy)propan-2-yl)acetamide | 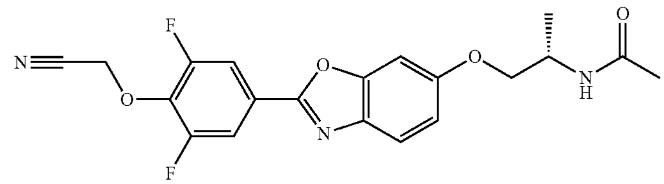 [SMILES: CC(=O)N[C@@H](C)COc1ccc2nc(-c3cc(F)c(OCC#N)c(F)c3)oc2c1] | 402.1 |
| 100 | N-((2S)-1-((2-(4-(cyclopropylmethoxy)-3-fluoro-5-methoxyphenyl)-1,3-benzoxazol-6-yl)oxy)propan-2-yl)acetamide | 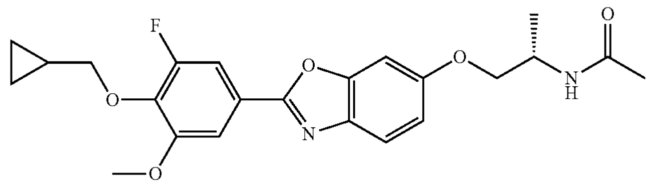 [SMILES: COc1cc(-c2nc3ccc(OC[C@H](C)NC(C)=O)cc3o2)cc(F)c1OCC1CC1] | 429.2 |
| 101 | 1-((2S)-1-((2-(4-(cyclopropylmethoxy)-2,5-difluorophenyl)[1,3]oxazolo[4,5-c]pyridin-6-yl)oxy)propan-2-yl)urea | 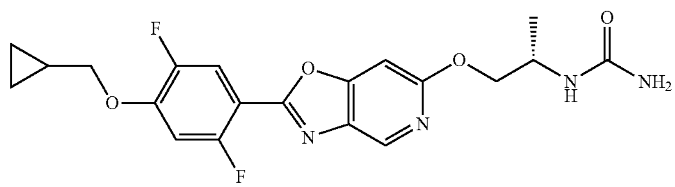 [SMILES: C[C@@H](COc1cc2oc(-c3cc(F)c(OCC4CC4)cc3F)nc2cn1)NC(N)=O] | 419.2 |
| 102 | N-((2S)-1-((2-(6-chloro-5-(cyclopropylmethoxy)pyridin-2-yl)[1,3]oxazolo[4,5-c]pyridin-6-yl)oxy)propan-2-yl)acetamide | 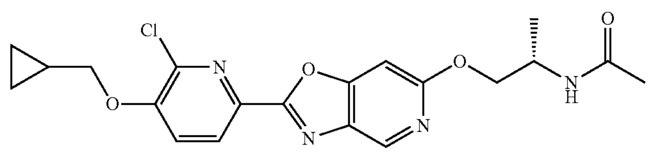 | 417.3 |
| 103 | 1-((2S)-1-((2-(4-(cyclopropylmethoxy)-3-fluoro-5-methoxyphenyl)[1,3]oxazolo[4,5-c]pyridin-6-yl)oxy)propan-2-yl)urea | 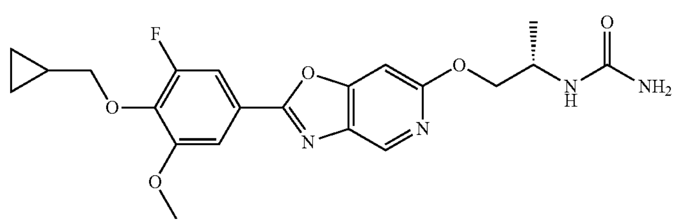 [SMILES: COc1cc(-c2nc3cnc(OC[C@H](C)NC(N)=O)cc3o2)cc(F)c1OCC1CC1] | 431.4 |
| 104 | N-((2S)-1-((2-(3-chloro-4-ethoxy-5-fluorophenyl)[1,3]oxazolo[4,5-c]pyridin-6-yl)oxy)propan-2-yl)acetamide | 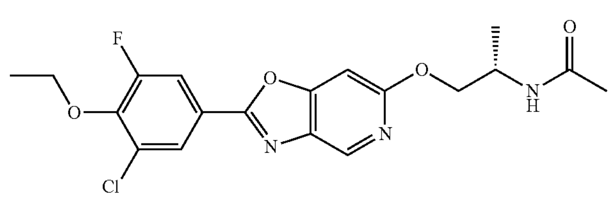 [SMILES: CCOc1c(F)cc(-c2nc3cnc(OC[C@H](C)NC(C)=O)cc3o2)cc1Cl] | 408.1 |
| 105 | N-((2S)-1-((2-(4-(((1R)-2,2-difluorocyclopropyl)methoxy)-3-methoxyphenyl)[1,3]oxazolo[4,5-c]pyridin-6-yl)oxy)propan-2-yl)acetamide | 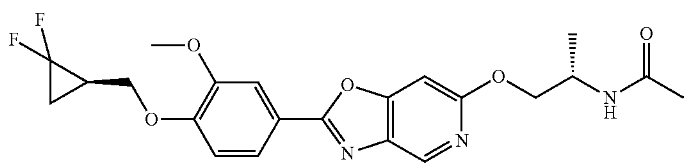 [SMILES: COc1cc(-c2nc3cnc(OC[C@H](C)NC(C)=O)cc3o2)ccc1OC[C@H]1CC1(F)F] | 448.3 |

TABLE 14

| Example | IUPAC name | Structure | MS |
|---|---|---|---|
| 106 | N-((2S)-1-((2-(4-(((1S)-2,2-difluorocyclopropyl)methoxy)-3-methoxyphenyl)[1,3]oxazolo[4,5-c]pyridin-6-yl)oxy)propan-2-yl)acetamide | 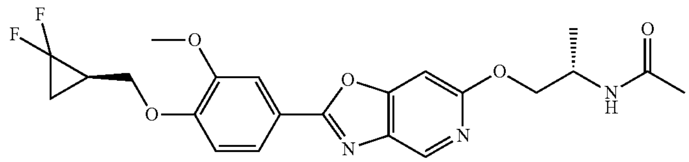 [SMILES: COc1cc(-c2nc3cnc(OC[C@H](C)NC(C)=O)cc3o2)ccc1OC[C@H]1CC1(F)F] | 448.3 |
| 107 | N-((2S)-1-((2-(5-(cyclopropylmethoxy)-6-fluoropyridin-2-yl)[1,3]oxazolo[4,5-c]pyridin-6-yl)oxy)propan-2-yl)acetamide | 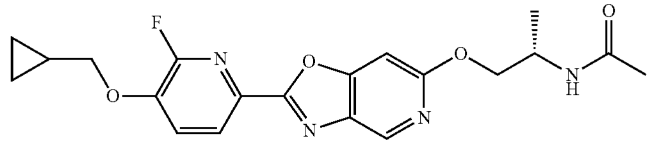 [SMILES: CC(=O)N[C@@H](C)COc1cc2oc(-c3ccc(OCC4CC4)c(F)n3)nc2cn1] | 401.2 |
| 108 | N-((2S)-1-((2-(4-(((1R)-2,2-difluorocyclopropyl)methoxy)-3-fluoro-5-methoxyphenyl)[1,3]oxazolo[4,5-c]pyridin-6-yl)oxy)propan-2-yl)acetamide | 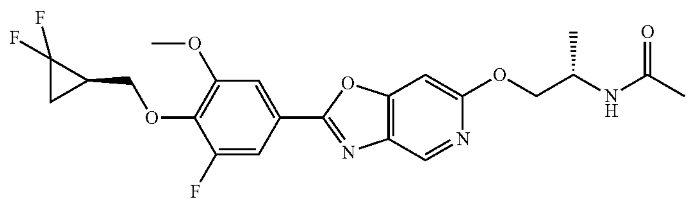 [SMILES: COc1cc(-c2nc3cnc(OC[C@H](C)NC(C)=O)cc3o2)cc(F)c1OC[C@H]1CC1(F)F] | 466.1 |
| 109 | N-((2S)-1-((2-(4-chloro-5-(cyclopropylmethoxy)pyridin-2-yl)[1,3]oxazolo[4,5-c]pyridin-6-yl)oxy)propan-2-yl)acetamide | 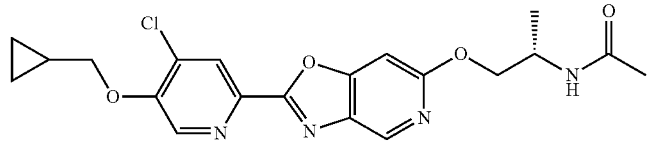 | 417.2 |
| 110 | 1-((2S)-1-((2-(4-(((1R)-2,2-difluorocyclopropyl)methoxy)-3-fluoro-5-methoxyphenyl)[1,3]oxazolo[4,5-c]pyridin-6-yl)oxy)propan-2-yl)urea | 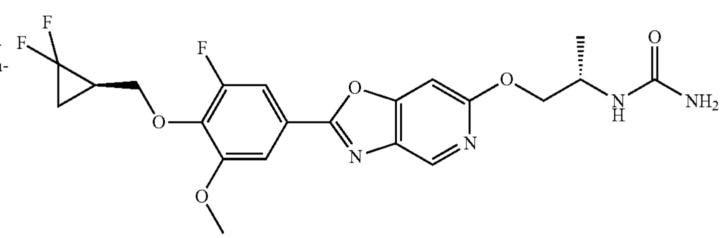 | 467.3 |
| 111 | N-((2S)-1-((2-(4-(cyclopropylmethoxy)-3-(trifluoromethyl)phenyl)[1,3]oxazolo[4,5-c]pyridin-6-yl)oxy)propan-2-yl)acetamide | 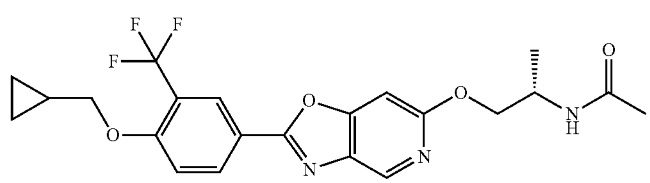 [SMILES: CC(=O)N[C@@H](C)COc1cc2oc(-c3ccc(OCC4CC4)c(C(F)(F)F)c3)nc2cn1] | 450.1 |
| 112 | N-((2S)-1-((2-(5-(((1R)-2,2-difluorocyclopropyl)methoxy)pyridin-2-yl)[1,3]oxazolo[4,5-c]pyridin-6-yl)oxy)propan-2-yl)acetamide | 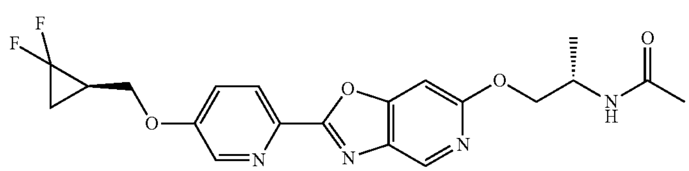 [SMILES: CC(=O)N[C@@H](C)COc1cc2oc(-c3ccc(OC[C@H]4CC4(F)F)cn3)nc2cn1] | 419.2 |
| 113 | N-((2S)-1-((2-(4-(cyclopropylmethoxy)-2-methoxyphenyl)[1,3]oxazolo[4,5-c]pyridin-6-yl)oxy)propan-2-yl)acetamide | 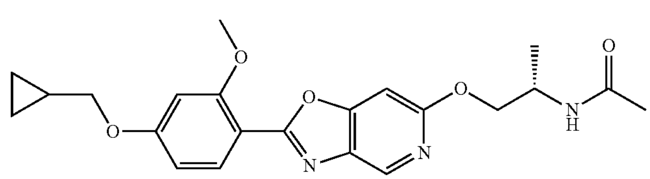 [SMILES: COc1cc(OCC2CC2)ccc1-c1nc2cnc(OC[C@H](C)NC(C)=O)cc2o1] | 412.3 |

TABLE 14-continued

| Example | IUPAC name | Structure | MS |
|---|---|---|---|
| 114 | N-((2S)-1-((2-(4-(cyclopropylmethoxy)-3-(difluoromethoxy)phenyl)[1,3]oxazolo[4,5-c]pyridin-6-yl)oxy)propan-2-yl)acetamide | 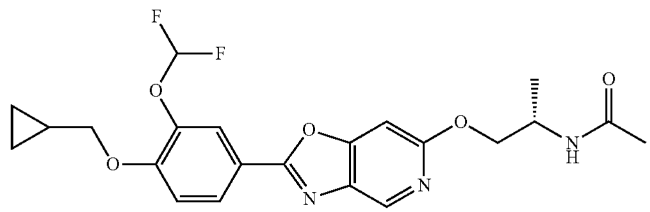 [SMILES: CC(=O)N[C@@H](C)COc1cc2oc(-c3ccc(OCC4CC4)c(OC(F)F)c3)nc2cn1] | 448.1 |

TABLE 15

| Example | IUPAC name | Structure | MS |
|---|---|---|---|
| 115 | N-((2S)-1-((2-(4-((2,2-difluorocyclopropyl)methoxy)-3-(difluoromethoxy)phenyl)[1,3]oxazolo[4,5-c]pyridin-6-yl)oxy)propan-2-yl)acetamide | 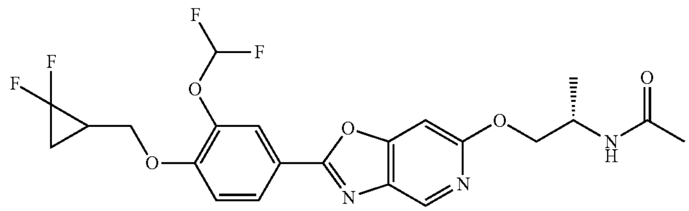 [SMILES: CC(=O)N[C@@H](C)COc1cc2oc(-c3ccc(OCC4CC4(F)F)c(OC(F)F)c3)nc2cn1] | 484.1 |
| 116 | N-((2S)-1-((2-(4-(cyclopropylmethoxy)-3-(2,2,2-trifluoroethoxy)phenyl)[1,3]oxazolo[4,5-c]pyridin-6-yl)oxy)propan-2-yl)acetamide | 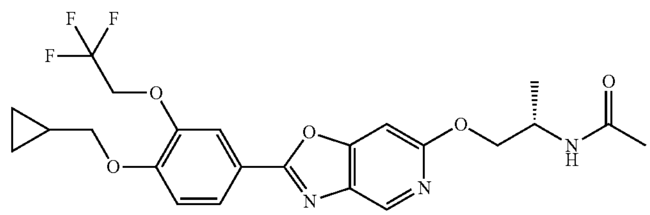 [SMILES: CC(=O)N[C@@H](C)COc1cc2oc(-c3ccc(OCC4CC4)c(OCC(F)(F)F)c3)nc2cn1] | 480.2 |
| 117 | N-((2S)-1-((2-(4-(cyclopropylmethoxy)-2-methylphenyl)[1,3]oxazolo[4,5-c]pyridin-6-yl)oxy)propan-2-yl)acetamide | 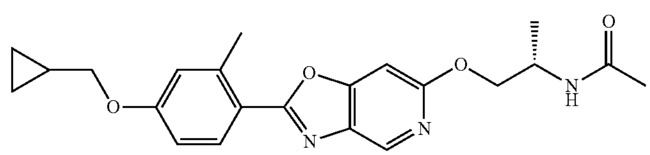 [SMILES: CC(=O)N[C@@H](C)COc1cc2oc(-c3ccc(OCC4CC4)cc3C)nc2cn1] | 396.2 |
| 118 | N-((2S)-1-((2-(5-(cyclopropylmethoxy)pyrazin-2-yl)[1,3]oxazolo[4,5-c]pyridin-6-yl)oxy)propan-2-yl)acetamide | 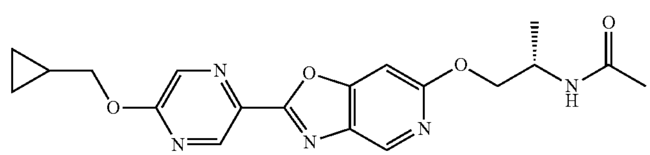 [SMILES: CC(=O)N[C@@H](C)COc1cc2oc(-c3cnc(OCC4CC4)cn3)nc2cn1] | 384.2 |
| 119 | N-((2S)-1-((2-(4-(cyclopropylmethoxy)-3-(trifluoromethoxy)phenyl)-1,3-benzoxazol-6-yl)oxy)propan-2-yl)acetamide | 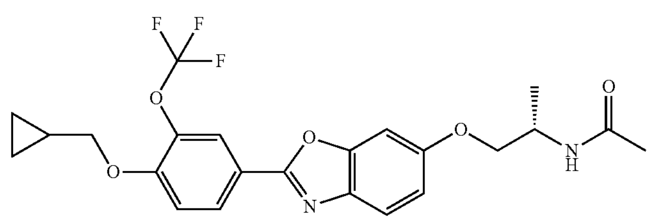 [SMILES: CC(=O)N[C@@H](C)COc1ccc2nc(-c3ccc(OCC4CC4)c(OC(F)(F)F)c3)oc2c1] | 465.2 |
| 120 | N-((2S)-1-((2-(5-(cyclopropylmethoxy)-3-methylpyridin-2-yl)[1,3]oxazolo[4,5-c]pyridin-6-yl)oxy)propan-2-yl)acetamide | 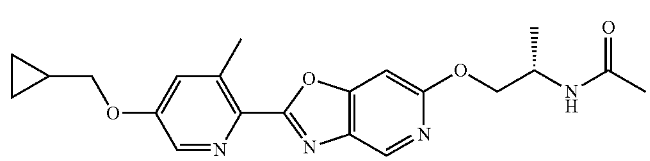 | 397.3 |

TABLE 15-continued

| Example | IUPAC name | Structure | MS |
|---|---|---|---|
| 121 | N-((2S)-1-((2-(6-(cyclopropylmethoxy)pyridazin-3-yl)[1,3]oxazolo[4,5-c]pyridin-6-yl)oxy)propan-2-yl)acetamide | 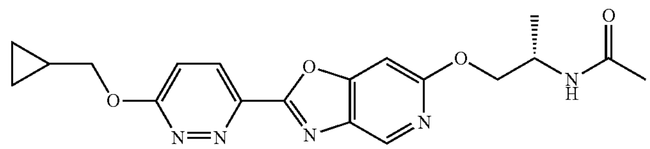 [SMILES: CC(=O)N[C@@H](C)COc1cc2oc(-c3ccc(OCC4CC4)nn3)nc2cn1] | 384.2 |
| 122 | N-((2S)-1-((2-(6-(cyclopropylmethoxy)-4-methylpyridin-3-yl)[1,3]oxazolo[4,5-c]pyridin-6-yl)oxy)propan-2-yl)acetamide | 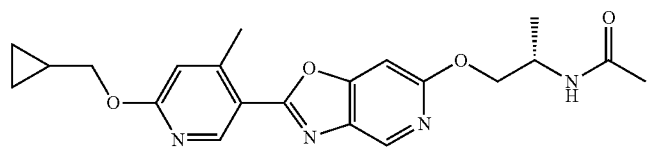 [SMILES: CC(=O)N[C@@H](C)COc1cc2oc(-c3cnc(OCC4CC4)cc3C)nc2cn1] | 397.4 |
| 123 | N-((2S)-1-((2-(4-(((1R)-2,2-difluorocyclopropyl)methoxy)phenyl)[1,3]oxazolo[4,5-c]pyridin-6-yl)oxy)propan-2-yl)-1H-pyrazole-4-carboxamide | 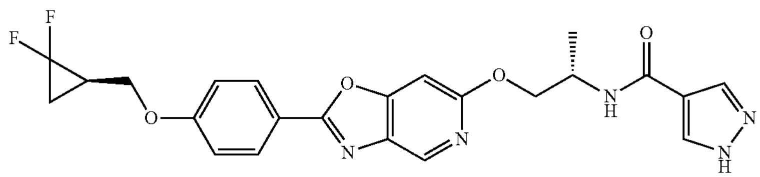 [SMILES: C[C@@H](COc1cc2oc(-c3ccc(OC[C@H]4CC4(F)F)cc3)nc2cn1)NC(=O)c1cn[nH]c1] | 470.2 |

TABLE 16

| Example | IUPAC name | Structure | MS |
|---|---|---|---|
| 124 | N-((2S)-1-((2-(4-((2,2-difluorocyclopropyl)methoxy)phenyl)[1,3]oxazolo[5,4-d]pyrimidin-5-yl)oxy)propan-2-yl)acetamide | 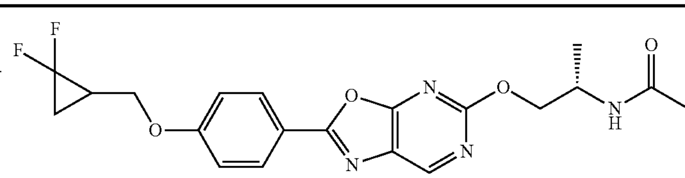 | 419.2 |
| 125 | N-((2S)-1-((2-(4-(cyclopropylmethoxy)-2-fluorophenyl)[1,3]oxazolo[4,5-c]pyridin-6-yl)oxy)propan-2-yl)acetamide | 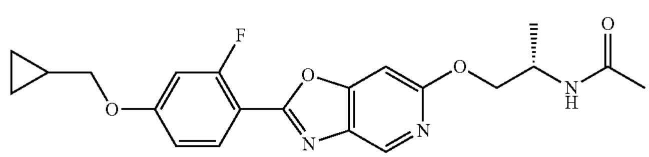 | 400.1 |
| 126 | N-((2S)-1-((2-(2-chloro-4-(cyclopropylmethoxy)phenyl)[1,3]oxazolo[4,5-c]pyridin-6-yl)oxy)propan-2-yl)acetamide | 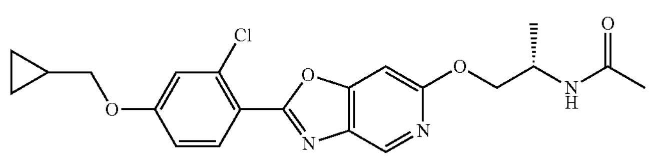 | 416.2 |
| 127 | N-((2S)-1-((2-(6-(cyclopropylmethoxy)-2-methylpyridin-3-yl)[1,3]oxazolo[4,5-c]pyridin-6-yl)oxy)propan-2-yl)acetamide | 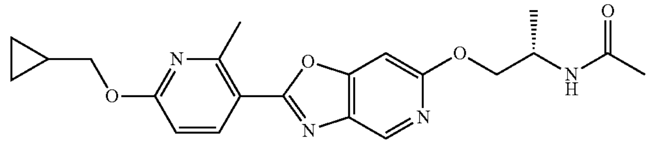 [SMILES: CC(=O)N[C@@H](C)COc1cc2oc(-c3ccc(OCC4CC4)nc3C)nc2cn1] | 397.1 |
| 128 | optically active form of N-((2S)-1-((2-(4-((2,2-difluorocyclopropyl)methoxy)-2,5-difluorophenyl)[1,3]oxazolo[4,5-c]pyridin-6-yl)oxy)propan-2-yl)acetamide | 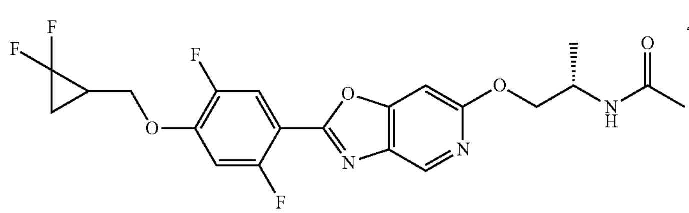 | 454.1 |

TABLE 16-continued

| Example | IUPAC name | Structure | MS |
|---|---|---|---|
| 129 | optically active form of N-((2S)-1-((2-(4-((2,2-difluorocyclopropyl)methoxy)-2,5-difluorophenyl)[1,3]oxazolo[4,5-c]pyridin-6-yl)oxy)propan-2-yl)acetamide | 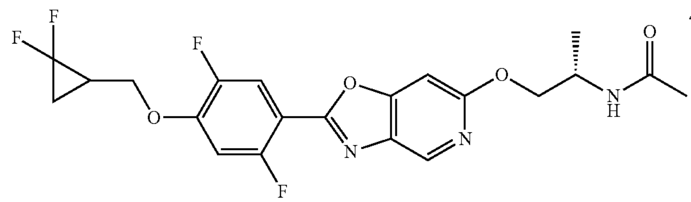 | 454.1 |
| 130 | optically active form of N-((2S)-1-((2-(4-((2,2-difluorocyclopropyl)methoxy)-3,5-difluorophenyl)[1,3]oxazolo[4,5-c]pyridin-6-yl)oxy)propan-2-yl)acetamide | 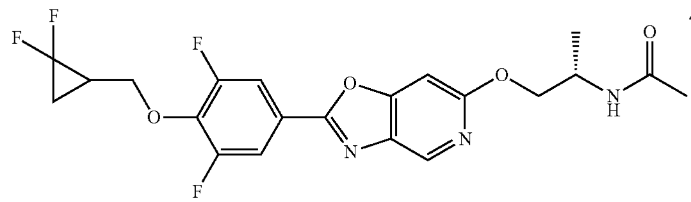 | 454.1 |
| 131 | optically active form of N-((2S)-1-((2-(4-((2,2-difluorocyclopropyl)methoxy)-3,5-difluorophenyl)[1,3]oxazolo[4,5-c]pyridin-6-yl)oxy)propan-2-yl)acetamide | 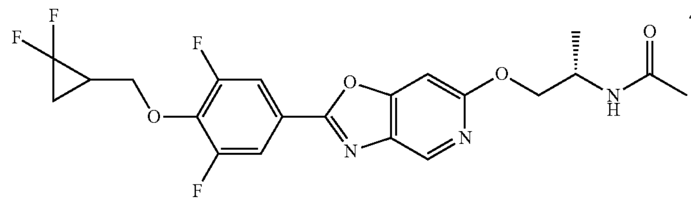 | 454.1 |
| 132 | N-((2S)-1-((2-(4-(cyclopropylmethoxy)-2-(trifluoromethyl)phenyl)[1,3]oxazolo[4,5-c]pyridin-6-yl)oxy)propan-2-yl)acetamide | 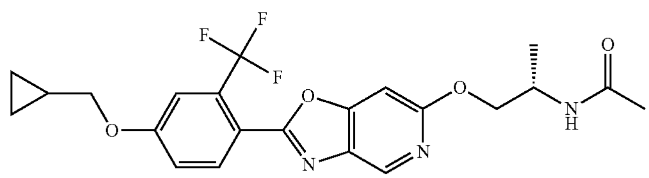 [SMILES: CC(=O)N[C@@H](C)COc1cc2oc(-c3ccc(OCC4CC4)cc3C(F)(F)F)nc2cn1] | 450.2 |

TABLE 17

| Example | IUPAC name | Structure | MS |
|---|---|---|---|
| 133 | N-((2S)-1-((2-(6-(cyclopropylmethoxy)-5-methylpyridin-3-yl)[1,3]oxazolo[4,5-c]pyridin-6-yl)oxy)propan-2-yl)acetamide | 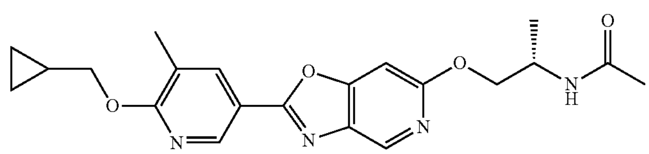 [SMILES: CC(=O)N[C@@H](C)COc1cc2oc(-c3cnc(OCC4CC4)c(C)c3)nc2cn1] | 397.1 |
| 134 | N-((2S)-1-((2-(6-((2,2-difluorocyclopropyl)methoxy)-5-methylpyridin-3-yl)[1,3]oxazolo[4,5-c]pyridin-6-yl)oxy)propan-2-yl)acetamide | 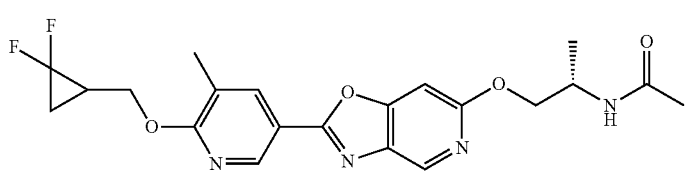 [SMILES: CC(=O)N[C@@H](C)COc1cc2oc(-c3cnc(OCC4CC4(F)F)c(C)c3)nc2cn1] | 433.1 |
| 135 | N-((2S)-1-((2-(4-(cyclopropylmethoxy)-2,6-dimethylphenyl)[1,3]oxazolo[4,5-c]pyridin-6-yl)oxy)propan-2-yl)acetamide | 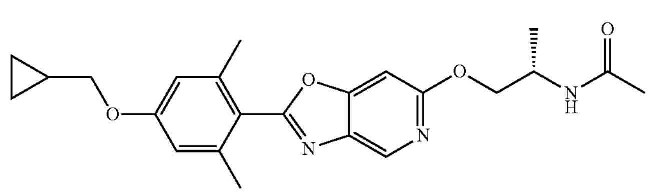 [SMILES: CC(=O)N[C@@H](C)COc1cc2oc(-c3c(C)cc(OCC4CC4)cc3C)nc2cn1] | 410.2 |

TABLE 17-continued

| Example | IUPAC name | Structure | MS |
|---|---|---|---|
| 136 | optically active form of N-((2S)-1-((2-(4-((2,2-difluorocyclopropyl)methoxy)phenyl)[1,3]oxazolo[5,4-d]pyrimidin-5-yl)oxy)propan-2-yl)acetamide | 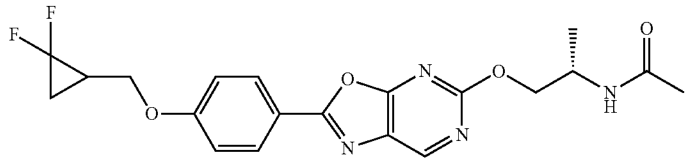 [SMILES: CC(=O)N[C@@H](C)COc1ncc2nc(-c3ccc(OCC4CC4(F)F)cc3)oc2n1] | 419.2 |
| 137 | optically active form of N-((2S)-1-((2-(4-((2,2-difluorocyclopropyl)methoxy)phenyl)[1,3]oxazolo[5,4-d]pyrimidin-5-yl)oxy)propan-2-yl)acetamide | 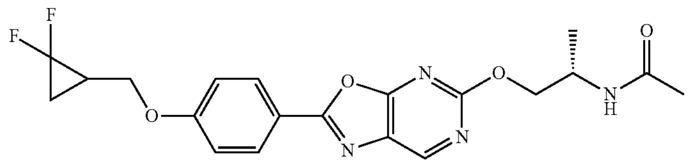 | 419.2 |
| 138 | N-((2S)-1-((2-(6-(((1R)-2,2-difluorocyclopropyl)methoxy)-5-methoxypyridin-3-yl)[1,3]oxazolo[4,5-c]pyridin-6-yl)oxy)propan-2-yl)acetamide | 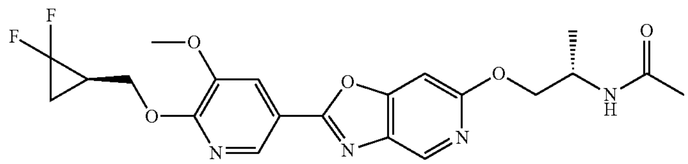 [SMILES: COc1cc(-c2nc3cnc(OC[C@H](C)NC(C)=O)cc3o2)cnc1OC[C@H]1CC1(F)F] | 449.2 |
| 139 | N-((2S)-1-((2-(5-(((1R)-2,2-difluorocyclopropyl)methoxy)-3-fluoropyridin-2-yl)[1,3]oxazolo[4,5-c]pyridin-6-yl)oxy)propan-2-yl)acetamide | 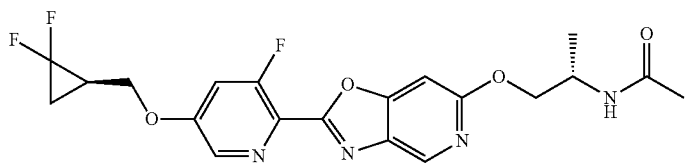 [SMILES: CC(=O)N[C@@H](C)COc1cc2oc(-c3ncc(OC[C@H]4CC4(F)F)cc3F)nc2cn1] | 437.2 |
| 140 | N-((2S)-1-((2-(4-(((1R)-2,2-difluorocyclopropyl)methoxy)phenyl)-7-fluoro[1,3]oxazolo[4,5-c]pyridin-6-yl)oxy)propan-2-yl)acetamide | 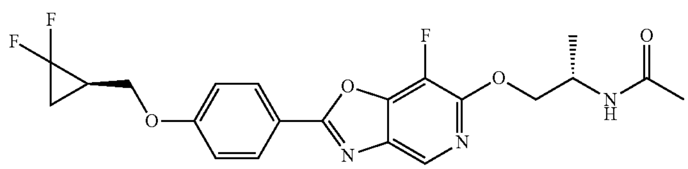 [SMILES: CC(=O)N[C@@H](C)COc1ncc2nc(-c3ccc(OC[C@H]4CC4(F)F)cc3)oc2c1F] | 436.1 |
| 141 | N-((2S)-1-((2-(5-(((1R)-2,2-difluorocyclopropyl)methoxy)-4-methylpyridin-2-yl)[1,3]oxazolo[4,5-c]pyridin-6-yl)oxy)propan-2-yl)acetamide | 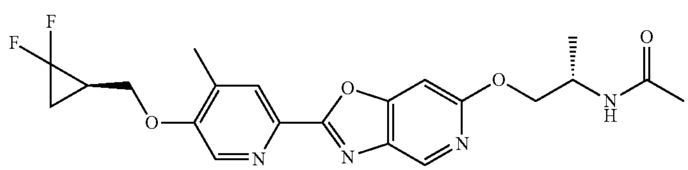 [SMILES: CC(=O)N[C@@H](C)COc1cc2oc(-c3cc(C)c(OC[C@H]4CC4(F)F)cn3)nc2cn1] | 433.1 |

TABLE 18

| Example | IUPAC name | Structure | MS |
|---|---|---|---|
| 142 | N-((2S)-1-((2-(4-(cyclopropylmethoxy)-2-ethylphenyl)[1,3]oxazolo[4,5-c]pyridin-6-yl)oxy)propan-2-yl)acetamide | 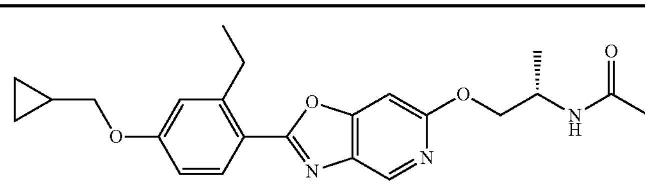 | 410.2 |
| 143 | N-((2S)-1-((2-(5-(((1R)-2,2-difluorocyclopropyl)methoxy)-3-fluoropyridin-2-yl)[1,3]oxazolo[5,4-d]pyrimidin-5-yl)oxy)propan-2-yl)acetamide | 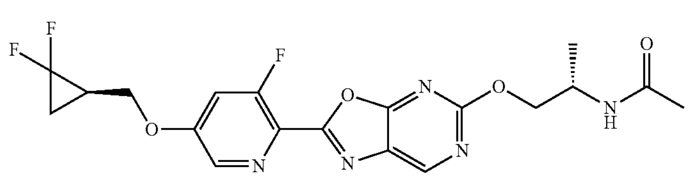 [SMILES: CC(=O)N[C@@H](C)COc1ncc2nc(-c3ncc(OC[C@H]4CC4(F)F)cc3F)oc2n1] | 438.1 |

TABLE 18-continued

| Example | IUPAC name | Structure | MS |
|---|---|---|---|
| 144 | N-((2S)-1-((2-(5-(cyclopropylmethoxy)-3-fluoropyridin-2-yl[1,3]oxazolo[4,5-c]pyridin-6-yl)oxy)propan-2-yl)acetamide | 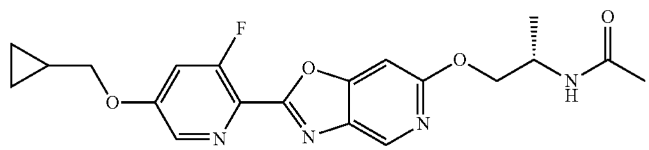 [SMILES: CC(=O)N[C@@H](C)COc1cc2oc(-c3ncc(OCC4CC4)cc3F)nc2cn1] | 401.2 |
| 145 | N-((2S)-1-((2-(3-chloro-5-(((1R)-2,2-difluorocyclopropyl)methoxy)pyridin-2-yl)[1,3]oxazolo[5,4-d]pyrimidin-5-yl)oxy)propan-2-yl)acetamide | 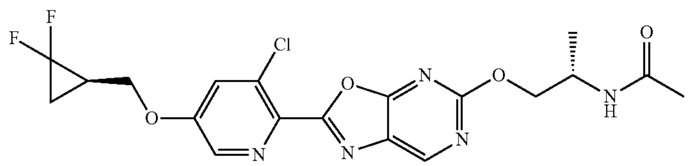 [SMILES: CC(=O)N[C@@H](C)COc1ncc2nc(-c3ncc(OC[C@H]4CC4(F)F)cc3Cl)oc2n1] | 454.1 |
| 146 | N-((2S)-1-((2-(4-(((1R)-2,2-difluorocyclopropyl)methoxy)phenyl[1,3]thiazolo[4,5-c]pyridin-6-yl)oxy)propan-2-yl)acetamide | 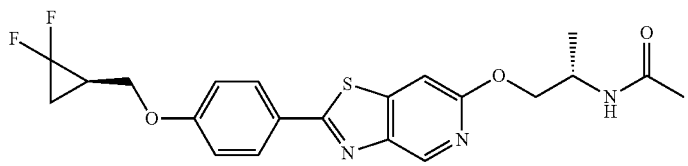 [SMILES: CC(=O)N[C@@H](C)COc1cc2sc(-c3ccc(OC[C@H]4CC4(F)F)cc3)nc2cn1] | 434.2 |
| 147 | N-((2S)-1-((2-(4-(cyclopropylmethoxy)-2-(2,2,2-trifluoroethoxy)phenyl)[1,3]oxazolo[4,5-c]pyridin-6-yl)oxy)propan-2-yl)acetamide | 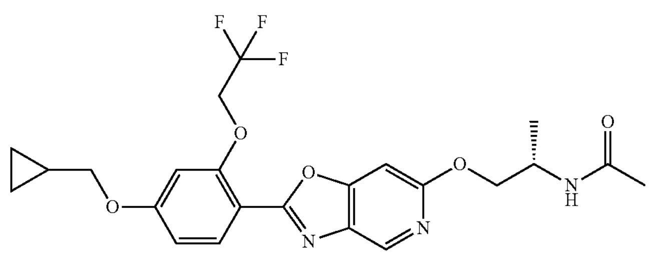 [SMILES: CC(=O)N[C@@H](C)COc1cc2oc(-c3ccc(OCC4CC4)cc3OCC(F)(F)F)nc2cn1] | 480.2 |
| 148 | N-((2S)-1-((2-(4-(((1R)-2,2-difluorocyclopropyl)methoxy)-2-(2,2,2-trifluoroethoxy)phenyl)[1,3]oxazolo[4,5-c]pyridin-6-yl)oxy)propan-2-yl)acetamide | 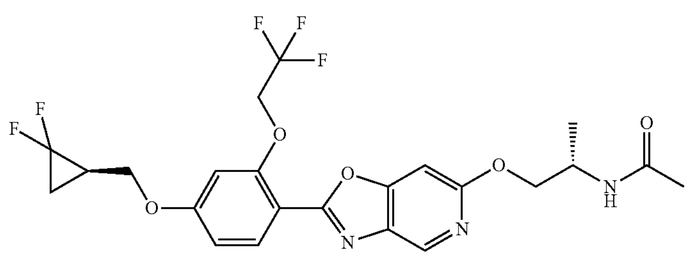 [SMILES: CC(=O)N[C@@H](C)COc1cc2oc(-c3ccc(OC[C@H]4CC4(F)F)cc3OCC(F)(F)F)nc2cn1] | 516.1 |
| 149 | N-((2S)-1-((2-(5-(((1R)-2,2-difluorocyclopropyl)methoxy)pyridin-2-yl)-7-fluoro[1,3]oxazolo[4,5-c]pyridin-6-yl)oxy)propan-2-yl)acetamide | 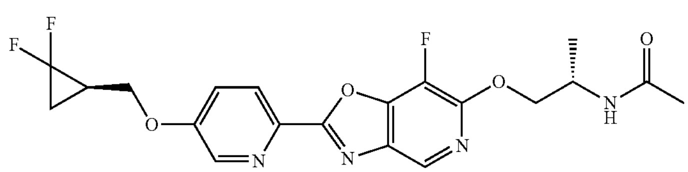 [SMILES: CC(=O)N[C@@H](C)COc1ncc2nc(-c3ccc(OC[C@H]4CC4(F)F)cn3)oc2c1F] | 437.2 |
| 150 | N-((2S)-1-((2-(4-(((1R)-2,2-difluorocyclopropyl)methoxy)-3-fluorophenyl)[1,3]oxazolo[5,4-d]pyrimidin-5-yl)oxy)propan-2-yl)acetamide | 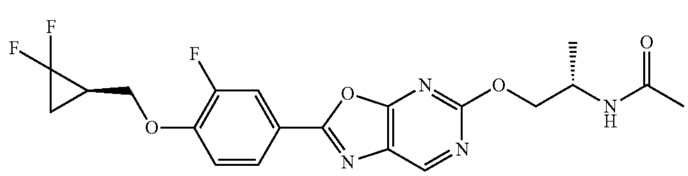 [SMILES: CC(=O)N[C@@H](C)COc1ncc2nc(-c3ccc(OC[C@H]4CC4(F)F)c(F)c3)oc2n1] | 437.2 |

TABLE 19

| Example | IUPAC name | Structure | MS |
|---|---|---|---|
| 151 | N-((2S)-1-((2-(4-((3,3-difluorocyclobutyl)methoxy)-3-fluorophenyl)[1,3]oxazolo[4,5-c]pyridin-6-yl)oxy)propan-2-yl)acetamide | 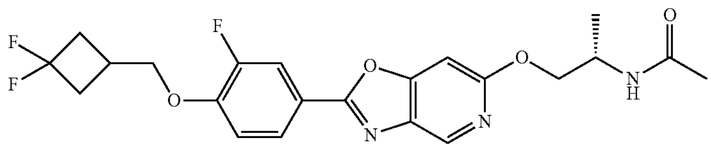 [SMILES: CC(=O)N[C@@H](C)COc1cc2oc(-c3ccc(OCC4CC(F)(F)C4)c(F)c3)nc2cn1] | 450.1 |
| 152 | N-((2S)-1-((2-(4-(2-(2,2-difluorocyclopropyl)ethoxy)-3-fluorophenyl)[1,3]oxazolo[4,5-c]pyridin-6-yl)oxy)propan-2-yl)acetamide | 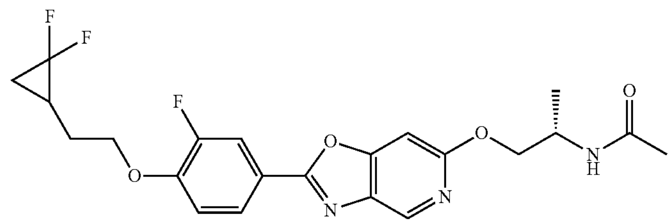 [SMILES: CC(=O)N[C@@H](C)COc1cc2oc(-c3ccc(OCCC4CC4(F)F)c(F)c3)nc2cn1] | 450.2 |
| 153 | N-((2S)-1-((2-(5-(((1R)-2,2-difluorocyclopropyl)methoxy)-3-fluoropyridin-2-yl)-7-fluoro[1,3]oxazolo[4,5-c]pyridin-6-yl)oxy)propan-2-yl)acetamide | 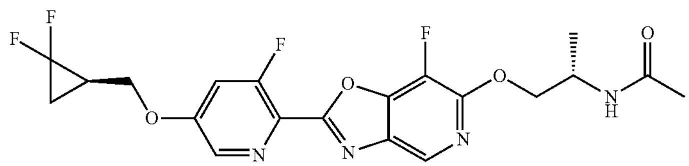 [SMILES: CC(=O)N[C@@H](C)COc1ncc2nc(-c3ncc(OC[C@H]4CC4(F)F)cc3F)oc2c1F] | 455.2 |
| 154 | N-((2S)-1-((2-(4-(cyclopropylmethoxy)phenyl)[1,3]oxazolo[5,4-c]pyridin-6-yl)oxy)propan-2-yl)acetamide | 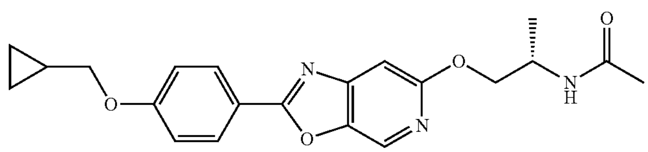 [SMILES: CC(=O)N[C@@H](C)COc1cc2nc(-c3ccc(OCC4CC4)cc3)oc2cn1] | 382.1 |
| 155 | N-((2S)-1-((2-(5-(cyclopropylmethoxy)pyrimidin-2-yl)[1,3]oxazolo[4,6-c]pyridin-6-yl)oxy)propan-2-yl)acetamide | 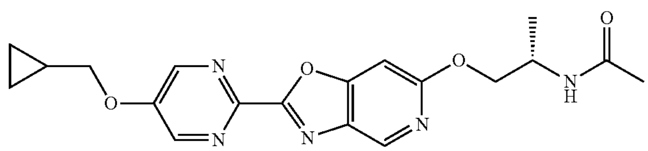 [SMILES: CC(=O)N[C@@H](C)COc1cc2oc(-c3ncc(OCC4CC4)cn3)nc2cn1] | 384.2 |
| 156 | N-((2S)-1-((2-(4-(cyclopropylmethoxy)-2-(difluoromethoxy)phenyl)[1,3]oxazolo[4,5-c]pyridin-6-yl)oxy)propan-2-yl)acetamide | 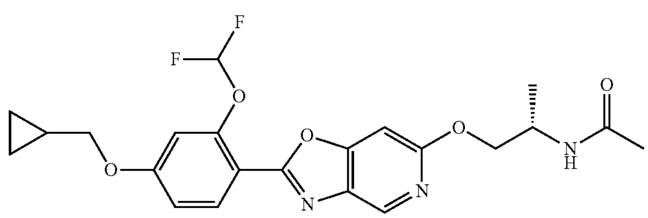 [SMILES: CC(=O)N[C@@H](C)COc1cc2oc(-c3ccc(OCC4CC4)cc3OC(F)F)nc2cn1] | 448.3 |
| 157 | N-((2S)-1-((2-(4-(((1R)-2,2-difluorocyclopropyl)methoxy)-2-difluoromethoxy)phenyl)[1,3]oxazolo[4,5-c]pyridin-6-yl)oxy)propan-2-yl)acetamide | 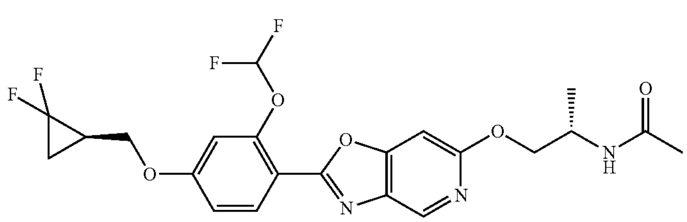 [SMILES: CC(=O)N[C@@H](C)COc1cc2oc(-c3ccc(OC[C@H]4CC4(F)F)cc3OC(F)F)nc2cn1] | 484.3 |
| 158 | N-((2S)-1-((2-(4-(3,3-difluorobutoxy)-3-fluorophenyl)[1,3]oxazolo[4,5-c]pyridin-6-yl)oxy)propan-2-yl)acetamide | 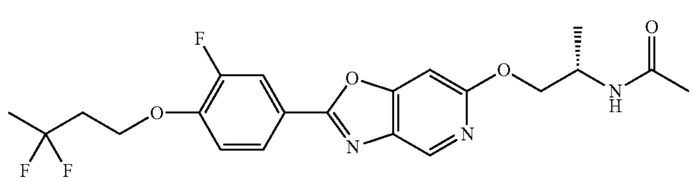 [SMILES: CC(=O)N[C@@H](C)COc1cc2oc(-c3ccc(OCCC(C)(F)F)c(F)c3)nc2cn1] | 438.2 |

TABLE 19-continued

| Example | IUPAC name | Structure | MS |
|---|---|---|---|
| 159 | N-((2S)-1-((2-(4-((2,2-difluoro-1-methylcyclopropyl)methoxy)-3-fluorophenyl)[1,3]oxazolo[4,5-c]pyridin-6-yl)oxy)propan-2-yl)acetamide | 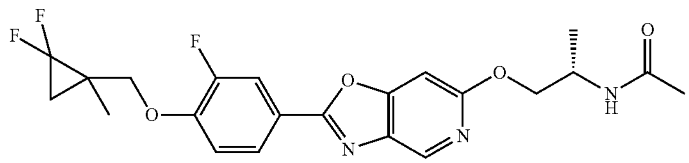 | 450.2 |

TABLE 20

| Example | IUPAC name | Structure | MS |
|---|---|---|---|
| 160 | N-((2S)-1-((2-(4-(2,2-difluorobutoxy)-3-fluorophenyl)[1,3]oxazolo[4,5-c]pyridin-6-yl)oxy)propan-2-yl)acetamide | 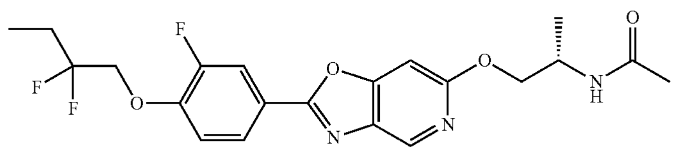 [SMILES: CCC(F)(F)COc1ccc(-c2nc3cnc(OC[C@H](C)NC(C)=O)cc3o2)cc1F] | 438.1 |
| 161 | optically active form of N-((2S)-1-((2-(4-((2,2-difluoro-1-methylcyclopropyl)methoxy)-3-fluorophenyl)[1,3]oxazolo[4,5-c]pyridin-6-yl)oxy)propan-2-yl)acetamide | 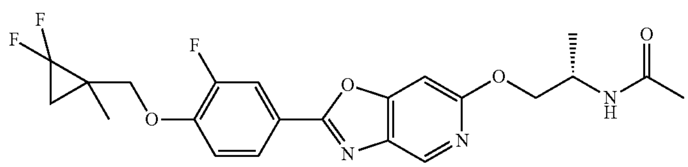 [SMILES: CC(=O)N[C@@H](C)COc1cc2oc(-c3ccc(OCC4(C)CC4(F)F)c(F)c3)nc2cn1] | 450.1 |
| 162 | optically active form of N-((2S)-1-((2-(4-((2,2-difluoro-1-methylcyclopropyl)methoxy)-3-fluorophenyl)[1,3]oxazolo[4,5-c]pyridin-6-yl)oxy)propan-3-yl)acetamide | 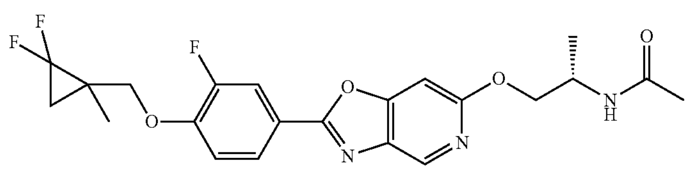 [SMILES: CC(=O)N[C@@H](C)COc1cc2oc(-c3ccc(OCC4(C)CC4(F)F)c(F)c3)nc2cn1] | 450.1 |
| 163 | N-((2S)-1-((2-(3-chloro-5-(((1R)-2,2-difluorocyclopropyl)methoxy)pyridin-2-yl)[1,3]oxazolo[4,5-c]pyridin-6-yl)oxy)propan-2-yl)acetamide | 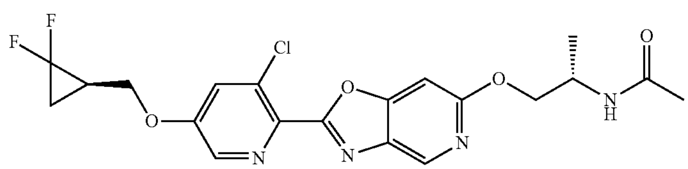 | 453.1 |
| 164 | N-((2S)-4-(2-(4-(((1R)-2,2-difluorocyclopropyl)methoxy)phenyl)[1,3]oxazolo[5,4-d]pyrimidin-5-yl)butan-2-yl)acetamide | 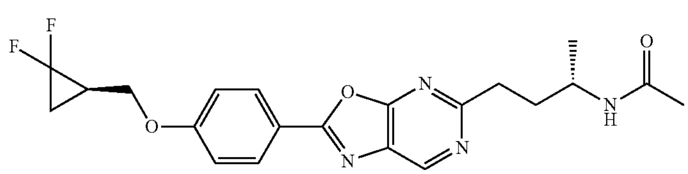 [SMILES: CC(=O)N[C@@H](C)CCc1ncc2nc(-c3ccc(OC[C@H]4CC4(F)F)cc3)oc2n1] | 417.1 |
| 165 | optically active form of N-((2S)-1-((2-(4-(2-(2,2-difluorocyclopropyl)ethoxy)-3-fluorophenyl)[1,3]oxazolo[4,5-c]pyridin-6-yl)oxy)propan-2-yl)acetamide | 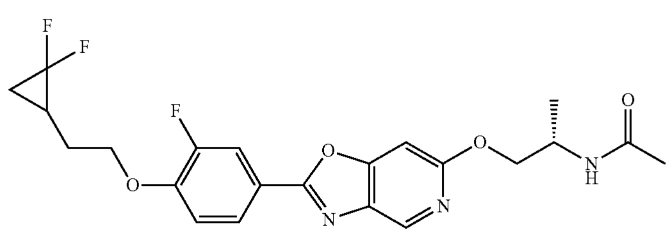 | 450.1 |

TABLE 20-continued

| Example | IUPAC name | Structure | MS |
|---|---|---|---|
| 166 | optically active form of N-((2S)-1-((2-(4-(2-(2,2-difluorocyclopropyl)ethoxy)-3-fluorophenyl)[1,3]oxazolo[4,5-c]pyridin-6-yl)oxy)propan-2-yl)acetamide | 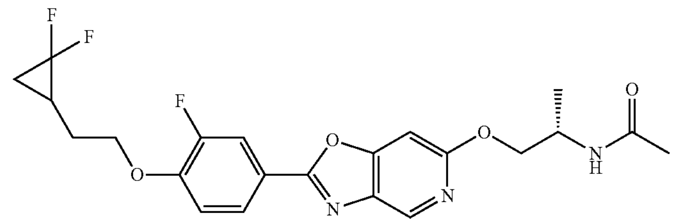 | 450.1 |
| 167 | N-((2S)-1-((2-(4-(((1R)-2,2-difluorocyclopropyl)methoxy)-3,5-difluorophenyl)[1,3]oxazolo[5,4-d]pyrimidin-5-yl)oxy)propan-2-yl)acetamide | 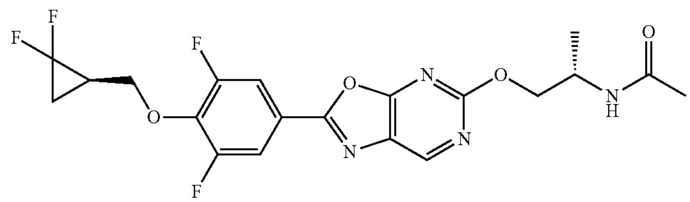 [SMILES: CC(=O)N[C@@H](C)COc1ncc2nc(-c3cc(F)c(OC[C@H]4CC4(F)F)c(F)c3)oc2n1] | 455.3 |
| 168 | N-((2S)-1-((2-(4-(2-(2,2-difluorocyclopropyl)ethoxy)phenyl)[1,3]oxazolo[4,5-c]pyridin-6-yl)oxy)propan-2-yl)acetamide | 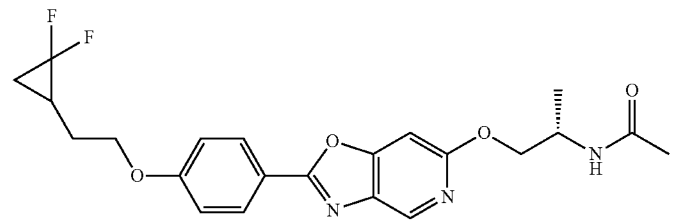 [SMILES: CC(=O)N[C@@H](C)COc1cc2oc(-c3ccc(OCCC4CC4(F)F)cc3)nc2cn1] | 432.2 |

Experimental Example 1

The ACC2 inhibitory action of the compound of the present invention was evaluated by the following method.

(1) Cloning of Human ACC2 Gene and Preparation of Recombinant Baculovirus

Human ACC2 gene was cloned by PCR using a human skeletal muscle cDNA library (Clontech) as a template and Primer 1 and Primer 2 shown below. Primer 1 and Primer 2 were prepared by adding SalI, XbaI restriction enzyme recognition sequences based on the information of the base sequence of human ACC2 gene (Genbank Accession U89344).

```
Primer 1:
                                        (SEQ ID NO: 1)
5'-AAAAGTCGACCCACCATGGTCTTGCTTCTTTGTCTATCTTG-3'

Primer 2:
                                        (SEQ ID NO: 2)
5'-TTTTTCTAGATCAGGTAGAGGCCGGGCTGTCCATG-3'
```

PCR was performed using Pyrobest DNA polymerase (TAKARA BIO INC.). The obtained PCR product was cloned to pT7 Blue vector (Novagen) and after confirmation of the base sequence, digested with restriction enzymes SalI and XbaI. The obtained DNA fragment was inserted into pFAST-BacHTa (Invitrogen) digested with restriction enzymes SalI and XbaI to give expression plasmid ACC2/pFAST-BacHTa.

A plasmid for expression of ACC2 without a mitochondrial targeting sequence was prepared by PCR using the expression plasmid as a template, and Primer 3 (SalI restriction enzyme recognition sequence was added) and Primer 4, which are prepared by reference to the information of human ACC2 gene base sequence (Genbank Accession U89344).

```
Primer 3:
                                        (SEQ ID NO: 3)
5'-CCAGGTCGACCCGCCAACGGGACTGGGACACAAGG-3'

Primer 4:
                                        (SEQ ID NO: 4)
5'-CGCACTCTCAGTTTCCCGGATTCCC-3'
```

PCR was performed using Pyrobest-DNA polymerase (TAKARA BIO INC.). The obtained PCR product was cloned to pT7 Blue vector (Novagen) and after confirmation of the base sequence, digested with restriction enzymes SalI and AflII. The obtained DNA fragment was inserted into ACC2/pFAST-BacHTa digested with restriction enzymes SalI and AflII to give expression plasmid ACC2mito7/pFAST-BacHTa.

Using the expression plasmid ACC2mito7/pFAST-BacHTa and BAC-TO-BAC Baculovirus Expression System (Invitrogen), virus stock BAC-ACC2 of recombinant Baculovirus (N terminal deleted (hereinafter Nd)) was prepared.

(2) Preparation of ACC2 (Nd) Protein

SF-9 cells (Invitrogen) were inoculated to a medium (10 L) for insect cells (Sf-900IISFM medium (Invitrogen) containing 5% fetal bovine serum (Trace), 50 mg/L Gentamicin (Wako), 0.1% Pluronic F-68 (Invitrogen)) at $1.0 \times 10^6$ cells/mL, and cultured with shaking in Wave Bioreactor (GE Health Care) at 27° C., 20 rpm, rocking angle 10°, oxygen concentration 30%.

On day 2 of the culture, recombinant Baculovirus BAC-ACC2 (Nd) was added, and the cells were cultured for 3 days. The culture medium was centrifuged at 1000×g for 10 min to give virus-infected cells. The cells were washed with phosphate buffered saline (Invitrogen) and centrifuged under the same conditions. The obtained cells were cryopreserved at −80° C.

The cryopreserved cells were thawed in ice and suspended in 900 mL of 25 mM HEPES buffer (pH 7.5) containing 10%

Glycerol, 0.3 M NaCl, 1 mM EDTA, 25 mM Sodium β-Glycerophosphate and 1 mM Sodium Orthovanadate, and supplemented with Complete Protease Inhibitor (Roche). The obtained suspension was homogenized three times in a polytron homogenizer (Kinematica) at 20,000 rpm for 30 sec. The obtained cell disruption solution was clarified by centrifugation at 186000×g for 60 min. To the supernatant was added 5 mL of AF-chelate 650M Ni chelated carrier (TOSOH), and the mixture was rotated at 4° C. for 1 hr, and centrifuged at 1000×g for 5 min, and the carrier was transferred to opened column. The column was washed with 50 mL of buffer A (50 mM HEPES (pH 7.5) containing 0.3 M NaCl), further washed with buffer A containing 20 mM Imidazole, and eluted with buffer A containing 250 mM Imidazole. The eluate was concentrated with Amicon Ultra 15 (Millipore) with a molecular weight cut off of 50K. The obtained concentrate was filtered using gelfiltration column (HiLoad 26/60 Superdex200 prep grade) (GE Health Care) with 50 mM HEPES buffer (pH 7.5) containing 10 mM $MgCl_2$, 2 mM Dithiothreitol, 10 mM Tripotassium Citrate and 0.3 M NaCl to give ACC2 (Nd). The obtained ACC2 (Nd) was cryopreserved at −80° C.

(3) Measurement of ACC2 Inhibitory Activity

ACC2 (Nd) (1.1 mg/ml) obtained in the above-mentioned (2) was diluted with an enzyme reaction buffer (50 mM HEPES (pH 7.5), 10 mM $MgCl_2$, 10 mM Tripotassium Citrate, 2 mM Dithiothreitol, 0.75 mg/ml Fatty acid free BSA) to a concentration of 6.4 μg/ml, and the mixture was added to each well of a 384 well assay plate (Nunc 265196) by 10 μl. A test compound dissolved in dimethyl sulfoxide (DMSO) was diluted with an enzyme reaction buffer and the resulting solution (5 μl) was added to each well. The mixture was incubated at 30° C. for 20 min. Then, a substrate solution (50 mM $KHCO_3$, 200 μM ATP, 200 μM Acetyl-CoA, 5 μl) was added to each well, and the mixture was reacted at 30° C. for 20 min (test compound addition group).

In addition, a reaction was performed in the same manner as above and without adding the test compound (test compound non-addition group).

Furthermore, a reaction was performed in the same manner as above and without adding the test compound and Acetyl-CoA (control group).

The reaction was quenched by adding a malachite green solution to each of the obtained reaction mixtures by 5 μl and stirring the mixtures. The obtained reaction mixture was left standing at room temperature for 20 min, and absorbance (620 nm) was measured using wallac1420 (PerkinElmer Japan Co., Ltd.). The above-mentioned malachite green solution was prepared by mixing Solution A (0.12% malachite green solution, prepared with 5N $H_2SO_4$, preserved at 4° C. in shading), Solution B (7.5% aqueous ammonium molybdate solution, prepared when in use) and Solution C (11% aqueous Tween 20 solution, preserved at room temperature) at a ratio of Solution A:Solution B:Solution C=100:25:2 (volume ratio).

ACC2 inhibitory rate (%) was determined according to the following calculation formula.

(1−(absorbance of test compound addition group−absorbance of control group)÷(absorbance of test compound non-addition group−absorbance of control group))×100

The inhibitory rates (%) against ACC2 at 10 μM of the test compound are shown in Table 21 and Table 22.

TABLE 21

| Example | ACC2 inhibitory rates (%) at 10 μM |
|---------|-----|
| 1 | 95 |
| 10 | 91 |
| 35 | 83 |
| 37 | 90 |
| 43 | 92 |
| 47 | 91 |
| 48 | 85 |
| 49 | 94 |
| 51c | 84 |
| 51d | 95 |

TABLE 22

| Example | ACC2 inhibitory rates (%) at 10 μM |
|---------|-----|
| 80 | 89 |
| 86 | 89 |
| 117 | 101 |
| 120 | 96 |
| 122 | 84 |
| 131 | 96 |
| 136 | 84 |
| 159 | 80 |
| 163 | 93 |
| 167 | 81 |

The inhibitory rates (%) against ACC2 at 1 μM of the test compound were determined in the same manner as in the above-mentioned method.

The inhibitory rates (%) against ACC2 at 1 μM of the test compound are shown in Table 23.

TABLE 23

| Example | ACC2 inhibitory rates (%) at 1 μM |
|---------|-----|
| 62 | 90 |
| 65 | 95 |
| 68 | 98 |
| 69 | 98 |

Formulation Example 1

Production of Capsule

| | |
|---|---|
| 1) compound of Example 1 | 30 mg |
| 2) finely-powdered cellulose | 10 mg |
| 3) lactose | 19 mg |
| 4) magnesium stearate | 1 mg |
| | total 60 mg |

1), 2), 3) and 4) are mixed and filled in a gelatin capsule.

Formulation Example 2

Production of Tablets

| | |
|---|---|
| 1) compound of Example 1 | 30 g |
| 2) lactose | 50 g |

| | |
|---|---|
| 3) cornstarch | 15 g |
| 4) calcium carboxymethylcellulose | 44 g |
| 5) magnesium stearate | 1 g |
| 1000 tablets | total 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention has ACC (acetyl-CoA carboxylase) inhibitory action, and is useful for the prophylaxis or treatment of obesity, diabetes, hypertension, hyperlipidemia, cardiac failure, diabetic complications, metabolic syndrome, sarcopenia, cancer and the like.

This application is based on patent application Nos. 233457/2011 and 122471/2012 filed in Japan, the contents of which are hereby incorporated by reference.

The invention claimed is:
1. A compound represented by formula (I):

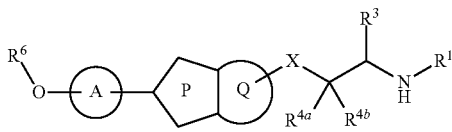

wherein:
R$^1$ is —COR$^2$ wherein R$^2$ is a C$_{1-6}$ alkyl group, a C$_{1-6}$ alkoxy group, an amino group optionally mono- or di-substituted by C$_{1-6}$ alkyl group(s), a 4- to 7-membered monocyclic non-aromatic heterocyclic group or a 5- to 7-membered monocyclic aromatic heterocyclic group;
R$^3$ is a C$_{1-6}$ alkyl group;
R$^{4a}$ and R$^{4b}$ are each independently a hydrogen atom or a C$_{1-6}$ alkyl group;
X is O, CO, or CH$_2$;
ring A is a 5- or 6-membered aromatic ring optionally further substituted by 1 to 4 substituents selected from the group consisting of:
 (1) a halogen atom,
 (2) a C$_{1-6}$ alkyl group optionally substituted by 1 to 3 substituents selected from the group consisting of:
  (a) a hydroxyl group, and
  (b) a halogen atom,
 (3) a C$_{1-6}$ alkoxy group optionally substituted by 1 to 3 halogen atoms,
 (4) a cyano group, and
 (5) a C$_{1-6}$ alkyl-carbonyl group;
ring P and ring Q form

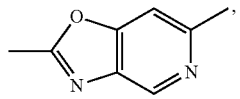

wherein ring Q is optionally further substituted by 1 to 3 halogen atoms; and
R$^6$ is a C$_{1-6}$ alkyl group optionally substituted by 1 to 3 substituents selected from the group consisting of:
 (a) C$_{3-6}$ cycloalkyl group optionally substituted by 1 to 5 substituents selected from the group consisting of:
  (i) a halogen atom, and
  (ii) a C$_{1-6}$ alkyl group,
 (b) a halogen atom,
 (c) a hydroxyl group,
 (d) a C$_{6-14}$ aryl group, and
 (e) a cyano group,
or a salt thereof.
2. The compound or salt of claim 1, wherein R$^1$ is —COR$^2$ wherein R$^2$ is a C$_{1-6}$ alkyl group, a C$_{1-6}$ alkoxy group, or an amino group optionally mono- or di-substituted by C$_{1-6}$ alkyl group(s).

3. The compound or salt of claim 1, wherein R$^{4a}$ and R$^{4b}$ are both hydrogen atoms.
4. The compound or salt of claim 1, wherein ring A is a 5- or 6-membered aromatic ring optionally further substituted by 1 to 4 substituents selected from the group consisting of:
 (1) a halogen atom,
 (2) a C$_{1-6}$ alkyl group, and
 (3) a C$_{1-6}$ alkoxy group.
5. The compound or salt of claim 1, wherein R$^6$ is a C$_{1-6}$ alkyl group optionally substituted by 1 to 3 substituents selected from the group consisting of:
 (a) a C$_{3-6}$ cycloalkyl group optionally substituted by 1 to 5 halogen atoms,
 (b) a halogen atom,
 (c) a hydroxy group, and
 (d) a C$_{6-14}$ aryl group.
6. The compound or salt of claim 1, wherein
R$^1$ is —COR$^2$ wherein R$^2$ is a C$_{1-6}$ alkyl group, a C$_{1-6}$ alkoxy group, or an amino group optionally mono- or di-substituted by C$_{1-6}$ alkyl group(s),
R$^{4a}$ and R$^{4b}$ are both hydrogen atoms,
ring A is benzene, pyridine or pyridazine, each of which is optionally further substituted by 1 to 4 substituents selected from the group consisting of:
 (1) a halogen atom,
 (2) a C$_{1-6}$ alkyl group, and
 (3) a C$_{1-6}$ alkoxy group,
and
R$^6$ is a C$_{1-6}$ alkyl group optionally substituted by 1 to 3 substituents selected from the group consisting of:
 (a) a C$_{3-6}$ cycloalkyl group optionally substituted by 1 to 5 halogen atoms,
 (b) a halogen atom,
 (c) a hydroxy group, and
 (d) a C$_{6-14}$ aryl group.
7. N-((2S)-1-((2-(4-(Cyclopropylmethoxy)-2,5-difluorophenyl)[1,3]oxazolo[4,5-c]pyridin-6-yl)oxy)propan-2-yl)acetamide or a salt thereof.
8. N-((2S)-1-((2-(4-(((1R)-2,2-Difluorocyclopropyl)methoxy)phenyl)[1,3]oxazolo[4,5-c]pyridin-6-yl)oxy)propan-2-yl)acetamide or a salt thereof.
9. N-((2S)-1-((2-(4-(((1R)-2,2-Difluorocyclopropyl)methoxy)-3-fluorophenyl)[1,3]oxazolo[4,5-c]pyridin-6-yl)oxy)propan-2-yl)acetamide or a salt thereof.
10. A pharmaceutical composition comprising the compound or salt of claim 1 and a pharmacologically acceptable carrier.
11. A method of inhibiting acetyl-CoA carboxylase in a mammal, which comprises administering an effective amount of the compound or salt of claim 1 to the mammal.
12. A method for the treatment of obesity or diabetes in a mammal, which comprises administering an effective amount of the compound or salt of claim 1 to the mammal.

* * * * *

```
SEQUENCE LISTING

<160> NUMBER OF SEQ ID NOS: 4

<210> SEQ ID NO 1
<211> LENGTH: 41
<212> TYPE: DNA
<213> ORGANISM: Artificial
<220> FEATURE:
<223> OTHER INFORMATION: PCR primer for hACC2 gene cloning

<400> SEQUENCE: 1
aaaagtcgac ccaccatggt cttgcttctt tgtctatctt g                    41

<210> SEQ ID NO 2
<211> LENGTH: 35
<212> TYPE: DNA
<213> ORGANISM: Artificial
<220> FEATURE:
<223> OTHER INFORMATION: PCR primer for hACC2 gene cloning

<400> SEQUENCE: 2
tttttctaga tcaggtagag gccgggctgt ccatg                           35

<210> SEQ ID NO 3
<211> LENGTH: 35
<212> TYPE: DNA
<213> ORGANISM: Artificial
<220> FEATURE:
<223> OTHER INFORMATION: PCR primer for construction of ACC2-expressing
      plasmid

<400> SEQUENCE: 3
ccaggtcgac ccgccaacgg gactgggaca caagg                           35

<210> SEQ ID NO 4
<211> LENGTH: 25
<212> TYPE: DNA
<213> ORGANISM: Artificial
<220> FEATURE:
<223> OTHER INFORMATION: PCR primer for construction of ACC2-expressing
      plasmid

<400> SEQUENCE: 4
cgcactctca gtttcccgga ttccc                                      25
```